United States Patent
Payton et al.

(10) Patent No.: US 12,128,101 B2
(45) Date of Patent: Oct. 29, 2024

(54) DOSAGE AND ADMINISTRATION OF ANTI-C5 ANTIBODIES FOR TREATMENT OF PAROXYSMAL NOCTURNAL HEMOGLOBINURIA (PNH) AND ATYPICAL HEMOLYTIC UREMIC SYNDROME (AHUS)

(71) Applicant: Alexion Pharmaceuticals, Inc., Boston, MA (US)

(72) Inventors: Lori Payton, Madison, CT (US); Scott T. Rottinghaus, Salem, CT (US); Rajendra Pradhan, New Haven, CT (US); Andrew Damokosh, West Hartford, CT (US); Xiang Gao, Guilford, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 388 days.

(21) Appl. No.: 16/757,512

(22) PCT Filed: Oct. 26, 2018

(86) PCT No.: PCT/US2018/057760
§ 371 (c)(1),
(2) Date: Apr. 20, 2020

(87) PCT Pub. No.: WO2019/084438
PCT Pub. Date: May 2, 2019

(65) Prior Publication Data
US 2020/0254092 A1 Aug. 13, 2020

Related U.S. Application Data

(60) Provisional application No. 62/685,425, filed on Jun. 15, 2018, provisional application No. 62/685,505, filed on Jun. 15, 2018, provisional application No. 62/662,503, filed on Apr. 25, 2018, provisional application No. 62/643,608, filed on Mar. 15, 2018, provisional application No. 62/643,056, filed on Mar. 14, 2018, provisional application No. 62/577,244, filed on Oct. 26, 2017.

(51) Int. Cl.
*A61K 39/395* (2006.01)
*A61K 9/00* (2006.01)
*A61K 39/00* (2006.01)
*A61P 7/00* (2006.01)
*C07K 16/18* (2006.01)

(52) U.S. Cl.
CPC ........ *A61K 39/3955* (2013.01); *A61K 9/0019* (2013.01); *A61P 7/00* (2018.01); *C07K 16/18* (2013.01); *A61K 2039/505* (2013.01); *A61K 2039/545* (2013.01); *C07K 2317/526* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |

(Continued)

FOREIGN PATENT DOCUMENTS

| AU | 2018201961 A1 | 4/2018 |
|---|---|---|
| CN | 106459189 A | 2/2017 |

(Continued)

OTHER PUBLICATIONS

History of Change for Study: NCT02949128: Single Arm Study of ALXN1210 in Complement Inhibitor Treatment-Naïve Adult and Adolescent Patients with Atypical Hemolytic Syndrome (aHUS); Study NCT02949128, Submitted Date: Oct. 27, 2016 (v1). (Year: 2016).*
NCT03056040 "ALXN1210 versus eculizumab in adult participants with paraoxysmal nocturnal hemolglobinuria (PNH) currently treated with eculizumab" Alexion Pharmaceuticals, Inc., first posted Feb. 16, 2017 (Year: 2017).*
NCT02946463 "ALXN1210 (Ravulizumab) versus eculizumab in complement inhibitor treatment-naive adult participants with paroxysmal nocturnall hemoglobinuria (PNH)" Alexion Pharmaceuticals, first posted Oct. 27, 2016. (Year: 2016).*

(Continued)

*Primary Examiner* — Maher M Haddad
(74) *Attorney, Agent, or Firm* — Nelson Mullins Riley & Scarborough LLP; Jane E. Remillard, Esq.; Jill Gorny Sloper, Esq.

(57) ABSTRACT

Provided are methods for clinical treatment of Paroxysmal Nocturnal Hemoglobinuria (PNH) and Atypical Hemolytic Uremic Syndrome (aHUS) using an anti-C5 antibody, or antigen binding fragment thereof.

12 Claims, 46 Drawing Sheets
Specification includes a Sequence Listing.

(56) References Cited

U.S. PATENT DOCUMENTS

| | | |
|---|---|---|
| 6,192,891 B1 | 2/2001 | Gravel et al. |
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |
| 6,302,855 B1 | 10/2001 | Lav et al. |
| 6,355,245 B1 | 3/2002 | Evans et al. |
| 6,737,056 B1 | 5/2004 | Presta |
| 6,933,368 B2 | 8/2005 | Co et al. |
| 7,112,341 B1 | 9/2006 | Nagarajan et al. |
| 7,371,826 B2 | 5/2008 | Presta |
| 7,390,786 B2 | 6/2008 | Warne et al. |
| 7,556,615 B2 | 7/2009 | Pettis et al. |
| 7,670,600 B2 | 3/2010 | Dall'Acqua et al. |
| 7,704,497 B2 | 4/2010 | Dall'Acqua et al. |
| 8,088,376 B2 | 1/2012 | Chamberlain et al. |
| 8,241,628 B2 | 8/2012 | Diefenbach-Streiber et al. |
| 8,323,962 B2 | 12/2012 | Dall'Acqua et al. |
| 8,367,805 B2 | 2/2013 | Chamberlain et al. |
| 8,802,820 B2 | 8/2014 | Chamberlain et al. |
| 8,883,158 B2 | 11/2014 | Diefenbach-Streiber et al. |
| 9,079,949 B1 | 7/2015 | Andrien, Jr. et al. |
| 9,107,861 B1 | 8/2015 | Andrien, Jr. et al. |
| 9,206,251 B2 | 12/2015 | Andrien, Jr. et al. |
| 9,371,377 B2 | 6/2016 | Andrien, Jr. et al. |
| 9,447,176 B2 | 9/2016 | Rother et al. |
| 9,663,574 B2 | 5/2017 | Andrien, Jr. et al. |
| 9,765,135 B2 | 9/2017 | Ruike et al. |
| 9,771,418 B2 | 9/2017 | Rother et al. |
| 9,803,007 B1 | 10/2017 | Andrien, Jr. et al. |
| 10,227,400 B2 | 3/2019 | Andrien, Jr. et al. |
| 10,584,164 B2 | 3/2020 | Andrien, Jr. et al. |
| 10,633,434 B2 | 4/2020 | Hu et al. |
| 11,434,280 B2 | 9/2022 | Andrien, Jr. et al. |
| 2002/0026176 A1 | 2/2002 | Varner et al. |
| 2005/0271660 A1 | 12/2005 | Wang |
| 2006/0141456 A1 | 6/2006 | Edwards et al. |
| 2007/0172483 A1 | 7/2007 | Schwaeble et al. |
| 2007/0235029 A1 | 10/2007 | Zhu et al. |
| 2008/0202513 A1 | 8/2008 | Birchall et al. |
| 2008/0241223 A1 | 10/2008 | Nivaggioli et al. |
| 2009/0110679 A1 | 4/2009 | Li et al. |
| 2010/0098730 A1 | 4/2010 | Lowman et al. |
| 2011/0111406 A1 | 5/2011 | Igawa et al. |
| 2012/0225056 A1 | 9/2012 | Rother et al. |
| 2012/0230982 A1 | 9/2012 | Zhou et al. |
| 2015/0299305 A1 | 10/2015 | Andrien, Jr. et al. |
| 2016/0108115 A1 | 4/2016 | Andrien, Jr. et al. |
| 2016/0251433 A1 | 9/2016 | Andrien, Jr. et al. |
| 2016/0355579 A1 | 12/2016 | Rother et al. |
| 2016/0355580 A1 | 12/2016 | Rother et al. |
| 2017/0298123 A1* | 10/2017 | Andrien, Jr. .......... A61P 5/14 |
| 2017/0355757 A1 | 12/2017 | Hu et al. |
| 2017/0369562 A1 | 12/2017 | Rother et al. |
| 2018/0009885 A1 | 1/2018 | Andrien, Jr. et al. |
| 2018/0311299 A1 | 11/2018 | Griffin et al. |
| 2018/0311345 A1 | 11/2018 | Pober et al. |
| 2019/0023775 A1* | 1/2019 | Bachman ............... C07K 16/40 |
| 2019/0263897 A1 | 8/2019 | Andrien, Jr. et al. |
| 2019/0276524 A1 | 9/2019 | Griffin et al. |
| 2019/0367599 A1* | 12/2019 | Shinomiya .............. A61P 7/00 |
| 2020/0140531 A1 | 5/2020 | Rother et al. |
| 2020/0157200 A1 | 5/2020 | Andrien, Jr. et al. |
| 2020/0254092 A1 | 8/2020 | Payton et al. |
| 2021/0000927 A1* | 1/2021 | Ricardo ................. A61K 38/12 |
| 2021/0122806 A1 | 4/2021 | Malanson et al. |
| 2021/0187054 A1 | 6/2021 | Griffin et al. |
| 2021/0214425 A1 | 7/2021 | Payton et al. |
| 2021/0332147 A1 | 10/2021 | Payton et al. |
| 2022/0235121 A1 | 7/2022 | Payton et al. |
| 2023/0002482 A1 | 1/2023 | Philominathan et al. |
| 2023/0106734 A1 | 4/2023 | Ortiz et al. |
| 2024/0141024 A1 | 5/2024 | Andrien, Jr. et al. |

FOREIGN PATENT DOCUMENTS

| | | |
|---|---|---|
| EP | 430539 A2 | 6/1991 |
| EP | 488401 A1 | 6/1992 |
| EP | 2006381 A1 | 12/2008 |
| EP | 1610820 B1 | 9/2010 |
| EP | 2275443 A1 | 1/2011 |
| EP | 3095795 A1 | 11/2016 |
| JP | 2002-500164 A | 1/2002 |
| JP | 2010-215674 A | 9/2010 |
| JP | 2010-529999 A | 9/2010 |
| JP | 2013-526861 A | 6/2013 |
| JP | 2015-536930 A | 12/2015 |
| JP | 2017-095440 A | 6/2017 |
| JP | 2018-503620 A | 2/2018 |
| WO | 8902468 A1 | 3/1989 |
| WO | 8905345 A1 | 6/1989 |
| WO | 8907136 A2 | 8/1989 |
| WO | 9207573 A1 | 5/1992 |
| WO | 94/02559 A1 | 2/1994 |
| WO | 94/04678 A1 | 3/1994 |
| WO | 94/28027 A1 | 12/1994 |
| WO | 9734631 A1 | 9/1997 |
| WO | 98/23289 A1 | 6/1998 |
| WO | 98/47531 A2 | 10/1998 |
| WO | 9919343 A1 | 4/1999 |
| WO | 0061178 A1 | 10/2000 |
| WO | 0069887 A2 | 11/2000 |
| WO | 0178693 A2 | 10/2001 |
| WO | 2002/013859 A1 | 2/2002 |
| WO | 2003/074679 A2 | 12/2003 |
| WO | 03105757 A2 | 12/2003 |
| WO | 2004024156 A1 | 3/2004 |
| WO | 2004026380 A2 | 4/2004 |
| WO | 2004029207 A2 | 4/2004 |
| WO | 2004060407 A1 | 7/2004 |
| WO | 2004073551 A2 | 9/2004 |
| WO | 2004091658 A1 | 10/2004 |
| WO | 2005011735 A1 | 2/2005 |
| WO | 2005040217 A2 | 5/2005 |
| WO | 2005/077981 A1 | 8/2005 |
| WO | 2005092925 A2 | 10/2005 |
| WO | 06/031994 A2 | 3/2006 |
| WO | 2006/053301 A2 | 5/2006 |
| WO | 2006094234 A1 | 9/2006 |
| WO | 2006/105338 A2 | 10/2006 |
| WO | 2006/122257 A2 | 11/2006 |
| WO | 2007041635 A2 | 4/2007 |
| WO | 2007/103134 A2 | 9/2007 |
| WO | 2007/106585 A1 | 9/2007 |
| WO | 2007114319 A1 | 10/2007 |
| WO | 08/043822 A2 | 4/2008 |
| WO | 2008048545 A2 | 4/2008 |
| WO | 2008092117 A2 | 7/2008 |
| WO | 2008/157356 A2 | 12/2008 |
| WO | 2009/041643 A1 | 4/2009 |
| WO | 2009058492 A2 | 5/2009 |
| WO | 2009086320 A1 | 7/2009 |
| WO | 2009125825 A1 | 10/2009 |
| WO | 2010/127069 A1 | 11/2010 |
| WO | 2010/151526 A1 | 12/2010 |
| WO | 2011/104381 A2 | 9/2011 |
| WO | 2011111007 A2 | 9/2011 |
| WO | 2011/122011 A2 | 10/2011 |
| WO | 2011/137362 A1 | 11/2011 |
| WO | 2011137395 A1 | 11/2011 |
| WO | 2012/073992 A1 | 6/2012 |
| WO | 2012133782 A1 | 10/2012 |
| WO | 2013046704 A2 | 4/2013 |
| WO | 2013047748 A1 | 4/2013 |
| WO | 2013/165690 A1 | 11/2013 |
| WO | 2014/068021 A1 | 5/2014 |
| WO | 2015021166 A2 | 2/2015 |
| WO | 2015/134894 A1 | 9/2015 |
| WO | 2016/106291 A1 | 6/2016 |
| WO | 2016098356 A1 | 6/2016 |
| WO | 2016/160756 A2 | 10/2016 |
| WO | 2016/209956 A1 | 12/2016 |
| WO | 2017/044811 A1 | 3/2017 |

(56) References Cited

FOREIGN PATENT DOCUMENTS

| | | |
|---|---|---|
| WO | 2017/051273 A1 | 3/2017 |
| WO | 2017/123636 A1 | 7/2017 |
| WO | 2017/218515 A1 | 12/2017 |
| WO | 2018/109588 A2 | 6/2018 |
| WO | 2018/143266 A1 | 8/2018 |
| WO | 2019/023564 A1 | 1/2019 |
| WO | 2019/084438 A1 | 5/2019 |
| WO | 2019/118556 A1 | 6/2019 |
| WO | 2019/231983 A1 | 12/2019 |
| WO | 2019/236345 A1 | 12/2019 |
| WO | 2020/006266 A1 | 1/2020 |
| WO | 2020/092549 A1 | 5/2020 |
| WO | 2020/154626 A1 | 7/2020 |
| WO | 2021/091937 A1 | 5/2021 |
| WO | 2022087339 A1 | 4/2022 |

OTHER PUBLICATIONS

Sheridan et al. Design and preclinical characterization of ALXN1210: A next generation anti-C5 monoclonal antibody with improved pharamacokinetics and duration of action. Immunobiology 221(10): 1131-1225, 2016, p. 1158, Abstract # 63 .. (Year: 2016).*
Ambati and Adamis, Prog Retin Eye Res 21(2): 145-151 (2002).
Amsterdam et al., Am J Physiol 268: H448-H457 (1995).
Anonymous: "Assessment report Soliris /Eculizumab,"pp. 1-28, Mar. 21, 2013, Retrieved from the Internet:URL: https://www.ema.europa.eu/en/documents/variation-report/soliris-h-c-791-ii-0050-epar-assessment-report-variation_en.pdf [retrieved on Aug. 7, 2019].
Anonymous: "Single Arm Study of ALXN1210 in Complement Inhibitor Treatment-Naive Adult and Adolescent Patients With Atypical Hemolytic Uremic Syndrome (aHUS)," pp. 1-6 (2016) XP055619305,Retrieved from the Internet:URL: https://clinicaltrials.gov/ct2/show/NCTO2949128?term=alxn1210&rank=8 [retrieved on Sep. 6, 2019].
Anonymous: "Study of Ravulizumab in Children and Adolescents With Atypical Hemolytic Uremic Syndrome (aHUS)", Apr. 27, 2017 (Apr. 27, 2017), pp. 1-6, XP055619309,Retrieved from the Internet: URL:https://clinicaltrials.gov/ct2/show/NCTO3131219?term=alxn1210&rank=5 [retrieved on Sep. 6, 2019].
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas and Balachandran, Expert Opin Drug Delivery 5(1): 1-10 (10) (2008).
Baudino et al.l, J Immunol 181: 6664-6669 (2008).
Berge et al., J Pharm Sci 66: 1-19 (1977).
Berkner et al., BioTechniques 6: 616 (1988).
Better et al., Science 240: 1041-1043 (1988).
Bieg et al., Autoimmunity 31(1): 15-24 (1999).
Bless et al., Am J Physiol 276(1): L57-L63 (1999).
Brodsky, R. et al., "Complement in hemolytic anemia," Blood, vol. 126(22):2459-2465 (2015).
Burmeister et al., Nature 372: 379-383 (1994).
Burton et al., Adv Immun 51:52 pages (1992).
Campistol, J., et al., "An update for atypical haemolytic uraemic syndrome: diagnosis and treatment. A consensus document," Nefrologia, vol. 33(1):27-45 (2013).
Canfield et al., J Exp Med 173: 1483-1491 (1991).
Caron et al., J Exp Med 176: 1191-1195 (1992).
Chaparro-Riggers, Biol Chem 287: 11090-11097 (2012).
Chothia et al., Nature 342: 877-883 (1989).
Chowdhury et al., Science 254: 1802-1805 (1991).
Christmann, M., et al., "Eculizumab as First-Line Therapy for Atypical Hemolytic Uremic Syndrome," Pediatrics, vol. 133, e1759: 7 pages (2014).
Co et al., Mol Immunol 30: 1361, 6 pages (1993).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117: 1129-1138 (2006).
Danos and Mulligan, Proc Natl Acad Sci USA 85; 6460-6464 (1988).
Datta-Mannan et al., J Biol Chem 282(3): 1709-1717 (2007).
Daugherty, A., et al., "Formulation and delivery issues for monoclonal antibody thera-peutics," Current Trends in Monoclonal Antibody Development and Manufacture, Chapter 8:103-129 (2010).
Deans et al., Proc Natl Acad Sci USA 81: 1292, 5 pages (1984).
Dong et al, Reviews in Mol Biotech 82: 303-323 (2002).
Duncan and Winter Nature 322: 738-40 (1988).
Eglitis et al., Science 230: 1395-1398 (1985).
Eppstein et al., Proc Natl Acad Sci USA 82: 3688, 5 pages (1985).
European Search Report, EP Application No. 161776562, dated Aug. 8, 2016, 8 pages.
Evans, et al., Mol Immunol 32(16): 1183-95 (1995).
Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).
Fearon et al., J Exp Med 142: 856-863 (1975).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Gulsen and Chauhan, Invest Opthalmol Vis Sci 45: 2342-2347 (2004).
Gupta et al., Vaccine 13(14): 1263-1276 (1995).
Hanauske et al., Clin Cancer Res 13(2, part 1): 523-531 (2007).
Heinen, S. et al., "Monitoring and modeling treatment of atypical hemolytic uremic syndrome," Molecular Immunology, vol. 54: 84-88 (2013).
Hetherington et al., Antimicrobial Agents and Chemotherapy 50(10): 3499-3500 (2006).
Hezareh et al., J Virol 75: 12161-12168 (2001).
Hillmen et al., N. Engl J Med 350(6): 552-559 (2004).
Hillmen, P. et al., "Long-term safety and efficacy of sustained eculizumab treatment in patients with paroxysmal nocturnal haemoglobinuria,"British Journal of Haematology doi: 10.1111/bjh.12347, 12 pages (2013).
Hinton et al., J Biol Chem 279: 6213-6216 (2004).
Hinton et al., J Immunol 176: 246-356 (2006).
Hirt-Minkowski, P. et al., "Atypical Hemolytic Uremic Syndrome: Update on the Complement System and What Is New," Nephron Clin Pract., 114:c219-c235 (2010).
Holers and Thurman, Molecular Immunology 41: 147-152 (2004).
Holers et al., Immunological Reviews 223: 300-316 (2008).
Homeister et al., J Immunol 150: 1055-1064 (1993).
Hou et al., Cytokine 10: 319-30 (1998).
Houdebine, Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030, 5 pages (1980).
Hwu et al., J Immunol 150: 4104-4115 (1993).
Igawa et al., "Antibody recycling by engineered pH-dependent antigen binding improves the duration of antigen neutralization," Nat. Biotechnol. 28(11):1203-1207 (2010).
International Preliminary Report on Patentability, PCT/US2018/044071, dated Jan. 28, 2020, 8 pages.
International Preliminary Report on Patentability, PCT/US2019/034293, dated Dec. 1, 2020, 9 pages.
International Preliminary Report on Patentability, PCT/US2019/034297, dated Dec. 8, 2020, 10 pages.
International Search Report and Written Opinion for Application No. PCT/US2015/019225, dated May 18, 2015.
International Search Report and Written Opinion, PCT/US2018/044071, dated Oct. 2, 2018, 12 pages.
International Search Report and Written Opinion, PCT/US2019/034293, dated Aug. 21, 2019, 14 pages.
International Search Report and Written Opinion, PCT/US2019/034297, dated Sep. 25, 2019, 13 pages.
Isaacs et al., J Immunol 161: 3862-3869 (1998).
Isenman et al., J Immunol 124: 326-331 (1980).

(56) References Cited

OTHER PUBLICATIONS

Ishii-Watabe, A. et al., "Molecular Design of Therapeutic Antibodies," Pharmaceutics 74 (1): 4-11: 17 pages (2014).
Israel et al, Immunology 89(4): 573-578 (1996).
Ito, W. et al., "The His-probe method: effects of histidine residues introduced into the complementarity-determining regions of antibodies on antigen-antibody interactions at different pH values," FEBS Letter, vol. 309(1): 85-88(1992).
Johne et al., J Immunol Meth 160: 191-198 (1993).
Johnson et al., J Med Chem 42: 4640-4649 (1999).
Jones et al., Nature 321: 522-525 (1986).
Jonsson et al., Ann Biol Clin 51: 19-26 (1993).
Jonsson et al., Biotechniques 11: 620-627 (1991).
Junghans, R. et al., "The protection receptor for IgG catabolismis the beta2-microglobulin-containing neonatal intestinal transport receptor," PNAS, USA, vol. 93(11):5512-5516 (1996).
Jungi and Pepys, Immunology 43(2): 271-279 (1981).
Kaszubska et al., Protein Expression and Purification 18: 213-220 (2000).
Kay et al., Human Gene Therapy 3: 641-647 (1992).
Kim et al., Ophthalmic Res 39: 244-254 (2007).
Kinstler et al., Advanced Drug Deliveries Reviews 54: 477-485.
Klein et al., Proc. Natl Acad Sci USA 78: 524-528 (1981).
Kroshus et al., Transplantation 60: 1194-1202 (1995).
Lee, CV., et al., "High-affinity human antibodies from phage-displayed synthetic Fab libraries with a single framework scaffold," J. Molecular Biology, vol. 340 (5):1073-1093 (2004).
Lee, et al., Bioconjug Chem 10(6): 973-81 (1999).
Legendre, CM, et al., "Terminal Complement Inhibitor Eculizumab in Atypical Hemolytic-Uremic Syndrome," N Engl J Med., vol. 368:2169-2181 (2013).
Levy and Ladda, Nat New Biol 229(2): 51-52 (1971).
Licht, C., et al., "The global aHUS registry: methodology and initial patient characteristics," BMC Nephrology, vol. 16 (207) 8 pages (2015) DOI 10.1186/s12882-015-0195-1.
Lodmell et al., Vaccine 18:1059-1066 (2000).
Loirat, C. et al., "Plasmatherapy in Atypical Hemolytic Uremic Syndrome," Seminars in Thrombosis and Hemostasis, vol. 36(6): 673-681 (2010).
Loirat, C. et al., "An international consensus approach to the management of atypical hemolytic uremic syndrome in children," Pediatr Nephrol., vol. 31:15-39 (2016).
Loirat, C. et al., "Atypical hemolytic uremic syndrome," Orphanet Journal of Rare Diseases, vol. 6:60: 30 pages (2011).
Lusky and Botchan, Nature 293: 79, 3 pages (1981).
Malina, M. et al., "Peripheral Gangrene in Children With Atypical Hemolytic Uremic Syndrome," Pediatrics, vol. 131: e331-e335 (2013).
Mclaughlin et al., J Virol 62: 1963-1973 (1989).
Medicus et al., J Exp Med 144: 1076-1093 (1976).
Mihu et al., J Gastrointestin Liver Dis 16(4): 419-424 (2007).
Moongkarndi et al., Immunobiol 165: 323 (1983).
Moongkarndi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Reviews in Molecular Biotechnology, 26: 230-235 (2001).
Newkirk et al., Clin Exp Immunol 106(2): 259-264 (1996).
Noris, M. et al., "STEC-HUS, atypical HUS and TTP are all diseases of complement activation," Nat. Rev. Nephrol., vol. 8: 622-633 (2012).
Nuttall et al., Curr Pharm Biotech 1: 253-263 (2000).
Park et al., Anesth Analg 99(1): 42-48 (1999).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raju, BioProcess International 1(4): 44-53 (2003).
Ranta and Uritti, Adv Drug Delivery Rev 58(11): 1164-1181 (2006).
Rawal and Pangburn, J Immunol 166(4): 2635-2642 (2001).
Reiss, U. et al., "Efficacy and safety of eculizumab in children and adolescents with paroxysmal nocturnal hemoglobinuria," Pediatric Blood and Cancer, vol. 61(9):1544-1550 (2014).
Rich et al., Curr Opin Biotechnol 11: 54-61 (2000).
Riechmann et al., J Immunol Meth 231: 25-38 (1999).
Riechmann et al., Nature 332: 323-327 (1988).
Rinder et al., J Clin Invest 96: 1564-1572 (1995).
Roberts et al.,PNAS, 54: 459-476 (2002).
Roeth, A. et al., "Optimization of Dose Regimen for ALXN1210, a Novel Complement C5 Inhibitor, in Patients with Paroxysmal Nocturnal Hemoglobinuria (PNH):Results of 2 Phase 1/2 Studies," Blood,vol. 130:3482 (2017).
Rogers et al., J Nucl Med 38: 1221-1229 (1997).
Rondon and Marasco, Annual Review of Microbiology 51: 257-284 (1997).
Roopenian et al., Methods Mol Blol 602: 93-104 (2010).
Roopenian, DC, et al., "FcRn: the neonatal Fc receptor comes of age," Nature Reviews Immunology, vol. 7(9): 115-725 (2007).
Rosenfeld et al., Cell 68: 143-155 (1992).
Rother , R. et al.,"Discovery and development of the complement inhibitor eculizumab for the treatment of paroxysmal nocturnal hemoglobinuria," Nature Biotechnology, 25 (11): 1256-1264 (1488 Supp) (2007).
Sawai et al., Am J Repr Immunol 34: 26-34 (1995).
Saland, J. et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9) 908-913 (2002).
Sarver et al., Proc Natl Acad Sci USA 79: 7147 (1982).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).
Sharma, V.K. et al., "The formulation and delivery of monoclonal antibodies", Therapeutic Monoclonal Antibodies, Chapter 30: 675-711 (2009).
Sheerin, N.S. et al., "A national specialized service in England for atypical haemolytic uraemic syndrome—the first year's experience," QJM: An International Journal of Medicine, 27-33: 7 pages (2016).
Sheridan, D. et al., "Design and preclinical characterization of ALXN1210: A next generation anti-C5 monoclonal antibody with improved pharmacokinetics and duration of action," Immunobiology, vol. 221(Issue 10): 1158 (2016).
Sheridan, D. et al., "Design and preclinical characterization of ALXN1210: A novel anti-C5 antibody with extended duration of action," PLoS One 13(4): e0195909, 15 pages (2018).
Shields et al., J Biol Chem 276(9): 6591-6604 (2001).
Shields et al., J Biol Chem 277(30): 26733-26740 (2002).
Shire, S. et al., "High-concentration antibody formulations," Formulation and Process De-velopment Strategies for Manufacturing Biopharmaceuticals, Chapter 15: 349-381 (2010).
Shopes, Immunol 148: 2918-2922 (1992).
Shu et al., Proc Natl Aced Sci USA 90: 7995-7999 (1993).
Sissons et al., Proc Natl Acad Sci USA 77: 559-562 (1980).
Skerra et al., Science 240: 1038-1040 (1988).
Southern and Berg, Mol Appl Genet 1:327, 15 pages (1982).
Staelens et al., Mol Immunol 43: 1243-1257 (2006).

(56) References Cited

OTHER PUBLICATIONS

Tabrizi, Ma et al., "Elimination mechanisms of therapeutic monoclonal antibodies ," Drug Discovery Today, vol. 11 (1-2):81-88 (2006).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 166(6): 1060-1068 (1998).
Tsai, H. et al., "A Mechanistic Approach to the Diagnosis and Management of Atypical Hemolytic Uremic Syndrome," Transfusion Medicine Reviews, vol. 28:187-197 (2014).
Van Beusechem et al., Proc Natl Acad Sci USA 89: 7640-7644 (1992).
Van Gurp et al., Am J Transplantation 8(8): 1711-1718 (2008).
Van Kuik-Romeijn et al., Transgenic Res 9(2): 155-159 (2000).
Verhoeyen et al., Science 239: 1534-1536 (1988).
Wang et al., Proc Natl Acad Sci USA 93: 8563-8568 (1996).
Wang, W. et al., "Antibody Structure, Instability, and Formulation," Journal of Pharmaceu-tical Sciences, American Chemical Society and American Pharmaceutical Association, vol. 96(1):1-26 (2007).
Ward and Zvaifler, J Clin Invest 50(3): 606-16 (1971).
Waters, A. et al., "aHUS caused by complement dysregulation: new therapies on the horizon," Pediatr Nephrol., vol. 26:41-57 (2011).
Weisman et al., Science 249: 146-151 (1990).
Wetsel et al., J Biol Chem 265: 2435-2440 (1990).
Wigler et al., Cell 16: 77, 9 pages (1979).
Wilson et al., Proc Natl Acad Sci USA 85: 3104-3018 (1988).
Wright et al., EMBO J 10(10): 2717-2723 (1991).
Wurzner et al., Complement Inflamm 8: 328-340 (1991).
Xu et al., Cell Immunol 200: 16-26 (2000).
Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Zuber, J. et al., "New insights into postrenal transplant hemolytic uremic syndrome," Nat. Rev. Nephrol., vol. 7: 23-35 (2011).
International Preliminary Report on Patentability, PCT/US2018/057760, dated Apr. 28, 2020 2019, 9 pages.
International Search Report and Written Opinion, PCT/US2018/057760, dated Mar. 21, 2019, 13 pages.
Lee, J-W et al., "Results from a Phase 3, Multicenter, Noninferiority Study of Ravulizumab (ALXN1210) Versus Eculizumab In Adult Patients with Paroxysmal Nocturnal Hemoglobinuria (PNH) Naïve To Complement Inhibitors," (2018), XP055550310, Retrieved from the Internet: URL:https://learningcenter.ehaweb.org/eha/2018/stockholm/218885/jong.wook.lee.results.from.a.phase.3.multicenter.noninferiority.study.of.html?f=media=1 [retrieved on Jan. 31, 2019] the whole document.
Lee, J-W et al., "Ravulizumab (ALXN1210) vs eculizumab in adult patients with PNH naive to complement inhibitors: the 301 study," Blood, (2018) ISSN: 0006-4971, DOI: 10.1182/blood-2018-09-876136.
Lee, J-W. et al., "2428 Immediate, Complete, and Sustained Inhibition of C5 with ALXN1210 Reduces Complement-Mediated Hemolysis in Patients with Paroxysmal Nocturnal Hemoglobinuria (PNH): Interim Analysis of a Dose-Escalation Study," Internet Citation, Dec. 4, 2016 (Dec. 4, 2016), XP002768543, Retrieved from the Internet: URL:https://ash.confex.com/ash/2016/webprogram/Paper90053.html [retrieved on Mar. 23, 2017] the whole document.
Roth, A. et al., "Ravulizumab (ALXN1210) in patients with paroxysmal nocturnal hemoglobinuria: results of phase lb/2 studies", Blood Adv., vol. 2 (17): 2176-2185 (2018).
Wong, E. et al., "Anticomplement C5 therapy with eculizumab for the treatment of paroxysmal nocturnal hemoglobinuria and atypical hemolytic uremic syndrome," Translational Research, vol. 165 (2): 306-320 (2017) XP055358380, NL ISSN: 1931-5244, DOI:10.1016/j.trsl.2014.10.010 the whole document.
Anonymous: "Alexion Receives FDA Approval for ULTOMIRIS (ravulizumab-cwvz) for Atypical Hemolytic Uremic Syndrome (aHUS)," Oct. 18, 2019.
Anonymous: "Ravulizumab for atypical haemolytic uraemic syndrome in adults and children—first line," Aug. 1, 2018, pp. 1-10.
International Search Report and Written Opinion, PCT/US2020/014998, dated Jun. 22, 2020, 13 pages.
Rondeau, E. et al., "The long-acting C5 inhibitor, Ravulizumab, is effective and safe in adult patients with atypical hemolytic uremic syndrome naive to complement inhibitor treatment," Kidney International, Mar. 6, 2020, pp. 1-10.
Tanaka, K. et al., "The long-acting C5 inhibitor, ravulizumab, is efficacious and safe in pediatric patients with atypical hemolytic uremic syndrome previously treated with eculizumab," Pediatric Nephrology, vol. 36(4):889-898 (2021).
International Search Report and Written Opinion, PCT/US2021/040802, dated Oct. 18, 2021, 9 pages.
Ito, N. et al., "Efficacy and safety of eculizumab in childhood atypical hemolytic uremic syndrome in Japan," Clin Exp Nephrol., vol. 20:265-272 (2016).
NCT02946463 ALXN1210 Versus Eculizumab in Complement Inhibitor Treatment-Native Adult Patients With Paroxysmal Nocturnal Hemoglobinuria (PNH), ClinicalTrials.gov, [online], Jul. 28, 2017, [retrieved on Jul. 21, 2022], 7 pags https://clinicaltrials.gov/ct2/history/NCT02946463?V_9 View#StudyPageTop>.
Al-Ani, Fatimah et al. "Eculizumab in the management of paroxysmal nocturnal hemoglobinuria: patient selection and special considerations," Therapeutics and Clinical Risk Management, vol. 12: 1161-1170 (2016).
Curran, K. J et al. "Paroxysmal nocturnal hemoglobinuria in pediatric patients," Pediatric Blood & Cancer, vol. 59(3): 525-529 (2012).
Greenbaum, L. et al. "Eculizumab is a safe and effective treatment in pediatric patients with atypical hemolytic uremic syndrome" Kidney International, vol. 89: 701-711 (2016).
History of Changes for Study: NCT03131219 Study of ALXN1210 in Children and Adolescents With Atypical Hemolytic Uremic Syndrome (aHUS), Nov. 16, 2022, 4 pages.
Hanafy, E. et al., "Characteristics and outcomes of patients with sickle cell disease admitted to pediatric intensive care, a retrospective review," Abstracts, British Journal of Haematology, John Wiley, Hoboken, USA, vol. 189, Abstract No. BSH2020-PO-158 , p. 148, XP071035211, ISSN: 0007-1048, Doi: 10.1111/BJH. 16638 (2020).
International Preliminary Report on Patentability, PCT/US2021/056153, dated Apr. 13, 2023, 8 pages.
International Search Report and Written Opinion, PCT/US2021/056153, dated Feb. 2, 2020, 12 pages.
Roth, A. et al., "The complement C5 inhibitor crovalimab in paroxysmal nocturnal hemoglobinuria," Blood, vol. 135 (12): 912-920 (2020).
Sostelly, A. et al.: "Characterizing C5 Inhibition with the SMART-Ig Anti-hC5 Antibody Crovalimab in PNH Patients Using Free Available Paratopes", Blood, vol. 134 (Supplement_1) : 1227: 6 pages (2019).
Anonymous, "Highlights of Prescribing Information—Ultomiris (ravulizumab-cwvz) injection, for intravenous use Inital U.S. Approval: 2018", (Oct. 1, 2019), URL: Ultomiris (ravulizumab-cwvz) injection, for intravenous use Inital U.S. Approval: 2018.
Anonymous, "Recipe: Sodium phosphate", doi: 10.1101/PDB.REC8303, ISSN 1559-6095, pp. 1-3, Cold Spring Harbor Protocols, URL: http://cshprotocols.cshlp.org/content/2006/1/pdb.rec8303.full?text_only=true, (Mar. 20, 2015), XP002737558.
International Preliminary Report on Patentability, PCT/US2019/039557, dated Dec. 29, 2020, 8 pages.
International Preliminary Report on Patentability, PCT/US2020/058779, dated May 10, 2022, 12 pages.
International Search Report and Written Opinion, PCT/US2019/039557, dated Oct. 11, 2019, 12 pages.
International Search Report and Written Opinion, PCT/US2020/058779, dated Feb. 18, 2021, 16 pages.
Janda A., et al., "lg Constant Regions Effects on Variable Region Structure and Function," Frontiers in Microbiology, vol. 7 (22): 10 pages. doi: 10.3389/fmicb.2016.00022 (2016).
Jorgensen L., et al., "Recent trends in stabilizing peptides and proteins in pharmaceutical formulation—considerations in the choice

(56) References Cited

OTHER PUBLICATIONS of excipients," Expert Opinion on Drug Delivery, vol. 6 (11): 1219-1230 (2009) doi: 10.1517/17425240903199143.

Licht. C. et al., "Efficacy and safety of eculizumab in atypical hemolytic uremic syndrome from 2-year extensions of phase 2 studies," Kidney International, vol. 87(5): 1061-1073 (2015).

Liu, et al., "Recovery and purification process development for monoclonal antibody production," MABS, vol. 2(5) 480-499 (2010).

Wang et al., "MINIREVIEW Antibody Structure, Instability and Formulation," Journal of Pharmaceutical Sciences, v.96 (1): 1-26 (2007).

Wang W., "Instability, stabilization and formulation of liquid protein pharmaceuticals," International Journal of Pharmaceutics, vol. 185(2): 129-188 (1999) doi: 10.1016/s0378-5173(99)00152-0.

Wong, E. et al., "Anticomplement C5 therapy with eculizumab for the treatment of parox-ysmal nocturnal hemoglobinuria and atypical hemolytic uremic syndrome," Translational Research, vol. 165 (2): 306-320 (2015) XP055358380, NL Issn: 1931-5244, DOI:10.1016/j.trsl.2014.10.010.

Cooper L. J., et al. "Role of heavy chain constant domains in antibody-antigen interaction, Apparent specificity differences among streptococcal IgG antibodies expressing identical variable domains," J. Immunol., vol. 50: 2231-2242 (1993).

Wei-Ching Liang, et al. "Dramatic activation of an antibody by a single amino acid change in framework," Scientifc Reports, vol. 11 (22365): 1-9 (2021).

* cited by examiner

Baseline Characteristics and Demographics

| Variable | Statistic | ALXN1210 (N=125) | Eculizumab (N=121) | Total (N=246) |
|---|---|---|---|---|
| Sex  Males  Females | N (%) | 65 (52%)  60 (48%) | 69 (57%)  52 (43%) | 134 (54%)  112 (46%) |
| Age at Infusion (yrs) | Mean (SD) | 44.8 (15.2) | 46.2 (16.2) | 45.5 (15.7) |
| Ethnicity (Not Hisp./Lat.) | N (%) | 116 (93%) | 102 (84%) | 218 (89%) |
| Race  Asian  Non-Japan  Japan  White  Other | N (%) | 72 (58%)  53 (42%)  19 (15%)  43 (34%)  10 (8%) | 57 (47%)  42 (35%)  15 (12%)  51 (42%)  13 (11%) | 129 (52%)  95 (39%)  34 (14%)  94 (38%)  23 (9%) |
| Body Weight (kg) | Mean (SD) | 68.2 (15.6) | 69.2 (14.9) | 68.7 (15.2) |
| Height (cm) | Mean (SD) | 166.3 (9.0) | 166.2 (10.7) | 166.2 (9.8) |
| LDH (Rando)  1.5 - <3xULN  > 3xULN | N (%) | 18 (14%)  107 (86%) | 16 (13%)  105 (87%) | 34 (14%)  212 (86%) |
| pRBC (Rando)  0 Units  1-14 Units  >14 Units | N (%) | 23 (18%)  79 (63%)  23 (18%) | 21 (17%)  78 (64%)  22 (18%) | 43 (18%)  156 (63%)  45 (19%) |

FIG. 3

Key Efficacy Results of Primary and Secondary Endpoints

| End Point | ALXN1210 (N=125) | Eculizumab (N=121) | Stat. for Trt. Comparison | Treatment Effect | NIM | Conclusion[1] |
|---|---|---|---|---|---|---|
| | | | CO-PRIMARY | | | |
| TA | 73.6% (65.9%, 81.3%) | 66.1% (57.7%, 74.6%) | Difference in rate | 6.8% (-4.7%, 18.1%) | -20% | Noninferior |
| LDH-N | 53.6% (45.9%, 61.2%) | 49.4% (41.7%, 57.0%) | Odds Ratio | 1.19 (0.80, 1.77) | 0.39 | Noninferior |
| | | | KEY SECONDARY | | | |
| LDH-PCHG | -76.8% (-80.0%, -73.7%) (N=124) | -76.0% (-79.2%, -72.8%) (N=118) | Difference in % change from baseline | -0.83% (-5.2%, 3.6%) | 20% | Noninferior |
| FACIT | 7.1 (5.6, 8.6) (N=125) | 6.4 (4.9, 8.0) (N=119) | Difference in change from baseline | 0.67 (-1.2, 2.6) | -5.0 | Noninferior |
| BTH | 4.0% (0.6%, 7.4%) | 10.7% (5.2%, 16.3%) | Difference in rate | -6.7% (-14.2%, 0.18%) | 20% | Noninferior |
| HGB-S | 68.0% (59.8%, 76.2%) | 64.5% (55.9%, 73.0%) | Difference in rate | 2.9% (-8.8%, 14.6%) | -20% | Noninferior |

FIG. 6

Sensitivity Analysis for TA

| Analysis | Treatment effect (95%CI) |
|---|---|
| Full Analysis | 6.8% (-4.7%, 18.1%) |
| Per Protocol | 7.2% (-4.1%, 18.9%) |
| pRBC categories:0, 1-4, >4-14 and >14 units | 7.5% (-4.1%, 18.9%) |
| Independent of protocol specified guidelines | 6.9% (-4.6%, 18.1%) |
| Independent of Randomization Factors | 7.5% (-4.0%, 18.7%) |

FIG. 7

Overview of Key Safety Results

| | ALXN1210 (N=125) | | Eculizumab (N=121) | | Total (N=246) | |
|---|---|---|---|---|---|---|
| | n (%) | E | n (%) | E | n (%) | E |
| Any Adverse Event (AE) | 110 (88.0) | 566 | 105 (86.8) | 556 | 215 (87.4) | 1122 |
| Any Serious AE (SAE) | 11 (8.8) | 15 | 9 (7.4) | 13 | 20 (8.1) | 28 |
| Death | 0 (0.0) | 0 | 1 (0.8) | 1 | 1 (0.4) | 1 |
| AEs Leading to Withdrawal of Study Drug | 0 (0.0) | 0 | 1 (0.8) | 1 | 1 (0.4) | 1 |
| SAEs Leading to Withdrawal of Study Drug | 0 (0.0) | 0 | 1 (0.8) | 1 | 1 (0.4) | 1 |
| AEs by Relationship | | | | | | |
| Related [a] | 51 (40.8) | 118 | 50 (41.3) | 117 | 101 (41.1) | 235 |
| Definitely Related | 3 (2.4) | 3 | 7 (5.8) | 15 | 10 (4.1) | 18 |
| Probably Related | 17 (13.6) | 27 | 22 (18.2) | 35 | 39 (15.9) | 62 |
| Possibly Related | 38 (30.4) | 88 | 30 (24.8) | 67 | 68 (27.6) | 155 |
| Not Related | 103 (82.4) | 448 | 101 (83.5) | 439 | 204 (82.9) | 887 |
| Unlikely Related | 32 (25.6) | 78 | 37 (30.6) | 77 | 69 (28.0) | 155 |
| Not Related | 94 (75.2) | 370 | 94 (77.7) | 362 | 188 (76.4) | 732 |
| AEs by Toxicity | | | | | | |
| Grade 1 | 98 (78.4) | 379 | 94 (77.7) | 388 | 192 (78.0) | 767 |
| Grade 2 | 65 (52.0) | 149 | 56 (46.3) | 130 | 121 (49.2) | 279 |
| Grade 3 | 21 (16.8) | 33 | 19 (15.7) | 35 | 40 (16.3) | 68 |
| Grade 4 | 5 (4.0) | 5 | 2 (1.7) | 2 | 7 (2.8) | 7 |
| Grade 5 | 0 (0.0) | 0 | 1 (0.8) | 1 | 1 (0.4) | 1 |
| SAEs by Relationship | | | | | | |
| Related [a] | 4 (3.2) | 5 | 1 (0.8) | 1 | 5 (2.0) | 6 |
| Definitely Related | 0 (0.0) | 0 | 0 (0.0) | 0 | 0 (0.0) | 0 |
| Probably Related | 0 (0.0) | 0 | 0 (0.0) | 0 | 0 (0.0) | 0 |
| Possibly Related | 4 (3.2) | 5 | 1 (0.8) | 1 | 5 (2.0) | 6 |
| Not Related | 7 (5.6) | 10 | 8 (6.6) | 12 | 15 (6.1) | 22 |
| Unlikely Related | 2 (1.6) | 2 | 3 (2.5) | 3 | 5 (2.0) | 5 |
| Not Related | 5 (4.0) | 8 | 5 (4.1) | 9 | 10 (4.1) | 17 |

FIG. 15

Most Common TEAEs (≥5%)

| System Organ Class<br>Preferred Term | ALXN1210<br>(N=125) n (%) | ALXN1210<br>(N=125) E | Eculizumab<br>(N=121) n (%) | Eculizumab<br>(N=121) E | Total<br>(N=246) n (%) | Total<br>(N=246) E |
|---|---|---|---|---|---|---|
| Gastrointestinal disorders | | | | | | |
| Nausea | 11 (8.8) | 14 | 10 (8.3) | 14 | 21 (8.5) | 28 |
| Diarrhea | 10 (8.0) | 12 | 5 (4.1) | 7 | 15 (6.1) | 19 |
| Abdominal pain | 7 (5.6) | 7 | 7 (5.8) | 7 | 14 (5.7) | 14 |
| Dyspepsia | 4 (3.2) | 6 | 6 (5.0) | 7 | 10 (4.1) | 13 |
| General disorders and administration site conditions | | | | | | |
| Pyrexia | 6 (4.8) | 7 | 13 (10.7) | 16 | 19 (7.7) | 23 |
| Infections and infestations | | | | | | |
| Nasopharyngitis | 11 (8.8) | 14 | 18 (14.9) | 20 | 29 (11.8) | 34 |
| Upper respiratory tract infection | 13 (10.4) | 15 | 7 (5.8) | 7 | 20 (8.1) | 22 |
| Viral upper respiratory tract infection | 9 (7.2) | 10 | 10 (8.3) | 12 | 19 (7.7) | 22 |
| Metabolism and nutrition disorders | | | | | | |
| Hypokalaemia | 6 (4.8) | 11 | 6 (5.0) | 8 | 12 (4.9) | 19 |
| Musculoskeletal and connective tissue disorders | | | | | | |
| Arthralgia | 8 (6.4) | 12 | 8 (6.6) | 9 | 16 (6.5) | 21 |
| Myalgia | 7 (5.6) | 8 | 9 (7.4) | 12 | 16 (6.5) | 20 |
| Pain in extremity | 9 (7.2) | 10 | 7 (5.8) | 8 | 16 (6.5) | 18 |
| Back pain | 7 (5.6) | 9 | 6 (5.0) | 6 | 13 (5.3) | 15 |
| Nervous system disorders | | | | | | |
| Headache | 45 (36.0) | 70 | 40 (33.1) | 72 | 85 (34.6) | 142 |
| Dizziness | 9 (7.2) | 9 | 7 (5.8) | 10 | 16 (6.5) | 19 |
| Psychiatric disorders | | | | | | |
| Insomnia | 2 (1.6) | 2 | 6 (5.0) | 7 | 8 (3.3) | 9 |
| Respiratory, thoracic and mediastinal disorders | | | | | | |
| Oropharyngeal pain | 8 (6.4) | 10 | 6 (5.0) | 6 | 14 (5.7) | 16 |
| Cough | 4 (3.2) | 4 | 8 (6.6) | 11 | 12 (4.9) | 15 |

FIG. 16

Treatment Emergent Serious Adverse Events

| System Organ Class | ALXN1210 (N=125) n (%) | E | Eculizumab (N=121) n (%) | E | Total (N=246) n (%) | E |
|---|---|---|---|---|---|---|
| Patients with Treatment-Emergent Serious Adverse Events | 11 (8.8) | 15 | 9 (7.4) | 13 | 20 (8.1) | 28 |
| Blood and lymphatic system disorders | 4 (3.2) | 5 | 0 (0.0) | 0 | 4 (1.6) | 5 |
| Cardiac disorders | 2 (1.6) | 2 | 0 (0.0) | 0 | 2 (0.8) | 2 |
| Gastrointestinal disorders | 0 (0.0) | 0 | 2 (1.7) | 3 | 2 (0.8) | 3 |
| General disorders and administration site conditions | 1 (0.8) | 1 | 2 (1.7) | 2 | 3 (1.2) | 3 |
| Infections and infestations | 2 (1.6) | 2 | 4 (3.3) | 5 | 6 (2.4) | 7 |
| Injury, poisoning and procedural complications | 1 (0.8) | 1 | 0 (0.0) | 0 | 1 (0.4) | 1 |
| Neoplasms benign, malignant and unspecified (including cysts and polyps) | 1 (0.8) | 2 | 2 (1.7) | 2 | 3 (1.2) | 4 |
| Renal and urinary disorders | 1 (0.8) | 1 | 1 (0.8) | 1 | 2 (0.8) | 2 |
| Vascular disorders | 1 (0.8) | 1 | 0 (0.0) | 0 | 1 (0.4) | 1 |

FIG. 17

Treatment Emergent AEs of Special Interest

| | ALXN1210 (N=125) | | Eculizumab (N=121) | | Total (N=246) | |
|---|---|---|---|---|---|---|
| | n (%) | E | n (%) | E | n (%) | E |
| AEs of Special Interest | | | | | | |
| Meningococcal Infections | 0 (0.0) | 0 | 0 (0.0) | 0 | 0 (0.0) | 0 |
| Aspergillus Infections | 0 (0.0) | 0 | 0 (0.0) | 0 | 0 (0.0) | 0 |
| Other Serious Infections | 2 (1.6) | 2 | 4 (3.3) | 5 | 6 (2.4) | 7 |
| Sepsis | 0 (0.0) | 0 | 0 (0.0) | 0 | 0 (0.0) | 0 |
| Infusion Reactions | 11 (8.8) | 12 | 10 (8.3) | 10 | 21 (8.5) | 22 |
| Serious Cutaneous Adverse Reactions | 0 (0.0) | 0 | 0 (0.0) | 0 | 0 (0.0) | 0 |
| Cardiac Disorders | 2 (1.6) | 2 | 0 (0.0) | 0 | 2 (0.8) | 2 |
| Angioedema | 3 (2.4) | 4 | 0 (0.0) | 0 | 3 (1.2) | 4 |

[a] : Related AEs are defined as AEs that are possibly, probably, or definitely related to study treatment. Not related AEs are defined as AEs that are unlikely or not related to study treatment.
Note: Patients are counted in each relationship and severity category in case of multiple events.
Note: %= n/N*100. E=number of events.
Note: Treatment emergent AEs are AEs with a start date on or after first dose date in the study.
Note: Grade 1=mild; Grade 2=moderate; Grade 3=severe; Grade 4=life-threatening; Grade 5=Fatal.
Note: The toxicity of AEs are graded using CTCAE version 4.03 or higher.
Note: AEs are coded using MedDRA Version 20.1.

FIG. 18

Drug Compliance

| Variable | ALXN1210 (N=125) | Eculizumab (N=121) |
|---|---|---|
| Compliance from Day 1 to Day 183, n (%) | | |
| >=100% | 125 (100) | 120 (99.2) |
| >= 90% to < 100% | 0 (0.0) | 1 (0.8) |
| >= 80% to < 90% | 0 (0.0) | 0 (0.0) |
| >= 70% to < 80% | 0 (0.0) | 0 (0.0) |
| >= 60% to < 70% | 0 (0.0) | 0 (0.0) |
| >= 50% to < 60% | 0 (0.0) | 0 (0.0) |
| >= 40% to < 50% | 0 (0.0) | 0 (0.0) |
| >= 30% to < 40% | 0 (0.0) | 0 (0.0) |
| >= 20% to < 30% | 0 (0.0) | 0 (0.0) |
| >= 10% to < 20% | 0 (0.0) | 0 (0.0) |
| >= 0% to < 10% | 0 (0.0) | 0 (0.0) |

FIG. 19

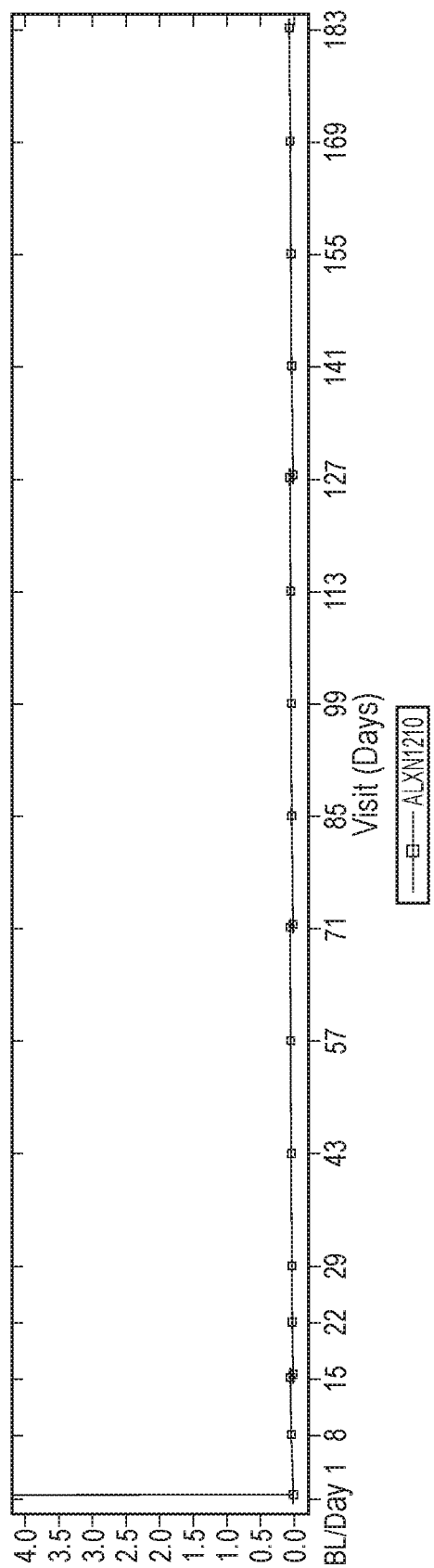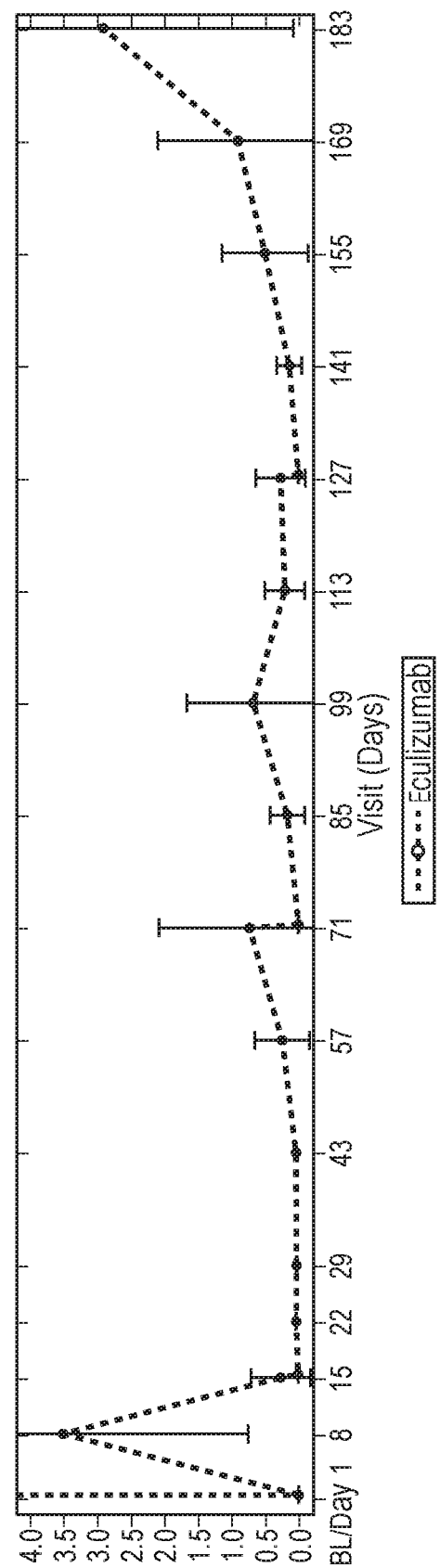
FIG. 22

Baseline Characteristics and Demographics

| Variable | Statistic | ALXN1210 (N=97) | Eculizumab (N=98) | Total (N=195) |
|---|---|---|---|---|
| Sex | N (%) | | | |
| Males | | 50 (52%) | 48 (49%) | 98 (50%) |
| Females | | 47 (48%) | 50 (51%) | 97 (50%) |
| Age at Infusion (yrs) | Mean (SD) | 46.6 (14.4) | 48.8 (14.0) | 47.7 (14.2) |
| Race | N (%) | | | |
| White | | 50 (52%) | 61 (62%) | 111 (57%) |
| Asian | | 24 (25%) | 19 (19%) | 43 (22%) |
| Non-Japan | | 19 (20%) | 12 (12%) | 31 (16%) |
| Japan | | 5 (5%) | 7 (7%) | 12 (6%) |
| Other | | 24 (24%) | 18 (18%) | 42 (21%) |
| Body Weight (kg) | Mean (SD) | 72.4 (16.8) | 73.4 (14.6) | 72.9 (15.7) |
| Height (cm) | Mean (SD) | 168.3 (10.1) | 168.8 (9.9) | 168.5 (10.0) |
| pRBC Hx at Randomization | N (%) | | | |
| Yes | | 12 (12%) | 12 (12%) | 24 (12%) |
| No | | 85 (88%) | 86 (88%) | 171 (88%) |

FIG. 28

Baseline Disease Characteristics

| Variable | Statistic | ALXN1210 (N=97) | Eculizumab (N=98) | Total (N=195) |
|---|---|---|---|---|
| Age at PNH Diagnosis | Mean (SD) | 34.1 (14.4) | 36.8 (14.1) | 35.5 (14.3) |
| Age at 1st Ecu Infusion | Mean (SD) | 40.7 (14.3) | 43.2 (13.9) | 42.0 (14.1) |
| Yrs PNH Diagnosis to Consent | Mean (SD) | 12.4 (8.4) | 11.9 (9.4) | 12.2 (8.9) |
| LDH (U/L) at Baseline | Mean (SD) | 228.0 (48.7) | 235.2 (49.7) | 231.6 (49.2) |
| Method PNH Diag. Flow Cytometry | N (%) | 78 (80%) | 75 (77%) | 153 (79%) |
| Ham's Test | | 9 (9%) | 10 (10%) | 18 (10%) |
| Sucrose Hemolysis | | 0 (0%) | 1 (1%) | 1 (0.5%) |
| Other | | 10 (10%) | 12 (12%) | 24 (11%) |
| PNH Clone Size RBC Type II | Mean (SD) | 14.9 (19.6) | 16.3 (23.6) | 15.6 (21.6) |
| RBC Type III | | 44.6 (30.5) | 43.5 (29.7) | 44.0 (30.0) |
| Total RBC | | 60.6 (32.5) | 59.5 (31.4) | 60.1 (31.9) |
| Granulocytes | | 82.6 (23.6) | 84.0 (21.4) | 83.3 (22.5) |
| Monocytes | | 85.6 (20.4) | 86.1 (19.7) | 85.9 (20.0) |

FIG. 29

Key Efficacy Results of Primary and Key Secondary Endpoints

| End Point | ALXN1210 (N=97) | Eculizumab (N=98) | Stat. for Trt. Comparison | Treatment Effect | NIM | Conclusion(1) |
|---|---|---|---|---|---|---|
| PRIMARY | | | | | | |
| LDH-PCHG | -0.82% (-7.8%, 6.1%) | 8.4% (1.5%, 15.3%) | Difference in % Change from baseline | -9.2% (-18.8%, 0.42%) | 15% | Noninferior |
| KEY SECONDARY | | | | | | |
| BTH | 0% (0%, 3.7%) | 5.1% (1.7%, 11.5%) | Difference in rate | -5.1% (-19.0, 8.9%) | 20% | Noninferior |
| FACIT | 2.0 (0.6, 3.4) | 0.54 (-0.8, 1.9) | Difference in change from baseline | 1.5 (-0.2, 3.2) | -3.0 | Noninferior |
| TA | 87.6% (81.1%, 94.2%) | 82.7% (75.2%, 90.2%) | Difference in rate | 5.5% (-4.3%, 15.7%) | -20% | Noninferior |
| HGB-S | 76.3% (67.8%, 84.8%) | 75.5% (67.0%, 84.0%) | Difference in rate | 1.4% (-10.4%, 13.3%) | -20% | Noninferior |

(1) A conclusion of statistically significant noninferiority is where the NIM is larger/smaller compared to the lower/upper bound of the 95% CI indicated in bold.

FIG. 31

Sensitivity Analysis for LDG-PCHG

| Analysis | Treatment effect (95%CI) |
|---|---|
| Full Analysis | -9.2 (-18.8%, 0.42%) |
| Per Protocol | -9.6 (-20.2%, 1.06%) |
| Independent of randomization Factors | -8.7 (-18.5%, 1.12%) |
| Adjustment for Missing pattern assumption. | Not done due to low dropout rate (2%) |

FIG. 32

Overview of Key Safety Results

| | ALXN1210 (N=97) | | Eculizumab (N=98) | | Total (N=195) | |
|---|---|---|---|---|---|---|
| | n (%) | E | n (%) | E | n (%) | E |
| Any Adverse Event (AE) | 85 (87.6) | 366 | 86 (87.8) | 366 | 171 (87.7) | 732 |
| Any Serious AE (SAE) | 4 (4.1) | 7 | 8 (8.2) | 8 | 12 (6.2) | 15 |
| Death | 0 (0.0) | 0 | 0 (0.0) | 0 | 0 (0.0) | 0 |
| AEs Leading to Withdrawal of Study Drug | 0 (0.0) | 0 | 0 (0.0) | 0 | 0 (0.0) | 0 |
| SAEs Leading to Withdrawal of Study Drug | 0 (0.0) | 0 | 0 (0.0) | 0 | 0 (0.0) | 0 |
| AEs by Relationship | | | | | | |
| Related [a] | 24 (24.7) | 61 | 14 (14.3) | 31 | 38 (19.5) | 92 |
| Definitely Related | 3 (3.1) | 3 | 0 (0.0) | 0 | 3 (1.5) | 3 |
| Probably Related | 9 (9.3) | 16 | 1 (1.0) | 1 | 10 (5.1) | 17 |
| Possibly Related | 21 (21.6) | 42 | 13 (13.3) | 30 | 34 (17.4) | 72 |
| Not Related | 82 (84.5) | 305 | 86 (87.8) | 335 | 168 (86.2) | 640 |
| Unlikely Related | 16 (16.5) | 37 | 19 (19.4) | 35 | 35 (17.9) | 72 |
| Not Related | 80 (82.5) | 268 | 82 (83.7) | 300 | 162 (83.1) | 568 |
| AEs by Toxicity | | | | | | |
| Grade 1 | 74 (76.3) | 270 | 75 (76.5) | 256 | 149 (76.4) | 528 |
| Grade 2 | 52 (53.6) | 79 | 50 (51.0) | 88 | 102 (52.3) | 167 |
| Grade 3 | 7 (7.2) | 11 | 14 (14.3) | 22 | 21 (10.8) | 33 |
| Grade 4 | 2 (2.1) | 4 | 0 (0.0) | 0 | 2 (1.0) | 4 |
| Grade 5 | 0 (0.0) | 0 | 0 (0.0) | 0 | 0 (0.0) | 0 |
| SAEs by Relationship | | | | | | |
| Related [a] | 1 (1.0) | 3 | 1 (1.0) | 1 | 2 (1.0) | 4 |
| Definitely Related | 0 (0.0) | 0 | 0 (0.0) | 0 | 0 (0.0) | 0 |
| Probably Related | 0 (0.0) | 0 | 0 (0.0) | 0 | 0 (0.0) | 0 |
| Possibly Related | 1 (1.0) | 3 | 1 (1.0) | 1 | 2 (1.0) | 4 |
| Not Related | 3 (3.1) | 4 | 7 (7.1) | 7 | 10 (5.1) | 11 |
| Unlikely Related | 1 (1.0) | 1 | 1 (1.0) | 1 | 2 (1.0) | 2 |
| Not Related | 2 (2.1) | 3 | 6 (6.1) | 6 | 8 (4.1) | 9 |

FIG. 38

Treatment Emergent Serious Adverse Events (TESAEs)

| System Organ Class<br>Preferred Term | ALXN1210<br>(N=97) n (%) | E | Eculizumab<br>(N=98) n (%) | E | Total<br>(N=195) n (%) | E |
|---|---|---|---|---|---|---|
| Patients with Treatment-Emergent Serious Adverse Events | 4 (4.1) | 7 | 8 (8.2) | 8 | 12 (6.2) | 15 |
| Blood and lymphatic system disorders | 0 (0.0) | 0 | 2 (2.0) | 2 | 2 (1.0) | 2 |
| Haemolysis | 0 (0.0) | 0 | 2 (2.0) | 2 | 2 (1.0) | 2 |
| Cardiac disorders | 0 (0.0) | 0 | 1 (1.0) | 1 | 1 (0.5) | 1 |
| Palpitations | 0 (0.0) | 0 | 1 (1.0) | 1 | 1 (0.5) | 1 |
| Gastrointestinal disorders | 1 (1.0) | 2 | 0 (0.0) | 0 | 1 (0.5) | 2 |
| Colitis | 1 (1.0) | 2 | 0 (0.0) | 0 | 1 (0.5) | 2 |
| General disorders and administration site conditions | 1 (1.0) | 1 | 3 (3.1) | 3 | 4 (2.1) | 4 |
| Pyrexia | 0 (0.0) | 0 | 3 (3.1) | 3 | 3 (1.5) | 3 |
| General disorders and administration site conditions | 1 (1.0) | 1 | 0 (0.0) | 0 | 1 (0.5) | 1 |
| Hyperthermia | | | | | | |
| Hepatobiliary disorders | 0 (0.0) | 0 | 1 (1.0) | 1 | 1 (0.5) | 1 |
| Cholelithiasis | 0 (0.0) | 0 | 1 (1.0) | 1 | 1 (0.5) | 1 |
| Infections and infestations | 2 (2.1) | 2 | 1 (1.0) | 1 | 3 (1.5) | 3 |
| Influenza | 1 (1.0) | 1 | 0 (0.0) | 0 | 1 (0.5) | 1 |
| Lower respiratory tract infection | 1 (1.0) | 1 | 0 (0.0) | 0 | 1 (0.5) | 1 |
| Pyelonephritis acute | 0 (0.0) | 0 | 1 (1.0) | 1 | 1 (0.5) | 1 |
| Nervous system disorders | 1 (1.0) | 1 | 0 (0.0) | 0 | 1 (0.5) | 1 |
| Epilepsy | 1 (1.0) | 1 | 0 (0.0) | 0 | 1 (0.5) | 1 |
| Respiratory, thoracic and mediastinal disorders | 1 (1.0) | 1 | 0 (0.0) | 0 | 1 (0.5) | 1 |
| Respiratory failure | 1 (1.0) | 1 | 0 (0.0) | 0 | 1 (0.5) | 1 |

FIG. 39

Most Common Treatment Emergent Adverse Events (TEAEs) (≥5%)

| System Organ Class Preferred Term | ALXN1210 (N=97) n (%) | | Eculizumab (N=98) n (%) | | Total (N=195) n (%) | |
|---|---|---|---|---|---|---|
| | n (%) | E | n (%) | E | n (%) | E |
| Blood and lymphatic system disorders | | | | | | |
| Anaemia | 6 (6.2) | 7 | 3 (3.1) | 4 | 9 (4.6) | 11 |
| Gastrointestinal disorders | | | | | | |
| Nausea | 8 (8.2) | 9 | 9 (9.2) | 9 | 17 (8.7) | 18 |
| Diarrhea | 9 (9.3) | 10 | 7 (7.1) | 7 | 16 (8.2) | 17 |
| Abdominal pain | 6 (6.2) | 9 | 9 (9.2) | 9 | 15 (7.7) | 18 |
| Constipation | 7 (7.2) | 7 | 5 (5.1) | 6 | 12 (6.2) | 13 |
| Vomiting | 6 (6.2) | 6 | 4 (4.1) | 4 | 10 (5.1) | 10 |
| General disorders and administration site conditions | | | | | | |
| Influenza like illness | 7 (7.2) | 8 | 8 (8.2) | 10 | 15 (7.7) | 18 |
| Pyrexia | 9 (9.3) | 11 | 5 (5.1) | 7 | 14 (7.2) | 18 |
| Chest pain | 3 (3.1) | 5 | 9 (9.2) | 12 | 12 (6.2) | 17 |
| Fatigue | 6 (6.2) | 8 | 6 (6.1) | 8 | 12 (6.2) | 16 |
| Infections and infestations | | | | | | |
| Nasopharyngitis | 21 (21.6) | 26 | 20 (20.4) | 21 | 41 (21.0) | 47 |
| Upper respiratory tract infection | 18 (18.6) | 22 | 10 (10.2) | 13 | 28 (14.4) | 35 |
| Rhinitis | 5 (5.2) | 7 | 4 (4.1) | 5 | 9 (4.6) | 12 |
| Musculoskeletal and connective tissue disorders | | | | | | |
| Pain in extremity | 5 (5.2) | 5 | 4 (4.1) | 6 | 9 (4.6) | 11 |
| Musculoskeletal pain | 2 (2.1) | 2 | 5 (5.1) | 5 | 7 (3.6) | 7 |
| Nervous system disorders | | | | | | |
| Headache | 26 (26.8) | 31 | 17 (17.3) | 26 | 43 (22.1) | 57 |
| Dizziness | 3 (3.1) | 3 | 7 (7.1) | 8 | 10 (5.1) | 11 |
| Respiratory, thoracic and mediastinal disorders | | | | | | |
| Cough | 5 (5.2) | 5 | 10 (10.2) | 11 | 15 (7.7) | 16 |
| Oropharyngeal pain | 4 (4.1) | 4 | 9 (9.2) | 9 | 13 (6.7) | 13 |
| Dyspnoea | 0 (0.0) | 0 | 6 (6.1) | 8 | 6 (3.1) | 8 |

FIG. 40

Upper Respiratory Tract Infections (URTI) as determined by Standard MedDRA Query (SMQ)

| Selected Category<br>Preferred Term | ALXN1210<br>(N=97) E | ALXN1210<br>(N=97) n (%) | Eculizumab<br>(N=98) E | Eculizumab<br>(N=98) n (%) | Total<br>(N=195) E | Total<br>(N=195) n (%) |
|---|---|---|---|---|---|---|
| URTI | 64 | 43 (44.3) | 50 | 43 (43.9) | 114 | 86 (44.1) |
| Nasopharyngitis | 26 | 21 (21.6) | 21 | 20 (20.4) | 47 | 41 (21.0) |
| Upper respiratory tract infection | 22 | 18 (18.6) | 13 | 10 (10.2) | 35 | 28 (14.4) |
| Oropharyngeal pain | 4 | 4 (4.1) | 9 | 9 (9.2) | 13 | 13 (6.7) |
| Rhinitis | 7 | 5 (5.2) | 5 | 4 (4.1) | 12 | 9 (4.6) |
| Respiratory tract infection | 2 | 2 (2.1) | 1 | 1 (1.0) | 3 | 3 (1.5) |
| Rhinorrhoea | 0 | 0 (0.0) | 1 | 1 (1.0) | 1 | 1 (0.5) |
| Viral upper respiratory tract infection | 3 | 1 (1.0) | 0 | 0 (0.0) | 3 | 1 (0.5) |

Note: % = n/N*100. E=total number of events.
Note: Treatment emergent AEs are events starting on or after the day of first dose of study drug.
Note: If a patient had more than one event for a particular PT, he/she is counted only once for that PT.
Note: AEs are coded using MedDRA Version 20.1.

FIG. 41

Treatment Emergent AEs of Special Interest (TEAESI)

| AEs of Special Interest | ALXN1210 (N=97) n (%) | E | Eculizumab (N=98) n (%) | E | Total (N=195) n (%) | E |
|---|---|---|---|---|---|---|
| Meningococcal Infections | 0 (0.0) | 0 | 0 (0.0) | 0 | 0 (0.0) | 0 |
| Aspergillus Infections | 0 (0.0) | 0 | 0 (0.0) | 0 | 0 (0.0) | 0 |
| Other Serious Infections | 2 (2.1) | 2 | 1 (1.0) | 1 | 3 (1.5) | 3 |
| Sepsis | 0 (0.0) | 0 | 0 (0.0) | 0 | 0 (0.0) | 0 |
| Infusion Reactions | 8 (8.2) | 10 | 3 (3.1) | 3 | 11 (5.6) | 13 |
| Serious Cutaneous Adverse Reactions | 0 (0.0) | 0 | 0 (0.0) | 0 | 0 (0.0) | 0 |
| Cardiac Disorders | 0 (0.0) | 0 | 1 (1.0) | 1 | 1 (0.5) | 1 |
| Angioedema | 1 (1.0) | 1 | 0 (0.0) | 0 | 1 (0.5) | 1 |

FIG. 42

Drug Compliance

| Variable | ALXN1210 (N=97) | Eculizumab (N=98) |
|---|---|---|
| Compliance from Day 1 to Day 183, n (%) | | |
| >=100% | 97 (100) | 98 (100) |
| >= 90% to < 100% | 0 (0.0) | 0 (0.0) |
| >= 80% to < 90% | 0 (0.0) | 0 (0.0) |
| >= 70% to < 80% | 0 (0.0) | 0 (0.0) |
| >= 60% to < 70% | 0 (0.0) | 0 (0.0) |
| >= 50% to < 60% | 0 (0.0) | 0 (0.0) |
| >= 40% to < 50% | 0 (0.0) | 0 (0.0) |
| >= 30% to < 40% | 0 (0.0) | 0 (0.0) |
| >= 20% to < 30% | 0 (0.0) | 0 (0.0) |
| >= 10% to < 20% | 0 (0.0) | 0 (0.0) |
| >= 0% to < 10% | 0 (0.0) | 0 (0.0) |

Note: Percentages are based on the total number of patients in each group.
Note: Study duration=date of completion of randomized treatment period/discontinuation-date of informed consent + 1.
Note: Treatment duration=Last study drug infusion date from the randomized treatment period-first study drug infusion date + 1.
Note: Percent compliance=Total number of infusions taken from Day 1 to end of randomized treatment period (excluding Day 183 infusion) / Total number of expected infusions to end of randomized treatment period (excluding Day 183 infusion)
[1] Note that dosing on Day 183 represents the start of the Extension Period and will not be included in these calculations.

FIG. 43

SEQUENCE LISTING

```
<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                    85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser
        115                 120
```

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105
```

<210> SEQ ID NO 9
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

-continued

```
Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
        210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160
```

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Val Val Thr
        180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80

Glu Asp Phe Ala Thr Tyr Tyr Cys Gln Asn Val Leu Asn Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 13
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Leu His Glu Ala Leu His Ser His Tyr Thr Gln Lys Ser Leu
305                 310                 315                 320

Ser Leu Ser Leu Gly Lys
                325

<210> SEQ ID NO 14
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
 1               5                  10                  15

Ser Val Lys Val Ser Cys Lys Ala Ser Gly His Ile Phe Ser Asn Tyr
                20                  25                  30
```

-continued

```
Trp Ile Gln Trp Val Arg Gln Ala Pro Gly Gln Gly Leu Glu Trp Met
            35                  40                  45
Gly Glu Ile Leu Pro Gly Ser Gly His Thr Glu Tyr Thr Glu Asn Phe
 50                  55                  60
Lys Asp Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Tyr Phe Phe Gly Ser Ser Pro Asn Trp Tyr Phe Asp Val Trp
                100                 105                 110
Gly Gln Gly Thr Leu Val Thr Val Ser Ser Ala Ser Thr Lys Gly Pro
            115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Leu His Glu Ala
            420                 425                 430
Leu His Ser His Tyr Thr Gln Lys Ser Leu Ser Leu Ser Leu Gly Lys
        435                 440                 445
```

```
<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

```
<210> SEQ ID NO 16
<211> LENGTH: 448
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 16
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Thr Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Gln Phe Asn Trp Tyr Val Asp Gly Met Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
            210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 21
<211> LENGTH: 5

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Tyr Ala Ile Ser
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Gly Pro Phe Phe Gly Thr Ala Asn Tyr Ala Gln Lys Phe Gln
1               5                   10                  15

Gly

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Thr Pro Tyr Phe Asp Tyr
1               5

<210> SEQ ID NO 24
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Gly Asp Ser Ile Pro Asn Tyr Tyr Val Tyr
1               5                   10

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 26

Gln Ser Phe Asp Ser Ser Leu Asn Ala Glu Val
1               5                   10

<210> SEQ ID NO 27
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 28
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105
```

```
<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asn Tyr Ile Ser
1

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Glu Tyr Gly Gly Phe Asp Ile
1               5

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Asp Asn Asp Arg Pro Ser
1               5

<210> SEQ ID NO 34
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Thr Tyr Asp Ile Glu Ser Tyr Val
1               5

<210> SEQ ID NO 35
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 36
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95
```

Phe Gly Gly Gly Thr Lys Leu Thr Val Leu
            100                 105

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Ser Tyr Tyr Val Ala
1               5

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ile Tyr Thr Gly Ser Gly Ala Thr Tyr Lys Ala Ser Trp Ala Lys
1               5                   10                  15

Gly

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Ala Ser Lys Thr His Ser
1               5

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

```
Gln Ser Thr Lys Val Gly Ser Ser Tyr Gly Asn His
1               5                   10
```

<210> SEQ ID NO 43
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
        35                  40                  45

Val Gly Ala Ile Tyr Thr Gly Ser Gly Ala Thr Tyr Lys Ala Ser Trp
50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
            100                 105                 110

Trp Gly Gln Gly Thr Leu Val Thr Val Ser Ser
        115                 120
```

<210> SEQ ID NO 44
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

```
Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Val Ala Thr Tyr Tyr Cys Gln Ser Thr Lys Val Gly Ser Ser
                85                  90                  95

Tyr Gly Asn His Phe Gly Gly Thr Lys Val Glu Ile Lys
            100                 105                 110

<210> SEQ ID NO 45
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
```

```
                    325                 330                 335
Ser Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
        435                 440                 445

Leu Ser Pro
    450

<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 47
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser
        115                 120

<210> SEQ ID NO 48
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
            100                 105

<210> SEQ ID NO 49
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Asp Ser Val Ser Ser Ser
            20                  25                  30
Tyr Trp Thr Trp Ile Arg Gln Pro Pro Gly Lys Gly Leu Glu Trp Ile
        35                  40                  45
Gly Tyr Ile Tyr Tyr Ser Gly Ser Ser Asn Tyr Asn Pro Ser Leu Lys
    50                  55                  60
Ser Arg Ala Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Glu Gly Asn Val Asp Thr Thr Met Ile Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
```

```
                      405                 410                 415
Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 50
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

DOSAGE AND ADMINISTRATION OF ANTI-C5 ANTIBODIES FOR TREATMENT OF PAROXYSMAL NOCTURNAL HEMOGLOBINURIA (PNH) AND ATYPICAL HEMOLYTIC UREMIC SYNDROME (AHUS)

CROSS-REFERENCE TO RELATED APPLICATIONS

This application is a 35 U.S.C. 371 national stage filing of International Application No. PCT/US2018/057760, filed on Oct. 26, 2018, which claims priority to, and the benefit of, U.S. Provisional Application No. 62/685,505, filed Jun. 15, 2018, U.S. Provisional Application No. 62/685,425, filed Jun. 15, 2018, U.S. Provisional Application No. 62/662,503, filed Apr. 25, 2018, U.S. Provisional Application No. 62/643,608, filed Mar. 15, 2018, U.S. Provisional Application No. 62/643,056, filed Mar. 14, 2018, and U.S. Provisional Application No. 62/577,244, filed Oct. 26, 2017. The entire contents of the aforementioned applications is incorporated herein by reference.

SEQUENCE LISTING

The instant application contains a Sequence Listing which has been submitted electronically in ASCII format and is hereby incorporated by reference in its entirety. Said ASCII copy, created on Apr. 20, 2020, is named AXJ-224US Sequence Listing.txt and is 59,151 bytes in size.

BACKGROUND

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

While a properly functioning complement system provides a robust defense against infecting microbes, inappropriate regulation or activation of the complement pathways has been implicated in the pathogenesis of a variety of disorders, including paroxysmal nocturnal hemoglobinuria (PNH) and atypical hemolytic uremic syndrome (aHUS). PNH and aHUS, are both ultra-rare disorders driven by chronic uncontrolled complement activation. The resulting inflammation and cellular damage lead to the devastating clinical manifestations of these diseases.

PNH is a condition in which uncontrolled complement activity leads to systemic complications, principally through intravascular hemolysis and platelet activation (see Socié G, et al., French Society of Haematology. Lancet. 1996; 348 (9027):573-577 and Brodsky, R., Blood. 2014; 124(18): 2804-2811). Persistent intravascular hemolysis may be triggered by various stressors, such as infection or physical exertion, and this leads to smooth muscle contraction (free hemoglobin), chronic anemia, and an increased risk of severe thromboembolism. Thromboembolism is the most common cause of mortality in patients with PNH, and pulmonary hypertension and end-organ damage of vital organs, such as the liver, kidneys, brain, and intestines, are sequelae of such events (Hillmen, P., et al, Am. J. Hematol. 2010; 85(8):553-559). Due to these adverse pathologic processes, patients with PNH have a decreased quality of life (QoL), which may include debilitating fatigue, chronic pain, poor physical function, shortness of breath, abdominal pain, erectile dysfunction, a need for anticoagulation, blood transfusions and in some instances, need for dialysis (Weitz, I C., et al., Thromb Res. 2012; 130(3):361-368).

Hemolytic uremic syndrome (HUS) is characterized by thrombocytopenia, microangiopathic hemolytic anemia, and acute renal failure. HUS is classified as one of two types: diarrheal-associated (D+ HUS; also referred to as shiga toxin producing *E. coli* (STEC)-HUS or typical HUS) and non-diarrheal or atypical HUS (aHUS). D+ HUS is the most common form, accounting for greater than 90% of cases and is caused by a preceding illness with a shiga-like toxin-producing bacterium, e.g., *E. coli* O157:H7.

aHUS can be genetic, acquired, or idiopathic. Hereditable forms of aHUS can be associated with mutations in a number of human complement components including, e.g., complement factor H (CFH), membrane cofactor protein (MCP), complement factor I (CFI), C4b-binding protein (C4BP), complement factor B (CFB), and complement component 3 (C3). See, e.g., Caprioli et al. (2006) *Blood* 108:1267-1279. Certain mutations in the gene encoding CD55, though not yet implicated in aHUS, are associated with the severity of aHUS. See, e.g., Esparza-Gordillo et al. (2005) *Hum Mol Genet* 14:703-712.

aHUS is rare and has a mortality rate of up to 25%. Many patients with this disease will sustain permanent neurological or renal impairment, e.g., at least 50% of aHUS patients progress to end-stage renal failure (ESRF). See, e.g., Kavanagh et al. (2006) *British Medical Bulletin* 77 and 78:5-22. Until recently, treatment options for patients with aHUS were limited and often involved plasma infusion or plasma exchange. In some cases, aHUS patients undergo uni- or bilateral nephrectomy or renal transplantation (see Artz et al. (2003) *Transplantation* 76:821-826). However, recurrence of the disease in treated patients is common.

Patients with PNH or aHUS are at risk of substantial morbidity and mortality. Accordingly, it is an object of the present invention to provide improved methods for treating patients with PNH or aHUS.

SUMMARY

Provided herein are compositions and methods for treating PNH or aHUS in a human patient, comprising administering to the patient an anti-C5 antibody, or antigen binding fragment thereof, wherein the anti-C5 antibody, or antigen binding fragment thereof, is administered (or is for administration) according to a particular clinical dosage regimen (i.e., at a particular dose amount and according to a specific dosing schedule).

Any suitable anti-C5 antibody, or antigen binding fragment thereof, can be used in the methods described herein. An exemplary anti-C5 antibody is ravulizumab (also known as Ultomiris™, ALXN1210 and antibody BNJ441) comprising the heavy and light chains having the sequences shown in SEQ ID NOs:14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2, and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively. In another embodiment, the antibody comprises VH and VL regions having the amino acid sequences set forth in SEQ ID NO:12 and SEQ ID NO:8, respectively. In another embodiment, the antibody comprises a heavy chain constant region as set forth in SEQ ID NO:13.

In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody binds to human C5 at pH 7.4 and 25° C. with an affinity dissociation constant ($K_D$) that is in the range 0.1 nM≤$K_D$≤1 nM. In another embodiment, the antibody binds to human C5 at pH 6.0 and 25° C. with a $K_D$≥10 nM. In yet another embodiment, the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] of the antibody is greater than 25.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs: 21, 22, and 23, respectively, and light chain CDR1, CDR2 and CDR3 domains having the sequences set forth in SEQ ID NOs: 24, 25, and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30, and 31, respectively, and light chain CDR1, CDR2 and CDR3 domains having the sequences set forth in SEQ ID NOs: 32, 33, and 34, respectively. In another embodiment, the antibody comprises the VH region of the 8110 antibody having the sequence set forth in SEQ ID NO: 35, and the VL region of the 8110 antibody having the sequence set forth in SEQ ID NO: 36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs: 37, 38, and 39, respectively, and light chain CDR1, CDR2 and CDR3 domains having the sequences set forth in SEQ ID NOs: 40, 41, and 42, respectively. In another embodiment, the antibody comprises the VH region of the 305LO5 antibody having the sequence set forth in SEQ ID NO: 43, and the VL region of the 305LO5 antibody having the sequence set forth in SEQ ID NO: 44.

Another exemplary anti-C5 antibody is the SKY59 antibody described in Fukuzawa T., et al., Rep. 2017 Apr. 24; 7(1):1080). In one embodiment, the antibody comprises the heavy and light chain CDRs or variable regions of the SKY59 antibody. In another embodiment, the antibody, or antigen binding fragment thereof, comprises a heavy chain comprising SEQ ID NO: 45 and a light chain comprising SEQ ID NO: 46.

Another exemplary anti-C5 antibody is the REGN3918 antibody (also known as H4H12166PP) described in US20170355757. In one embodiment, the antibody comprises a heavy chain variable region comprising SEQ ID NO:47 and a light chain variable region comprising SEQ ID NO:48. In another embodiment, the antibody comprises a heavy chain comprising SEQ ID NO:49 and a light chain comprising SEQ ID NO:50.

In another embodiment, the antibody competes for binding with, and/or binds to the same epitope on C5 as, the above-mentioned antibodies (e.g., eculizumab, ravulizumab, 7086 antibody, 8110 antibody, 305LO5 antibody, SKY59 antibody, or REGN3918 antibody). In another embodiment, the antibody has at least about 90% variable region amino acid sequence identity with the above-mentioned antibodies (e.g., at least about 90%, 91%, 92%, 93%, 94%, 95%, 96%, 97%, 98% or 99% variable region identity).

In one embodiment, the dose of the anti-C5 antibody, or antigen binding fragment thereof, is based on the weight of the patient. For example, in one embodiment, 2400 mg or 3000 mg of the anti-C5 antibody, or antigen binding fragment thereof, is administered to a patient weighing ≥40 to <60 kg. In another embodiment, 2700 mg or 3300 mg of the anti-C5 antibody, or antigen binding fragment thereof, is administered to a patient weighing ≥60 to <100 kg. In another embodiment, 3000 mg or 3600 mg of the anti-C5 antibody, or antigen binding fragment thereof, is administered to a patient weighing ≥100 kg. In certain embodiments, dosage regimens are adjusted to provide the optimum desired response (e.g., an effective response).

In another embodiment, the anti-C5 antibody, or antigen binding fragment thereof, is administered for one or more administration cycles. In one embodiment, the administration cycle is 26 weeks. In one embodiment, the anti-C5 antibody, or antigen binding fragment thereof, is administered once on Day 1 of the administration cycle, once on Day 15 of the administration cycle, and every eight weeks thereafter. In one embodiment, the anti-C5 antibody, or antigen binding fragment thereof, is administered every eight weeks after the administration cycle for an extension period up to two years (e.g., at a dose of 3000 mg, 3300 mg, or 3600 mg).

In another embodiment, the anti-C5 antibody, or antigen binding fragment thereof, is administered for one or more administration cycles. In one embodiment, the administration cycle is 26 weeks. In another embodiment, the treatment comprises at least 1, 2, 3, 4, 5, 6, 7, 8, 9, 10, or 11 cycles. In another embodiment, the treatment is continued for the lifetime of the human patient.

In another embodiment, a method of treating a human patient with PNH or aHUS is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:
  (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, a method of treating a human patient with PNH or aHUS is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
  (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, the anti-C5 antibody, or antigen binding fragment thereof, is administered to a patient weighing ≥40 to <60 kg:
  (a) once on Day 1 of the administration cycle at a dose of 2400 mg; and
  (b) on Day 15 of the administration cycle and every eight weeks thereafter at a dose of 3000 mg.

In another embodiment, the anti-C5 antibody, or antigen binding fragment thereof, is administered to a patient weighing ≥60 to <100 kg:
  (a) once on Day 1 of the administration cycle at a dose of 2700 mg; and
  (b) on Day 15 of the administration cycle and every eight weeks thereafter at a dose of 3300 mg.

In another embodiment, the anti-C5 antibody, or antigen binding fragment thereof, is administered to a patient weighing ≥100 kg:
  (a) once on Day 1 of the administration cycle at a dose of 3000 mg; and
  (b) on Day 15 of the administration cycle and every eight weeks thereafter at a dose of 3600 mg.

In some embodiments, the patient has not previously been treated with a complement inhibitor (e.g., the patient is a complement inhibitor treatment-naïve patient).

In other embodiments, the patient has previously been treated with one anti-C5 antibody, or antigen binding fragment thereof, and is switched to another anti-C5 antibody during the course of treatment. For example, in certain embodiments, different anti-C5 antibodies are administered during the course of treatment. In one embodiment, different anti-C5 antibodies are administered during separate treatment and extension periods. For example, in one embodiment, the patient is treated with eculizumab during a treatment period (e.g., for 26 weeks), followed by treatment with another anti-C5 antibody (e.g., ravulizumab, 7086 antibody, 8110 antibody, 305LO5 antibody, SKY59 antibody, or REGN3918 antibody), for example, during an extension period. In another embodiment, eculizumab is administered to the patient at a dose of 600 mg on Days 1, 8, 15, and 22 of the administration cycle during an induction phase, followed by a maintenance dose of 900 mg of eculizumab on Day 19 of the administration cycle and every two weeks thereafter (e.g., for a total of 26 weeks), followed by treatment with ravulizumab for an extension period of up to two years. In another embodiment, the patient is treated with ravulizumab (e.g., for 26 weeks), followed by treatment with another anti-C5 antibody (e.g., eculizumab, 7086 antibody, 8110 antibody, 305LO5 antibody, SKY59 antibody, or REGN3918 antibody) during, for example, an extension period.

Exemplary alternative anti-C5 antibodies include, but are not limited to, (i) ALXN1210, (ii), an antibody, or antigen binding fragment thereof, comprising heavy chain CDR1, CDR2 and CDR3 domains comprising SEQ ID NOs: 21, 22, and 23, respectively, and light chain CDR1, CDR2 and CDR3 domains comprising SEQ ID NOs: 24, 25, and 26, respectively, (iii) an antibody, or antigen binding fragment thereof, comprising a heavy chain variable region comprising SEQ ID NO:27 and a light chain variable region comprising SEQ ID NO:28, (iv) an antibody, or antigen binding fragment thereof, comprising heavy chain CDR1, CDR2 and CDR3 domains comprising SEQ ID NOs: 29, 30, and 31, respectively, and light chain CDR1, CDR2 and CDR3 domains comprising SEQ ID NOs: 32, 33, and 34, respectively, (v) an antibody, or antigen binding fragment thereof, comprising a heavy chain variable region comprising SEQ ID NO: 35 and a light chain variable region comprising SEQ ID NO: 36, (vi) an antibody, or antigen binding fragment thereof, comprising heavy chain CDR1, CDR2 and CDR3 domains comprising SEQ ID NOs: 37, 38, and 39, respectively, and light chain CDR1, CDR2 and CDR3 domains comprising SEQ ID NOs: 40, 41, and 42, respectively, (vii) an antibody, or antigen binding fragment thereof, comprising a heavy chain variable region comprising SEQ ID NO: 43 and a light chain variable region comprising SEQ ID NO: 44, (viii) an antibody, or antigen binding fragment thereof, comprising a heavy chain comprising SEQ ID NO: 45 and a light chain comprising SEQ ID NO: 46, (ix) an antibody, or antigen binding fragment thereof, comprising a heavy chain variable region comprising SEQ ID NO: 47 and a light chain variable region comprising SEQ ID NO: 48, and (x) an antibody, or antigen binding fragment thereof, comprising a heavy chain comprising SEQ ID NO: 49 and a light chain comprising SEQ ID NO: 50.

In some embodiments, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with an anti-C5 antibody, or antigen binding fragment thereof, (e.g., eculizumab) before switching to another anti-C5 antibody, or antigen binding fragment thereof (e.g., ravulizumab). In a particular embodiment, the patient has previously been treated for at least 6 months with eculizumab.

In another embodiment, where a patient (e.g., PNH or aHUS patient) is treated with a first anti-C5 antibody and then switched to treatment with a second different anti-C5 antibody, especially where the second different anti-C5 antibody binds to a different epitope on C5 than the first anti-C5 antibody, the administration schedules takes into account the half-life of the first anti-C5 antibody. For example, to ensure that the first anti-C5 antibody is cleared (e.g., "washed out") from the patient before the second (different) anti-C5 antibody is administered (e.g., to avoid issues associated with aggregation, immune complex formation, etc.), the half-life of the first anti-C5 antibody is taken into consideration. In one embodiment, the second (different) anti-C5 antibody is not administered until a duration of time corresponding to 2, 2.5, 3, 3.5, 4, 4.5, 5, 5.5, 6, 6.5, 7, or 7.5 times the half-life of the first anti-C5 antibody has passed after the final administration of the first anti-C5 antibody.

In another embodiment, the patient has previously been treated with eculizumab and then is switched to treatment with a second (different) anti-C5 antibody (e.g., ravulizumab, 7086 antibody, 8110 antibody, 305LO5 antibody, SKY59 antibody, or REGN3918 antibody). In one embodiment where eculizumab is the first administered antibody, the second (different) anti-C5 antibody is not administered, for example, until at least 36, 45, 54, 63, 72, 81, 90, 99, 108, 117, or 126 days have passed after the final administration of eculizumab.

In another embodiment, the patient has previously been treated with ravulizumab and then is switched to treatment with a different anti-C5 antibody (e.g., eculizumab, 7086 antibody, 8110 antibody, 305LO5 antibody, SKY59 antibody, or REGN3918 antibody). In one embodiment where ravulizumab is the first administered antibody, the second (different) anti-C5 antibody is not administered, for example, until at least 100, 125, 150, 175, 200, 225, 250, 275, 300, 325, 375, or 400 days have passed after the final administration of ravulizumab.

Additionally or alternatively, techniques are used to clear or enhance clearance of the first anti-C5 antibody before switching to treatment with a second (different) anti-C5 antibody. Exemplary techniques include, but are not limited to, plasmapheresis or blood transfusions. In another embodiment, an antibody against the first anti-C5 antibody (e.g., an anti-eculizumab antibody, an anti-ravulizumab antibody, an anti-7086 antibody, an anti-8110 antibody, an anti-305LO5 antibody, an anti-SKY59 antibody, or an anti-REGN3918 antibody) is administered to clear or enhance clearance of the first anti-C5 antibody before a second (different) anti-C5 antibody is administered.

In another embodiment, the anti-C5 antibody, or antigen binding fragment thereof (e.g., ALXN1210), is administered to a patient, wherein the administration cycle starts at least about two weeks, at least about three weeks, at least about four weeks, at least about six weeks, at least about seven weeks, or at least about eight weeks after the patient's last dose of eculizumab. In another embodiment, the anti-C5 antibody, or antigen binding fragment thereof (e.g., ALXN1210), is administered to a patient, wherein the administration cycle starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

In another aspect, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In another embodiment, to obtain an effective response, the anti-C5 antibody is administered to the patient in an amount and with a frequency to maintain at least 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

In another embodiment, to obtain an effective response, the anti-C5 antibody is administered to the patient in an amount and with a frequency to maintain a minimum free C5 concentration. For example, in one embodiment, the anti-C5 antibody is administered to the patient in an amount and with a frequency to maintain a free C5 concentration of 0.2 µg/mL, 0.3 µg/mL, 0.4 µg/mL, 0.5 µg/mL or below. In another embodiment, the anti-C5 antibody is administered to the patient in an amount and with a frequency to maintain a free C5 concentration of 0.309 to 0.5 µg/mL or below. In another embodiment, the treatment described herein reduces free C5 concentration by greater than 99% throughout the treatment period. In another embodiment, the treatment reduces free C5 concentration greater than 99.5% throughout the treatment period.

The anti-C5 antibodies, or antigen binding fragments thereof, can be administered to a patient by any suitable means. In one embodiment, the antibodies are formulated for intravenous administration.

The efficacy of the treatment methods provided herein can be assessed using any suitable means. In one embodiment, for a PNH patient, the treatment produces at least one therapeutic effect selected from the group consisting of a reduction or cessation in fatigue, abdominal pain, dyspnea, dysphagia, chest pain, and erectile dysfunction. In another embodiment, for an aHUS patient, the treatment produces at least one therapeutic effect selected from the group consisting of a reduction or cessation in severe hypertension, proteinuria, uremia, lethargy/fatigue, irritability, thrombocytopenia, microangiopathic hemolytic anemia, and renal function impairment (e.g., acute renal failure).

In other embodiments, the treatment results in terminal complement inhibition.

In other embodiments, the treatment produces a shift toward normal levels of a hemolysis-related hematologic biomarker selected from the group consisting of free hemoglobin, haptoglobin, reticulocyte count, PNH red blood cell (RBC) clone and D-dimer. In another embodiment, the treatment produces an increase in hemoglobin stabilization from the patient's pre-treatment baseline.

In other embodiments, the treatment produces a shift toward normal levels of a chronic disease associated biomarker selected from the group consisting estimated glomerular filtration rate (eGFR) and spot urine:albumin:creatinine and plasma brain natriuretic peptide (BNP).

In other embodiments, the treatment produces a reduction in the need for blood transfusions. In another embodiment, the treatment produces a greater than 70% increase in transfusion avoidance.

In other embodiments, the treatment results in a reduction in breakthrough hemolysis relative to treatment with eculizumab. In another embodiment, the treatment results in a elimination of breakthrough hemolysis during the treatment period. In another embodiment, the treatment results in a reduction of breakthrough hemolysis compared to pretreatment baseline amount of breakthrough hemolysis.

In other embodiments, the treatment produces a reduction in major adverse vascular events (MAVEs).

In other embodiments, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale. In another embodiment, the treatment produces a change from baseline in quality of life, assessed via the Functional Assessment of Chronic Illness Therapy (FACIT)-Fatigue Scale, version 4 and the European Organisation for Research and Treatment of Cancer, Quality of Life Questionnaire-Core 30 Scale by at least 7 points from the patients untreated baseline score.

In another embodiment, the treatment results in no change in quality of life (QoL) as assessed via the Functional Assessment of Chronic Illness Therapy (FACIT)-Fatigue Scale, Version 4, from Baseline to Day 183. In another embodiment, the treatment results in an increase in quality of life (QoL) assessed via the Functional Assessment of Chronic Illness Therapy (FACIT)-Fatigue Scale, Version 4, from Baseline to Day 183. In another embodiment, the treatment results in transfusion avoidance from Baseline to Day 183. In another embodiment, the treatment results in avoidance of a ≥2 g/dL decrease in hemoglobin level from baseline in the absence of transfusion from Baseline to Day 183.

In other embodiments, lactate dehydrogenase (LDH) levels are used to evaluate responsiveness to a therapy (e.g., a reduction of hemolysis as assessed by lactate dehydrogenase (LDH) levels is indicative of an improvement in at least one sign of PNH). For example, in one embodiment, the treatments described herein result in a normalization of LDH levels. In another embodiment, patients treated according to the disclosed methods experience reductions in LDH levels to near normal levels or to within 10%, or within 20% above what is considered the normal level (e.g., within 105-333 IU/L (international units per liter). In another embodiment, the patient's LDH levels are normalized throughout maintenance period of treatment. In another embodiment, the treated patient's LDH levels are normalized at least at least 95% of the time while on the maintenance period of treatment. In another embodiment, the treated patient's LDH levels are normalized at least at least 90%, 85% or 80% of the time while on the maintenance period of treatment. In one embodiment, the patient's LDH levels are ≥1.5 fold above the upper limit of normal (LDH≥1.5×ULN) prior to initiating treatment. In another embodiment, the treatment results in a normalization of LDH levels by at least day 24 of treatment. In one embodiment, patients treated according to the disclosed methods experience reductions in LDH levels to within normal levels or to within 10%, 20%, 30%, 40% or within 50% below what is considered the upper limit of normal level (e.g., within 105-333 IU/L (international units per liter). In one embodiment, the patient's LDH levels are ≥1.5 fold above the upper limit of normal (LDH≥1.5× ULN) prior to initiating treatment. In one embodiment, the treatment results in LDH levels less than 2× upper limit of normal (ULN).

In another aspect, an anti-C5 antibody, or antigen binding fragment thereof, is provided, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8, for administration to a patient having PNH or aHUS:

(a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In one embodiment, the antibody is determined to be safe, tolerable and sufficiently non-immunogenic after multiple IV doses for use in PNH and aHUS patients.

Further provided are kits that include a pharmaceutical composition containing an anti-C5 antibody, or antigen binding fragment thereof, such as antibody ravulizumab, and a pharmaceutically-acceptable carrier, in a therapeutically effective amount adapted for use in the methods described herein. In one embodiment, the kit comprises:

(a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and (b) instructions for using the anti-C5 antibody, or antigen binding fragment thereof, in the methods described herein.

In one embodiment, 2400 mg or 3000 mg of the anti-C5 antibody, or antigen binding fragment thereof, is administered to a patient weighing ≥40 to <60 kg. In another embodiment, 2700 mg or 3300 mg of the anti-C5 antibody, or antigen binding fragment thereof, is administered to a patient weighing ≥60 to <100 kg. In another embodiment, 3000 mg or 3600 mg of the anti-C5 antibody, or antigen binding fragment thereof, is administered to a patient weighing ≥100 kg.

In another aspect, methods of treating a human patient having a complement-associated disorder are provided. In one embodiment, the method comprises treating a human patient having a complement-associated disorder who is being treated with eculizumab, wherein the method comprises discontinuing treatment with eculizumab and switching the patient to treatment with a different complement inhibitor. In another embodiment, the method comprises treating a human patient having a complement-associated disorder who is being treated with ravulizumab, wherein the method comprises discontinuing treatment with ravulizumab and switching the patient to treatment with a different complement inhibitor. In one embodiment the different complement inhibitor is selected from the group consisting of: a small molecule, a polypeptide, a polypeptide analog, a peptidomimetic, an siRNA or an aptamer. In another embodiment, the different complement inhibitor inhibits one or more of complement components C1, C2, C3, C4, C5, C6, C7, C8, C9, Factor D, Factor B, properdin, MBL, MASP-1, MASP-2, or biologically active fragments thereof. In another embodiment, the different complement inhibitor is a different anti-C5 antibody (e.g., ravulizumab, 7086 antibody, 8110 antibody, 305LO5 antibody, SKY59 antibody, or REGN3918 antibody).

Exemplary complement-associated conditions that can be treated according to the methods described herein include, but are not limited to, rheumatoid arthritis, antiphospholipid antibody syndrome, lupus nephritis, ischemia-reperfusion injury, atypical hemolytic uremic syndrome (aHUS), typical hemolytic uremic syndrome, paroxysmal nocturnal hemoglobinuria (PNH), dense deposit disease, neuromyelitis optica, multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, myasthenia gravis, cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection, Hashimoto's thyroiditis, type I diabetes, psoriasis, pemphigus, autoimmune hemolytic anemia, idiopathic thrombocytopenic purpura, Goodpasture's syndrome, Degos disease, and catastrophic antiphospholipid syndrome. In one embodiment, the complement-associated condition is PNH. In another embodiment, the complement-associated condition is aHUS.

BRIEF DESCRIPTION OF THE DRAWINGS

FIG. 3 is a schematic that shows the baseline characteristics and demographics of the patients in the Phase III ALXN1210-PNH-301 clinical trial.

FIG. 6 is a tabulation of key results from both the primary and secondary endpoints.

FIG. 7 shows the results from multiple sensitivity analyses of the efficacy results

FIG. 15 is a tabulation of the key safety results in the Phase III ALXN1210-PNH-301 clinical trial.

FIG. 16 is a tabulation of the most common treatment emergent adverse events (TEAE) in the Phase III ALXN1210-PNH-301 clinical trial.

FIG. 17 is a tabulation of the treatment emergent serious adverse events (TESAE) in the Phase III ALXN1210-PNH-301 clinical trial.

FIG. 18 is a tabulation of the treatment emergent adverse events (TEAE) of special interest in the Phase III ALXN1210-PNH-301 clinical trial.

FIG. 19 is a tabular display of the patient drug compliance results in the Phase III ALXN1210-PNH-301 clinical trial.

FIG. 22 is a graphical depiction of the pharmacodynamics (PD) of ravulizumab (ALXN1210) and eculizumab showing the mean C5 concentration in the presence of each drug over time.

FIG. 28 is a schematic that shows the baseline characteristics and demographics of the patients enrolled in the Phase III ALXN1210-PNH-302 clinical trial.

FIG. 29 is a schematic that shows the baseline disease characteristics of the patients enrolled in the Phase III ALXN1210-PNH-302 clinical trial.

FIG. 31 is a tabulation of key efficacy results from both the primary and secondary endpoints from the Phase III ALXN1210-PNH-302 clinical trial.

FIG. 32 shows the results from multiple sensitivity analyses of the efficacy results for the primary endpoint from the Phase III ALXN1210-PNH-302 clinical trial.

FIG. 38 is a tabulation of the key safety results from the Phase III ALXN1210-PNH-302 clinical trial.

FIG. 39 is a tabulation of the treatment emergent serious adverse events (TESAEs) from the Phase III ALXN1210-PNH-302 clinical trial.

FIG. 40 is a tabulation of the most common treatment emergent adverse events (TEAEs) from the Phase III ALXN1210-PNH-302 clinical trial.

FIG. 41 is a tabulation of upper respiratory tract infections (URTI) from the Phase III ALXN1210-PNH-302 clinical trial, as determined by standard MedDRA query (SMQ).

FIG. 42 is a tabulation of the treatment emergent adverse events of special interest (TEAESI) from the Phase III ALXN1210-PNH-302 clinical trial.

FIG. 43 is a tabular display of the patient drug compliance results from the Phase III ALXN1210-PNH-302 clinical trial.

DETAILED DESCRIPTION

I. Anti-C5 Antibodies

Figure 1:
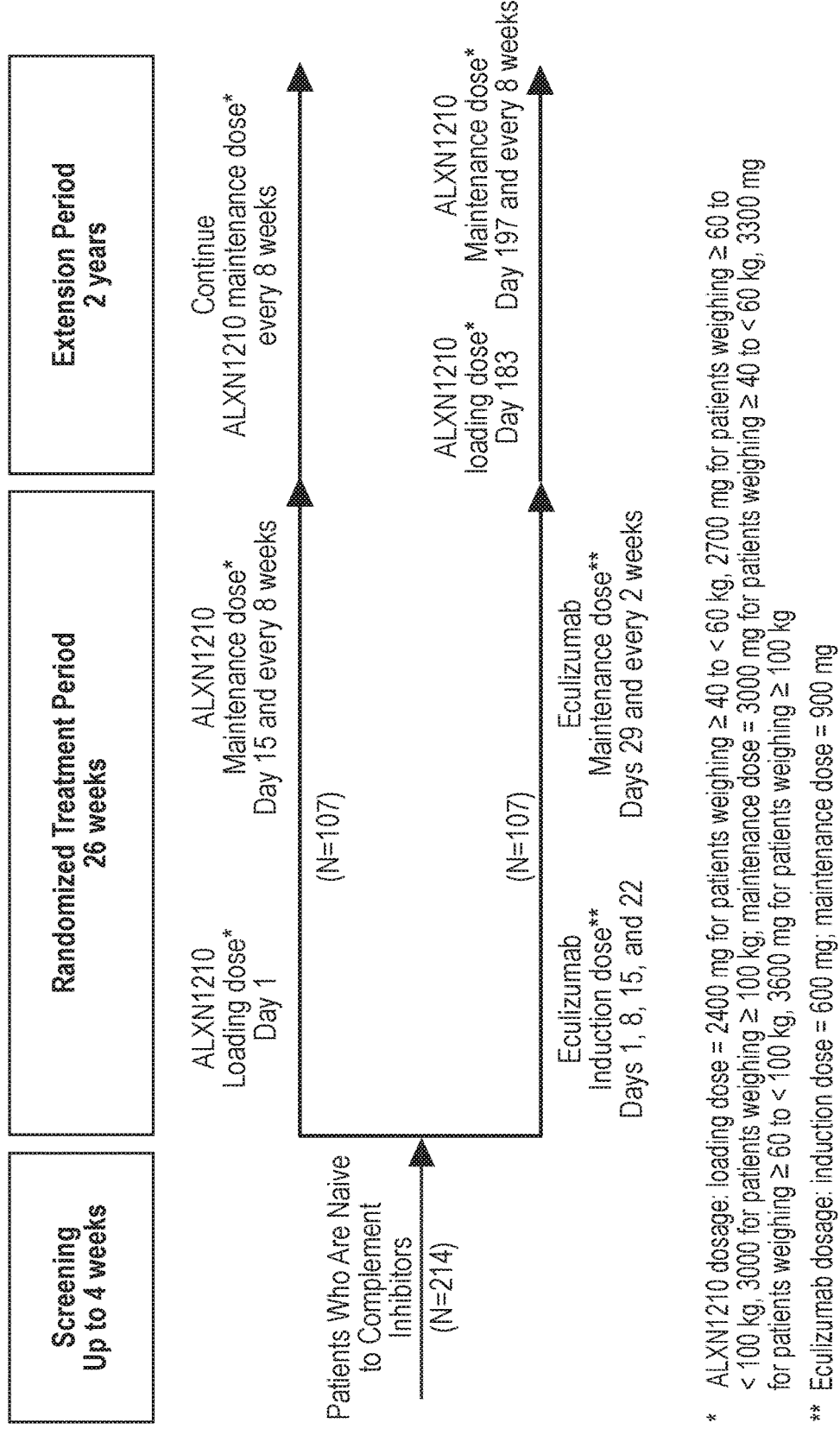
FIG. 1 is a schematic depicting the design of a Phase III ALXN1210-PNH-301 clinical trial in PNH patients naïve to treatment with a complement inhibitor.

The anti-C5 antibodies described herein bind to complement component C5 (e.g., human C5) and inhibit the cleavage of C5 into fragments C5a and C5b. As described above, such antibodies also have, for example, improved pharmacokinetic properties relative to other anti-C5 antibodies (e.g., eculizumab) used for therapeutic purposes.

The term "antibody" describes polypeptides comprising at least one antibody derived antigen binding site (e.g., VH/VL region or Fv, or CDR). Antibodies include known forms of antibodies. For example, the antibody can be a human antibody, a humanized antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which changes a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

Anti-C5 antibodies (or VH/VL domains derived therefrom) suitable for use in the invention can be generated using methods well known in the art. Alternatively, art recognized anti-C5 antibodies can be used. Antibodies that compete with any of these art-recognized antibodies for binding to C5 also can be used.

Eculizumab (also known as Soliris®) is an anti-C5 antibody comprising heavy chain CDR1, CDR2 and CDR3 domains having the sequences set forth in SEQ ID NOs: 1, 2, and 3, respectively, and light chain CDR1, CDR2 and CDR3 domains having the sequences set forth in SEQ ID NOs: 4, 5, and 6, respectively. Eculizumab comprises a heavy chain variable region having the amino acid sequence set forth in SEQ ID NO: 7 and a light chain variable region having the amino acid sequence set forth in SEQ ID NO: 8. The variable regions of eculizumab are described in PCT/US1995/005688 and U.S. Pat. No. 6,355,245, the teachings of which are hereby incorporated by reference. Eculizumab comprises a heavy chain comprising the amino acid sequence set forth in SEQ ID NO:10 and a light chain having the amino acid sequence set forth in SEQ ID NO:11. The full heavy and light chains of eculizumab are described in PCT/US2007/006606, the teachings of which are hereby incorporated by reference.

An exemplary anti-C5 antibody is ravulizumab comprising heavy and light chains having the sequences shown in SEQ ID NOs:14 and 11, respectively, or antigen binding fragments and variants thereof. Ravulizumab (also known as Ultomiris™, BNJ441 and ALXN1210) is described in PCT/US2015/019225 and U.S. Pat. No. 9,079,949, the teachings or which are hereby incorporated by reference. The terms ravulizumab, BNJ441, and ALXN1210 may be used interchangeably throughout this document, but all refer to the same antibody. Ravulizumab selectively binds to human complement protein C5, inhibiting its cleavage to C5a and C5b during complement activation. This inhibition prevents the release of the proinflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. For example, in one embodiment, the antibody comprises the CDR1, CDR2, and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively. In another embodiment, the antibody comprises VH and VL regions having the amino acid sequences set forth in SEQ ID NO:12 and SEQ ID NO:8, respectively.

Another exemplary anti-C5 antibody is antibody BNJ421 comprising heavy and light chains having the sequences shown in SEQ ID NOs:20 and 11, respectively, or antigen binding fragments and variants thereof. BNJ421 (also known as ALXN1211) is described in PCT/US2015/019225 and U.S. Pat. No. 9,079,949, the teachings or which are hereby incorporated by reference.

In other embodiments, the antibody comprises the heavy and light chain CDRs or variable regions of BNJ421. Accordingly, in one embodiment, the antibody comprises the CDR1, CDR2, and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18, and 3, respectively, and light chain CDR1, CDR2 and CDR3 domains having the sequences set forth in SEQ ID NOs:4, 5, and 6, respectively.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, MD]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (1989) Nature 342:877-883. Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. [(1996) Mol Immunol 33(17/18):1389-1401] exemplifies the identification of CDR boundaries according to Kabat and Chothia definitions.

In another embodiment, the antibody comprises VH and VL regions having the amino acid sequences set forth in SEQ ID NO: 12 and SEQ ID NO: 8, respectively. In another embodiment, the antibody comprises a heavy chain constant region as set forth in SEQ ID NO:13. In another embodiment, the antibody comprises a heavy chain polypeptide as set forth in SEQ ID NO:14 and a light chain polypeptide as set forth in SEQ ID NO:11. In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering.

In another embodiments, an anti-C5 antibody described herein comprises a heavy chain CDR1 comprising, or consisting of, the following amino acid sequence: GHIFSNY-WIQ (SEQ ID NO:19). In another embodiment, an anti-C5 antibody described herein comprises a heavy chain CDR2 comprising, or consisting of, the following amino acid sequence: EILPGSGHTEYTENFKD (SEQ ID NO:18).

In another embodiment, the antibody binds to human C5 at pH 7.4 and 25° C. with an affinity dissociation constant ($K_D$) that is in the range 0.1 nM≤$K_D$≤1 nM. In another embodiment, the antibody binds to human C5 at pH 6.0 and 25° C. with a $K_D$≥10 nM. In yet another embodiment, the

[(K_D of the antibody or antigen-binding fragment thereof for human C5 at pH 6.0 and at 25° C.)/(K_D of the antibody or antigen-binding fragment thereof for human C5 at pH 7.4 and at 25° C.)] of the antibody is greater than 25.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs: 21, 22, and 23, respectively, and light chain CDR1, CDR2 and CDR3 domains having the sequences set forth in SEQ ID NOs: 24, 25, and 26, respectively. In another embodiment, the antibody, or antigen binding fragment thereof, comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30, and 31, respectively, and light chain CDR1, CDR2 and CDR3 domains having the sequences set forth in SEQ ID NOs: 32, 33, and 34, respectively. In another embodiment, the antibody comprises the VH region of the 8110 antibody having the sequence set forth in SEQ ID NO: 35, and the VL region of the 8110 antibody having the sequence set forth in SEQ ID NO: 36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs: 37, 38, and 39, respectively, and light chain CDR1, CDR2 and CDR3 domains having the sequences set forth in SEQ ID NOs: 40, 41, and 42, respectively. In another embodiment, the antibody comprises the VH region of the 305LO5 antibody having the sequence set forth in SEQ ID NO: 43, and the VL region of the 305LO5 antibody having the sequence set forth in SEQ ID NO: 44.

Another exemplary anti-C5 antibody is the SKY59 antibody described in Fukuzawa T., et al., Rep. 2017 Apr. 24; 7(1):1080). In one embodiment, the antibody comprises the heavy and light chain CDRs or variable regions of the SKY59 antibody. In another embodiment, the antibody, or antigen binding fragment thereof, comprises a heavy chain comprising SEQ ID NO: 45 and a light chain comprising SEQ ID NO: 46.

Another exemplary anti-C5 antibody is the REGN3918 antibody (also known as H4H12166PP) described in US20170355757. In one embodiment, the antibody comprises a heavy chain variable region comprising SEQ ID NO:47 and a light chain variable region comprising SEQ ID NO:48. In another embodiment, the antibody comprises a heavy chain comprising SEQ ID NO:49 and a light chain comprising SEQ ID NO:50.

In another embodiment, the antibody competes for binding with, and/or binds to the same epitope on C5 as, the above-mentioned antibodies (e.g., eculizumab, ravulizumab, 7086 antibody, 8110 antibody, 305LO5 antibody, SKY59 antibody, or REGN3918 antibody). In another embodiment, the antibody has at least about 90% variable region amino acid sequence identity with the above-mentioned antibodies (e.g., at least about 90%, 91%, 92%, 93%, 94%, 95%, 96%, 97%, 98% or 99% variable region identity).

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. For example, the Fc constant region can comprise one or more (e.g., two, three, four, five, six, seven, or eight or more) amino acid substitutions relative to the native human Fc constant region from which the variant human Fc constant region was derived. The substitutions can increase the binding affinity of an IgG antibody containing the variant Fc constant region to FcRn at pH 6.0, while maintaining the pH dependence of the interaction. Methods for testing whether one or more substitutions in the Fc constant region of an antibody increase the affinity of the Fc constant region for FcRn at pH 6.0 (while maintaining pH dependence of the interaction) are known in the art and exemplified in the working examples. See, e.g., PCT/US2015/019225 and U.S. Pat. No. 9,079,949 the disclosures of each of which are incorporated herein by reference in their entirety.

Substitutions that enhance the binding affinity of an antibody Fc constant region for FcRn are known in the art and include, e.g., (1) the M252Y/S254T/T256E triple substitution described by Dall'Acqua et al. (2006) *J Biol Chem* 281: 23514-23524; (2) the M428L or T250Q/M428L substitutions described in Hinton et al. (2004) *J Biol Chem* 279:6213-6216 and Hinton et al. (2006) *J Immunol* 176: 346-356; and (3) the N434A or T307/E380A/N434A substitutions described in Petkova et al. (2006) *Int Immunol* 18(12):1759-69. The additional substitution pairings: P257I/Q311I, P257I/N434H, and D376V/N434H are described in, e.g., Datta-Mannan et al. (2007) *J Biol Chem* 282(3):1709-1717, the disclosure of which is incorporated herein by reference in its entirety.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three, or two) amino acid substitutions, insertions, or deletions relative to the native constant region from which it was derived. In some embodiments, the variant Fc constant region comprises one or more amino acid substitutions selected from the group consisting of: M252Y, S254T, T256E, N434S, M428L, V259I, T250I, and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376.

In some embodiments the precise location of these mutations may be shifted from the native human Fc constant region position due to antibody engineering. For example, the 428L/434S double substitution when used in a IgG2/4 chimeric Fc may correspond to 429L and 435S as in the M429L and N435S variants found in BNJ441 (ravulizumab) and described in U.S. Pat. No. 9,079,949 the disclosure of which is incorporated herein by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434, or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan, or tyrosine for threonine at position 250; phenylalanine, tryptophan, or tyrosine for methionine at position 252; threonine for serine at position 254; glutamic acid for arginine at position 255; aspartic acid, glutamic acid, or glutamine for threonine at position 256; alanine, glycine, isoleucine, leucine, methionine, asparagine, serine, threonine, or valine for proline at position 257; histidine for glutamic acid at position 258; alanine for aspartic acid at position 265; phenylalanine for aspartic acid at position 270; alanine, or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan, or tyrosine for threonine at position 307; alanine, phenylalanine, isoleucine, leucine, methionine, proline, glutamine, or threonine for valine at position 308; alanine, aspartic acid, glutamic acid, proline, or arginine for leucine or valine at position 309; alanine, histidine, or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan, or tyrosine for methionine at position 428; lysine for histidine at position 433; alanine, phenylalanine, histidine, serine, tryptophan, or tyrosine for asparagine at position 434; and histidine for tyrosine or phenylalanine at position 436, all in EU numbering.

Suitable anti-C5 antibodies for use in the methods described herein, in some embodiments, comprise a heavy chain polypeptide comprising the amino acid sequence depicted in SEQ ID NO:14 and/or a light chain polypeptide comprising the amino acid sequence depicted in SEQ ID NO:11. Alternatively, the anti-C5 antibodies for use in the methods described herein, in some embodiments, comprise a heavy chain polypeptide comprising the amino acid sequence depicted in SEQ ID NO:20 and/or a light chain polypeptide comprising the amino acid sequence depicted in SEQ ID NO:11.

In one embodiment, the antibody binds to C5 at pH 7.4 and 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3, or 0.2) nM.

In other embodiments, the [($K_D$ of the antibody for C5 at pH 6.0 at C)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500, or 8000).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Benny K. C. Lo (2004) "Antibody Engineering: Methods and Protocols," Humana Press (ISBN: 1588290921); Johne et al. (1993) *J Immunol Meth* 160:191-198; Jonsson et al. (1993) *Ann Biol Clin* 51:19-26; and Jonsson et al. (1991) *Biotechniques* 11:620-627. In addition, methods for measuring the affinity (e.g., dissociation and association constants) are set forth in the working examples.

As used herein, the term "$k_a$" refers to the rate constant for association of an antibody to an antigen. The term "$k_d$" refers to the rate constant for dissociation of an antibody from the antibody/antigen complex. And the term "$K_D$" refers to the equilibrium dissociation constant of an antibody-antigen interaction. The equilibrium dissociation constant is deduced from the ratio of the kinetic rate constants, $K_D = k_a/k_d$. Such determinations preferably are measured at 25° C. or 37° C. (see the working examples). For example, the kinetics of antibody binding to human C5 can be determined at pH 8.0, 7.4, 7.0, 6.5 and 6.0 via surface plasmon resonance (SPR) on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, e.g., the pro-inflammatory effects of C5a and the generation of the C5b-9 membrane attack complex (MAC) at the surface of a cell.

Methods for determining whether a particular antibody described herein inhibits C5 cleavage are known in the art. Inhibition of human complement component C5 can reduce the cell-lysing ability of complement in a subject's body fluids. Such reductions of the cell-lysing ability of complement present in the body fluid(s) can be measured by methods well known in the art such as, for example, by a conventional hemolytic assay such as the hemolysis assay described by Kabat and Mayer (eds.), "Experimental Immunochemistry, 2$^{nd}$ Edition," 135-240, Springfield, IL, CC Thomas (1961), pages 135-139, or a conventional variation of that assay such as the chicken erythrocyte hemolysis method as described in, e.g., Hillmen et al. (2004) *N Engl J Med* 350(6):552. Methods for determining whether a candidate compound inhibits the cleavage of human C5 into forms C5a and C5b are known in the art and described in Evans et al. (1995) *Mol Immunol* 32(16):1183-95. For example, the concentration and/or physiologic activity of C5a and C5b in a body fluid can be measured by methods well known in the art. For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody, or antigen binding fragment thereof, on complement activation. In order to determine the effect of an anti-C5 antibody, or antigen binding fragment thereof, on classical complement pathway-mediated hemolysis in a serum test solution in vitro, for example, sheep erythrocytes coated with hemolysin or chicken erythrocytes sensitized with anti-chicken erythrocyte antibody are used as target cells. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-05b-9 antibody and a fluorogenic substrate and measuring the absorbance at the appropriate wavelength. As a control, the test serum is incubated in the absence of the anti-05 antibody, or antigen binding fragment thereof. In some embodiments, the test serum is a C5-deficient serum reconstituted with a C5 polypeptide.

To determine the effect of an anti-C5 antibody, or antigen binding fragment thereof, on alternative pathway-mediated hemolysis, unsensitized rabbit or guinea pig erythrocytes can be used as the target cells. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, the activated sera are diluted in microas say wells, which are coated with a capture reagent (e.g., an antibody that binds to one or more components of the TCC). The TCC present in the activated samples bind to the monoclonal antibodies coating the surface of the microas say wells. The wells are washed and to each well is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %. In some embodiments, an anti-C5 antibody described herein contains one or more amino acid substitutions relative to the CDRs of eculizumab (i.e., SEQ ID NOs:1-6), yet retains at least 30 (e.g., at least 31, 32, 33, 34, 35, 36, 37, 38, 39, 40, 41, 42, 43, 44, 45, 46, 47, 48, 49, 50, 55, 60, 65, 70, 75, 80, 85, 90, or 95) % of the complement inhibitory activity of eculizumab in a hemolytic assay or CH50eq assay.

An anti-C5 antibody described herein has a serum half-life in humans that is at least 20 (e.g., at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55) days. In another embodiment, the anti-C5 antibody described herein has a serum half-life in humans that is at least 40 days. In another embodiment, the anti-C5 antibody described herein has a serum half-life in humans that is approximately 43 days. In another embodiment, the anti-C5 antibody described herein has a serum half-life in humans that is between 39-48 days. Methods for measuring the serum half-life of an antibody are known in the art. In some embodiments, an anti-C5 antibody, or antigen binding fragment thereof, described herein has a serum half-life that is at least 20 (e.g., at least 30, 35, 40, 45, 50, 55, 60, 65, 70, 75, 80, 85, 90, 95, 100, 125, 150, 175, 200, 250, 300, 400, 500) % greater than the serum half-life of eculizumab, e.g., as measured in one of the mouse model systems described in the working examples (e.g., the C5-deficient/NOD/scid mouse or hFcRn transgenic mouse model system).

In one embodiment, the antibody competes for binding with, and/or binds to the same epitope on C5 as, the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competing antibodies bind to the same epitope, an overlapping epitope or to adjacent epitopes (e.g., as evidenced by steric hindrance).

Anti-C5 antibodies, or antigen-binding fragments thereof described herein, used in the methods described herein can be generated using a variety of art-recognized techniques. Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246: 1275-1281 (1989).

II. Compositions

Also, provided herein are compositions comprising an anti-C5 antibody, or antigen binding fragment thereof. In one embodiment, the composition comprises an anti-C5 antibody comprising the CDR1, CDR2 and CDR3 domains in a heavy chain variable region having the sequence set forth in SEQ ID NO:12, and the CDR1, CDR2 and CDR3 domains in a light chain variable region having the sequence set forth in SEQ ID NO:8. In another embodiment, the anti-C5 antibody comprises heavy and light chains having the sequences shown in SEQ ID NOs:14 and 11, respectively. In another embodiment, the anti-C5 antibody comprises heavy and light chains having the sequences shown in SEQ ID NOs:20 and 11, respectively.

The compositions can be formulated as a pharmaceutical solution, e.g., for administration to a subject for the treatment or prevention of a complement-associated disorder, such as PNH or aHUS. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods. Pharmaceutical formulation is a well-established art, and is further described in, e.g., Gennaro (2000) "Remington: The Science and Practice of Pharmacy," $20^{th}$ Edition, Lippincott, Williams & Wilkins (ISBN: 0683306472); Ansel et al. (1999) "Pharmaceutical Dosage Forms and Drug Delivery Systems," $7^{th}$ Edition, Lippincott Williams & Wilkins Publishers (ISBN: 0683305727); and Kibbe (2000) "Handbook of Pharmaceutical Excipients American Pharmaceutical Association," $3^{rd}$ Edition (ISBN: 091733096X). In some embodiments, a composition can be formulated, for example, as a buffered solution at a suitable concentration and suitable for storage at 2-8° C. (e.g., 4° C.). In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, in some embodiments, the compositions described herein are stable in storage for at least 1 year at 2-8° C. (e.g., 4° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

In one embodiment, the composition comprises ALXN1210 (also known as Ultomiris™, antibody BNJ441, or ravulizumab) for injection. In one embodiment, the injection is a sterile, clear to translucent, slight whitish color, preservative-free solution for intravenous use. In another embodiment, each single-dose vial contains 300 mg ALXN1210 for injection at a concentration of 10 mg/mL with a pH of 7.0. In another embodiment, ALXN1210 for injection requires dilution to a final concentration of 5 mg/mL. In another embodiment, each mL further comprises polysorbate 80 (0.2 mg) (vegetable origin), sodium chloride (8.77 mg), sodium phosphate dibasic (1.78 mg), sodium phosphate monobasic (0.46 mg), and Water for Injection.

III. Methods of Treatment

Provided herein are methods for treating PNH or aHUS in a human patient, comprising administering to the patient an anti-C5 antibody, or antigen binding fragment thereof, wherein the anti-C5 antibody, or antigen binding fragment thereof, is administered (or is for administration) according to a particular clinical dosage regimen (i.e., at a particular dose amount and according to a specific dosing schedule).

As used herein, the terms "induction" and "induction phase" are used interchangeably and refer to the first phase of treatment in the clinical trial.

As used herein, the terms "maintenance" and "maintenance phase" are used interchangeably and refer to the second phase of treatment in the clinical trial. In certain embodiments, treatment is continued as long as clinical benefit is observed or until unmanageable toxicity or disease progression occurs.

As used herein, the term "subject" or "patient" is a human patient (e.g., a patient having complement-associated condition, such as PNH or aHUS).

In one embodiment, the complement-associated condition is paroxysmal nocturnal hemoglobinuria (PNH). PNH is an acquired hemolytic disorder that occurs most frequently in adults (Brodsky R A., *Blood.* 2015; 126:2459-65). The disease begins with the clonal expansion of a hematopoietic stem cell that has acquired a somatic mutation in the PIGA gene (Brodsky R A., *Blood.* 2014; 124:2804-1). Consequently, PNH blood cells lack the glycophosphatidylinositol (GPI) anchor protein and are deficient in the membrane-bound complement inhibitory proteins CD55 and CD59. In the absence of CD55, there is increased deposition of complement protein C3 cleavage products on blood cell membrane surfaces, in turn leading to cleavage of C5 into C5a and C5b. The pathology and clinical presentations in patients with PNH are driven by uncontrolled terminal complement activation.

C5a is a potent anaphylatoxin, chemotactic factor, and cell-activating molecule that mediates multiple pro-inflammatory and pro-thrombotic activities (Matis L A, et al., *Nat. Med.* 1995; 1:839-42; Prodinger et al., Complement. In: Paul W E, editor. Fundamental immunology (4th ed). Philadelphia: Lippincott-Raven Publishers; 1999. p. 967-95). C5b recruits the terminal complement components C6, C7, C8, and C9 to form the pro-inflammatory, pro-thrombotic cytolytic pore molecule C5b-9, a process that under normal circumstances would be blocked on the red blood cell (RBC) membrane by CD59. In patients with PNH, however, these final steps proceed unchecked, culminating in hemolysis and the release of free hemoglobin, as well as platelet activation (Hill, et al., *Blood* 2013; 121:4985-96). The signs and symptoms of PNH can be attributed to chronic, uncontrolled complement C5 cleavage, and release of C5a and C5b-9 leading to RBC hemolysis, which together result in (Hill, et al., Blood 2013; 121:4985-96; Brodsky R A., *Blood.* 2014; 124:2804-1): release of intracellular free hemoglobin and lactate dehydrogenase (LDH) into circulation as a direct consequence of hemolysis, irreversible binding to and inactivation of nitric oxide (NO) by hemoglobin, and inhibition of NO synthesis, vasoconstriction and tissue-bed ischemia due to absence of vasodilatory NO, as well as possible microthrombi manifesting as abdominal pain, dysphagia, and erectile dysfunction, platelet activation, and/or pro-inflammatory and prothrombotic state. A substantial proportion of patients with PNH experience renal dysfunction and pulmonary hypertension (Hillmen, et al., *Am J Hematol.* 2010; 85:553-9. [erratum in Am J Hematol. 2010; 85:911.]; Hill, et al., *Br. J Haematol.* 2012; 158:409-14.; Hill, et al., *Blood* 2013; 121:4985-96). Patients also experience venous or arterial thrombosis in diverse sites, including the abdomen or central nervous system (Brodsky R A., *Blood.* 2014; 124:2804-1).

In another embodiment, the complement-associated condition is atypical hemolytic uremic syndrome (aHUS). The pathology and clinical presentations of patients with aHUS are also driven by terminal complement activation. More specifically, activation of C5 and dysregulation of complement activation lead to endothelial damage, platelet consumption, and thrombotic microangiopathic (TMA) events, characterized by thrombocytopenia, mechanical intravascular hemolysis, and kidney injury. Importantly, approximately 20% of patients experience extra-renal manifestations of disease as well, including central nervous system, cardiac, gastrointestinal, distal extremities, and severe systemic organ involvement (Loirat, et al., *Orphanet. J. Rare Dis.* 2011; 6:60). Symptoms of aHUS are well-known to those of skill in the art of rare disease or kidney disease medicine and include, e.g., severe hypertension, proteinuria, uremia, lethargy/fatigue, irritability, thrombocytopenia, microangiopathic hemolytic anemia, and renal function impairment (e.g., acute renal failure).

aHUS can be genetic, acquired, or idiopathic. aHUS can be considered genetic when two or more (e.g., three, four, five, or six or more) members of the same family are affected by the disease at least six months apart and exposure to a common triggering agent has been excluded, or when one or more aHUS-associated gene mutations (e.g., one or more mutations in CFH, MCP/CD46, CFB, or CFI) are identified in a subject. For example, a subject can have CFH-associated aHUS, CFB-associated aHUS, CFI-associated aHUS, or MCP-associated aHUS. Up to 30% of genetic aHUS is associated with mutations in CFH, 12% with mutations in MCP, 5-10% with mutations in CFI, and less than 2% with mutations in CFB. Genetic aHUS can be multiplex (i.e., familial; two or more affected family members) or simplex (i.e., a single occurrence in a family). aHUS can be considered acquired when an underlying environmental factor (e.g., a drug, systemic disease, or viral or bacterial agents that do not result in Shiga-like exotoxins) or trigger can be identified. aHUS can be considered idiopathic when no trigger (genetic or environmental) is evident.

Laboratory tests can be performed to determine whether a human subject has thrombocytopenia, microangiopathic hemolytic anemia, or acute renal insufficiency. Thrombocytopenia can be diagnosed by a medical professional as one or more of: (i) a platelet count that is less than 150,000/mm$^3$ (e.g., less than 60,000/mm$^3$); (ii) a reduction in platelet survival time that is reduced, reflecting enhanced platelet disruption in the circulation; and (iii) giant platelets observed in a peripheral smear, which is consistent with secondary activation of thrombocytopoiesis. Microangiopathic hemolytic anemia can be diagnosed by a medical professional as one or more of: (i) hemoglobin concentrations that are less than 10 mg/dL (e.g., less than 6.5 mg/dL); (ii) increased serum lactate dehydrogenase (LDH) concentrations (>460 U/L); (iii) hyperbilirubinemia, reticulocytosis, circulating free hemoglobin, and low or undetectable haptoglobin concentrations; and (iv) the detection of fragmented red blood cells (schistocytes) with the typical aspect of burr or helmet cells in the peripheral smear together with a negative Coombs test. See, e.g., Kaplan et al. (1992) "Hemolytic Uremic Syndrome and Thrombotic Thrombocytopenic Purpura," Informa Health Care (ISBN 0824786637) and Zipfel (2005) "Complement and Kidney Disease," Springer (ISBN 3764371668). Blood concentrations of C3 and C4 can also be used as a measure of complement activation or dysregulation. In addition, a subject's condition can be further characterized by identifying the subject as harboring one or more mutations in a gene associated with aHUS such as CFI, CFB, CFH, or MCP (supra). Suitable methods for detecting a mutation in a gene include, e.g., DNA sequencing and nucleic acid array techniques. See, e.g., Breslin et al. (2006) *Clin Am Soc Nephrol* 1:88-99 and Goicoechea de Jorge et al. (2007) *Proc Nall Acad Sci USA* 104:240-245.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. In the context of PNH, for example, effective treatment may refer to alleviation of one more symptoms selected from the group consisting of fatigue, abdominal pain, dyspnea, dysphagia, chest pain, and/or erectile dysfunction). In the context of aHUS, for example, effective treatment may refer to the alleviation of one or more symptoms selected from the group consisting of severe hypertension, proteinuria, uremia, lethargy/fatigue, irritability, thrombocytopenia, microangiopathic hemolytic anemia, and/or renal function impairment (e.g., acute renal failure)).

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In one example, an "effective amount" is the amount of anti-C5 antibody, or antigen binding fragment thereof, clinically proven to alleviate at least one symptom of PNH (e.g., fatigue, abdominal pain, dyspnea, dysphagia, chest pain, or erectile dysfunction) or at least one symptom of aHUS (e.g., severe hypertension, proteinuria, uremia, lethargy/fatigue, irritability, thrombocytopenia, microangiopathic hemolytic anemia, and renal function impairment (e.g., acute renal failure)). An effective amount can be administered in one or more administrations.

In one embodiment, the dose of the anti-C5 antibody, or antigen binding fragment thereof, is based on the weight of the patient. For example, in one embodiment, 2400 mg or 3000 mg of the anti-C5 antibody, or antigen binding fragment thereof, is administered to a patient weighing ≥40 to <60 kg. In another embodiment, 2700 mg or 3300 mg of the anti-C5 antibody, or antigen binding fragment thereof, is administered to a patient weighing ≥60 to <100 kg. In another embodiment, 3000 mg or 3600 mg of the anti-C5 antibody, or antigen binding fragment thereof, is administered to a patient weighing ≥100 kg. In certain embodiments, dosage regimens are adjusted to provide the optimum desired response (e.g., an effective response). In another embodiment, the anti-C5 antibody, or antigen binding fragment thereof, is administered for one or more administration cycles. In one embodiment, the administration cycle is 26 weeks. In one embodiment, the anti-C5 antibody, or antigen binding fragment thereof, is administered once on Day 1 of the administration cycle, once on Day 15 of the administration cycle, and every eight weeks thereafter. In one embodiment, the anti-C5 antibody, or antigen binding fragment thereof, is administered every eight weeks after the administration cycle for an extension period up to two years (e.g., at a dose of 3000 mg, 3300 mg, or 3600 mg).

In another embodiment, a method of treating a human patient with PNH or aHUS is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:
  (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, a method of treating a human patient with PNH or aHUS is provided, the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
  (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

In another embodiment, the anti-C5 antibody, or antigen binding fragment thereof, is administered to a patient weighing ≥40 to <60 kg:
  (a) once on Day 1 of the administration cycle at a dose of 2400 mg; and
  (b) on Day 15 of the administration cycle and every eight weeks thereafter at a dose of 3000 mg.

In another embodiment, the anti-C5 antibody, or antigen binding fragment thereof, is administered to a patient weighing ≥60 to <100 kg:
  (a) once on Day 1 of the administration cycle at a dose of 2700 mg; and
  (b) on Day 15 of the administration cycle and every eight weeks thereafter at a dose of 3300 mg.

In another embodiment, the anti-C5 antibody, or antigen binding fragment thereof, is administered to a patient weighing ≥100 kg:
(a) once on Day 1 of the administration cycle at a dose of 3000 mg; and
(b) on Day 15 of the administration cycle and every eight weeks thereafter at a dose of 3600 mg.

In some embodiments, the patient has not previously been treated with a complement inhibitor (e.g., the patient is a complement inhibitor treatment-naïve patient).

In other embodiments, the patient has previously been treated with one anti-C5 antibody, or antigen binding fragment thereof, and is switched to another anti-C5 antibody during the course of treatment. For example, in certain embodiments, different anti-C5 antibodies are administered during the course of treatment. In one embodiment, different anti-C5 antibodies are administered during separate treatment and extension periods. For example, in one embodiment, the patient is treated with eculizumab during a treatment period (e.g., for 26 weeks), followed by treatment with another anti-C5 antibody (e.g., ravulizumab, 7086 antibody, 8110 antibody, 305LO5 antibody, SKY59 antibody, or REGN3918 antibody), for example, during an extension period. In another embodiment, eculizumab is administered to the patient at a dose of 600 mg on Days 1, 8, 15, and 22 of the administration cycle during an induction phase, followed by a maintenance dose of 900 mg of eculizumab on Day 19 of the administration cycle and every two weeks thereafter (e.g., for a total of 26 weeks), followed by treatment with ravulizumab for an extension period of up to two years. In another embodiment, the patient is treated with ravulizumab (e.g., for 26 weeks), followed by treatment with another anti-C5 antibody (e.g., eculizumab, 7086 antibody, 8110 antibody, 305LO5 antibody, SKY59 antibody, or REGN3918 antibody) during, for example, an extension period.

Exemplary alternative anti-C5 antibodies include, but are not limited to, (i) ALXN1210, (ii), an antibody, or antigen binding fragment thereof, comprising heavy chain CDR1, CDR2 and CDR3 domains comprising SEQ ID NOs: 21, 22, and 23, respectively, and light chain CDR1, CDR2 and CDR3 domains comprising SEQ ID NOs: 24, 25, and 26, respectively, (iii) an antibody, or antigen binding fragment thereof, comprising a heavy chain variable region comprising SEQ ID NO:27 and a light chain variable region comprising SEQ ID NO:28, (iv) an antibody, or antigen binding fragment thereof, comprising heavy chain CDR1, CDR2 and CDR3 domains comprising SEQ ID NOs: 29, 30, and 31, respectively, and light chain CDR1, CDR2 and CDR3 domains comprising SEQ ID NOs: 32, 33, and 34, respectively, (v) an antibody, or antigen binding fragment thereof, comprising a heavy chain variable region comprising SEQ ID NO: 35 and a light chain variable region comprising SEQ ID NO: 36, (vi) an antibody, or antigen binding fragment thereof, comprising heavy chain CDR1, CDR2 and CDR3 domains comprising SEQ ID NOs: 37, 38, and 39, respectively, and light chain CDR1, CDR2 and CDR3 domains comprising SEQ ID NOs: 40, 41, and 42, respectively, (vii) an antibody, or antigen binding fragment thereof, comprising a heavy chain variable region comprising SEQ ID NO: 43 and a light chain variable region comprising SEQ ID NO: 44, (viii) an antibody, or antigen binding fragment thereof, comprising a heavy chain comprising SEQ ID NO: 45 and a light chain comprising SEQ ID NO: 46, (ix) an antibody, or antigen binding fragment thereof, comprising a heavy chain variable region comprising SEQ ID NO: 47 and a light chain variable region comprising SEQ ID NO: 48, and (x) an antibody, or antigen binding fragment thereof, comprising a heavy chain comprising SEQ ID NO: 49 and a light chain comprising SEQ ID NO: 50.

In some embodiments, the patient has previously been treated for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months with an anti-C5 antibody, or antigen binding fragment thereof, (e.g., eculizumab) before switching to another anti-C5 antibody, or antigen binding fragment thereof (e.g., ravulizumab). In a particular embodiment, the patient has previously been treated for at least 6 months with eculizumab.

In another embodiment, where a patient (e.g., PNH or aHUS patient) is treated with a first anti-C5 antibody and then switched to treatment with a second different anti-C5 antibody, especially where the second different anti-C5 antibody binds to a different epitope on C5 than the first anti-C5 antibody, the administration schedules takes into account the half-life of the first anti-C5 antibody. For example, to ensure that the first anti-C5 antibody is cleared (e.g., "washed out") from the patient before the second (different) anti-C5 antibody is administered (e.g., to avoid issues associated with aggregation, immune complex formation, etc.), the half-life of the first anti-C5 antibody is taken into consideration. In one embodiment, the second (different) anti-C5 antibody is not administered until a duration of time corresponding to 2, 2.5, 3, 3.5, 4, 4.5, 5, 5.5, 6, 6.5, 7, or 7.5 times the half-life of the first anti-C5 antibody has passed after the final administration of the first anti-C5 antibody.

In another embodiment, the patient has previously been treated with eculizumab and then is switched to treatment with a second (different) anti-C5 antibody (e.g., ravulizumab, 7086 antibody, 8110 antibody, 305LO5 antibody, SKY59 antibody, or REGN3918 antibody). In one embodiment where eculizumab is the first administered antibody, the second (different) anti-C5 antibody is not administered, for example, until at least 36, 45, 54, 63, 72, 81, 90, 99, 108, 117, or 126 days have passed after the final administration of eculizumab.

In another embodiment, the patient has previously been treated with ravulizumab and then is switched to treatment with a different anti-C5 antibody (e.g., eculizumab, 7086 antibody, 8110 antibody, 305LO5 antibody, SKY59 antibody, or REGN3918 antibody). In one embodiment where ravulizumab is the first administered antibody, the second (different) anti-C5 antibody is not administered, for example, until at least 100, 125, 150, 175, 200, 225, 250, 275, 300, 325, 375, or 400 days have passed after the final administration of ravulizumab.

Additionally or alternatively, techniques are used to clear or enhance clearance of the first anti-C5 antibody before switching to treatment with a second (different) anti-C5 antibody. Exemplary techniques include, but are not limited to, plasmapheresis or blood transfusions. In another embodiment, an antibody against the first anti-C5 antibody is administered to clear or enhance clearance of the first anti-C5 antibody (e.g., an anti-eculizumab antibody, an anti-ravulizumab antibody, an anti-7086 antibody, an anti-8110 antibody, an anti-305LO5 antibody, an anti-SKY59 antibody, or an anti-REGN3918 antibody) before a second (different) anti-C5 antibody is administered.

In another embodiment, the anti-C5 antibody, or antigen binding fragment thereof (e.g., ALXN1210), is administered to a patient, wherein the administration cycle starts at least about two weeks, at least about three weeks, at least about four weeks, at least about six weeks, at least about seven weeks, or at least about eight weeks after the patient's last dose of eculizumab. In another embodiment, the anti-C5 antibody, or antigen binding fragment thereof (e.g., ALXN1210), is administered to a patient, wherein the administration cycle starts at least two weeks after the patient's last dose of eculizumab.

In some embodiments, the patients treated according to the methods described herein have been vaccinated against meningococcal infections within 3 years prior to, or at the time of, initiating treatment. In one embodiment, patients who received treatment less than 2 weeks after receiving a meningococcal vaccine are also treated with appropriate prophylactic antibiotics until 2 weeks after vaccination. In another embodiment, patients treated according to the methods described herein are vaccinated against meningococcal serotypes A, C, Y, W135, and/or B.

As used herein, the term "serum trough level" refers to the lowest level that the agent (e.g., the anti-C5 antibody, or antigen binding fragment thereof) or medicine is present in the serum. In contrast, a "peak serum level", refers to the highest level of the agent in the serum. The "average serum level", refers to the mean level of the agent in the serum over time.

In one embodiment, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395, or 400 µg/ml or greater. In one embodiment, the treatment maintains a serum trough concentration of the anti-C5 antibody, or antigen binding fragment thereof, of 100 µg/ml or greater. In another embodiment, the treatment maintains a serum trough concentration of the anti-C5 antibody, or antigen binding fragment thereof, of 150 µg/ml or greater. In another embodiment, the treatment maintains a serum trough concentration of the anti-C5 antibody, or antigen binding fragment thereof, of 200 µg/ml or greater. In another embodiment, the treatment maintains a serum trough concentration of the anti-C5 antibody, or antigen binding fragment thereof, of 250 µg/ml or greater. In another embodiment, the treatment maintains a serum trough concentration of the anti-C5 antibody, or antigen binding fragment thereof, of 300 µg/ml or greater. In another embodiment, the treatment maintains a serum trough concentration of the anti-C5 antibody, or antigen binding fragment thereof, of between 100 µg/ml and 200 µg/ml. In another embodiment, the treatment maintains a serum trough concentration of the anti-C5 antibody, or antigen binding fragment thereof, of about 175 µg/ml.

In another embodiment, to obtain an effective response, the anti-C5 antibody is administered to the patient in an amount and with a frequency to maintain at least 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, or 260 µg of antibody per milliliter of the patient's blood. In another embodiment, the anti-C5 antibody is administered to the patient in an amount and with a frequency to maintain between 50 µg and 250 µg of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

In another embodiment, to obtain an effective response, the anti-C5 antibody is administered to the patient in an amount and with a frequency to maintain a minimum free C5 concentration. For example, in one embodiment, the anti-C5 antibody is administered to the patient in an amount and with a frequency to maintain a free C5 concentration of 0.2 µg/mL, 0.3 µg/mL, 0.4 µg/mL, 0.5 µg/mL or below. In another embodiment, the anti-C5 antibody is administered to the patient in an amount and with a frequency to maintain a free C5 concentration of 0.309 to 0.5 µg/mL or below. In another embodiment, the treatment described herein reduces free C5 concentration by greater than 99% throughout the treatment period. In another embodiment, the treatment reduces free C5 concentration greater than 99.5% throughout the treatment period.

In another aspect, methods of treating a human patient having a complement-associated disorder are provided. In one embodiment, the method comprises treating a human patient having a complement-associated disorder who is being treated with eculizumab, wherein the method comprises discontinuing treatment with eculizumab and switching the patient to treatment with a different complement inhibitor. In another embodiment, the method comprises treating a human patient having a complement-associated disorder who is being treated with ravulizumab, wherein the method comprises discontinuing treatment with ravulizumab and switching the patient to treatment with a different complement inhibitor. In one embodiment the different complement inhibitor is selected from the group consisting of: a small molecule, a polypeptide, a polypeptide analog, a peptidomimetic, an siRNA or an aptamer. In another embodiment, the different complement inhibitor inhibits one or more of complement components C1, C2, C3, C4, C5, C6, C7, C8, C9, Factor D, Factor B, properdin, MBL, MASP-1, MASP-2, or biologically active fragments thereof. In another embodiment, the different complement inhibitor is a different anti-C5 antibody (e.g., ravulizumab, 7086 antibody, 8110 antibody, 305LO5 antibody, SKY59 antibody, or REGN3918 antibody).

Exemplary complement-associated conditions that can be treated according to the methods described herein include, but are not limited to, rheumatoid arthritis, antiphospholipid antibody syndrome, lupus nephritis, ischemia-reperfusion injury, atypical hemolytic uremic syndrome (aHUS), typical hemolytic uremic syndrome, paroxysmal nocturnal hemoglobinuria (PNH), dense deposit disease, neuromyelitis optica, multifocal motor neuropathy, multiple sclerosis, macular degeneration, HELLP syndrome, spontaneous fetal loss, thrombotic thrombocytopenic purpura, Pauci-immune vasculitis, epidermolysis bullosa, recurrent fetal loss, traumatic brain injury, myocarditis, a cerebrovascular disorder, a peripheral vascular disorder, a renovascular disorder, a mesenteric/enteric vascular disorder, vasculitis, Henoch-Schönlein purpura nephritis, systemic lupus erythematosus-associated vasculitis, vasculitis associated with rheumatoid arthritis, immune complex vasculitis, Takayasu's disease, dilated cardiomyopathy, diabetic angiopathy, Kawasaki's disease, venous gas embolus, restenosis following stent placement, rotational atherectomy, percutaneous transluminal coronary angioplasty, myasthenia gravis, cold agglutinin disease, dermatomyositis, paroxysmal cold hemoglobinuria, antiphospholipid syndrome, Graves' disease, atherosclerosis, Alzheimer's disease, systemic inflammatory response sepsis, septic shock, spinal cord injury, glomerulonephritis, transplant rejection, Hashimoto's thyroiditis, type I diabetes, psoriasis, pemphigus, autoimmune hemolytic anemia, idiopathic thrombocytopenic purpura, Goodpasture's syndrome, Degos disease, and catastrophic antiphospholipid syndrome. In one embodiment, the complement-associated condition is PNH. In another embodiment, the complement-associated condition is aHUS.

IV. Outcomes

Provided herein are methods for treating PNH or aHUS in a patient comprising administering to the patient an anti-C5 antibody, or antigen binding fragment thereof.

Symptoms of PNH include, but are not limited to, fatigue (e.g., tiredness, difficultly performing daily activities, trouble concentrating, dizziness, weakness), pain (e.g., stomach pain, leg pain or swelling, chest pain, back pain), dark-colored urine, shortness of breath, difficulty swallowing, yellowing of the skin and/or eyes, erectile dysfunction, blood clots, kidney disease, damage to organs, stroke, or heart attack. Patients treated according to the methods disclosed herein preferably experience improvement in at least one sign of PNH. For example, the treatment may produce at least one therapeutic effect selected from the group consisting of a reduction or cessation in fatigue, abdominal pain, dyspnea, dysphagia, chest pain, and erectile dysfunction.

Symptoms of aHUS include, but are not limited to, severe hypertension, proteinuria, uremia, lethargy/fatigue, irritability, thrombocytopenia, microangiopathic hemolytic anemia, and renal function impairment (e.g., acute renal failure). Patients treated according to the methods disclosed herein preferably experience improvement in at least one sign of aHUS For example, the treatment may produce at least one therapeutic effect selected from the group consisting of a reduction or cessation in hypertension, proteinuria, uremia, lethargy/fatigue, irritability, thrombocytopenia, microangiopathic hemolytic anemia, and renal function impairment.

In other embodiments, the treatment results in terminal complement inhibition.

In other embodiments, the treatment produces a shift toward normal levels of a hemolysis-related hematologic biomarker selected from the group consisting of free hemoglobin, haptoglobin, reticulocyte count, PNH red blood cell (RBC) clone and D-dimer. In another embodiment, the treatment produces an increase in hemoglobin stabilization from the patient's pre-treatment baseline.

In other embodiments, the treatment produces a shift toward normal levels of a chronic disease associated biomarker selected from the group consisting estimated glomerular filtration rate (eGFR) and spot urine:albumin:creatinine and plasma brain natriuretic peptide (BNP).

In other embodiments, the treatment produces a reduction in the need for blood transfusions. In another embodiment, the treatment produces a greater than 70% increase in transfusion avoidance.

In other embodiments, the treatment results in a reduction in breakthrough hemolysis relative to treatment with eculizumab. In another embodiment, the treatment results in a elimination of breakthrough hemolysis during the treatment period. In another embodiment, the treatment results in a reduction of breakthrough hemolysis compared to pretreatment baseline amount of breakthrough hemolysis.

In other embodiments, the treatment produces a reduction in major adverse vascular events (MAVEs).

In other embodiments, the treatment produces a change from baseline in quality of life as assessed via the Functional Assessment of Chronic Illness Therapy (FACIT)-Fatigue Scale, version 4 and the European Organisation for Research and Treatment of Cancer, Quality of Life Questionnaire-Core 30 Scale. In another embodiment, the treatment produces a change from baseline in quality of life, assessed via the Functional Assessment of Chronic Illness Therapy (FACIT)-Fatigue Scale, version 4 and the European Organisation for Research and Treatment of Cancer, Quality of Life Questionnaire-Core 30 Scale by at least 7 points from the patients untreated baseline score.

In another embodiment, the treatment results in no change in quality of life (QoL) as assessed via the Functional Assessment of Chronic Illness Therapy (FACIT)-Fatigue Scale, Version 4, from Baseline to Day 183. In another embodiment, the treatment results in an increase in quality of life (QoL) assessed via the Functional Assessment of Chronic Illness Therapy (FACIT)-Fatigue Scale, Version 4, from Baseline to Day 183. In another embodiment, the treatment results in transfusion avoidance from Baseline to Day 183. In another embodiment, the treatment results in avoidance of a ≥2 g/dL decrease in hemoglobin level from baseline in the absence of transfusion from Baseline to Day 183.

In other embodiments, lactate dehydrogenase (LDH) levels are used to evaluate responsiveness to a therapy (e.g., a reduction of hemolysis as assessed by lactate dehydrogenase (LDH) levels is indicative of an improvement in at least one sign of PNH). LDH is a marker of intravascular hemolysis (Hill, A. et al., *Br. J. Haematol.*, 149:414-25, 2010; Hillmen, P. et al., *N. Engl. J. Med.,* 350:552-9, 2004; Parker, C. et al., *Blood,* 106:3699-709, 2005). Red blood cells contain large amounts of LDH, and a correlation between cell-free hemoglobin and LDH concentration has been reported in vitro (Van Lente, F. et al., *Clin. Chem.,* 27:1453-5, 1981) and in vivo (Kato, G. et al., *Blood,* 107:2279-85, 2006). The consequences of hemolysis are independent of anemia (Hill, A. et al., Haematologica, 93(s1):359 Abs.0903, 2008; Kanakura, Y et al., *Int. J. Hematol.,* 93:36-46, 2011). LDH concentration obtained at baseline and then serially throughout a treatment period, is an important measure of hemolysis. Baseline levels of cell-free plasma hemoglobin are highly elevated in patients with PNH with LDH ≥1.5-fold above the upper limit of normal (LDH≥1.5×ULN), with a significant correlation between LDH and cell-free plasma hemoglobin (Hillmen, P. et al., *N. Engl. J. Med.,* 355:1233-43, 2006). The normal LDH value range is 105-333 IU/L (international units per liter).

LDH levels can be measured using any suitable test or assay, such as those described by Ferri F F, ed. *Ferri's Clinical Advisor* 2014. Philadelphia: Pa: Elsevier Mosby; 2014: Section IV—Laboratory tests and interpretation of results. LDH concentration can be measured in various samples obtained from a patient, in particular, serum samples. As used herein, the term "sample" refers to biological material from a subject. Although serum LDH concentration is of interest, samples can be derived from other sources, including, for example, single cells, multiple cells, tissues, tumors, biological fluids, biological molecules or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are known in the art and can be readily adapted to obtain a sample that is compatible with the method utilized.

In one embodiment, the treatments described herein result in a normalization of LDH levels. In another embodiment, patients treated according to the disclosed methods experience reductions in LDH levels to near normal levels or to within 10%, or within 20% above what is considered the normal level (e.g., within 105-333 IU/L (international units per liter). In another embodiment, the patient's LDH levels are normalized throughout maintenance period of treatment. In another embodiment, the treated patient's LDH levels are normalized at least at least 95% of the time while on the maintenance period of treatment. In another embodiment, the treated patient's LDH levels are normalized at least at least 90%, 85% or 80% of the time while on the maintenance period of treatment. In one embodiment, the patient's LDH levels are ≥1.5 fold above the upper limit of normal (LDH≥1.5×ULN) prior to initiating treatment. In another embodiment, the treatment results in a normalization of LDH levels by at least day 24 of treatment. In one embodiment, patients treated according to the disclosed methods experience reductions in LDH levels to within normal levels or to within 10%, 20%, 30%, 40% or within 50% below what is considered the upper limit of normal level (e.g., within 105-333 IU/L (international units per liter). In one embodiment, the patient's LDH levels are ≥1.5 fold above the upper limit of normal (LDH≥1.5×ULN) prior to initiating treatment. In one embodiment, the treatment results in LDH levels less than 2× upper limit of normal (ULN).

V. Kits and Unit Dosage Forms

Also provided herein are kits which include a pharmaceutical composition containing an anti-05 antibody, or antigen binding fragment thereof, such as ravulizumab, and a pharmaceutically-acceptable carrier, in a therapeutically effective amount adapted for use in the methods described herein. The kits optionally also can include instructions, e.g., comprising administration schedules, to allow a practitioner (e.g., a physician, nurse, or patient) to administer the composition contained therein to administer the composition to a patient having PNH or aHUS. The kit also can include a syringe.

Optionally, the kits include multiple packages of the single-dose pharmaceutical compositions each containing an effective amount of the anti-C5 antibody, or antigen binding fragment thereof, for a single administration in accordance with the methods provided above. Instruments or devices necessary for administering the pharmaceutical composition(s) also may be included in the kits. For instance, a kit may provide one or more pre-filled syringes containing an amount of the anti-C5 antibody, or antigen binding fragment thereof.

In one embodiment, the present invention provides a kit for treating PNH or aHUS in a human patient, the kit comprising:
(a) a dose of an anti-C5 antibody, or antigen binding fragment thereof, comprising CDR1, CDR2 and CDR3 domains of the heavy chain variable region having the sequence set forth in SEQ ID NO:12, and CDR1, CDR2 and CDR3 domains of the light chain variable region having the sequence set forth in SEQ ID NO:8; and
(b) instructions for using the anti-C5 antibody, or antigen binding fragment thereof, according to any of the methods described herein.

In one embodiment, the kit comprises a dose of an anti-C5 antibody, or antigen binding fragment thereof, wherein the anti-C5 antibody, or antigen binding fragment thereof, is administered to a patient weighing ≥40 to <60 kg:
(a) once on Day 1 of the administration cycle at a dose of 2400 mg; and
(b) on Day 15 of the administration cycle and every eight weeks thereafter at a dose of 3000 mg.

In another embodiment, the kit comprises a dose of an anti-C5 antibody, or antigen binding fragment thereof, wherein the anti-C5 antibody, or antigen binding fragment thereof, is administered to a patient weighing ≥60 to <100 kg:
(a) once on Day 1 of the administration cycle at a dose of 2700 mg; and
(b) on Day 15 of the administration cycle and every eight weeks thereafter at a dose of 3300 mg.

In another embodiment, the kit comprises a dose of an anti-C5 antibody, or antigen binding fragment thereof, wherein the anti-C5 antibody, or antigen binding fragment thereof, is administered to a patient weighing ≥100 kg:
(a) once on Day 1 of the administration cycle at a dose of 3000 mg; and
(b) on Day 15 of the administration cycle and every eight weeks thereafter at a dose of 3600 mg.

The following examples are merely illustrative and should not be construed as limiting the scope of this disclosure in any way as many variations and equivalents will become apparent to those skilled in the art upon reading the present disclosure.

The contents of all references, Genbank entries, patents and published patent applications cited throughout this application are expressly incorporated herein by reference.

EXAMPLES

Example 1: A Phase 3, Randomized, Open-Label, Active-Controlled Study of ALXN1210 (Ravulizumab) Versus Eculizumab in Complement Inhibitor-Naïve Adult Patients with Paroxysmal Nocturnal Hemoglobinuria (PNH)

In phase 1b/2 studies, treatment with ravulizumab administered at extended dosing intervals, achieved a rapid and sustained reduction in complement-mediated hemolysis in patients with PNH. These studies demonstrated drug/exposure versus response relationships, with higher ravulizumab trough exposure (1800-mg-q4w cohort) being associated with a greater proportion of patients reaching plasma LDH levels considered to be of low risk for hemolysis (normalization [or below 1.5×ULN]), reductions in free hemoglobin, and lack of breakthrough hemolysis relative to all other cohorts. Based on these results and subsequent exposure-response analyses, a phase 3, open-label, randomized, active-controlled, multicenter study was conducted to evaluate the safety and efficacy of ALXN1210 (ravulizumab) versus eculizumab administered by intravenous (IV) infusion to adult patients with PNH who are naïve to complement inhibitor treatment. In the phase 3 study herein, patients randomized to ravulizumab received a loading dose (2400 mg for patients ≥40 kg to <60 kg, 2700 mg for patients ≥60 kg to <100 kg, 3000 mg for patients ≥100 kg) on day 1, followed by maintenance doses of ravulizumab (3000 mg for patients ≥40 kg to <60 kg, 3300 mg for patients ≥60 to <100 kg, 3600 mg for patients ≥100 kg) on day 15 and q8w thereafter.

1. Objectives

The primary objective of the study was to assess the non-inferiority of ALXN1210 (ravulizumab) compared to eculizumab in adult patients with PNH who have never been treated with a complement inhibitor.

Non-inferiority was claimed if after 26 weeks of treatment: 1) the lower bound of the 95% confidence interval (CI) for the difference (ALXN1210-eculizumab) in transfusion avoidance (TA) rate is greater than −20%, and 2) the lower bound of the 95% CI for the odds ratio of ALXN1210 compared to eculizumab for lactate dehydrogenase normalization (LDH-N) is greater than 0.39.

Secondary objectives included characterizing the safety and tolerability of ALXN1210 in this patient population, evaluating the efficacy of ALXN1210 by additional efficacy measures characterizing the pharmacokinetics/pharmacodynamics (PK/PD) and immunogenicity of ALXN1210, and evaluating the long-term safety and efficacy of ALXN1210.

2. Study Design

The overall study design, treatments and study durations are depicted in FIG. 1. Study ALXN1210-PNH-301 is a Phase 3, open-label, randomized, active-controlled, multicenter study to evaluate the safety and efficacy of ALXN1210 versus eculizumab administered by intravenous (IV) infusion to adult patients with PNH who are naïve to complement inhibitor treatment. The study as designed included approximately 214 patients (107 patients per treatment group), but ultimately 246 subjects were enrolled and completed at least 183 days of treatment. Upon completion of the study, 246 subjects went on to enroll in the extension study and 2 subjects discontinued. The study consisted of a 4-week screening period, a 26-week randomized treatment period, and an extension period of up to 2 years. Patients were stratified into 1 of 6 groups based on their transfusion history (0, 1 to 14, or >14 units of pRBCs in the 1 year prior to first dose of study drug) and screening LDH levels (1.5 to <3×ULN or ≥3×ULN). The patients within each of the 6 groups were randomly assigned in a 1:1 ratio to receive ALXN1210 or eculizumab. Enrollment of patients without a history of transfusion in the past year was capped at 20%.

Prior to randomization and within 5 days prior to study drug administration on Day 1, each patient's hemoglobin was evaluated by either local or central laboratory. If at that time the patient's hemoglobin value meets protocol-specified transfusion guidelines, the patient was transfused with pRBCs to a hemoglobin level above the protocol-specified transfusion threshold to be eligible for randomization. The patient's post-transfusion hemoglobin value was confirmed by local or central laboratory to be above the protocol-specified transfusion threshold.

Patients randomly assigned to the ALXN1210 group received a loading dose of ALXN1210 (2400 mg for patients weighing ≥40 to <60 kg, 2700 mg for patients weighing ≥60 to <100 kg, 3000 mg for patients weighing ≥100 kg) on Day 1, followed by maintenance doses of ALXN1210 (3000 mg for patients weighing ≥40 to <60 kg, 3300 mg for patients weighing ≥60 to <100 kg, 3600 mg for patients weighing ≥100 kg) on Day 15 and every 8 weeks (q8w) thereafter for a total of 26 weeks of treatment. Patients randomly assigned to the eculizumab group received induction treatment with 600 mg of eculizumab IV on Days 1, 8, 15, and 22, followed by maintenance treatment with eculizumab 900 mg on Day 29 and every 2 weeks (q2w) thereafter for a total of 26 weeks of treatment. After completion of all assessments on Day 183, patients entered an extension period during which patients received ALXN1210 until the product is registered or approved (in accordance with country-specific regulations) or for up to 2 years, whichever occurs first. Beginning on Day 183, patients who had been randomized to the ALXN1210 treatment group received a maintenance dose (as described above) of ALXN1210 q8w for up to two years, and patients who had been randomized to the eculizumab group received a loading dose (as described above) of ALXN1210 followed 2 weeks later and q8w thereafter by a weight-based maintenance dose of ALXN1210. A pRBC transfusion was administered when a patient has a hemoglobin value of 9 g/dL or lower with signs or symptoms of sufficient severity to warrant a transfusion, or a hemoglobin value of 7 g/dL or lower regardless of presence of clinical signs or symptoms.

3. Endpoints

The coprimary efficacy endpoints of the study were (1) transfusion avoidance, defined as the proportion of patients who remain transfusion-free and do not require a transfusion per protocol-specified guidelines through Day 183 (Week 26) and (2) hemolysis as directly measured by LDH-N levels from Day 29 (first scheduled evaluation status post initiation of maintenance dosing) through Day 183 (Week 26).

The key secondary efficacy endpoints of the study (tested in a hierarchical manner) were:
1. Percentage change in LDH from Baseline to Day 183 (Week 26); 2. Change in quality of life (QoL) assessed via the Functional Assessment of
Chronic Illness Therapy (FACIT)-Fatigue Scale, Version 4, from Baseline to Day 183 (Week 26);
3. Proportion of patients with breakthrough hemolysis, defined as at least one new or worsening symptom or sign of intravascular hemolysis (fatigue, hemoglobinuria, abdominal pain, shortness of breath [dyspnea], anemia [hemoglobin <10 g/dL], major adverse vascular event [MAVE, including thrombosis], dysphagia, or erectile dysfunction) in the presence of elevated LDH≥2× upper limit of normal [ULN], after prior LDH reduction to <1.5×ULN on therapy; and
4. Proportion of patients with stabilized hemoglobin, defined as avoidance of a ≥2 g/dL decrease in hemoglobin level from baseline in the absence of transfusion through Day 183 (Week 26).

Other secondary efficacy endpoints of the study were:
Change in the European Organisation for Research and Treatment of Cancer (EORTC) Quality of Life Questionnaire-Core 30 Scale (QLQ-C30), Version 3.0, from Baseline to Day 183 (Week 26);
Time to first occurrence of LDH-N;
Total number of units of packed red blood cells (pRBCs) transfused through Day 183 (Week 26);
Change in clinical manifestations of PNH (fatigue, hemoglobinuria, abdominal pain, shortness of breath, anemia, dysphagia, and erectile dysfunction) from Baseline to Day 183 (Week 26); and
Proportion of patients experiencing MAVEs through Day 183 (Week 26).

Pharmacokinetic and pharmacodynamic endpoints of the study were: change in serum ALXN1210 and eculizumab concentration over time, change in chicken red blood cell (cRBC) hemolytic activity over time (exploratory), and change in free complement component 5 (C5) concentrations over time.

Exploratory endpoints included patient-reported PNH symptoms and healthcare resource utilization. The safety and tolerability of ALXN1210 compared with eculizumab is evaluated by physical examinations, vital signs, electrocardiograms (ECGs), laboratory assessments, and incidence of adverse events (AEs) and serious adverse events (SAEs). The proportion of patients who develop antidrug antibodies (ADAs) was also assessed.

TABLE 1

Schedule of Study Visits and Assessments: Screening Through End of Randomized Treatment Period

| | Period | | | | | | | | | | | | | | | | |
|---|---|---|---|---|---|---|---|---|---|---|---|---|---|---|---|---|---|
| | Screening | Randomized Treatment Period | | | | | | | | | | | | | | | |
| | Study Day | | | | | | | | | | | | | | | | |
| | −28 to −1 | 1 | 8 | 15 | 22 | 29 | 43 | 57 | 71 | 85 | 99 | 113 | 127 | 141 | 155 | 169 | 183/ET |
| | | | | | | | | Window (day) | | | | | | | | | |
| | N/A | | ±2 | ±2 | ±2 | ±2 | ±2 | ±2 | ±2 | ±2 | ±2 | ±2 | ±2 | ±2 | ±2 | ±2 | ±2 |
| Informed consent | X | | | | | | | | | | | | | | | | |
| Confirmation or administration of meningococcal vaccination[a] | X | X | | | | | | | | | | | | | | | |
| Medical history and demographics | X | | | | | | | | | | | | | | | | |
| HIV testing | X | | | | | | | | | | | | | | | | |
| PNH clone size[b] | X | X | | | | | | | X | | | | | | | | X |
| Height | X | | | | | | | | | | | | | | | | |
| Weight | X | X | X | X | X | X | X | X | X | X | X | X | X | X | X | X | X |
| Pregnancy test[c] | X | X | | X | | | | | X | | | | X | | | | X |
| Record transfusions and transfusion parameters[d] | X[e] | X | X | X | X | X | X | X | X | X | X | X | X | X | X | X | X |
| PNH symptomatology[f,g] | X | X | X | X | X | X | X | X | X | X | X | X | X | X | X | X | X |
| FACIT-Fatigue[g] | X | X | X | | | X | | | X | | | | X | | | | X |
| EORTC QLQ-C30[g] | X | X | X | | | X | | | X | | | | X | | | | X |
| PNH symptoms patient questionnaire[g] | | X | X | X | X | X | X | X | X | X | X | X | X | X | X | X | X |
| Resource utilization patient questionnaire[g] | | X | | | | X | | | X | | | | X | | | | X |
| Physical examination | X | | | | | | | | | | | | | | | | |
| Abbreviated physical examination[h] | | X | | | | | | | X | | | | | | | | X |
| Vital signs[i] | X | X | X | X | X | X | X | X | X | X | X | X | X | X | X | X | X |
| Safety 12-Lead ECG[j] | X | | | | | | | | X | | | | | | | | X |
| Chemistry including LDH[k] | X | X | X | X | X | X | X | X | X | X | X | X | X | X | X | X | X |
| Hematology including free hemoglobin and coagulation[k] | X | X | X | X | X | X | X | X | X | X | X | X | X | X | X | X | X |
| Urinalysis and urine chemistry[k] | X | X | | X | | X | | | X | | | | X | | | | X |
| PK/PD sampling | | X[l] | X[m] | X[l] | X[m] | X[m] | X[m] | X[m] | X[l] | X[m] | X[m] | X[m] | X[l] | X[m] | X[m] | X[m] | X[l] |
| Immunogenicity (ADA)[n] | | X | | | | | | | X | | | | X | | | | X |
| Review safety card | | X | X | X | X | X | X | X | X | X | X | X | X | X | X | X | X |
| Breakthrough hemolysis[o] | | | | | | | | ←Monitor continuously→ | | | | | | | | | |
| Concomitant medications | X | | | | | | | ←Monitor continuously→ | | | | | | | | | |
| Adverse events | X | | | | | | | ←Monitor continuously→ | | | | | | | | | |
| Randomization[p] | | X | | | | | | | | | | | | | | | |
| ALXN1210 administration[q] | | X | | X | | | | | X | | | | X | | | | —[r] |

TABLE 1-continued

Schedule of Study Visits and Assessments: Screening Through End of Randomized Treatment Period

| | Screening | Randomized Treatment Period | | | | | | | | | | | | | | |
|---|---|---|---|---|---|---|---|---|---|---|---|---|---|---|---|---|
| | | Study Day | | | | | | | | | | | | | | |
| | −28 to −1 | 1 | 8 | 15 | 22 | 29 | 43 | 57 | 71 | 85 | 99 | 113 | 127 | 141 | 155 | 169 | 183/ET |
| | | | | | | | | | Window (day) | | | | | | | |
| | N/A | ±2 | ±2 | ±2 | ±2 | ±2 | ±2 | ±2 | ±2 | ±2 | ±2 | ±2 | ±2 | ±2 | ±2 | ±2 | ±2 |
| Eculizumab administration | | X | X | X | X | X | X | X | X | X | X | X | X | X | X | | X |

Abbreviations: ADA = antidrug antibody;
ECG = electrocardiogram;
EORTC QLQ-C30 = European Organisation for Research and Treatment of Cancer, Quality of Life Questionnaire-Core 30 Scale;
ET = early termination;
FACIT-Fatigue = Functional Assessment of Chronic Illness Therapy-Fatigue Scale;
LDH = lactate dehydrogenase;
N/A = not applicable;
PD = pharmacodynamics;
PK = pharmacokinetics;
PNH = paroxysmal nocturnal hemoglobinuria;
RBC = red blood cell;
WBC = white blood cell

[a]All patients were vaccinated against meningococcal infections within 3 years prior to, or at the time of, initiating study drug. Patients who initiate study drug treatment less than 2 weeks after receiving a meningococcal vaccine must receive treatment with appropriate prophylactic antibiotics until 2 weeks after vaccination.
[b]WBC (granulocyte and monocyte) and RBC clone size measured by high-sensitivity flow cytometry at Screening and Day 1; RBC clone size only on Day 71 and Day 183.
[c]Female patients of childbearing potential only. Serum pregnancy test at Screening and Day 183; urine pregnancy test at all other required time points. A negative urine test result was required prior to administering ALXN1210 or eculizumab to female patients of childbearing potential at the indicated visits.
[d]Transfusions given during and between visits were recorded.
[e]Prior to randomization and within 5 days prior to study drug administration on Day 1, each patient's hemoglobin was evaluated by either local or central laboratory. If at that time the patient's hemoglobin value meets protocol-specified transfusion guidelines, the patient was transfused with pRBCs to a hemoglobin level above the protocol-specified transfusion threshold in order to be eligible for randomization. The patient's post-transfusion hemoglobin value was confirmed by local or central laboratory to be above the protocol-specified transfusion threshold.
[f]Investigator or designee assessment of the following events: fatigue, abdominal pain, dyspnea, dysphagia, chest pain, and erectile dysfunction.
[g]Physician- and patient-reported assessments were performed prior to study drug administration.
[h]Abbreviated physical examination consists of a body system relevant examination based upon Investigator (or designee) judgment and patient symptoms. At least 1 body system was checked for an abbreviated physical examination.
[i]Vital sign measurements were taken after the patient has been resting for at least 5 minutes and include systolic and diastolic BP (millimeters of mercury [mmHg]), heart rate (beats/minute), respiratory rate (breaths/minute), and oral or tympanic temperature (degrees Celsius [° C.] or degrees Fahrenheit [° F.]). On dosing days, vital signs were taken before study drug administration.
[j]Single 12-lead ECG is collected at Screening and predose on Day 57 and Day 183. Patients must be supine for approximately 5 to 10 minutes before ECG collection and remain supine but awake during ECG collection.
[k]Clinical laboratory measurements were collected predose on dosing days. Follicle stimulating hormone levels were measured during Screening only in order to confirm postmenopausal status.
[l]Serum samples for PK/PD analyses were collected predose (within 0.5 hours prior to the start of infusion) and at end-of-infusion (within 0.5 hours after the end of infusion). End-of-infusion samples were drawn from the patient's opposite, noninfused arm. All collection times were recorded in the eCRF. In the event of breakthrough hemolysis, a serum sample for PK/PD analysis is collected.
[m]Serum samples for PK/PD analyses were collected predose (within 0.5 hours prior to the start of infusion) for eculizumab-treated patients and at any time for ALXN1210-treated patients. All collection times were recorded in the eCRF. In the event of breakthrough hemolysis, a serum sample for PK/PD analysis is collected.
[n]Samples for ADA were collected predose. If results of the test were positive, the test can be repeated every 3 months until results become negative or stabilize, based on the measured titer and the safety assessments.
If a suspected event of breakthrough hemolysis occurs, LDH, PK, and PD parameters were analyzed at the central laboratory. If the suspected event of breakthrough does not occur at a scheduled visit, an unscheduled visit occurs for evaluation of the patient and collection of the required LDH, PK, and PD parameters.
Patients were randomly assigned to treatment based on screening LDH result and history of blood transfusions through an interactive voice or web response system (IxRS).
The dose of ALXN1210 is based on the patient's last recorded study visit body weight.
The primary efficacy endpoint assessment is before dosing on Day 183. Dosing on Day 183 is the start of the Extension Period. Please refer to additional Day 183 post dose procedures in Table 2 and Table 3.

TABLE 2

Schedule of Study Visits and Assessments: Extension Period Patients Entering from ALXN1210 Group

| | Period Extension Period | | | | | | | | | | | | | |
|---|---|---|---|---|---|---|---|---|---|---|---|---|---|---|
| | Study Day | | | | | | | | | | | | | |
| | 183[a] | 239 | 295 | 351 | 407 | 463 | 519 | 575 | 631 | 687 | 743 | 799 | 855 | 911 EOS/ET |
| | | | | | | | Window (day) | | | | | | | |
| | ±2 | ±7 | ±7 | ±7 | ±7 | ±7 | ±7 | ±7 | ±7 | ±7 | ±7 | ±7 | ±7 | ±7 |
| PNH clone size[b] | | X | X | X | X | X | X | X | X | X | X | X | X | X |
| Weight | | X | X | X | X | X | X | X | X | X | X | X | X | X |
| Pregnancy test[c] | | X | X | X | X | X | X | X | X | X | X | X | X | X |
| Record transfusions and transfusion parameters[d] | | X | X | X | X | X | X | X | X | X | X | X | X | X |

TABLE 2-continued

Schedule of Study Visits and Assessments: Extension Period Patients Entering from ALXN1210 Group

| | Period |
|---|---|
| | Extension Period |

| | Study Day | | | | | | | | | | | | | |
|---|---|---|---|---|---|---|---|---|---|---|---|---|---|---|
| | 183[a] | 239 | 295 | 351 | 407 | 463 | 519 | 575 | 631 | 687 | 743 | 799 | 855 | 911 EOS/ET |
| | | | | | | | Window (day) | | | | | | | |
| | ±2 | ±7 | ±7 | ±7 | ±7 | ±7 | ±7 | ±7 | ±7 | ±7 | ±7 | ±7 | ±7 | ±7 |
| PNH symptomatology[e] | | X | X | X | X | X | X | X | X | X | X | X | X | X |
| FACIT-Fatigue[f] | | | X | | | | X | | | X | | | | X |
| EORTC QLQ-C30[f] | | | X | | | | X | | | X | | | | X |
| PNH symptoms patient questionnaire[f] | | X | X | X | X | X | X | X | X | X | X | X | X | X |
| Resource utilization patient questionnaire[f] | | X | X | X | X | X | X | X | X | X | X | X | X | X |
| Abbreviated physical examination[g] | | X | | X | | X | | X | | X | | X | | X |
| Vital signs[h] | | X | X | X | X | X | X | X | X | X | X | X | X | X |
| Safety 12-Lead ECG[i] | | | | | | | | | | | | | | X |
| Chemistry including LDH[j] | | X | X | X | X | X | X | X | X | X | X | X | X | X |
| Hematology including free hemoglobin and coagulation[j] | | X | X | X | X | X | X | X | X | X | X | X | X | X |
| Urinalysis and urine chemistry[j] | | X | X | X | X | X | X | X | X | X | X | X | X | X |
| PK/PD sampling[k] | X | | | X | | | X | | | X | | | | X |
| Immunogenicity (ADA)[l] | | X | | X | | X | X | | X | | | X | | X |
| Review safety card | | X | X | X | X | X | X | X | X | X | X | X | X | X |
| Breakthrough hemolysis[m] | | | | | | | ←Monitor continuously→ | | | | | | | |
| Concomitant medications | | | | | | | ←Monitor continuously→ | | | | | | | |
| Adverse events | | | | | | | ←Monitor continuously→ | | | | | | | |
| ALXN1210 administration[n] | X | X | X | X | X | X | X | X | X | X | X | X | X | |

Abbreviations: ADA = antidrug antibody;
ECG = electrocardiogram;
EORTC QLQ-C30 = European Organisation for Research and Treatment of Cancer, Quality of Life Questionnaire-Core 30 Scale;
EOS = end of study;
ET = early termination;
FACIT-Fatigue = Functional Assessment of Chronic Illness Therapy-Fatigue Scale;
LDH = lactate dehydrogenase;
PD = pharmacodynamics;
PK = pharmacokinetics;
PNH = paroxysmal nocturnal hemoglobinuria;
RBC = red blood cell

[a]All patients who roll over into the Extension Period receive ALXN1210 on Day 183 after all assessments have been performed.
[b]Granulocyte and RBC clone size measured by high-sensitivity flow cytometry on Days 351 and 743; RBC clone size only at other visits.
[c]Female patients of childbearing potential only. Serum pregnancy test at ET only; urine pregnancy test at all other time points. A negative urine test result is required prior to administering ALXN1210 to female patients of childbearing potential on dosing days.
[d]Transfusions given during and between visits were recorded.
[e]Investigator or designee assessment of the following events: fatigue, abdominal pain, dyspnea, dysphagia, chest pain, and erectile dysfunction.
[f]Physician- and patient-reported assessments were performed prior to study drug administration.
[g]Abbreviated physical examination consists of a body system relevant examination based upon Investigator (or designee) judgment and patient symptoms. At least one body system must be checked for an abbreviated physical examination.
[h]Vital sign measurements were taken after the patient has been resting for at least 5 minutes and include systolic and diastolic BP (millimeters of mercury [mmHg]), heart rate (beats/minute), respiratory rate (breaths/minute), and oral or tympanic temperature (degrees Celsius [° C.] or degrees Fahrenheit [° F.]). Vital signs were taken before each study drug administration.
[i]Single 12-lead ECG is collected at Day 911 or ET. Patients must be supine for approximately 5 to 10 minutes before ECG collection and remain supine but awake during ECG collection.
[j]Clinical laboratory measurements were collected predose on dosing days.

TABLE 2-continued

Schedule of Study Visits and Assessments: Extension Period Patients Entering from ALXN1210 Group

| | | | | | | Period | | | | | | | |
|---|---|---|---|---|---|---|---|---|---|---|---|---|---|
| | | | | | | Extension Period | | | | | | | |
| | | | | | | Study Day | | | | | | | |
| 183[a] | 239 | 295 | 351 | 407 | 463 | 519 | 575 | 631 | 687 | 743 | 799 | 855 | 911 EOS/ET |
| | | | | | | Window (day) | | | | | | | |
| ±2 | ±7 | ±7 | ±7 | ±7 | ±7 | ±7 | ±7 | ±7 | ±7 | ±7 | ±7 | ±7 | ±7 |

[k]Serum samples for PK/PD analyses were collected at end-of-infusion on Day 183; predose (within 0.5 hours prior to the start of infusion) and at end-of-infusion (within 0.5 hours after the end of infusion) on Days 351, 575, and 743; and at any time on Day 911 or ET. End-of-infusion samples were drawn from the patient's opposite, noninfused arm. All collection times were recorded in the eCRF. In the event of breakthrough hemolysis, a serum sample for PK/PD analysis is collected.

[l]Samples for ADA were collected predose. If results of the test were positive, the test can be repeated every 3 months until results become negative or stabilize, based on the measured titer and the safety assessments.

[m]If a suspected event of breakthrough hemolysis occurs, LDH, PK, and PD parameters were analyzed at the central laboratory. If the suspected event of breakthrough does not occur at a scheduled visit, an unscheduled visit occurs for evaluation of the patient and collection of the required LDH, PK, and PD parameters.

[n]The dose of ALXN1210 is based on the patient's last recorded study visit body weight.

TABLE 3

Schedule of Study Visits and Assessments: Extension Period Patients Entering from Eculizumab Group

| | | | | | | | Period | | | | | | | |
|---|---|---|---|---|---|---|---|---|---|---|---|---|---|---|
| | | | | | | | Extension Period | | | | | | | |
| | | | | | | | Study Day | | | | | | | |
| | 183[a] | 197 | 253 | 309 | 365 | 421 | 477 | 533 | 589 | 645 | 701 | 757 | 813 | 869 | 925 EOS/ET |
| | | | | | | | Window (day) | | | | | | | |
| | ±2 | ±3 | ±7 | ±7 | ±7 | ±7 | ±7 | ±7 | ±7 | ±7 | ±7 | ±7 | ±7 | ±7 | ±7 |
| PNH clone size[b] | | X | X | X | X | X | X | X | X | X | X | X | X | X | X |
| Weight | | X | X | X | X | X | X | X | X | X | X | X | X | X | X |
| Pregnancy test[c] | | X | X | X | X | X | X | X | X | X | X | X | X | X | X |
| Record transfusions and transfusion parameters[d] | | X | X | X | X | X | X | X | X | X | X | X | X | X | X |
| PNH symptomatology[e] | | X | X | X | X | X | X | X | X | X | X | X | X | X | X |
| FACIT-Fatigue[f] | | | | | X | | | | X | | | X | | | X |
| EORTC QLQ-C30[f] | | | | | X | | | | X | | | X | | | X |
| PNH symptoms patient questionnaire[f] | | X | X | X | X | X | X | X | X | X | X | X | X | X | X |
| Resource utilization patient questionnaire[f] | | X | X | X | X | X | X | X | X | X | X | X | X | X | X |
| Abbreviated physical examination[g] | | X | X | | X | | X | | X | | X | | X | | X |
| Vital signs[h] | | X | X | X | X | X | X | X | X | X | X | X | X | X | X |
| Safety 12-Lead ECG[i] | | | | | | | | | | | | | | | X |
| Chemistry including LDH[j] | | X | X | X | X | X | X | X | X | X | X | X | X | X | X |
| Hematology including free hemoglobin and coagulation[j] | | X | X | X | X | X | X | X | X | X | X | X | X | X | X |
| Urinalysis and urine chemistry[j] | | X | X | X | X | X | X | X | X | X | X | X | X | X | X |
| PK/PD sampling[k] | X | X | | | X | | | X | | | X | | X | | X |
| Immunogenicity (ADA)[l] | | | X | | X | | X | | X | | X | | X | | X |
| Review safety card | | X | X | X | X | X | X | X | X | X | X | X | X | X | X |
| Breakthrough hemolysis[m] | | | | | | | ←Monitor continuously→ | | | | | | | | |
| Concomitant medications | | | | | | | ←Monitor continuously→ | | | | | | | | |
| Adverse events | | | | | | | ←Monitor continuously→ | | | | | | | | |

TABLE 3-continued

Schedule of Study Visits and Assessments: Extension Period Patients Entering from Eculizumab Group

| | Period |
|---|---|
| | Extension Period |

| | Study Day | | | | | | | | | | | | | | |
|---|---|---|---|---|---|---|---|---|---|---|---|---|---|---|---|
| | 183[a] | 197 | 253 | 309 | 365 | 421 | 477 | 533 | 589 | 645 | 701 | 757 | 813 | 869 | 925 EOS/ET |
| | Window (day) | | | | | | | | | | | | | | |
| | ±2 | ±3 | ±7 | ±7 | ±7 | ±7 | ±7 | ±7 | ±7 | ±7 | ±7 | ±7 | ±7 | ±7 | ±7 |
| ALXN1210 administration[n] | X | X | X | X | X | X | X | X | X | X | X | X | X | X | |

Abbreviations: ADA = antidrug antibody;
ECG = electrocardiogram;
EORTC QLQ-C30 = European Organisation for Research and Treatment of Cancer, Quality of Life Questionnaire-Core 30 Scale;
EOS = end of study;
ET = early termination;
FACIT-Fatigue = Functional Assessment of Chronic Illness Therapy-Fatigue Scale;
LDH = lactate dehydrogenase;
PD = pharmacodynamics;
PK = pharmacokinetics;
PNH = paroxysmal nocturnal hemoglobinuria;
RBC = red blood cell
[a]All patients who roll over into the Extension Period receive ALXN1210 on Day 183 after all assessments have been performed.
[b]Granulocyte and RBC clone size measured by high-sensitivity flow cytometry on Days 365 and 757; RBC clone size only at other visits.
[c]Female patients of childbearing potential only. Serum pregnancy test at ET only; urine pregnancy test at all other time points. A negative urine test result is required prior to administering ALXN1210 to female patients of childbearing potential on dosing days.
[d]Transfusions given during and between visits were recorded.
[e]Investigator or designee assessment of the following events: fatigue, abdominal pain, dyspnea, dysphagia, chest pain, and erectile dysfunction.
[f]Physician- and patient-reported assessments is performed prior to study drug administration.
[g]Abbreviated physical examination consists of a body system relevant examination based upon Investigator (or designee) judgment and patient symptoms. At least one body system is checked for an abbreviated physical examination.
[h]Vital sign measurements were taken after the patient has been resting for at least 5 minutes and include systolic and diastolic BP (millimeters of mercury [mmHg]), heart rate (beats/minute), respiratory rate (breaths/minute), and oral or tympanic temperature (degrees Celsius [° C.] or degrees Fahrenheit [° F.]). Vital signs were taken before each study drug administration.
[i]Single 12-lead ECG is collected at Day 925 or ET. Patients must be supine for approximately 5 to 10 minutes before ECG collection and remain supine but awake during ECG collection.
[j]Clinical laboratory measurements were collected predose on dosing days.
[k]Serum samples for PK/PD analyses were collected predose (within 0.5 hours prior to the start of infusion) and at end-of-infusion (within 0.5 hours after the end of infusion) on Days 197, 365, 589, and 757; at end-of-infusion on Day 183; and at any time on Day 925 or ET. End-of-infusion samples were drawn from the patient's opposite, noninfused arm. All collection times were recorded in the eCRF. In the event of breakthrough hemolysis, a serum sample for PK/PD analysis is collected.
[l]Samples for ADA were collected predose. If results of the test were positive, the test can be repeated every 3 months until results become negative or stabilize, based on the measured titer and the safety assessments.
[m]If a suspected event of breakthrough hemolysis occurs, LDH, PK, and PD parameters were analyzed at the central laboratory. If the suspected event of breakthrough does not occur at a scheduled visit, an unscheduled visit should occur for evaluation of the patient and collection of the required LDH, PK, and PD parameters.
[n]The dose of ALXN1210 is based on the patient's last recorded study visit body weight.

4. Study Population

A total of approximately 246 patients with documented PNH were enrolled and randomly assigned to treatment with either ALXN1210 or eculizumab at approximately 300 investigative sites globally. Individuals who did not meet the criteria for participation in this study (screen failure) could be rescreened. Prospective approval of protocol deviations to recruitment and enrollment criteria, also known as protocol waivers or exemptions, was not permitted.

Patients were eligible for enrollment in the study only if they met all of the following criteria and none of the exclusion criteria:

1. Male or female, 18 years of age or older at the time of consent.
2. Documented diagnosis of PNH, confirmed by high-sensitivity flow cytometry evaluation (Borowitz M J, et al., "Guidelines for the diagnosis and monitoring of paroxysmal nocturnal hemoglobinuria and related disorders by flow cytometry", Cytometry Part B. 2010; 78B:211-230) of RBCs and white blood cells (WBCs), with granulocyte or monocyte clone size of ≥5%.
3. Presence of 1 or more of the following PNH-related signs or symptoms within 3 months of Screening: fatigue, hemoglobinuria, abdominal pain, shortness of breath (dyspnea), anemia (hemoglobin <10 g/dL), history of a major adverse vascular event (including thrombosis), dysphagia, or erectile dysfunction; or history of pRBC transfusion due to PNH.
4. LDH level ≥1.5×ULN at Screening.
5. To reduce the risk of meningococcal infection (*Neisseria meningitidis*), all patients must be vaccinated against meningococcal infections within 3 years prior to, or at the time of, initiating study drug. Patients who initiate study drug treatment less than 2 weeks after receiving a meningococcal vaccine must receive treatment with appropriate prophylactic antibiotics until 2 weeks after vaccination.
6. Female patients of childbearing potential and male patients with female partners of childbearing potential must follow protocol-specified guidance for avoiding pregnancy while on treatment and for 8 months after last dose of study drug.
7. Patients must give written informed consent and to comply with all study visits and procedures, including the use of any data collection device(s) to directly record patient data.

Patients were excluded from study enrollment if they met any of the following criteria:

1. Current or previous treatment with a complement inhibitor.
2. Platelet count <30,000/mm$^3$ (30×10$^9$/L) at Screening.

3. Absolute neutrophil count <500/µL (0.5×10⁹/L) at Screening.
4. History of bone marrow transplantation.
5. Body weight <40 kg at Screening.
6. History of *N. meningitidis* infection.
7. History of unexplained, recurrent infection.
8. Active systemic bacterial, viral, or fungal infection within 14 days prior to study drug administration on Day 1.
9. Presence of fever ≥38° C. (100.4° F.) within 7 days prior to study drug administration on Day 1.
10. Human immunodeficiency virus (HIV) infection (evidenced by HIV-1 or HIV-2 antibody titer).
11. Immunized with a live-attenuated vaccine 1 month prior to study drug administration on Day 1.
12. History of malignancy within 5 years of Screening, with the exception of nonmelanoma skin cancer or carcinoma in situ of the cervix that has been treated with no evidence of recurrence.
13. History of or ongoing major cardiac, pulmonary, renal, endocrine, or hepatic disease (e.g., active hepatitis) that, in the opinion of the Investigator or Sponsor, precludes the patient's participation in an investigational clinical trial.
14. Unstable medical conditions (e.g., myocardial ischemia, active gastrointestinal bleed, severe congestive heart failure, anticipated need for major surgery within 6 months of randomization, coexisting chronic anemia unrelated to PNH that make them unlikely to tolerate the requirements of the protocol (e.g., transfusion guidelines).
15. Concomitant use of any of the following medications was prohibited if not on a stable regimen for the time period indicated prior to Screening:
    a) Erythropoietin or immunosuppressants for at least 8 weeks
    b) Systemic corticosteroids for at least 4 weeks
    c) Vitamin K antagonists (eg, warfarin) with a stable international normalized ratio (INR) for at least 4 weeks
    d) Iron supplements or folic acid for at least 4 weeks
    e) Low-molecular-weight heparin for at least 4 weeks
16. History of hypersensitivity to murine proteins or to any of the study drug excipients (eg, polysorbate 80).
17. Females who plan to become pregnant or were currently pregnant or breastfeeding.
18. Females who have a positive pregnancy test result at Screening or on Day 1.
19. Participation in another interventional treatment study or use of any experimental therapy within 30 days before initiation of study drug on Day 1 in this study or within 5 half-lives of that investigational product, whichever is greater.
20. Known or suspected history of drug or alcohol abuse or dependence within 1 year prior to the start of Screening.
21. Known medical or psychological condition(s) or risk factor that, in the opinion of the Investigator, might interfere with the patient's full participation in the study, pose any additional risk for the patient, or confound the assessment of the patient or outcome of the study.

A patient has the right to withdraw from the study at any time. If a patient withdraws consent, the assessments specified for the Early Termination (ET) visit were performed. Patients who withdraw from the study were not replaced.

A patient can be discontinued from study drug if it is in the best interest of the patient to stop treatment. If a patient was discontinued from study drug, the patient was encouraged to return for the remainder of his or her scheduled protocol visits until starting a different complement-targeted therapy.

If a patient was discontinued from the study with an ongoing adverse event or an unresolved laboratory result that is significantly outside of the reference range and clinically significant, the Investigator attempted to provide follow-up until a satisfactory clinical resolution of the laboratory result or adverse event was achieved.

The Sponsor or Competent Authority could terminate the study for reasonable cause. The end of the study is defined as the date of the last patient's last visit in the Extension Period.

5. Study Treatment

The study drugs in this study were ALXN1210 (ravulizumab) and eculizumab (active control). Both ALXN1210 and eculizumab were humanized, anti-C5 monoclonal antibodies.

Eculizumab is an IgG2/4 kappa immunoglobulin consisting of human constant regions, and murine complementarity-determining regions grafted onto human framework light- and heavy-chain variable regions. To be clear, IgG2/4 is a short hand way of describing the non-naturally occurring, protein engineered, heavy chain comprising elements from both an IgG2 and an IgG4 heavy chains. This unique heavy chain was first described for use in an anti-C5 antibody for eculizumab. Eculizumab is composed of two 448 amino acid heavy chains and two 214 amino acid light chains.

ALXN1210 was derived through minimal targeted engineering of eculizumab by introducing 4 unique amino acid substitutions to its heavy chain to extend antibody half-life. ALXN1210 and eculizumab share over 99% primary amino acid sequence identity and have very similar pharmacology.

ALXN1210 and eculizumab drug products were supplied for clinical studies as sterile, preservative-free 10-mg/mL solutions in single-use vials and designed for infusion by diluting into commercially available saline (0.9% sodium chloride injection; country-specific pharmacopeia) for administration via IV infusion. Table 4, the current ALXN1210 IB, and the approved eculizumab local labeling or current eculizumab IB provide additional information.

TABLE 4

| | Study Drug | |
|---|---|---|
| Product Name | ALXN1210 | Eculizumab |
| Dosage Form | Concentrated solution (10 mg/mL) for infusion | Concentrated solution (10 mg/mL) for infusion |
| Route of Administration | Intravenous infusion | Intravenous infusion |
| Physical Description | Clear to translucent, slight whitish color, practically free from particles | Clear, colorless solution practically free from particles |
| Manufacturer | Alexion Pharmaceuticals, Inc. or Contracted Manufacturing Organization | Alexion Pharmaceuticals, Inc. or Contracted Manufacturing Organization |

ALXN1210 and eculizumab were packaged in US Pharmacopeia/European Pharmacopeia Type 1 borosilicate glass vials and stoppered with a butyl rubber stopper with an aluminum overseal and a flip-off cap. Study drug is supplied in kits. Study drug is released to each site upon receipt of all required essential documents based upon applicable regulations.

Upon arrival of the study drug kits at the study site, the pharmacist or designee promptly removes the study drug kits from the shipping cooler and stores them in their original cartons under refrigerated conditions at 2° C. to 8° C. (35° F. to 47° F.) and protected from light. ALXN1210 and eculizumab were not to be frozen. Study drug is stored in a secure, limited-access storage area, and the temperature must be monitored daily.

The drug product is at room temperature prior to administration. The material is not heated (e.g., by using a microwave or other heat source) other than by ambient air temperature.

Eculizumab or ALXN1210 were not administered as an IV push or bolus injection. Infusions of study drug were prepared using aseptic technique. The patient's required dose of ALXN1210 or eculizumab is further diluted into commercially available saline (0.9% sodium chloride; country-specific pharmacopeia) at the volume specified in Table 5 for ALXN1210 or Table 6 for eculizumab (see also approved local labeling or current IB for eculizumab). ALXN1210 or eculizumab solution in diluent is administered to the patient using an IV tubing administration set via an infusion pump. Use of an in-line filter for infusion is required.

This study involves a direct comparison of ALXN1210 versus the active control, eculizumab. Patients were randomly assigned in a 1:1 ratio to receive either ALXN1210 or eculizumab for 26 weeks. Study drug was administered as a slow IV infusion (see Table 5 and Table 6).

The dose regimen for ALXN1210 was a loading dose on Day 1 followed by maintenance doses on Day 15 and q8w thereafter. The dosage of ALXN1210 was based on the patient's body weight at the time of dose administration, as indicated in Table 7.

TABLE 7

ALXN1210 Weight-Based Dosages

| ALXN1210 Treatment Group Body Weight | Loading Dose | Maintenance Dose |
| --- | --- | --- |
| ≥40 to <60 kg | 2400 mg | 3000 mg |
| ≥60 to <100 kg | 2700 mg | 3300 mg |
| ≥100 kg | 3000 mg | 3600 mg |

Patients randomly assigned to the eculizumab group received eculizumab according to the approved dosing regimen for the PNH indication, which is 4 weekly induction doses, followed by maintenance doses q2w starting at Week 5 (Table 8).

TABLE 5

Dosing Reference Chart for ALXN1210 Dose Preparation

| Dose Type | Body Weight (kg)[a] | Dose (mg) | ALXN1210 Volume (mL) | Saline Volume (mL) | Total Volume (mL) | Minimum Infusion Duration minutes (hours) | Maximum Infusion Rate (mL/hour) |
| --- | --- | --- | --- | --- | --- | --- | --- |
| Loading | ≥40 to <60 | 2400 | 240 | 240 | 480 | 114 (1.9) | 253 |
| | ≥60 to <100 | 2700 | 270 | 270 | 540 | 102 (1.7) | 333 |
| | ≥100 | 3000 | 300 | 300 | 600 | 108 (1.8) | 333 |
| Maintenance | ≥40 to <60 | 3000 | 300 | 300 | 600 | 138 (2.3) | 267 |
| | ≥60 to <100 | 3300 | 330 | 330 | 660 | 120 (2.0) | 333 |
| | ≥100 | 3600 | 360 | 360 | 720 | 132 (2.2) | 333 |

Note:
Please refer to the Pharmacy Manual for additional dose preparation instructions.
[a]Body weight as recorded at the last study visit.

TABLE 6

Dosing Reference Chart for Eculizumab Dose Preparation

| Dose Type | Dose (mg) | Eculizumab Volume (mL) | Saline Volume (mL) | Total Volume (mL) | Infusion Duration (minutes) | Approximate Infusion Rate (mL/hour) |
| --- | --- | --- | --- | --- | --- | --- |
| Induction | 600 | 60 | 60 | 120 | 35 | 200 |
| Maintenance | 900 | 90 | 90 | 180 | 35 | 300 |

Doses of study drug were only prepared and dispensed by a pharmacist or a medically qualified staff member. Study drug is dispensed only to enrolled patients who were confirmed eligible for participation in this study. Once study drug is prepared for a patient, it is only administered to that patient. Vials of study drug were for one-time use only and any drug product remaining in the vial were not used for another patient. Any drug remaining in the infusion tubing or infusion bag were not used for another patient.

TABLE 8

Eculizumab Dosages

| Eculizumab Treatment Group | Induction Dose | Maintenance Dose |
| --- | --- | --- |
| All patients | 600 mg | 900 mg |

After the randomized treatment period all patients enteed the Extension Period and received ALXN1210 until the product was registered or approved (in accordance with country-specific regulations) or for up to 2 years, whichever occurs first. Beginning on Day 183, patients who had been randomized to the ALXN1210 treatment group receive their weight-based maintenance dose of ALXN1210 q8w, and patients who had been randomized to the eculizumab group receive a weight-based loading dose of ALXN1210 followed 2 weeks later and q8w thereafter by a weight-based maintenance dose of ALXN1210 (Table 7).

The actual time of all dose administrations was recorded on the patient's eCRF. Patients who meet all criteria for enrollment were randomly assigned to study treatment with ALXN1210 or eculizumab at the Baseline Visit (Day 1). Treatment group assignment were determined by a computer-generated random sequence using an interactive voice- or web-response system (IxRS). The randomization was a stratified randomization. Patients were stratified into 1 of 6 groups based on their transfusion history (0, 1 to 14, or >14 units of pRBCs in the 1 year prior to first dose of study drug) and screening lactate dehydrogenase (LDH) levels (1.5 to <3×ULN or ≥3×ULN). The patients within each of the 6 groups were then randomly assigned in a 1:1 ratio to receive ALXN1210 or eculizumab during the 26-week randomized treatment period.

The weight-based dosages of ALXN1210 in this study (Table 7) were premised on PK/PD data from early development studies in healthy adult volunteers, as well as the available data from patients with PNH in an ongoing Phase 1b dose-finding study (ALXN1210-PNH-103) and an ongoing Phase 2 proof-of-concept study (ALXN1210-PNH-201). The selection of ALXN1210 dose regimen is based on targeting immediate, complete and sustained inhibition of terminal complement in patients with PNH.

The eculizumab dosage is the labelled dose for the treatment of patients with PNH (Soliris® USPI and SmPC).

Infusion of other monoclonal antibodies has been associated with infusion reactions, with onset typically during or shortly after completion of the infusion. Prior medications (including vitamins and herbal preparations)—including those discussed in the exclusion criteria and procedures (any therapeutic intervention, such as surgery/biopsy or physical therapy) the patient takes or undergoes within 28 days (or 3 years for documentation of meningococcal vaccination) prior to the start of Screening until the first dose of study drug—were recorded on the patient's eCRF.

Transfusions of pRBCs received within 1 year prior to first study drug administration were recorded on the patient's eCRF.

All medication use and procedures undertaken during the study is recorded in the patient's source document/medical chart and eCRF. This record includes all prescription drugs, herbal products, vitamins, minerals, over-the-counter medications, and current medications for PNH. Concomitant medications were recorded from the first infusion of study drug through 56 days after the patient's last dose of study drug. Any changes in concomitant medications also were recorded in the patient's source document/medical chart and eCRF. Any concomitant medication deemed necessary for the patient's standard of care during the study, or for the treatment of any AE, along with the allowed medications described below is given at the discretion of the Investigator. However, it is the responsibility of the Investigator to ensure that details regarding all medications were recorded in full in the patient's source document/medical chart and eCRF.

The following concomitant medications were allowed if the following conditions apply, and dose adjustments were not expected during the randomized treatment period:

Erythropoietin, if the patient has been receiving a stable dose for at least 8 weeks before Screening.

Immunosuppressants, if the patient has been receiving a stable dose for at least 8 weeks before Screening.

Corticosteroids, if the patient has been receiving a stable dose for at least 4 weeks before Screening.

Vitamin K antagonists (eg, warfarin) with a stable INR for at least 4 weeks before Screening.

Iron supplements or folic acid, if the patient has been receiving a stable dose for at least 4 weeks before Screening.

Low-molecular-weight heparin, if the patient has been receiving a stable dose for at least 4 weeks before Screening.

If deemed in the best interest of the patient, the frequency or dose level of any of the above medications could be adjusted.

Due to their mechanism of action, the use of eculizumab or ALXN1210 increases the patient's susceptibility to meningococcal infection (*N. meningitidis*). To reduce the risk of meningococcal infection, all patients were vaccinated against meningococcal infections within 3 years prior to, or at the time of, initiating study drug. Patients who initiated study drug treatment less than 2 weeks after receiving a meningococcal vaccine received treatment with appropriate prophylactic antibiotics until 2 weeks after vaccination. Vaccines against serotypes A, C, Y, W135, and B, where available, were recommended to prevent common pathogenic meningococcal serotypes. Patients were vaccinated or revaccinated according to current national vaccination guidelines or local practice for vaccination use with complement inhibitors (e.g., eculizumab).

Vaccination may not be sufficient to prevent meningococcal infection. Consideration was given per official guidance and local practice on the appropriate use of antibacterial agents. All patients were monitored for early signs of meningococcal infection, evaluated immediately if infection is suspected, and treated with appropriate antibiotics, if necessary.

6. Efficacy Assessments

A pRBC transfusion was administered when a patient had a hemoglobin value of 9 g/dL or lower with signs or symptoms of sufficient severity to warrant a transfusion or hemoglobin value of 7 g/dL or lower regardless of presence of clinical signs or symptoms.

Signs or symptoms typically associated with or that precipitated the patient's need for transfusion were documented on the eCRF for each individual patient. Typical anemia-related symptoms warranting transfusions included angina, change in mental status (e.g., syncope, light headedness, confusion, stroke, transient ischemic attack), severe or worsening shortness of breath, and severe or worsening fatigue.

If a patient met either transfusion criterion during the study, the Investigator determined the appropriate number of units of pRBCs to be transfused. It was recommended that the transfusion be performed within 48 hours of the hemoglobin determination responsible for the transfusion. Administration of a transfusion, including the hemoglobin result and symptoms that triggered the transfusion, and the number of units transfused, were documented in the eCRF.

Prior to randomization and within 5 days prior to study drug administration on Day 1, each patient's hemoglobin was evaluated by either local or central laboratory. If at that time the patient's hemoglobin value met these transfusion guidelines, the patient was transfused with pRBCs to a hemoglobin level above the transfusion threshold in order to be eligible for randomization. The patient's post-transfusion hemoglobin value was confirmed by local or central laboratory to be above the transfusion threshold.

A. LDH and Other Disease-Related Laboratory Parameters

Blood and urine samples were collected. The following disease-related laboratory parameters were measured during the study: LDH, free hemoglobin, occult blood, urine, total C5, haptoglobin, reticulocyte count, PNH RBC clone size evaluated by high-sensitivity flow cytometry, D-dimer concentration, estimated glomerular filtration rate (calculated using the Modification of Diet in Renal Disease formula), spot urine albumin:creatinine ratio, and C-reactive protein.

B. Patient-Reported Outcome Measures

Two validated QoL scales were administered to patients before study drug administration. The FACIT-Fatigue scale, Version 4.0, is a collection of QoL questionnaires pertaining to the management of fatigue symptoms due to a chronic illness. The FACIT-Fatigue is a 13-item questionnaire that assesses self-reported fatigue and its impact upon daily activities and function over the preceding 7 days. Patients score each item on a 5-point scale: 0 (Not at all) to 4 (Very much). Total scores range from 0 to 52, with higher score indicating better QoL.

The European Organization for Research and Treatment of Cancer (EORTC) Quality of Life Questionnaire-Core 30 Scale (QLQ-C30), Version 3.0, is a questionnaire developed to assess the QoL of cancer patients. The questionnaire includes the following subscales: global health status, functional scales (physical functioning, role functioning, emotional functioning, cognitive functioning, and social activity), symptom scales (fatigue, nausea and vomiting, and pain), and single items (dyspnea, insomnia, appetite loss, constipation, diarrhea, and financial difficulties). Thirty questions related to QoL, with the first 28 questions scored on a 4-point scale (1=not at all to 4=very much) and the final 2 questions that probe the patient's overall health and QoL scored on a scale of 1 (very poor) to 7 (excellent). Each subscale has a range of 0 to 100%, with a high score representing a higher response level. Thus, a high score for a functional scale represents a high level of functioning but a high score for a symptom scale represents a high level of symptomatology/problem. Two additional questionnaires were completed by patients to assess disease burden.

These questionnaires were administered to patients before study drug is infused. The PNH Symptoms Questionnaire lists the following symptoms: yellow discoloration of eyes, discoloration of urine, chest pain, shortness of breath, headache, fatigue, abdominal pain, confusion, erectile dysfunction, trouble swallowing, and other. Patients indicate whether they have experienced each of the symptoms in the past week, and if so, they rate the frequency (4-point scale ranging from rarely to almost constantly), severity (4-point scale ranging from slight to very severe), and extent of distress/bother associated with it (5-point scale ranging from not at all to very much).

The Resource Utilization Questionnaire asks patients to provide the number of times within the past month that they have: visited their health care provider primarily for treatment of their PNH (excluding protocol-specified study visits), gone to an emergency room primarily for treatment of their PNH, been admitted to a hospital primarily for treatment of their PNH, had darkened urine, and/or missed work as a result of symptoms of PNH.

C. Major Adverse Vascular Events

Major adverse vascular events (MAVEs) were assessed as part of the planned evaluation for adverse events (AEs). The description of the MAVE, anatomical site, method of diagnosis (e.g., magnetic resonance imaging, ultrasound, angiogram), date of diagnosis, and date resolved (or ongoing) were collected on the eCRF as part of the patient's medical history (prior to baseline) and during the study.

A MAVE is defined as follows:
a) Thrombophlebitis/deep vein thrombosis
b) Pulmonary embolus
c) Myocardial infarction
d) Transient ischemic attack
e) Unstable angina
f) Renal vein thrombosis
g) Acute peripheral vascular occlusion
h) Mesenteric/visceral vein thrombosis or infarction
i) Mesenteric/visceral arterial thrombosis or infarction
j) Hepatic/portal vein thrombosis (Budd-Chiari syndrome)
k) Cerebral arterial occlusion/cerebrovascular accident
l) Cerebral venous occlusion
m) Renal arterial thrombosis
n) Gangrene (nontraumatic; nondiabetic)
o) Amputation (nontraumatic; nondiabetic)
p) Dermal thrombosis
q) Other, specify D. Major Adverse Vascular Events A review of demographic parameters, including age, gender, race, and ethnicity was performed. A complete medical history was taken and documented. Weight and height were recorded. Height was measured at Screening only.

The patient's PNH medical history, including onset of first PNH symptom, date of diagnosis, PNH clone size, pRBC transfusions, and history of any MAVEs, was documented at the Screening visit.

The patient's medical history, including prior and concomitant conditions/disorders and transfusion history, was recorded at the Screening Visit. Medication (prescription or over-the-counter, including vitamins and/or herbal supplements) use over the 28 days (or 3 years for documentation of meningococcal vaccination) prior to the start of Screening was also recorded, in addition to meningococcal vaccination.

A physical examination included the following assessments: general appearance; skin; head, ear, eye, nose, and throat; neck; lymph nodes; chest; heart; abdominal cavity; limb; central nervous system; and musculoskeletal system. An abbreviated physical examination consisted of a body system relevant examination based upon Investigator judgment and patient symptoms.

Vital sign measurements were taken after the patient has been resting for at least 5 minutes, and include systolic and diastolic blood pressure (BP; millimeters of mercury [mmHg]), heart rate (beats/minute), respiratory rate (breaths/minute), and oral or tympanic temperature (degrees Celsius [° C.] or degrees Fahrenheit [° F.]).

Samples for serum pregnancy, hematology, chemistry, coagulation, and urinalysis were performed. Samples for laboratory assessments were collected before each study drug administration. If a suspected event of breakthrough hemolysis occurs, an unscheduled visit takes place at which a sample is collected for analysis of LDH and PK/PD by the central laboratory.

It was anticipated that some laboratory values would be outside the normal value range due to the underlying disease. The Investigators used their medical judgment when assessing the clinical significance of these values. Clinical significance is defined as any variation in laboratory measurements that has medical relevance and which results in a change in medical care. If clinically significant laboratory changes from baseline value were noted, the changes were documented as AEs on the AE eCRF. The Investigator also assessed the relationship to study treatment for all clinically significant out-of-range values. The Investigator continued to monitor the patient through additional laboratory assessments until (1) values returned to the normal range or baseline level, or (2) in the judgment of the Investigator, values that were outside the normal range were not related to the administration of study drug or other protocol-specific procedures.

Blood samples were analyzed for serum chemistry parameters. Indirect bilirubin is calculated from total and direct bilirubin values; therefore, indirect bilirubin results were not be available if direct bilirubin is below the limit of quantification. Serum FSH levels were measured during Screening for postmenopausal female patients to confirm their postmenopausal status. Chemistry assessments were performed. Estimated glomerular filtration rate was calculated using the Modification of Diet in Renal Disease formula for all visits at which serum chemistries were collected. Blood samples were analyzed for coagulation parameters.

Urine samples were analyzed. A microscopic examination of urine samples was performed if the results of the macroscopic analysis were abnormal. Urine samples were also analyzed to measure proteins and creatinine in order to calculate the urine protein:creatinine ratio.

HIV testing for human immunodeficiency virus type 1 (HIV-1) and human immunodeficiency virus type 2 (HIV-2) is required for all patients prior to enrollment. Known HIV positive patients were not enrolled.

For each patient, single 12-lead digital ECGs were collected. Patients must be supine for approximately 5 to 10 minutes before ECG collection and remain supine but awake during ECG collection.

Blood samples were collected to test for presence and titer of ADAs to ALXN1210 or eculizumab in serum prior to study drug administration. If results of the test were positive, the test was repeated every 3 months until results become negative or stabilize, based on the measured titer and the safety assessments. Further characterization of antibody responses was conducted as appropriate, including binding and neutralizing antibodies, PK/PD, safety, and activity of ALXN1210 or eculizumab.

An AE is any untoward medical occurrence in a patient administered a pharmaceutical product and which does not necessarily have a causal relationship with this treatment. An AE can therefore be any unfavorable or unintended sign (e.g., an abnormal laboratory finding), symptom, or disease temporally associated with the use of a medicinal product, whether or not considered related to the medicinal product.

Situations in which an untoward medical occurrence did not occur (e.g., hospitalization for elective surgery if planned before the start of the study, admissions for social reasons or for convenience), and anticipated day-to-day fluctuations of pre-existing disease(s) or condition(s) present or detected at the start of the study that do not worsen were not AEs.

Lack of drug effect is not an AE in clinical studies, because the purpose of the clinical study is to establish drug effect.

A medication error (including intentional misuse, abuse, and overdose of the product) or use other than what is defined in the protocol is not considered an AE unless there is an untoward medical occurrence as a result of a medication error.

Cases of pregnancy that occur during maternal or paternal exposure to investigational product were reported within 24 hours of Investigator/site awareness. Data on fetal outcome and breastfeeding is collected for regulatory reporting and safety evaluation.

Adverse events were recorded from the time of signed consent. An AE reported after informed consent but before study drug administration is considered a pretreatment AE.

C5 inhibition is known to increase susceptibility to infections caused by encapsulated bacteria, particularly *N. meningitidis*. The following events were important identified risks in this study: Meningococcal infections, Sepsis, Serious infections, *Aspergillus* infection, and Infusion reactions. Additional events of interest in this study included the following: Serious cutaneous adverse reactions, Cardiac disorders (including ventricular fibrillation), and Angioedema.

The severity of AEs was graded using Common Terminology Criteria for Adverse Events (CTCAE) version 4.03 or higher. A grading (severity) scale was provided for each AE term. Each CTCAE term is a Lowest Level Term (LLT) per the Medical Dictionary for Regulatory Activities (MedDRA®). Each LLT is coded to a MedDRA preferred term (PT).

Grade refers to the severity of the AE. The CTCAE assigns a grade of 1 through 5, with unique clinical descriptions of severity for each AE (Table 9).

TABLE 9

Adverse Event Severity Grading Scale

| Grade | Description |
|---|---|
| Grade 1 | Mild; asymptomatic or mild symptoms; clinical or diagnostic observations only; intervention not indicated |
| Grade 2 | Moderate; minimal, local or noninvasive intervention indicated; limiting age-appropriate instrumental activities of daily living (ADL)[a] |
| Grade 3 | Severe or medically significant, but not immediately life-threatening; hospitalization or prolongation of hospitalization indicated; disabling; limiting self-care ADL[b] |
| Grade 4 | Life-threatening consequences; urgent intervention indicated. |
| Grade 5 | Death related to AE. |

Abbreviations: ADL = activities of daily living;
AE = adverse event
[a]Instrumental ADL refers to preparing meals, shopping for groceries or clothes, using the telephone, managing money, etc.
[b]Self-care ADL refers to bathing, dressing and undressing, feeding self, using the toilet, taking medications, and not bedridden.

An Investigator must have provided a causality assessment (Unrelated, Unlikely, Possible, Probable, or Definite) for all AEs (both serious and nonserious) based upon the Investigator's medical judgment and the observed symptoms associated with the event (Table 10). This assessment was recorded on the eCRF and any additional forms as appropriate.

TABLE 10

Causality Assessment Descriptions

| Assessment | Description |
|---|---|
| Not Related/Unrelated | Suggests that there is no causal association between the investigational product and the reported event. |

TABLE 10-continued

Causality Assessment Descriptions

| Assessment | Description |
|---|---|
| Unlikely Related | Suggests that the clinical picture is highly consistent with a cause other than the investigational product but attribution cannot be made with absolute certainty and a relationship between the investigational product and AE cannot be excluded with complete confidence. |
| Possibly Related | Suggests that treatment with the investigational product may have caused or contributed to the AE (i.e., the event follows a reasonable temporal sequence from the time of drug administration and/or follows a known response pattern to the investigational product, but could also have been produced by other factors). |
| Probably Related | Suggests that a reasonable temporal sequence of the event with the investigational product administration exists and the likely causal association of the event with the investigational product. This is based upon the known pharmacological action of the investigational product, known or previously reported adverse reactions to the investigational product or class of drugs, or judgment based on the Investigator's clinical experience. |
| Definitely Related | Temporal relationship to the investigational product, other conditions (concurrent illness, concurrent medication reaction, or progression/expression of disease state) do not appear to explain event, corresponds with the known pharmaceutical profile, improvement on discontinuation, reappearance on rechallenge. |

A serious adverse event (SAE) is any untoward medical occurrence that: results in death, is life-threatening (i.e., patient was at risk of death at the time of the event), requires inpatient hospitalization or prolongation of existing hospitalization, results in persistent or significant disability/incapacity, and/or is a congenital anomaly/birth defect.

Important medical events that may not result in death, be immediately life-threatening, or require hospitalization could be considered a serious adverse event when, based upon appropriate medical judgment, they could have jeopardized the patient or required intervention to prevent one of the outcomes listed above.

Suspected unexpected serious adverse reactions (SUSARs) were serious events that were not listed in the IB and that the Investigator identifies as related to investigational product or procedure.

All AEs (serious and nonserious) were collected from the signing of the ICF until 56 days after the last dose of study drug for patients with ET or until 56 days after the last dose of study drug for patients who complete the study.

7. Pharmacokinetics and Pharmacodynamics

Blood samples for determination of serum drug concentrations and PD assessments were collected before and after administration of study drug. The actual date and time (24-hour clock time) of each sampling is recorded. The number of PK sampling time points for any given patient did not exceed the currently planned number of time points; in the event of breakthrough hemolysis, an additional PK/PD sample was required.

The blood samples for PK and PD assessment were collected from the arm opposite to the arm used for infusing drug.

Assessments for PK/PD were as follows: change in serum ALXN1210 and eculizumab concentration over time, change in cRBC hemolytic activity over time (exploratory), and change in free and total C5 concentrations over time.

8. Statistical Methods and Planned Analyses

All data collected is presented in summary tabulations. All data, as well as any outcomes derived from the data, is presented in detailed data listings. Graphical displays were also provided, when appropriate. All analyses were performed using SAS® release, version 9.4 or higher (SAS Institute Inc., Cary, NC, USA) or other validated statistical software. Continuous variables were summarized using descriptive statistics, including number of observations and mean, standard deviation, median, minimum, and maximum values. Categorical variables were summarized by frequency counts and percentage of patients. All statistical tests performed were based on a 2-sided 5% level of significance unless otherwise specified. Prior to finalizing and locking the database, all decisions concerning the inclusion or exclusion of data from the analysis for each patient were determined by appropriate medical and statistical personnel. Any and all exclusions were documented in patient listings.

Details of the statistical analyses described below were specified in a separate Statistical Analysis Plan (SAP) before database lock and analysis. Any change to the data analysis methods described in the protocol requires an amendment only if it changes the primary or key secondary objectives or the study conduct. Any other change to the data analysis methods described in the protocol or SAP, and the justification for making the change, is described in the clinical study report (CSR). Additional exploratory analyses of the data were conducted as deemed appropriate.

A CSR was produced based on efficacy, safety, PK, and PD data collected through the end of the 26-week randomized treatment period (Day 183). A final CSR to summarize long-term efficacy, safety, PK, and PD parameters was produced at study completion.

Approximately 246 patients were randomly assigned in a 1:1 ratio to receive ALXN1210 (N=107) or eculizumab (N=107) to ensure at least 193 evaluable patients (assumes no more than a 10% drop-out rate). The sample size estimation was based on a noninferiority design comparing patients treated with ALXN1210 to those treated with eculizumab. Coprimary endpoints of hemolysis as directly measured by the normalization of LDH (LDH-N) from Day 29 through Day 183 and the proportion of patients who achieved transfusion avoidance (TA) through Day 183 were used to assess noninferiority. The sample size is based on the endpoint that requires the larger number of patients.

For the coprimary endpoint of LDH-N, using a noninferiority margin (NIM) based on the relative benefit of eculizumab with respect to placebo of 0.39 and a type I error of 1-sided 2.5%, a minimum of 142 patients provides 80% power to demonstrate noninferiority of ALXN1210 to eculizumab. The NIM was determined based on a randomized placebo-controlled study (Hillmen P., et al., N. Engl. J. Med., 2006; 355:1233-1243) which showed a relative benefit of eculizumab over placebo with an odds ratio of 6.5. This was based on several factors. As baseline LDH is a predictor of the rate of normalization, in order to preserve the constancy assumption, the rate of LDH-N was calculated adjusted to the observed baseline LDH-N of the current ALXN1210 Phase 1b and 2 data. The estimate of LDH-N for eculizumab was then calculated to be a weighted average of the proportions of LDH-N from Day 29 to Day 183 to be consistent with the proposed analysis plan for this study. As the proportion of LDH-N for placebo treated patients was 0% at all visits, the upper bound of the 95% CI was used in order to be able to calculate an odds ratio. The final estimate of benefit was based on a LDH-N proportion of 42% for eculizumab-treated patients and 10% for placebo. A traditional choice of NIM is one with ≤50% loss of benefit resulting in a NIM of an odds ratio of 0.39. The calculation of NIM follows Ng T-H (Statist. Med. 2008; 27:5392-5406) in which the NIM is given by $1/\{OR^{0.5}\}$ where OR represents the odds ratio of eculizumab compared to placebo and is given by [0.42/(1−0.42)]/[0.1/(1−0.1)], and 0.5 is the fraction of benefit to be preserved. This approach chooses the NIM on the log odds scale, as described in Section IV of the 2010 Food and Drug Administration (FDA) Guidance for Industry: Non-Inferiority Clinical Trials. While more conservative approaches for constructing NIMs could be used, such as using the lower bound of the 95% CI for eculizumab, the resulting estimated sample size makes this study operationally infeasible in light of the rarity of PNH and the paucity of eculizumab-naïve patients.

For the other co-primary endpoint of proportion of patients not receiving any transfusions through Day 183, using a NIM of −20% and a type I error of 1-sided 2.5%, a minimum of 193 patients provides 80% power to demonstrate noninferiority between the treatment arms. The NIM was determined based on the global PNH Registry for eculizumab-treated patients enrolling into the registry in 2012 or later (Soliris Type II Variation Procedure No. EMEA/H/C/000791/II/66). History of transfusion is a predictor of on-treatment transfusion so to preserve the constancy assumption, the NIM was assessed based on available data from treated and untreated patients in proportion to enrollment expectations in the current study. Patients treated with eculizumab (TA rate of 57.1%) showed a benefit over untreated patients (TA rate of 18.6%) with a difference of approximately 40% (38.5%) after adjustment for history of transfusions 12 months prior to enrollment. The adjustment comes from an expected proportion of patients without a history of transfusions to be no more than 20%. Enrollment of patients for this study is capped at 20% for patients without a history of transfusions to ensure constancy is satisfied.

A traditional choice of NIM is one with ≤50% loss of benefit which gives a NIM of approximately −20%. A more conservative NIM can be used using the lower bound of the 95% CI for the difference in rates, but the resulting estimated sample size makes the study operationally infeasible in light of the rarity of PNH and the paucity of eculizumab-naïve patients with and without a history of transfusions. Further, given the proportion of patients with TA observed in preliminary results from the Phase 1b/2 program, noninferiority can be demonstrated with more conservative NIMs for the given sample size with limited loss of power.

Because the sample size estimate based on LDH-N is smaller than that based on TA (Table 11), the final sample size estimate selected for this study was based on the TA endpoint. Adjusting for a possible 10% dropout rate, approximately 246 patients were enrolled in this study.

TABLE 11

Summary of Parameters Used in Estimating Sample Size with Coprimary Endpoints

| Parameters | LDH Normalization (LDH-N) | Transfusion Avoidance (TA) |
|---|---|---|
| Power | 80% | 80% |
| Type I error | 1-sided 0.025 | 1-sided 0.025 |
| Noninferiority margin | 0.39 | −0.20 |
| Allocation ratio | 1:1 | 1:1 |
| Mean eculizumab response | 0.42[a] | 0.57[b] |
| Standard deviation of eculizumab response | NA | NA |
| Assumed treatment difference | 1 | 0 |
| Estimated sample size (SS) | 142 | 193 |
| Adjusted SS for 10% dropouts | 158 | 214 |

Note:
Software package: Hintze, J. (2011). PASS 11. NCSS, LLC. Kaysville, Utah, US. www.ncss.com.
[a]Response rate from TRIUMPH study adjusted for baseline LDH.
[b]Response rate from Global PNH Registry adjusted for history of transfusion.

Efficacy analyses were performed on the Full Analysis Set (FAS). The coprimary efficacy endpoint analyses, as well as key secondary endpoint analyses, were performed on the Per Protocol (PP) set. The FAS is the primary population for all efficacy analyses. The FAS includes all patients who received at least 1 dose of ALXN1210 or eculizumab and have at least 1 efficacy assessment post first infusion.

The PP set, which is finalized prior to database lock, consists of FAS patients who meet all of the following criteria:
a) Missed no doses of ALXN1210 or no more than 1 dose of eculizumab during the 26-week randomized treatment period
b) Met inclusion criteria #2, 3, and 4
c) Did not meet exclusion criteria #1, 2, 3, or 4
d) Never received the wrong randomized treatment
e) Followed the protocol-specified transfusion guidelines Safety analyses were performed on the Safety Set, defined as all patients who receive at least 1 dose of study drug. Pharmacokinetic and PD analyses were performed on all patients who receive at least 1 dose of study drug and who have evaluable PK and PD data.

Patient demographic and baseline characteristics, including medical history and transfusion history, were summarized by treatment group and overall for the FAS, Safety, and PP sets. No formal statistical comparisons were made.

All patients were included in the summaries of patient disposition, which describe the frequency and percentage of patients screened and treated and who completed or discontinued from the study, along with reason for discontinuation, by treatment group. All patients who discontinue from the study were identified, and the extent of their participation in the study were reported. If known, a reason for their discontinuation is given. The numbers of patients who were treated, discontinue treatment (along with reason for treatment discontinuation), enter the Extension Period, and discontinue the Extension Period (along with reason for discontinuation) were tabulated by treatment group and overall.

Each patient's prior and concomitant medication use were coded using the World Health Organization Drug Dictionary, and the frequency and percentage of concomitant medications is summarized. Medications were summarized by Anatomic-Therapeutic-Chemical (ATC) class and preferred drug name using frequency counts and percentages of patients in the FAS, Safety, and PP sets.

The coprimary efficacy endpoints were 1) the difference between treatment groups in the proportion of patients who achieve TA through Day 183, and 2) the relative effect between treatments in LDH-N from Day 29 through Day 183 expressed as an odds ratio. Transfusion avoidance is achieved only by those patients who did not receive a transfusion and did not meet the protocol-specified guidelines for transfusion. The percentage of patients who achieve TA with 95% CIs is computed at Day 183 for both the ALXN1210 and eculizumab treatment groups and the randomization strata. A difference in the percentage of patients achieving TA in the 2 treatment groups is calculated between ALXN1210 and eculizumab treatment groups, along with a 95% CI for the difference. The difference between the ALXN1210 and eculizumab treatment groups is computed as a weighted combination of the differences between the ALXN1210 and eculizumab treatment groups within stratification groups (using Mantel-Haenszel). The 95% CI for the difference between ALXN1210 and eculizumab treatment groups is calculated using the stratified Newcombe confidence interval method.

LDH-N was analyzed using a generalized estimating equation (GEE) approach which accounts for the repeated measures of LDH-N at each visit (Liang K-Y, et al., Biometrika. 1986; 73(1):13-22). The GEE approach provides odds ratios and CIs of treatment effect while controlling for the correlation between visits for a given patient and other baseline factors. LDH-N from Day 29 through Day 183 is used as the dependent variable and an indicator variable for treatment, history of transfusion (as a categorical variable based on the stratification factor levels), and baseline LDH level (as a continuous variable) is included in the model as explanatory variables. The within-patient correlation assumes a first-order autoregressive structure which assumes the highest correlation is between visits that were closest in time. Day 29 was the first scheduled assessment after initiation of maintenance dosing, and experience with eculizumab and Phase 1b/2 ALXN1210 data demonstrate near maximal suppression of LDH by 4 weeks of treatment. Results from the model were presented as odds ratios with 95% confidence intervals.

In order to conclude ALXN1210 is noninferior to eculizumab, both coprimary endpoints individually needed to demonstrate noninferiority. If the lower-bound of the 95% CI for the difference (ALXN1210-eculizumab) was greater than the NIM of −20% for TA and the lower-bound of the 95% CI for the odds ratio of ALXN1210 compared to eculizumab is greater than the NIM of 0.39 for LDH-N, then ALXN1210 treatment was concluded to be noninferior to eculizumab. If noninferiority is met for both coprimary endpoints and a larger effect for ALXN1210 was observed in either coprimary endpoint, then superiority was assessed using a Hochberg multiple comparison approach.

The 4 key secondary efficacy endpoints were summarized by randomization strata and by treatment group at baseline and at the study visits where these assessments were collected during the 26-week randomized treatment period. Change in FACIT-Fatigue (and percent change in LDH) from baseline to Week 26 is analyzed using a mixed model for repeated measures (MMRM; see, e.g., Mallinckrodt C H, et al., *J. Biopharm. Stat.* 2001; 11:9-21 and Mallinckrodt C H, et al., *Clinical Trials.* 2004; 1:477-489) with the fixed, categorical effects of treatment, the stratification randomization indicators of transfusion history (0, 1 to 14, or >14 units of pRBCs in the 1 year prior to first dose of study drug) and screening LDH levels (1.5 to <3×ULN or ≥3×ULN), study visit and study visit by treatment group interaction, as well as the continuous, fixed covariates of baseline FACIT-Fatigue (or LDH) and baseline FACIT-Fatigue (or LDH)-by-visit interaction as covariates. For percent change in LDH, the baseline LDH level as a continuous variable is included. The Kenward-Roger approximation is used to estimate denominator degrees of freedom. A difference between the ALXN1210 and eculizumab treatment groups along with a 2-sided 95% CI is calculated.

For breakthrough hemolysis and stabilized hemoglobin, the same approach used for TA was employed. These key secondary endpoints were tested in a hierarchical manner provided that noninferiority was declared for the coprimary endpoints. If noninferiority was established for a key secondary endpoint and a larger effect for ALXN1210 is observed, then superiority was assessed using a 2-sided 0.05 test for each parameter.

When performing the analyses for the key secondary efficacy endpoints, a closed-testing procedure was used so that the lack of significance of a test precludes assessment of subsequent tests. Estimates and CIs were computed for all these key secondary efficacy endpoints irrespective of whether a lack of significance of a test precludes assessment of subsequent tests. If the upper bound of the 95% CI for the difference between the ALXN1210 and eculizumab treatment groups in the percentage change from Baseline to Week 26 in LDH was less than the NIM of 20%, then ALXN1210 was declared noninferior for this parameter and the next parameter was tested. If the lower bound of the 95% CI for the difference between the ALXN1210 and eculizumab treatment groups in change from baseline in FACIT-Fatigue was greater than the NIM of −5, then ALXN1210 was declared noninferior for this parameter and the next parameter was tested. If the upper bound of the 95% CI for the difference between the ALXN1210 and eculizumab treatment groups in the proportion of patients with breakthrough hemolysis was less than the NIM of 20%, then ALXN1210 was declared noninferior for this parameter and the next parameter is tested. If the lower bound of the 95% CI for the difference between the ALXN1210 and eculizumab treatment groups in the proportion of patients with stabilized hemoglobin was greater than the NIM of −20%, then ALXN1210 was declared noninferior for this parameter. Due to the hierarchical testing order being prespecified, no adjustment of the type I error was required.

Changes from baseline in EORTC-QLQ-C30 were summarized by treatment group at baseline and at the study visits where these assessments were collected. Shifts from baseline in clinical manifestations of PNH were summarized by treatment group and at the study visits where these assessments were collected. The number of any treatment-emergent MAVEs (n) and number of patients with events (n, %) were displayed by treatment group. Total number of units of pRBCs transfused during treatment were summarized by treatment group. Kaplan-Meier curves for both treatment groups and estimates of time to first occurrence of LDH-N since first study drug were produced. No statistical inference of these parameters is planned.

All safety analyses were performed for the Safety set, defined as all patients who received at least 1 dose of ALXN1210 or eculizumab. Up to Day 183, safety results were reported by treatment group.

The following definitions were used for AEs:
a) Pretreatment adverse events: Any AE that starts after providing informed consent, but before the first infusion of study drug
b) Treatment-emergent adverse event: Any AE that starts during or after the first infusion of study drug.
c) Treatment-emergent SAE: A treatment-emergent AE (TEAE) that is serious. The incidence of TEAEs, discontinuations due to TEAEs, drug-related TEAEs, TEAEs during study drug administration, severe TEAEs, and SAEs were summarized. All AEs were coded using MedDRA version 18 or higher, and were summarized by system organ class (SOC) and PT. Detailed by-patient listings of TEAEs, SAEs, TEAEs, related TEAEs, TEAEs during study drug administration, and discontinuations due to TEAEs were provided. Adverse changes from Baseline in physical examination findings were classified as AEs and analyzed accordingly.

Vital signs were summarized descriptively at Baseline and postbaseline time points and for changes from Baseline by treatment group. By-patient data listings were provided. Changes in clinical chemistry, hematology, and urinalysis results from Baseline to post-baseline study time points were summarized descriptively by treatment group. Shift tables over time were presented for all central laboratory values, where applicable, using grading criteria from CTCAE v4.03. Listings of patients with abnormal results were provided.

By-patient data listings of ECG parameters were provided. Changes from baseline in electrocardiogram intervals (PR, RR, QT, and QTcF) were provided by treatment group. QT interval is corrected for heart rate using Fridericia's formula (QTcF).

Abnormal immunogenicity findings, including the incidence and titers for ADAs to ALXN1210 or eculizumab, was summarized in tabular format by treatment group. The proportion of patients ever positive and the proportion of patients always negative was explored.

Individual serum concentration data for all patients who received at least 1 dose of study drug (i.e., ALXN1210 or eculizumab) and who had evaluable PK data were used to derive PK parameters for ALXN1210 and eculizumab. Graphs of mean serum concentration-time profiles were constructed. Graphs of serum concentration-time profiles for individual patients were also provided. Actual dose administration and sampling times was used for all calculations. Descriptive statistics were calculated for serum concentration data at each sampling time, as appropriate. Assessment of population-PK was considered using data from this study or in combination with data from other studies.

PD analyses was performed for all patients who received at least 1 dose of ALXN1210 or eculizumab and who have evaluable PD data. Descriptive statistics were presented for all ALXN1210 and eculizumab PD endpoints at each sampling time. The PD effects of ALXN1210 and eculizumab administered IV were evaluated by assessing the absolute values and changes and percentage changes from baseline in total and free C5 serum concentrations and cRBC hemolysis over time, as appropriate.

Example 2: Results from Phase 3, Randomized, Open-Label, Active-Controlled Study of ALXN1210 (Ravulizumab) Versus Eculizumab in Complement Inhibitor-Naïve Adult Patients with PNH The following is a summary of data obtained from an ongoing open-label, phase 3 clinical study conducted according to the protocol described above in Example 1. A summary of the efficacy and safety results are presented below.

1. Summary of Trial

This phase III human clinical trial was a randomized open label active controlled study comparing non-inferiority of ALXN1210 versus Soliris® (eculizumab) in adult patients with PNH patients who were naïve to treatment with a complement inhibitor. The study enrolled 246 patients in total. A total of 244 patients completed the study and were included in this per-protocol analysis. Only 2 subjects discontinued during the course of the study.

This phase III study met its primary objective and demonstrated that ALXN1210 (ravulizumab) was noninferior to Soliris® (eculizumab). Specifically, the study met the pre-designated non-inferiority margins (NIM) for LDH normalization (LDH-N) and transfusion avoidance (TA) by better than the 10% margins required by the FDA. In addition, the TA endpoint achieved NIM of less than 5%. In addition, all 4 key secondary endpoints favored ALXN1210 and demonstrated non-inferiority to Soliris® (eculizumab). Breakthrough hemolysis (BTH) also demonstrated a numerical trend favoring ravulizumab to eculizumab by 4% versus 10.7% respectively, but did not quite achieve tab in this study (p<0.074). The incidence of breakthrough hemolysis was more than 2-fold higher in the Soliris® group than in the ALXN1210 group and the difference was associated with suboptimal C5 inhibition in the Soliris® group, suggesting that AXLN1210 reduces a patient's risk of breakthrough hemolysis through constant complete C5 inhibition.

In sum, Ravulizumab was statistically significantly non-inferior to eculizumab for both coprimary and all key secondary endpoints: transfusion avoidance (73.6% versus 66.1%; difference of 6.8% [95% CI, −4.7, 18.1]), LDH normalization (53.6% versus 49.4%, odds ratio [1.19 (0.80, 1.77)]), percent reduction in LDH (76.8% versus 76.0%; difference [95% CI], −0.83% [−5.2, 3.6]), change in FACIT-Fatigue score (7.1 versus 6.4; difference [95% CI], 0.67 [−1.2, 2.6]), breakthrough hemolysis (4.0% versus 10.7%; difference [95% CI], −6.7% [−14.21, 0.18]), and stabilized hemoglobin (68.0% versus 64.5%; difference [95% CI], 2.9 [−8.8, 14.6]). Importantly, the sensitivity analysis demonstrated robust results on all efficacy endpoints. The data is presented in the attached Figures and Tables and discussed more fully below.

The design of the non-inferiority study comparing ALXN1210 and eculizumab is shown in FIG. 1. The study compares a personalized weight based dosing scheme for ALXN1210 to the existing approved dosing scheme for eculizumab in PNH in an attempt to show non-inferiority in PNH patients naïve to treatment with a complement inhibitor. The dose chosen for ALXN1210 is weight based and comprises a loading dose (2400 mg for patients ≥40 kg to <60 kg, 2700 mg for patients ≥60 kg to <100 kg, 3000 mg for patients ≥100 kg) on day 1, followed by maintenance doses of ALXN1210 (3000 mg for patients ≥40 kg to <60 kg, 3300 mg for patients ≥60 to <100 kg, 3600 mg for patients ≥100 kg) on day 15 and q8w thereafter. See FIG. 1. In contrast, the eculizumab dose comprises four 600 mg inductions doses on days 1, 8, 15 and 22, followed by a maintenance dose of 900 mg administered IV on day 29 and every 2 weeks thereafter. See FIG. 1.

Figure 2:
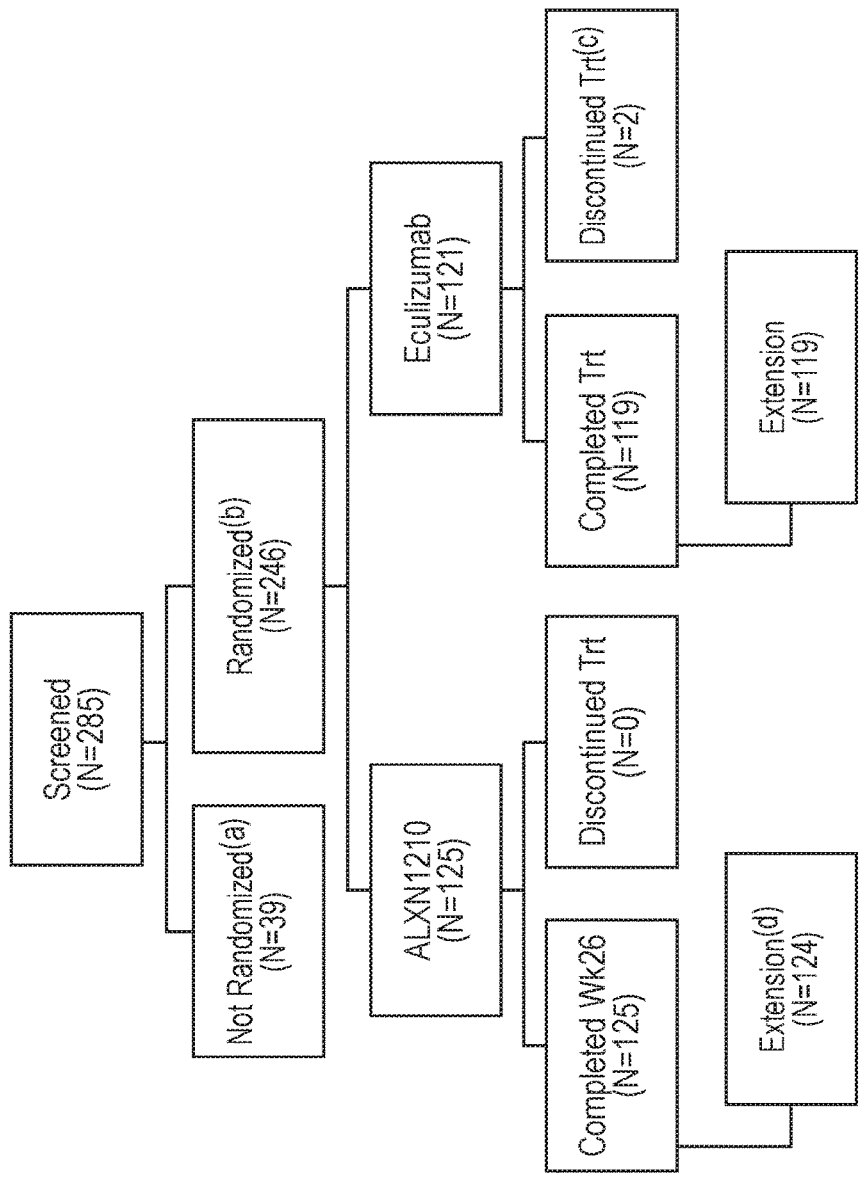
FIG. 2 is a schematic showing the disposition of patients in Phase III ALXN1210-PNH-301.

The study enrolled more patients than originally planned. Specifically, 246 patients enrolled in the study and were randomized to either the ALXN1210 group or the eculizumab group. See FIG. 2. A total of 39 subjects failed the screening. Of the 246 patients to enter and complete the 26 week treatment period, 243 proceeded into the ongoing extension study. See FIG. 2. The baseline characteristics and demographics of the study population are shown in FIG. 3.

All 246 treated patients (125 patients in the ALXN1210 group and 121 patients in the eculizumab group) were included in the FAS and Safety Set, as set forth in Table 12. Two patients were excluded from the PP Set. One patient in the ALXN1210 group and 1 patient in the eculizumab group met the protocol-specified criteria for pRBC transfusion (hemoglobin <7 g/dL) but were not transfused at that time or at any other time during the Primary Evaluation Period. Although other patients met the transfusion criteria at a particular visit but did not receive a transfusion, these patients were included in the PP Set because they received at least 1 transfusion according to the transfusion criteria.

TABLE 12

Analysis Data Sets (All Randomized Patients)

|  | ALXN1210 n (%) | Eculizumab n (%) | Total n (%) |
|---|---|---|---|
| Number of randomized patients | 125 (100) | 121 (100) | 246 (100) |
| Number of patients in the FAS | 125 (100) | 121 (100) | 246 (100) |
| Number of patients excluded from the FAS | 0 | 0 | 0 |
| Number of patients in the PP Set | 124 (99.2) | 120 (99.2) | 244 (99.2) |
| Number of patients excluded from the PP Set | 1 (0.8) | 1 (0.8) | 2 (0.8) |
| Number of patients in the Safety Set | 125 (100) | 121 (100) | 246 (100) |
| Number of patients excluded from the Safety Set | 0 | 0 | 0 |
| Number of patients in the PK Analysis Set | 125 (100) | 121 (100) | 246 (100) |
| Number of patients excluded from the PK Analysis Set | 0 | 0 | 0 |

Abbreviations: FAS = Full Analysis Set; PP = Per Protocol

There were no differences in the actual stratification at the time of randomization compared to the observed stratification for the LDH groups (LDH 1.5 to <3×ULN versus LDH ≥3×ULN) (see Table 13). Of the 44 patients stratified to 0 unit of pRBCs, 1 patient was observed to have received 1 to 14 unit(s) of pRBCs. Of the 157 patients stratified to 1 to 14 unit(s) of pRBCs, 3 patients were observed to have received >14 units of pRBCs. Of the 45 patients stratified to >14 units unit of pRBCs, 1 patient was observed to have received 1 to 14 unit(s) of pRBCs.

TABLE 13

Stratification Groups at Randomization and Observed (Full Analysis Set)

| Variable | ALXN1210 (N = 125) | Eculizumab (N = 121) | Total (N = 246) |
|---|---|---|---|
| LDH stratification groups at Randomization, n (%) | | | |
| 1.5 to <3 × ULN | 18 (14.4) | 16 (13.2) | 34 (13.8) |
| ≥3 × ULN | 107 (85.6) | 105 (86.8) | 212 (86.2) |
| LDH observed stratification groups, n (%) | | | |
| 1.5 to <3 × ULN | 18 (14.4) | 16 (13.2) | 34 (13.8) |
| ≥3 × ULN | 107 (85.6) | 105 (86.8) | 212 (86.2) |
| pRBC stratification groups at Randomization, n (%) | | | |
| 0 unit | 23 (18.4) | 21 (17.4) | 44 (17.9) |
| 1-14 units | 79 (63.2) | 78 (64.5) | 157 (63.8) |
| >14 units | 23 (18.4) | 22 (18.2) | 45 (18.3) |
| pRBC observed stratification groups, n (%) | | | |
| 0 unit | 22 (17.6) | 21 (17.4) | 43 (17.5) |
| 1 to 14 units | 80 (64.0) | 76 (62.8) | 156 (63.4) |
| >14 units | 23 (18.4) | 24 (19.8) | 47 (19.1) |
| Overall stratification groupings at Randomization, n (%) | | | |
| pRBC = 0 unit and LDH = 1.5 to <3 × ULN | 9 (7.2) | 8 (6.6) | 17 (6.9) |
| pRBC = 1 to 14 units and LDH = 1.5 to <3 × ULN | 6 (4.8) | 6 (5.0) | 12 (4.9) |
| pRBC > 14 units and LDH = 1.5 to <3 × ULN | 3 (2.4) | 2 (1.7) | 5 (2.0) |
| pRBC = 0 unit and LDH ≥ 3 × ULN | 14 (11.2) | 13 (10.7) | 27 (11.0) |
| pRBC = 1 to 14 units and LDH ≥ 3 × ULN | 73 (58.4) | 72 (59.5) | 145 (58.9) |
| pRBC > 14 units and LDH ≥ 3 × ULN | 20 (16.0) | 20 (16.5) | 40 (16.3) |
| Overall observed stratification groupings, n (%) | | | |
| pRBC = 0 unit and LDH = 1.5 to <3 × ULN | 8 (6.4) | 8 (6.6) | 16 (6.5) |

TABLE 13-continued

Stratification Groups at Randomization and Observed (Full Analysis Set)

| Variable | ALXN1210 (N = 125) | Eculizumab (N = 121) | Total (N = 246) |
|---|---|---|---|
| pRBC = 1 to 14 units and LDH = 1.5 to <3 × ULN | 7 (5.6) | 6 (5.0) | 13 (5.3) |
| pRBC > 14 units and LDH = 1.5 to <3 × ULN | 3 (2.4) | 2 (1.7) | 5 (2.0) |
| pRBC = 0 unit and LDH ≥ 3 × ULN | 14 (11.2) | 13 (10.7) | 27 (11.0) |
| pRBC = 1 to 14 units and LDH ≥ 3 × ULN | 73 (58.4) | 70 (57.9) | 143 (58.1) |
| pRBC > 14 units and LDH ≥ 3 × ULN | 20 (16.0) | 22 (18.2) | 42 (17.1) |

Note:
Baseline was defined as the last non-missing value prior to first dose of study drug. The ULN for LDH is 246 U/L.
Abbreviations: LDH = lactate dehydrogenase;
pRBC = packed red blood cells;
ULN = upper limit of normal The baseline disease characteristics were similar between the 2 treatment groups (Table 14). In the total population, the mean time from PNH diagnosis to informed consent was 6.6 years (median=3.9 years).

All patients had PNH diagnosis confirmed by flow cytometry at Screening. The mean total PNH RBC clone size was 38.57%; mean total PNH granulocyte clone size was 84.74%, and the mean total PNH monocyte clone size was 87.99%.

TABLE 14

Disease Characteristics (Full Analysis Set)

| Variable Category | ALXN1210 (N = 125) | Eculizumab (N = 121) | Total (N = 246) |
|---|---|---|---|
| Age (years) at PNH diagnosis | | | |
| n | 123 | 118 | 241 |
| Mean (SD) | 37.9 (14.90) | 39.6 (16.65) | 38.7 (15.77) |
| Median | 34.0 | 36.5 | 35.0 |
| Min, Max | 15, 81 | 13, 82 | 13, 82 |
| Method of initial PNH diagnosis, n (%) | | | |
| Flow cytometry | 94 (75.2) | 96 (79.3) | 190 (77.2) |
| Ham's test | 10 (8.0) | 5 (4.1) | 15 (6.1) |
| Sucrose hemolysis test | 0 (0.0) | 2 (1.7) | 2 (0.8) |
| Other[a] | 21 (16.8) | 18 (14.9) | 39 (15.9) |
| Years from diagnosis to informed consent | | | |
| n | 123 | 118 | 241 |
| Mean (SD) | 6.7 (8.14) | 6.4 (7.54) | 6.6 (7.84) |
| Median | 3.8 | 3.9 | 3.9 |
| Min, max | 0, 41 | 0, 34 | 0, 41 |
| PNH clone size at baseline PNH RBC type II clone size (%) | | | |
| n | 124 | 120 | 244 |
| Mean (SD) | 12.36 (20.539) | 13.70 (17.672) | 13.02 (19.155) |
| Median | 4.00 | 6.15 | 5.00 |
| Min, max | 0.1, 99.5 | 0.1, 95.3 | 0.1, 99.5 |
| PNH RBC type III clone size (%) | | | |
| n | 124 | 120 | 244 |
| Mean (SD) | 26.29 (17.246) | 25.21 (16.944) | 25.76 (17.071) |
| Median | 26.35 | 21.20 | 24.10 |
| Min, max | 0.1, 82.0 | 0.4, 75.6 | 0.1, 82.0 |
| Total PNH RBC | | | |

TABLE 14-continued

Disease Characteristics (Full Analysis Set)

| Variable Category | ALXN1210 (N = 125) | Eculizumab (N = 121) | Total (N = 246) |
|---|---|---|---|
| clone size (%) | | | |
| n | 125 | 121 | 246 |
| Mean (SD) | 38.40 (23.748) | 38.74 (23.194) | 38.57 (23.430) |
| Median | 33.60 | 34.20 | 33.75 |
| Min, max | 3.0, 99.6 | 2.2, 98.0 | 2.2, 99.6 |
| Total PNH granulocyte clone size (%) | | | |
| n | 125 | 121 | 246 |
| Mean (SD) | 84.22 (20.956) | 85.28 (18.977) | 84.74 (19.973) |
| Median | 93.80 | 92.40 | 92.55 |
| Min, max | 4.2, 99.9 | 8.0, 100.0 | 4.2, 100.0 |
| Total PNH monocyte clone size (%) | | | |
| n | 125 | 121 | 246 |
| Mean (SD) | 86.86 (18.078) | 89.15 (15.189) | 87.99 (16.725) |
| Median | 94.00 | 95.10 | 94.80 |
| Min, max | 8.5, 99.9 | 17.0, 99.9 | 8.5, 99.9 |

Note:
Total RBC, Granulocyte, Monocyte Clone Size = Sum Type II and Type III RBC, Granulocyte, Monocyte clone size, respectively. Baseline was defined as the last non-missing value prior to first dose of study drug.
*"Other" category included Coombs test, Flaer test, clinical signs/symptoms (ie, clinical data, presentation, or diagnosis), immunophenotyping, combination of methods used for diagnosis, osmotic fragility test, diagnosed at another hospital, and unknown.
Abbreviations: max = maximum;
min = minimum;
SD = standard deviation;
PNH = paroxysmal nocturnal hemoglobinuria;
RBC = red blood cell Enrollment into the 0 prior units of RBCs stratum was closed once the protocol-specified 20% cap on enrollment of patients with a history of no transfusions in the prior year was reached. Therefore, the majority of patients (82.5%) had a history of pRBC transfusions in the year prior to first dose of study drug, as set forth in Table 15. In the total population, a mean of 6.2 pRBC/whole blood transfusions were administered and a mean of 8.8 units were transfused during the 12 months prior to first dose. The number of transfusions and number of units transfused were similar between the 2 treatment groups.

TABLE 15

Red Blood Cell Transfusions within 12 Months Prior to First Dose (Full Analysis Set)

| Variable Category | ALXN1210 (N = 125) | Eculizumab (N = 121) | Total (N = 246) |
|---|---|---|---|
| Number of patients with pRBC/whole blood transfusions within 12 months prior to first dose, n (%) | 103 (82.4) | 100 (82.6) | 203 (82.5) |
| pRBC/whole blood transfusions within 12 months prior to first dose | | | |
| Total | 677 | 572 | 1249 |
| Mean (SD) | 6.6 (6.04) | 5.7 (5.53) | 6.2 (5.80) |
| Median | 4.0 | 3.0 | 4.0 |
| Min, Max | 1, 28 | 1, 28 | 1, 28 |
| Units of pRBC/whole blood transfused within 12 months prior to first dose | | | |
| Total | 925 | 861 | 1786 |
| Mean (SD) | 9.0 (7.74) | 8.6 (7.90) | 8.8 (7.81) |
| Median | 6.0 | 6.0 | 6.0 |
| Min, Max | 1, 44 | 1, 32 | 1, 44 |

Abbreviations: max = maximum;
min = minimum;
pRBC = packed red blood cells;
SD = standard deviation As required by the protocol, all patients had at least 1 PNH-associated symptom at baseline. The types of PNH symptoms that patients experienced prior to informed consent were similar between the treatment groups, with the most common (>20% of all patients) being fatigue or asthenia (generalized weakness), red or dark urine, shortness of breath (dyspnea), jaundice (yellowing of skin or eyes), abdominal pain, and CNS-related symptoms such as headache, dizziness, or difficulty concentrating.

In the total population, 98.0% of patients had documented PNH-associated conditions that were diagnosed prior to informed consent, as shown in Table 16. The majority (84.6%) of patients had a prior diagnosis of anemia; 32.1% of patients had aplastic anemia, 12.2% of patients had a history of renal failure, and 5.3% of patients had myelodysplastic syndrome.

TABLE 16

PNH-Associated Conditions Diagnosed at Any Time
Prior to Informed Consent (Full Analysis Set)

| PNH-Associated Conditions, n (%) | ALXN1210 (N = 125) | Eculizumab (N = 121) | Total (N = 246) |
|---|---|---|---|
| Patients with any PNH conditions prior to informed consent | 121 (96.8) | 120 (99.2) | 241 (98.0) |
| Anemia | 103 (82.4) | 105 (86.8) | 208 (84.6) |
| Hematuria or hemoglobinuria | 81 (64.8) | 75 (62.0) | 156 (63.4) |
| Aplastic anemia | 41 (32.8) | 38 (31.4) | 79 (32.1) |
| Renal failure | 19 (15.2) | 11 (9.1) | 30 (12.2) |
| Myelodysplastic syndrome | 7 (5.6) | 6 (5.0) | 13 (5.3) |
| Pregnancy complication | 3 (2.4) | 4 (3.3) | 7 (2.8) |
| Other[a] | 27 (21.6) | 13 (10.7) | 40 (16.3) |

Note:
Patients could have been counted in more than one category.
[a]"Other" category included the most commonly (n ≥ 2) reported conditions in the "other" category also had a history of at least 1 other PNH-associated condition included thrombocytopenia (n = 5), chronic kidney disease (n = 4), pancytopenia (n = 3), AST increased (n = 2), renal parenchymal disease (n = 2), leukopenia/thrombocytopenia (n = 2), gallstones (n = 2), and 1 patient each reported a history of hepatosplenomegaly, myeloid and megakaryocytic hypoplasia, hemolitic event, hypocellular bone marrow, pancytopenia, marrow hypoplasia, signs of hemolysis, chronic hemolysis, bilateral renal parenchymal disease/hypokalaemia, suspected aplastic anemia, miscarriage, ischemic stroke/chronic kidney disease, marrow hyperplasy, thrombocytopenia/epistaxis, increased bilirubin, bone marrow aplasia, or leukopenia/thrombocytopenia/splenectomy
Abbreviation: PNH = paroxysmal nocturnal hemoglobinuria All 246 patients had a history of prior medication use. All patients received meningococcal vaccine no later than Day 1. The most commonly reported (>10% of patients) groupings of prior medications other than meningococcal vaccine were vitamin B12 and folic acid (52.8%), antithrombotic agents (29.7%), corticosteroids for systemic use (24.8%), drugs for peptic ulcer and gastro-esophageal reflux disease (22.8%), iron preparations (15.4%), beta-lactam antibacterials (penicillins) (15.0%), antihistamines for systemic use (13.0%), selective calcium channel blockers with mainly vascular effects (11.4%), and other analgesics and antipyretics (11.0%).

Overall, 95.9% of patients (98.4% in the ALXN1210 group and 93.4% in the eculizumab group) took at least one concomitant medication. The most commonly reported (≥10% of patients) groupings of concomitant medications were vitamin B12 and folic acid (54.9%), other analgesics and antipyretics (38.6%), beta-lactam antibacterials (penicillins) (38.6%), antithrombotic agents (31.3%), drugs for peptic ulcer and gastro-esophageal reflux disease (29.3%), quinolone antibacterials (26.0%), antihistamines for systemic use (24.8%), corticosteroids for systemic use (24.4%), anti-inflammatory and antirheumatic products (21.1%), iron preparations (17.1%), other beta-lactam antibacterials (13.0%), expectorants excluding combinations with cough suppressants (11.4%), selective calcium channel blockers with mainly vascular events (12.6%) and immunosuppressants (10.2%). During the study, a total of 30.9% patients underwent a nonpharmacologic medical procedure.

2. Primary/Secondary Endpoints and Disease-Related Parameters

Figure 4:
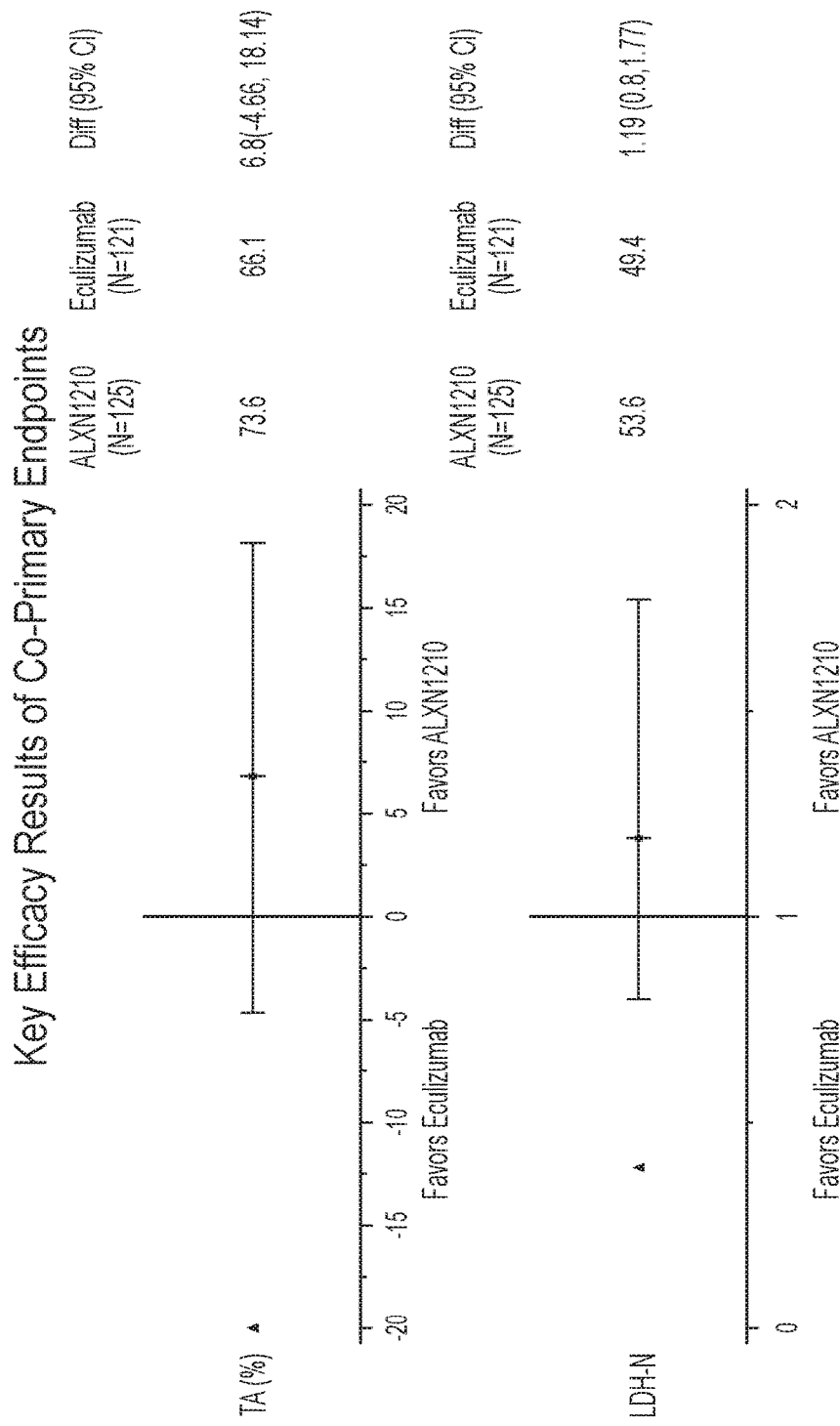
FIG. 4 is a graphical schematic showing the key efficacy results of the two co-primary endpoints.

The two co-primary efficacy endpoints of transfusion avoidance (TA) and LDH normalization (LDH-N) were very clearly met and exceeded as shown in FIG. 4. The red triangle in FIG. 4 indicates the non-inferiority margin required by the FDA. For both the TA and LDH-N endpoints, the 20% non-inferiority margins were exceeded substantially. In fact, the TA endpoint didn't just meet the 20% margin, it met a 5% margin. Likewise, the LDH-N exceeded the 20% margin and further met the equivalent of a 10% margin. See FIG. 4.

Figure 5:
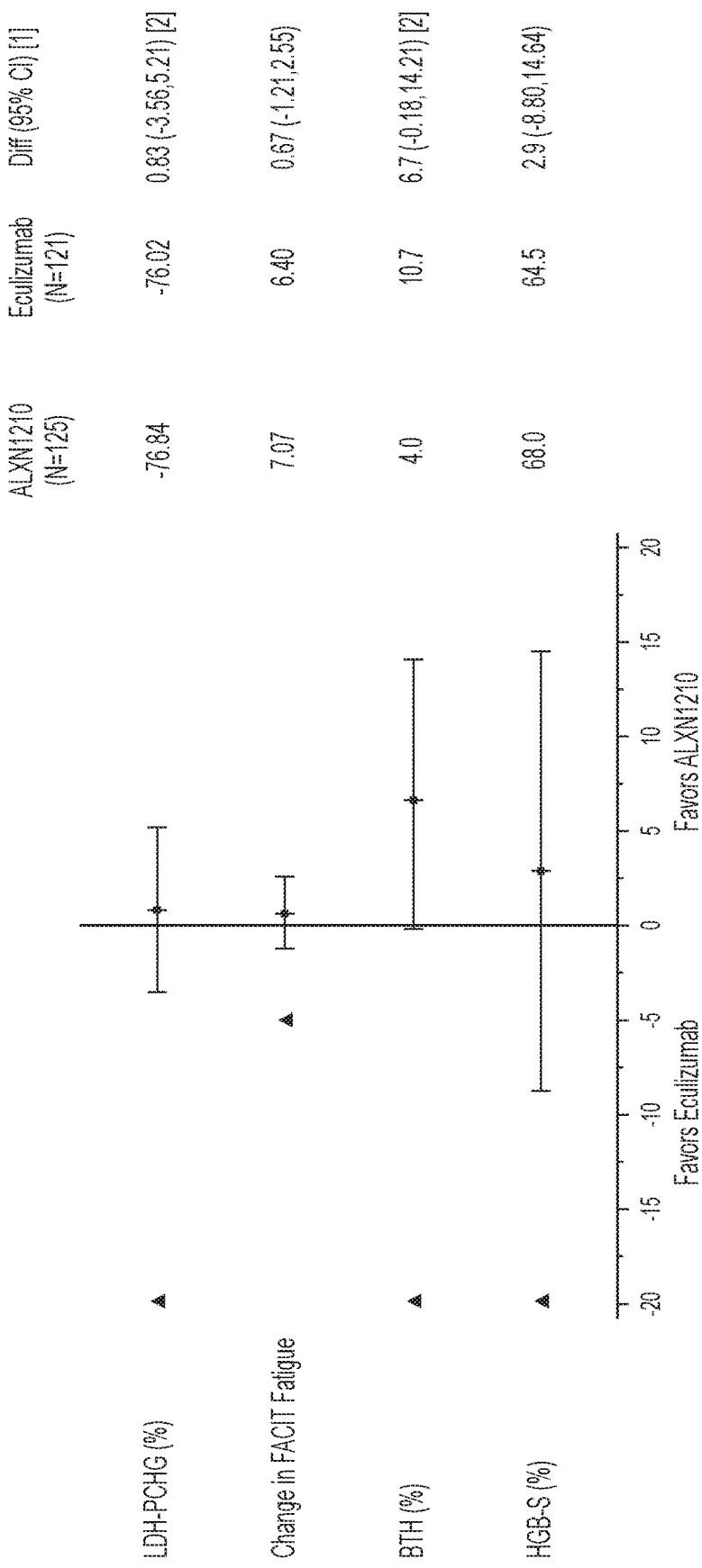
FIG. 5 is a graphical display of the key secondary endpoints showing that all endpoints favor ravulizumab (ALXN1210) and exceeded the non-inferiority margins shown by the red triangles in the graph.

The key secondary endpoints LDH percent change (LDH-PCHG), change in FACIT fatigue score, breakthrough hemoloysis (BTH) and hemoglobin stabilization (HGB-S) were also positive and favored ALXN1210 over eculizumab. See FIG. 5. Moreover, not only did all the secondary endpoints favor ALXN1210, but they all substantially exceeded the non-inferiority margins shown by the red triangles in the graph. See FIG. 5.

The key primary and secondary endpoints are tabulated in FIG. 6. Also shown is the treatment effect for each endpoint in favor of ALXN1210 over that for eculizumab. For example the first row shows the treatment effect for transfusion avoidance for ALXN120 over eculizumab was 6.8%, much greater than the −20% required non-inferior margin and renders a finding of non-inferior. Likewise, all the primary and secondary endpoints led to the same conclusion of non-inferior for ALXN1210 over eculizumab. Stated another way, ALXN1210 was found to be better than eculizumab, but the sample size was insufficient to reach a statistical conclusion of superior. See FIG. 6.

The efficacy data from this study was subjected to multiple different sensitivity analyses. The results are shown in FIG. 7. For example, the treatment effect (point estimate) for 1210 was 6.8% better than for eculizumab, with a 95% confidence intervals (CI) of −4.7% to 18.1%. The −4.7% number is substantially better that the predefined non-inferiority margin of −20%. This table shows a variety of sensitivity analysis, which all support the robust finding of the primary analysis. It is worth noting that this consistency is unusual for a clinical trial of this type and supports the idea that this study was conducted with very high quality.

Figure 8:
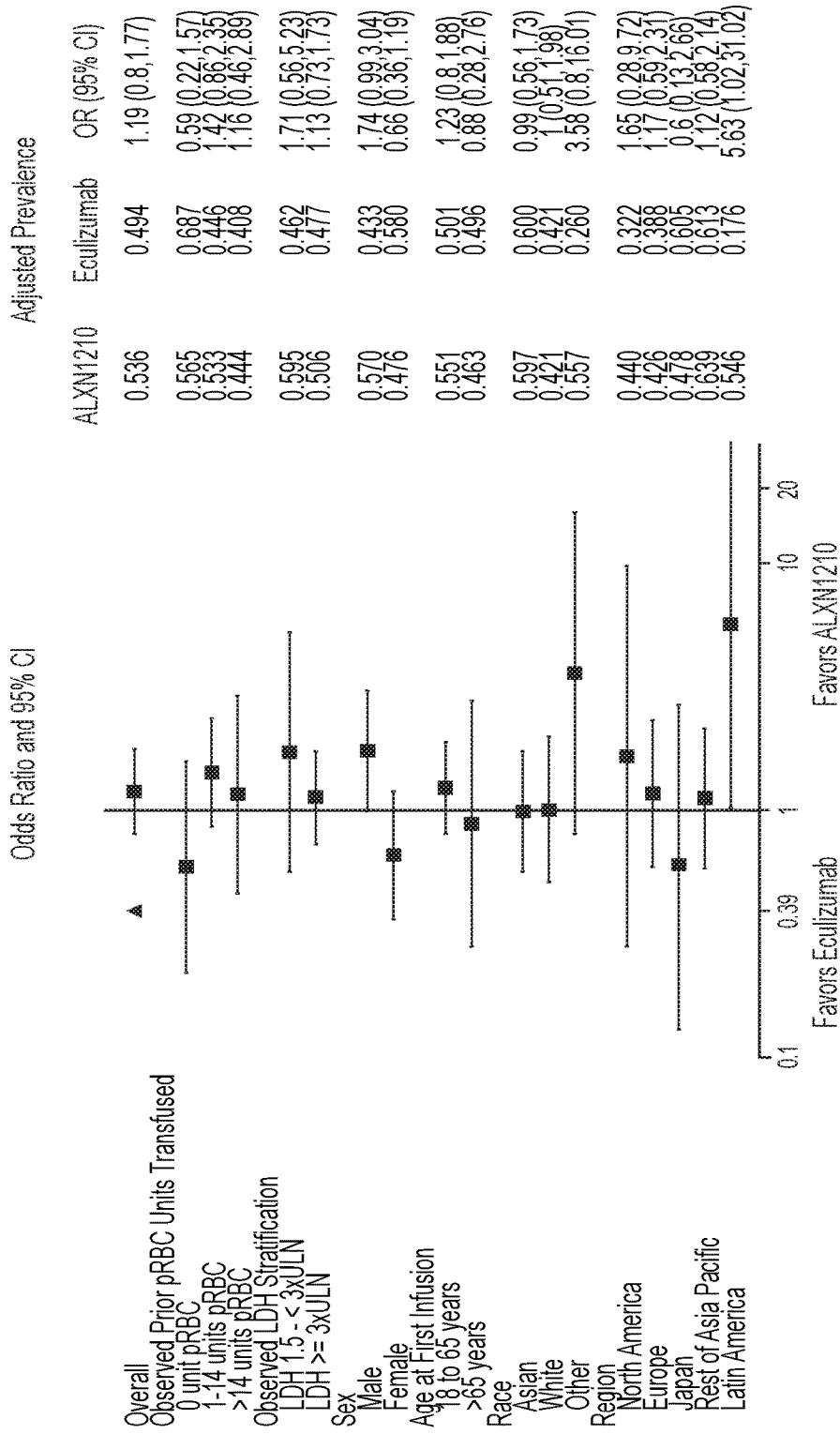
FIG. 8 is a graphical schematic showing subgroup favorability for ravulizumab (ALXN1210) versus eculizumab.

The efficacy results for the LDH-N primary endpoint were analyzed as subgroups of the patient population and are shown in FIG. 8. LDH-N (lactate dehydrogenase normalization) refers to LDH levels less than or equal to 1×ULN, from Day 29 through Day 183. Subgroup analyses for LDH-N revealed that the preponderance of evidence favored ALXN1210. Grey lines are 95% confidence intervals and blue squares are point estimates. Estimation was based on a generalized estimating equation (GEE) approach. The model included the following terms: treatment group, history of transfusion and baseline LDH levels. Estimates to the right of 1 favor ALXN1210 and estimates to the left favor eculizumab. All point estimates were to right of the pre-defined non inferiority margin (red triangle) (−20%) There were only 3 endpoints that favored eculizumab that didn't, and two of those had small sample sizes. In conclusion, most of the subgroups clearly favored ALXN1210 over eculizumab. See FIG. 8.

Figure 9:
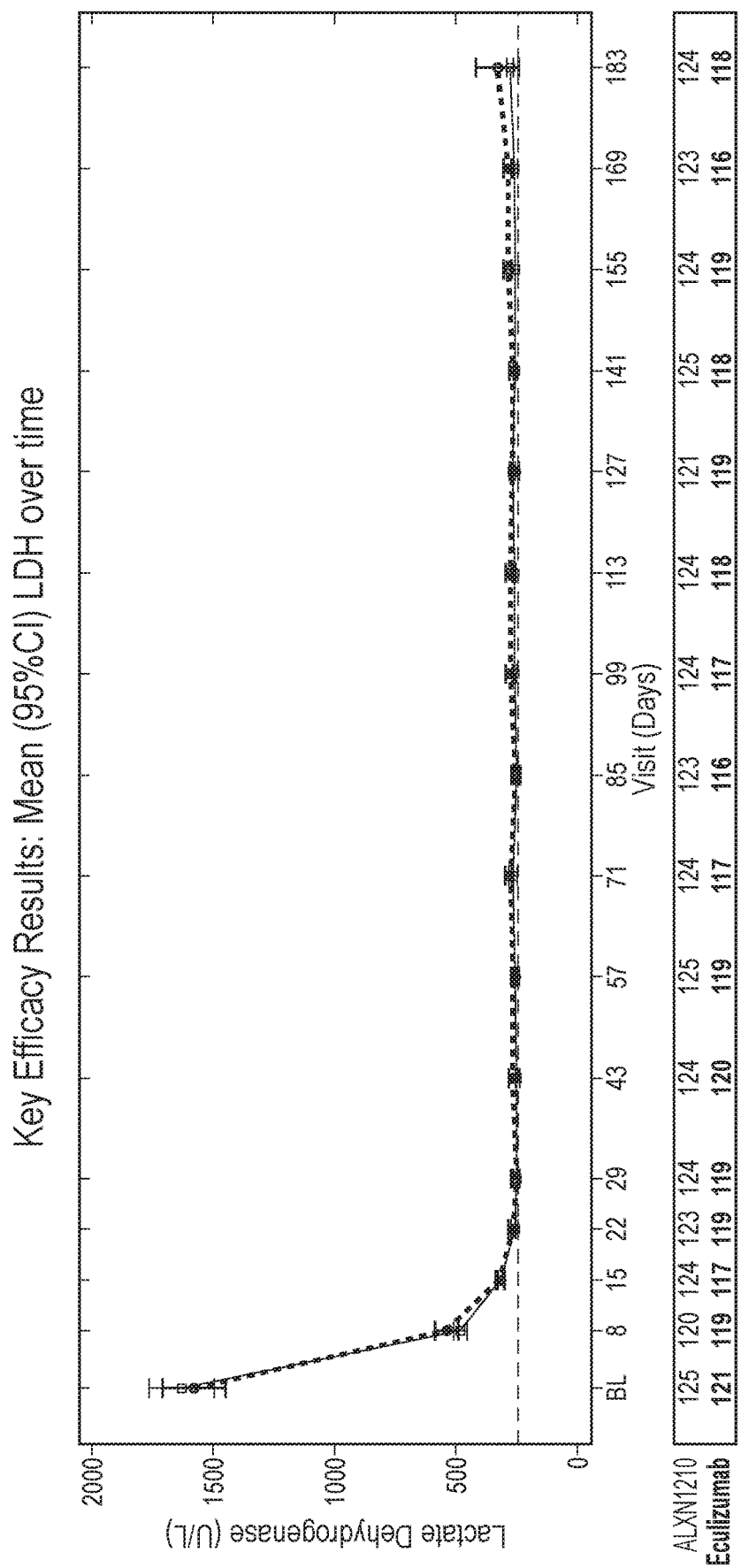
FIG. 9 is a graphical display of LDH levels over time for patients treated with either ravulizumab (ALXN1210) or eculizumab.

As shown in FIG. 9, the mean values for LDH were normalized in the patient population to the upper limit of normal (1×ULN LDH) by about day 22 to day 24 and remained at that level throughout the study. The dotted line in FIG. 9 shows the value of the upper limit of normal for LDH or 1×ULN LDH. The box below the graph shows the number of patients in each group that contributed to the mean on that day. In conclusion, it is clear the mean value of LDH in patients on ALXN1210 remained below the critical level of 1.5×ULN. See FIG. 9.

Figure 10:
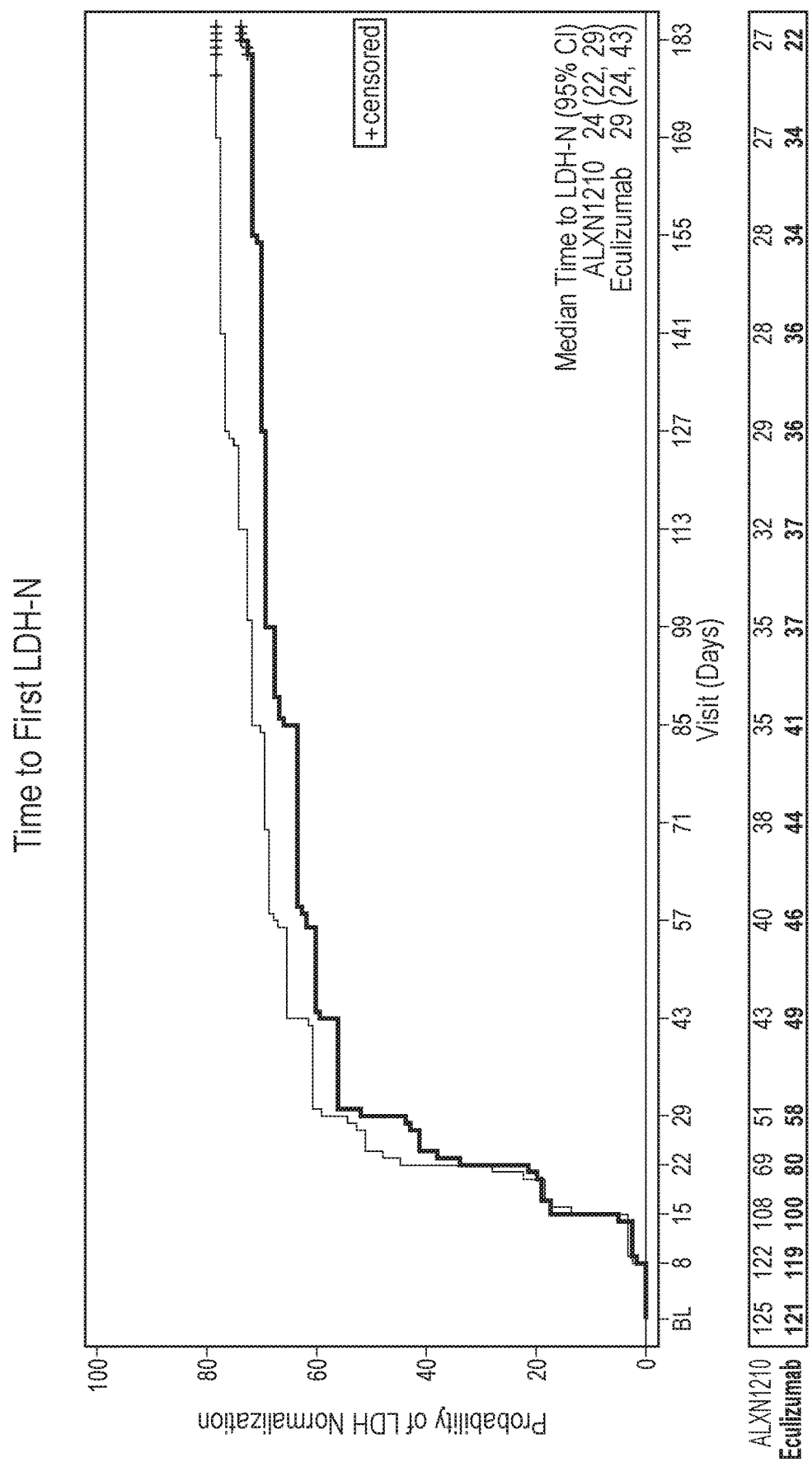
FIG. 10 is a graphical display of the time to reach normalization of LDH (LDH-N) for patients treated with either ravulizumab (ALXN1210) or eculizumab.

The time to reach LDH normalization is shown in FIG. 10 for both ALXN1210 and eculizumab treated groups. Patients on ALXN1210 reached normalization about 5 days sooner than patients on eculizumab. See FIG. 10. The mean of ALXN120 patients reached normalization by day 24 versus day 29 for patients treated with eculizumab. The box with numbers under the graph shows the number of patients of each group used to calculate the mean on that day. See FIG. 10.

Figure 11:
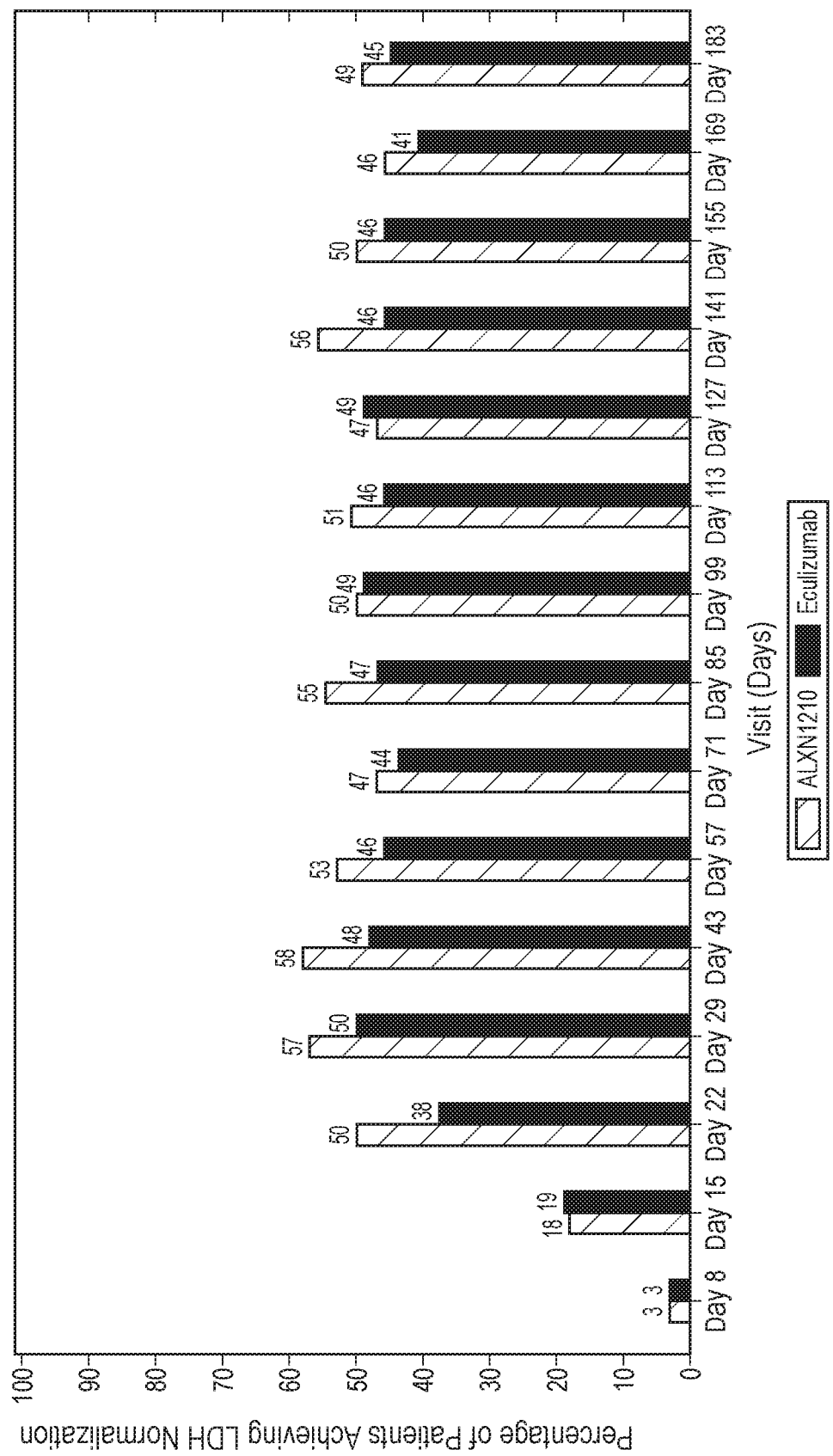
FIG. 11 is a graphical display of the percentage of patients achieving normalized LDH on ravulizumab (ALXN1210) or eculizumab at various time points from day 8 to day 183.

The percentage of patients achieving LDH normalization at various time points during the course of the study is shown in FIG. 11. Generally, more than 50% of ALXN1210 patients stayed in the normal range throughout the study, while less than 50% of eculizumab treated patients remained in the normal range during the study and through day 183. See FIG. 11.

Figure 12:
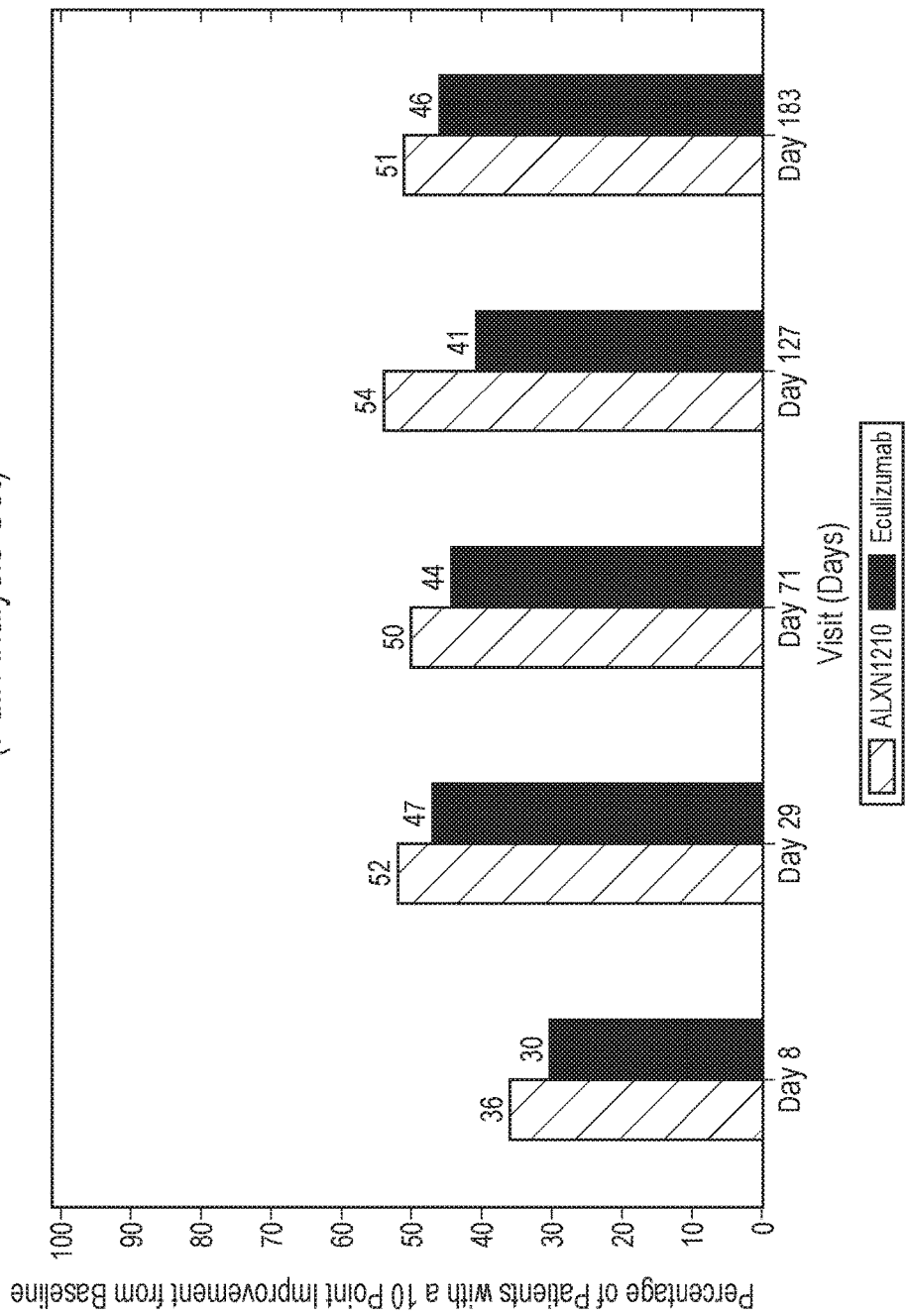
FIG. 12 is a graphical display of the percentage of patients with a 10-point improvement from baseline, by visit (full analysis set), per the European Organisation for Research and Treatment of Cancer, Quality of Life Questionnaire-Core 30 Global Health Status Subscale.
Figure 13:
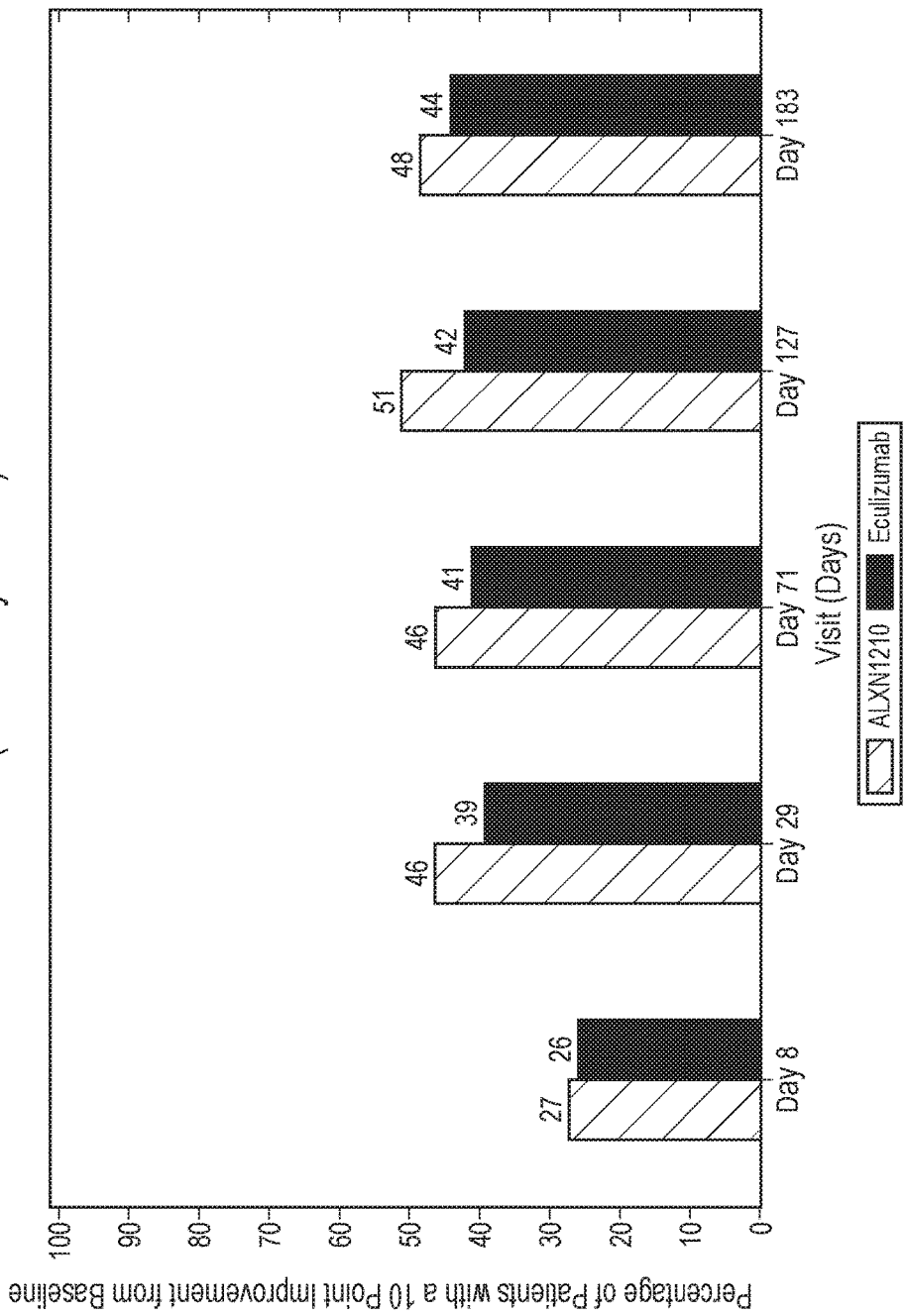
FIG. 13 is a graphical display of the percentage of patients with a 10-point improvement from baseline, by visit (full analysis set), per the European Organisation for Research and Treatment of Cancer, Quality of Life Questionnaire-Core 30 Physical Functioning Subscale.
Figure 14:
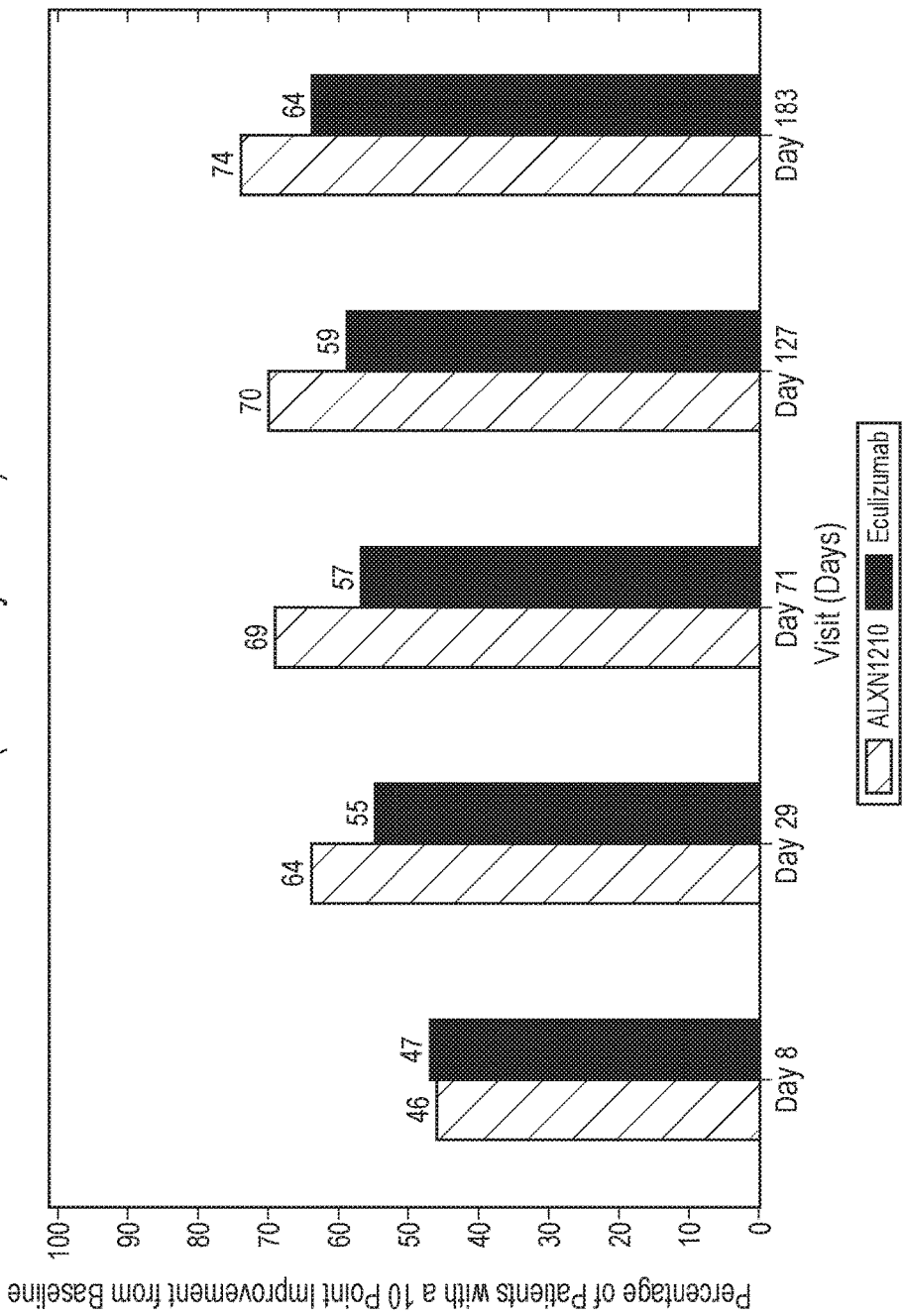
FIG. 14 is a graphical display of the percentage of patients with a 10-point improvement from baseline, by visit (Full Analysis Set), per the European Organisation for Research and Treatment of Cancer, Quality of Life Questionnaire-Core 30 Fatigue Subscale.

In addition, at baseline, the mean EORTC QLQ-C30 Global Health Status subscale scores were 56.13 for the ALXN1210 group and 57.51 for the eculizumab group. An improvement of ≥10 points in 3 subscales of the EORTC QLQ-C30, Global Health Status, Physical Functioning, and EORTC-Fatigue, are considered to indicate a clinically meaningful improvement (King, 1996; Osoba, 1998). A higher percentage of patients in the ALXN1210 group had at least a 10-point improvement in the EORTC QLQ-C30, Global Health Status, Physical Functioning, and Fatigue subscale scores at Day 29 and throughout the Primary Evaluation Period compared with the eculizumab group, as shown in FIGS. 12, 13, and 14.

3. Safety

There were no notable safety differences in adverse events (AEs) or serious adverse events (SAE) observed between ALXN1210 and eculizumab treated patients. See FIGS. 15 and 16. In addition, there were no meningococcal infections, no discontinuations due to AEs and no deaths observed during the primary evaluation period. See FIGS. 17 and 18. The most frequent AE was headache at 35%. See FIG. 16.

A history of one or more MAVEs was reported for 17.1% of patients overall, as set forth in Table 17.

TABLE 17

Major Adverse Vascular Events History (Full Analysis Set)

| MAVE Categories | ALXN1210 (N = 125) | Eculizumab (N = 121) | Total (N = 246) |
|---|---|---|---|
| Patients with a history of MAVE | 17 (13.6) | 25 (20.7) | 42 (17.1) |
| Thrombophlebitis/deep vein thrombosis | 4 (3.2) | 8 (6.6) | 12 (4.9) |
| Hepatic/portal vein thrombosis (Budd-Chiari syndrome) | 4 (3.2) | 4 (3.3) | 8 (3.3) |
| Cerebral arterial occlusion/cerebrovascular accident | 4 (3.2) | 2 (1.7) | 6 (2.4) |
| Mesenteric/visceral vein thrombosis or infarction | 3 (2.4) | 2 (1.7) | 5 (2.0) |
| Cerebral venous occlusion | 1 (0.8) | 3 (2.5) | 4 (1.6) |
| Pulmonary embolus | 0 | 4 (3.3) | 4 (1.6) |
| Dermal thrombosis | 2 (1.6) | 1 (0.8) | 3 (1.2) |
| Myocardial infarction | 0 | 3 (2.5) | 3 (1.2) |
| Acute peripheral vascular occlusion | 1 (0.8) | 1 (0.8) | 2 (0.8) |
| Mesenteric/visceral arterial thrombosis or infarction | 0 | 2 (1.7) | 2 (0.8) |
| Transient ischemic attack | 1 (0.8) | 1 (0.8) | 2 (0.8) |
| Amputation (non-traumatic; non-diabetic) | 0 | 0 | 0 |
| Gangrene (non-traumatic; non-diabetic) | 0 | 0 | 0 |
| Renal arterial thrombosis | 0 | 0 | 0 |
| Renal vein thrombosis | 0 | 0 | 0 |
| Unstable angina | 0 | 0 | 0 |
| Other | 0 | 2 (1.7) | 2 (0.8) |

Note:
Patients could have been counted in more than one category.
Abbreviation: MAVE = major adverse vascular event There was one treatment emergent case of anti-drug antibody (ADA) observed for each of ALXN1210 and eculizumab. Neither one produced neutralizing antibodies and there was no effect on PK,PD, efficacy or safety by these apparently transient ADAs. FIG. 15 is a tabulation of the key safety results in the Phase III ALXN1210-PNH-301 clinical trial.

Drug compliance was near perfect for this clinical trial, as shown in FIG. 19. There was only a single incidence of drug non-compliance in the eculizumab arm, as shown in FIG. 19.

4. Pharmacokinetic Results

Figure 20:
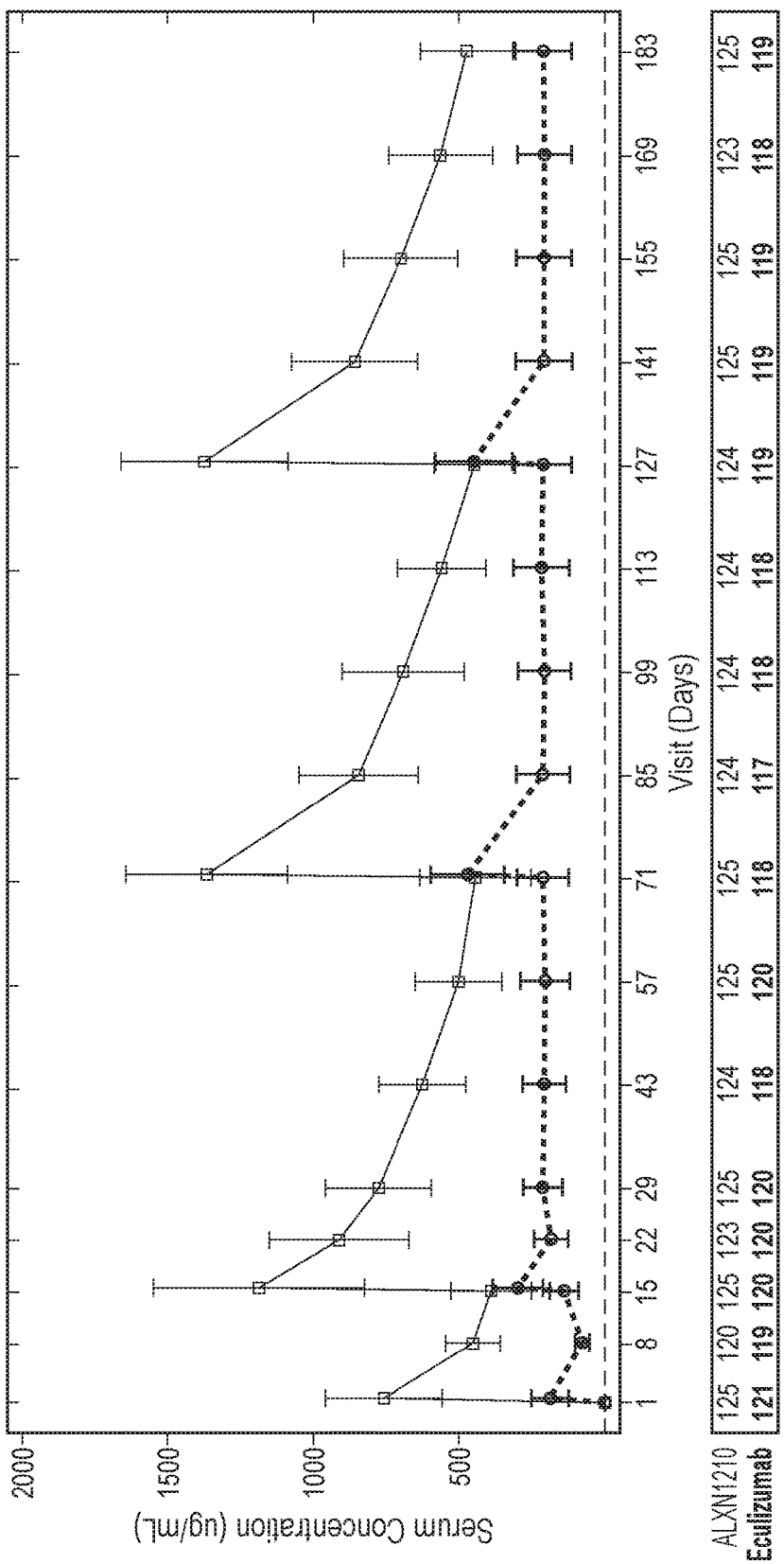
FIG. 20 is a graphical depiction of the pharmacokinetics (PK) of ravulizumab (ALXN1210) and eculizumab showing the serum concentration of each drug over time (linear scale).
Figure 21:
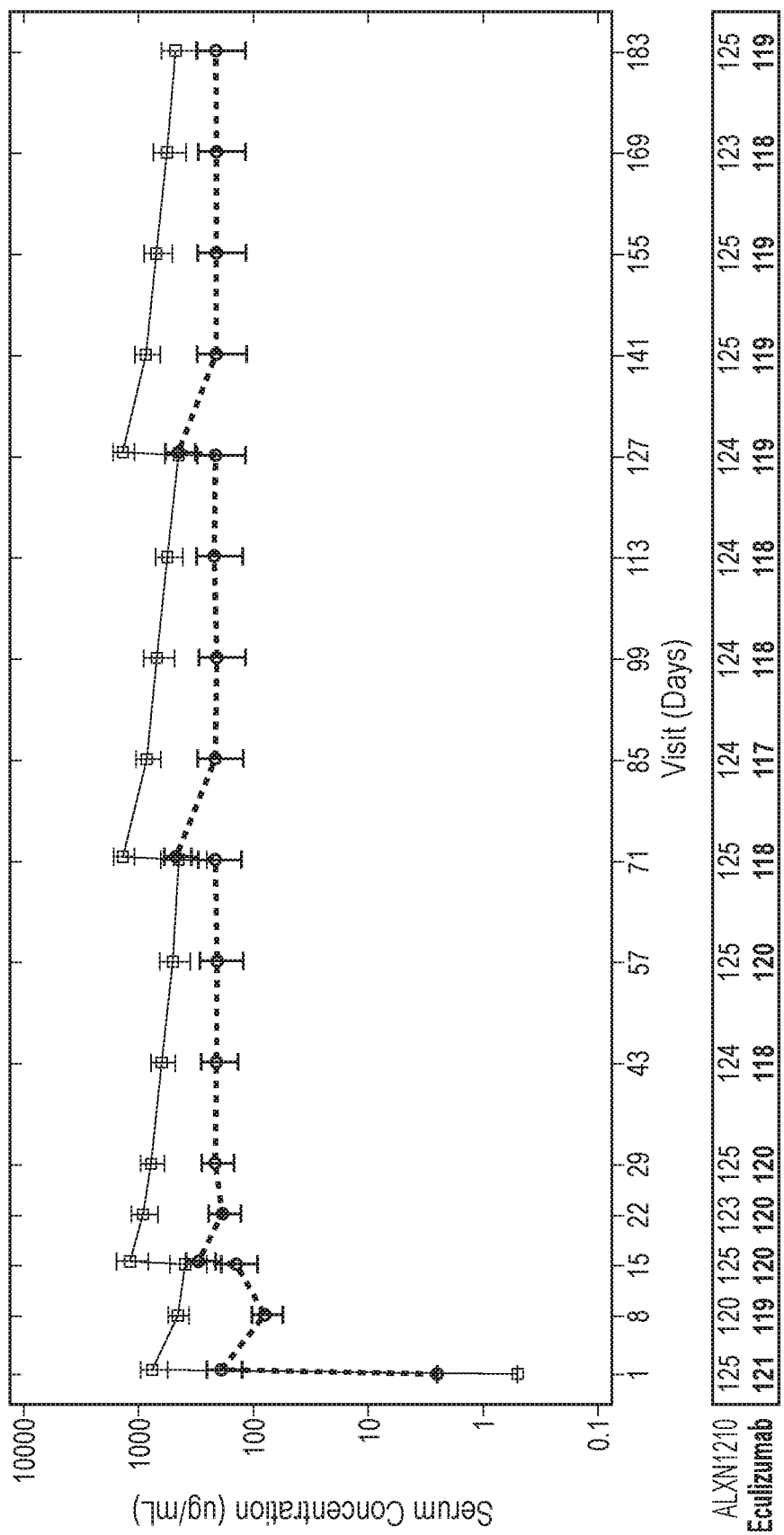
FIG. 21 is a graphical depiction of the pharmacokinetics (PK) of ravulizumab (ALXN1210) and eculizumab showing the serum concentration of each drug over time (semi-log scale).

The mean (±SD) ALXN1210 and eculizumab serum concentration versus time profile for the respective treatment groups (linear scale) is presented in FIG. 20. The mean (±SD) ALXN1210 and eculizumab serum concentration versus time profile for the respective treatment groups (semi-log scale) is presented in FIG. 21.

Pharmacokinetic parameters for ALXN1210 are summarized in Table 18 and Table 19 for the first (induction) and last (maintenance) doses, respectively. The geometric mean (geometric CV %) $C_{max}$ and $C_{trough}$ of ALXN1210 following the first dose in all patients was 753.7 (22.45) and 376.44 (26.17) m/mL, respectively. Following the last dose of ALXN1210, the geometric mean (% CV) $C_{max}$ and $C_{trough}$ in all patients were 1350.5 (20.8) and 446.1 (36.2) μg/mL, respectively.

TABLE 18

ALXN1210 Pharmacokinetic Parameters ($C_{max}$ and $C_{trough}$) Following the First (Loading) Dose of ALXN1210 (Pharmacokinetic Analysis Set)

| Parameter | Statistics | All Patients (N = 125) | ≥40 to <60 kg (N = 41) | ≥60 to <100 kg (N = 79) | ≥100 kg (N = 5) |
|---|---|---|---|---|---|
| $C_{max}$ (μg/mL) | Mean | 771.4 | 846.7 | 740.3 | 645.0 |
| | SD | 165.89 | 174.34 | 146.62 | 181.25 |
| | CV % | 21.51 | 20.59 | 19.80 | 28.10 |
| | Median | 761.0 | 846.0 | 736.0 | 656.0 |
| | Minimum | 403 | 470 | 414 | 403 |
| | Maximum | 1310 | 1160 | 1310 | 905 |
| | Geometric Mean | 753.7 | 828.6 | 726.2 | 623.9 |
| | Geometric CV % | 22.45 | 21.60 | 20.99 | 29.96 |
| $C_{trough}$ (μg/mL) | Mean | 391.21 | 424.15 | 377.8 | 333.6 |
| | SD | 136.774 | 116.191 | 146.30 | 93.26 |
| | CV % | 34.96 | 27.39 | 38.73 | 27.96 |
| | Median | 358.00 | 412.00 | 351.0 | 308.0 |
| | Minimum | 199.0 | 199.0 | 257 | 252 |
| | Maximum | 1500.0 | 775.0 | 1500 | 482 |
| | Geometric Mean | 376.44 | 409.51 | 363.8 | 324.2 |
| | Geometric CV % | 26.17 | 27.30 | 24.56 | 26.71 |

Abbreviations: $C_{max}$ = maximum serum concentration;
$C_{trough}$ = trough serum concentration;
CV = coefficient of variation;
SD = standard deviation

TABLE 19

ALXN1210 Pharmacokinetic Parameters ($C_{max}$ and $C_{trough}$) Following the Final Maintenance Dose of ALXN1210 (Pharmacokinetic Analysis Set)

| Parameter | Statistics | All Patients (N = 124) | ≥40 to <60 kg (N = 41) | ≥60 to <100 kg (N = 77) | ≥100 kg (N = 6) |
|---|---|---|---|---|---|
| $C_{max}$ (μg/mL) | Mean | 1378.5 | 1528.8 | 1292.9 | 1450.0 |
| | SD | 275.94 | 279.47 | 242.83 | 219.00 |
| | CV % | 20.02 | 18.28 | 18.78 | 15.10 |
| | Median | 1365.0 | 1520.0 | 1280.0 | 1365.0 |
| | Minimum | 780 | 909 | 780 | 1260 |
| | Maximum | 2100 | 2100 | 1790 | 1790 |
| | Geometric Mean | 1350.5 | 1502.8 | 1269.6 | 1436.9 |
| | Geometric CV % | 20.80 | 19.17 | 19.63 | 14.63 |
| $C_{trough}$ (μg/mL) | Mean | 472.7 | 548.3 | 438.8 | 391.8 |
| | SD | 157.94 | 167.99 | 139.25 | 143.75 |
| | CV % | 33.41 | 30.64 | 31.74 | 36.69 |
| | Median | 463.5 | 538.0 | 433.0 | 353.5 |
| | Minimum | 135 | 257 | 135 | 250 |
| | Maximum | 1000 | 1000 | 790 | 579 |
| | Geometric Mean | 446.1 | 524.0 | 415.5 | 370.8 |
| | Geometric CV % | 36.22 | 31.47 | 35.61 | 37.44 |

Abbreviations: $C_{max}$ = maximum serum concentration; $C_{trough}$ = trough serum concentration; CV = coefficient of variation; SD = standard deviation Noncompartmental PK parameters were measured for the ALXN1210 group only. Results following the last maintenance dose of ALXN1210 are presented in Table 20. ALXN1210 PK steady state was achieved following multiple dose administration for all weight-based maintenance doses (Table 21).

TABLE 20

Summary of ALXN1210 Noncompartmental Analysis Pharmacokinetic Parameters Following the Last ALXN1210 Maintenance Dose (Pharmacokinetic Analysis Set)

| PK Parameter (Units) | All Patients (N = 124) Mean ± SD (% CV) | ≥40 to <60 kg (N = 41) Mean ± SD (% CV) | ≥60 to <100 kg (N = 77) Mean ± SD (% CV) | ≥100 kg (N = 6) Mean ± SD (% CV) |
|---|---|---|---|---|
| $t_{max}$ (h)[a] | 2.5 (2.0, 335.8) | 2.75 (2.4, 309.1) | 2.3 (2.0, 335.8) | 2.6 (2.3, 2.9) |
| $C_{max}$ (μg/mL) | 1378.5 ± 275.9 (20.0) | 1528.8 ± 279.5 (18.3) | 1292.9 ± 242.8 (18.8) | 1450.0 ± 219.0 (15.1) |
| $C_{trough}$ (μg/mL) | 472.7 ± 157.9 (33.4) | 548.3 ± 168.0 (30.6) | 438.8 ± 139.25 (31.7) | 391.8 ± 143.75 (36.7) |
| $AUC_\tau$ (h · μg/mL) | 1007169.4 ± 237539.3 (23.6) | 1148146.3 ± 235621.5 (20.5) | 939779.2 ± 205402.5 (21.9) | 908666.7 ± 240977.7 (26.5) |
| CL (mL/h) | 2.0 ± 0.8 (41.6) | 1.5 ± 0.5 (34.3) | 2.2 ± 0.9 (38.9) | 2.5 ± 0.9 (36.6) |
| $V_z$ (mL) | 2989.4 ± 715.0 (23.9) | 2494.8 ± 568.0 (22.8) | 3194.7 ± 646.0 (20.2) | 3653.3 ± 691.1 (18.9) |

Note:
Mean half-life could not be reliably estimated due to continuous therapeutic maintenance dosing.
[a] $t_{max}$ values are presented as median (minimum, maximum).
Abbreviations: $AUC_\tau$ = area under the serum concentration versus time curve over the dosing interval; $C_{max}$ = maximum observed serum concentration; $C_{trough}$ = concentrations at the end of the dosing interval; CL = total clearance; CV = coefficient of variation; SD = standard deviation; $t_{max}$ = time to maximum observed serum concentration; $V_z$ = volume of distribution at steady state

TABLE 21

Assessment of ALXN1210 Pharmacokinetic Steady State Attainment (Pharmacokinetic Analysis Set)

| Steady State Attainment | Maintenance Dose in mg (Body Weight Group) | Slope | Lower 95% CI | Upper 95% CI | Steady State Reached? |
|---|---|---|---|---|---|
| Days 15, 71, 127, 183 | 3000 (≥40 to <60 kg) | 0.00007432 | −0.00010259 | 0.00025123 | Yes |
| Days 15, 71, 127, 183 | 3300 (≥60 to <100 kg) | 0.00000884 | −0.00008491 | 0.00010259 | Yes |
| Days 15, 71, 127, 183 | 3600 (≥100 kg) | 0.00001494 | −0.00026602 | 0.00029591 | Yes |
| Days 15, 71, 127, 183 | All Patients | 0.00001751 | −0.00007316 | 0.00010817 | Yes |

Abbreviations: CI = confidence interval

5. Pharmacodynamic Results

Treatment with ALXN1210 resulted in immediate, complete and sustained complement C5 inhibition throughout the entire 8 week dose interval. See FIG. 19. Weight based dosing every 8 weeks resulted in maximal steady state and trough exposures as shown in FIG. 19.

Table 22 summarizes mean percent change from baseline in serum free C5 concentrations following treatment with ALXN1210 (body weight-based dose q8w) or eculizumab (900 mg q2w). Some free C5 samples were excluded as they were considered biologically implausible. The exclusions were corroborated with the paired PK data, as the PK and free C5 samples were collected from the same blood draw. These exclusions are as follows: ALXN1210 group: For 3 (2.4%) patients, the Day 1 free C5 samples at end of infusion had values similar to pretreatment values. Eculizumab group: For 3 (2.5%) patients, the Day 1 free C5 samples were below the limit of quantification (BLQ) at pretreatment; for 5 (4.1%) patients, the Day 1 free C5 samples at EOI had values similar to pretreatment values.

Figure 23:
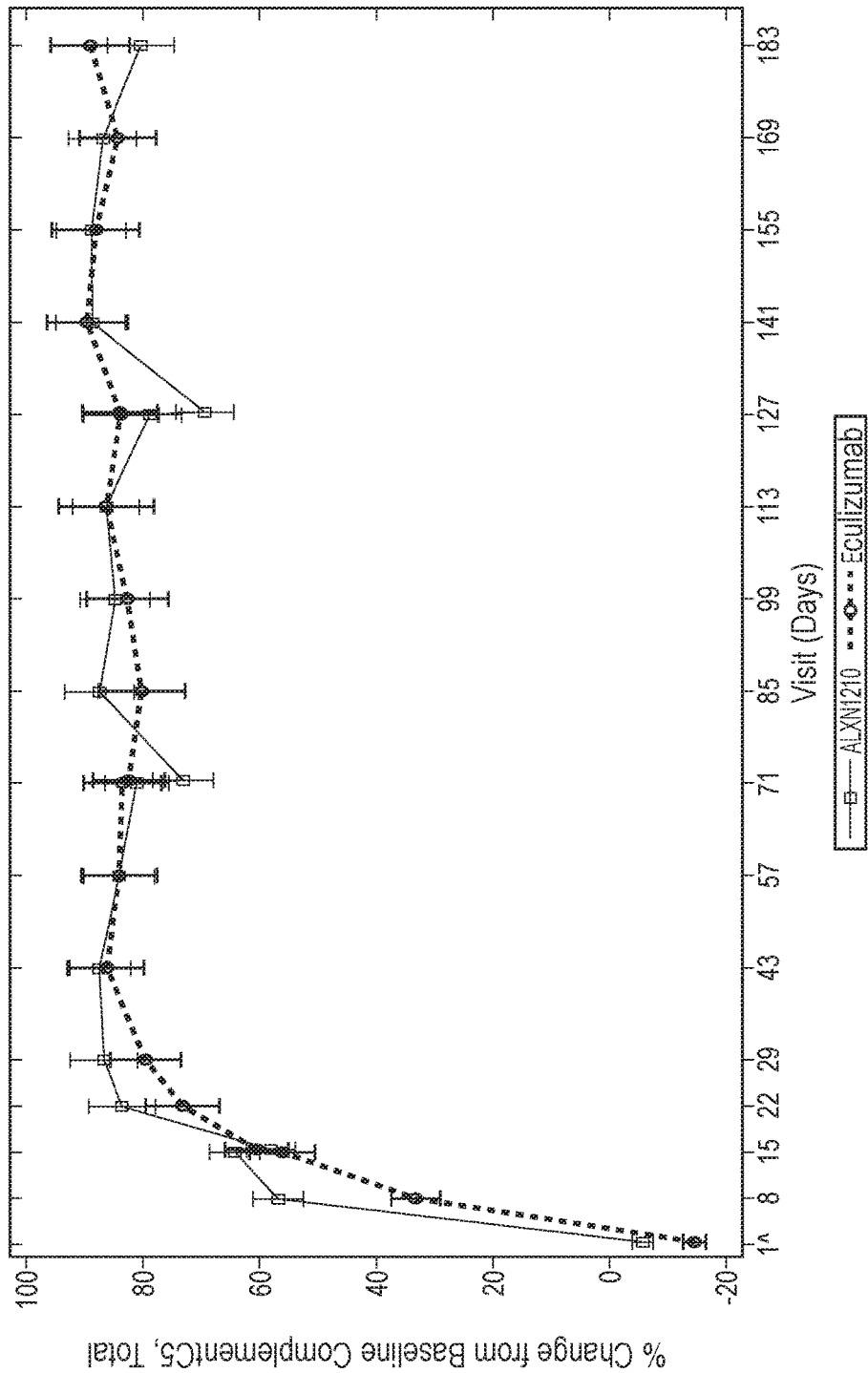
FIG. 23 is a graphical depiction of the pharmacodynamics (PD) of ravulizumab (ALXN1210) and eculizumab showing the mean (±95% CI) percent change from baseline for total serum C5 concentration in the presence of each drug over time.

Mean serum free C5 concentration as early as the first end of infusion and at all subsequent troughs was <0.5 μg/mL in the ALXN1210 group. This threshold was not consistently met in the eculizumab group. Additionally, more individual free C5 values greater than the target free C5 threshold of 0.5 μg/mL were noted in the eculizumab group than in the ALXN1210 group. The imbalance in free C5 control appears to account for the difference noted in breakthrough hemolysis events between treatment groups (ALXN1210: n=5, eculizumab: n=15).

profile is shown in FIG. 23. The rate and magnitude of change in serum total C5 was similar between treatments. Baseline was defined as the last non-missing assessment value prior to first dose of study drug. ˆindicates that the Day 1 data are from end of infusion, while at Days 8, 22, 29, 43, 57, 85, 99, 113, 141, 155, and 169, the data are from anytime for the ALXN1210 group and predose for the eculizumab group; at Days 15, 71, and 127 data are from predose for both treatment groups; and at Day 183 data are from end of the Randomized Treatment Period for both treatment groups.

Example 3: A Phase 3, Single Arm, Multicenter Study of ALXN1210 in Complement Inhibitor-Naïve Adult Patients with Atypical Hemolytic Uremic Syndrome (aHUS)

A single arm study of ALXN1210 (ALXN1210-aHUS-311) is conducted in complement inhibitor treatment-naïve adult and adolescent patients with atypical hemolytic uremic syndrome (aHUS).

aHUS is a thrombotic microangiopathy (TMA), most often caused by mutations in genes encoding proteins involved in the alternative pathway of complement (APC) or by autoantibodies against APC regulatory proteins (Noris, et al., Clin. J. Am. Soc. Nephrol. 2010; 5:1844-59). Patients with aHUS are at risk for life-threatening manifestations of disease resulting from endothelial damage, including thrombocytopenia, intravascular hemolysis, acute renal failure, and extra-renal tissue damage. Importantly, approximately

TABLE 22

Mean Serum Free C5 Concentration and Number (Percentage) of Patients With Serum Free C5 Concentration >0.05 μg/mL Over Time (Full Analysis Set)

| | ALXN1210 | | | Eculizumab | | |
|---|---|---|---|---|---|---|
| Visit[a] | n | Mean Serum Free C5 Concentration, μg/mL | n (%) of Patients With Serum Free C5 Concentration >0.5 μg/mL | n | Mean Serum Free C5 Concentration, μg/mL | n (%) of Patients With Serum Free C5 Concentration >0.5 μg/mL |
| Day 1 | 122 | 0.01 | 0 | 114 | 0.01 | 10 (8.62) |
| Day 8 | 120 | 0.04 | 0 | 116 | 3.60 | 1 (0.85) |
| Day 15 | 125 | 0.05 | 0 | 117 | 0.28 | 0 |
| Day 22 | 124 | 0.03 | 0 | 117 | 0.05 | 0 |
| Day 29 | 125 | 0.03 | 0 | 116 | 0.05 | 0 |
| Day 43 | 125 | 0.04 | 0 | 116 | 0.05 | 1 (0.87) |
| Day 57 | 124 | 0.05 | 0 | 115 | 0.26 | 2 (1.74) |
| Day 71 | 125 | 0.06 | 0 | 115 | 0.76 | 1 (0.88) |
| Day 85 | 124 | 0.03 | 0 | 114 | 0.18 | 3 (2.61) |
| Day 99 | 124 | 0.04 | 0 | 115 | 0.70 | 2 (1.74) |
| Day 113 | 124 | 0.05 | 0 | 115 | 0.22 | 2 (1.72) |
| Day 127 | 124 | 0.06 | 0 | 116 | 0.29 | 1 (0.86) |
| Day 141 | 125 | 0.04 | 0 | 116 | 0.15 | 4 (3.45) |
| Day 155 | 125 | 0.05 | 0 | 116 | 0.53 | 4 (3.48) |
| Day 169 | 123 | 0.06 | 0 | 115 | 0.94 | 5 (4.31) |
| Day 183 | 125 | 0.07 | 0 | 116 | 3.00 | 10 (8.62) |

The mean free C5 levels were inhibited by greater than 99% by the end of the first infusion with ALXN1210 and remained inhibited by greater than 99% for the duration of the study treatment period. In contrast, the free C5 did not remain inhibited by greater than 99% at all times in the eculizumab group (see FIG. 22).

Total C5 levels were similar for both the ALXN1210 and eculizumab groups. The mean (±95% CI) percent change from baseline for total serum C5 concentration versus time 20% of patients experience extra-renal manifestations of disease, including central nervous system, cardiac, GI, distal extremity, and severe systemic organ involvement (Loirat, et al., Orphanet J. Rare Dis. 2011; 6:60 and Brodsky, Blood. 2015; 126:2459-65). Before the availability of eculizumab, mortality rates among patients with aHUS were as high as 15% during the acute progressing phase of the disease (Noris, et al., Clin. J. Am. Soc. Nephrol. 2010; 5:1844-59) and Sellier-Leclerc, J. Am. Soc. Nephrol. 2007; 18:2392-

2400). Up to 50% of patients progressed to end-stage kidney disease (ESKD), often within a year of disease onset, and required dialysis or kidney transplant to sustain life. Chronic, uncontrolled terminal complement activation, specifically, activation of complement component 5 (C5) and dysregulation of complement activity, is central to the pathogenesis of aHUS and the devastating manifestations of this disease. As a result, the targeted blockade of C5, with selective inhibition of generation of C5a and C5b-9, represents an important therapeutic mechanism of treatment.

1. Objectives

The primary objective of the study is to assess the efficacy of ALXN1210 in complement inhibitor treatment naïve adolescent and adult patients with aHUS to inhibit complement-mediated TMA as characterized by thrombocytopenia, hemolysis, and renal impairment.

The secondary objectives of the study are to (1) characterize the safety and tolerability of ALXN1210 in this patient population, (2) evaluate the efficacy of ALXN1210 by additional measures (e.g., dialysis requirement status, time to complete TMA response, complete TMA Response status over time, observed value and change from baseline in estimated glomerular filtration rate (eGFR), chronic kidney disease (CKD) stage (as evaluated at select target days and classified as improved, stable (no change), or worsened compared to baseline), observed value and change from baseline in hematologic parameters (platelets, LDH, hemoglobin), increase in hemoglobin of ≥20 g/L from baseline (sustained for at least 2 consecutive measurements obtained at least 4 weeks apart), change from baseline in quality of life (QoL) (as measured by EuroQol 5 dimensions 3 level (EQ-5D-3L; all patients), Functional Assessment of Chronic Therapy (FACIT) Fatigue version 4 (patients <18 years of age), and Pediatric FACIT Fatigue (patients <18 years of age) questionnaires)), (3) characterize the PK/pharmacodynamics (PD) of ALXN1210 by changes in serum ALXN1210 concentration over time and changes in free C5 concentrations over time, and (4) evaluate the long-term safety and efficacy of ALXN1210.

2. Endpoints

The primary efficacy endpoint of the study is Complete TMA Response during the 26-week Initial Evaluation Period, as evidenced by normalization of hematological parameters (platelet count and LDH) and ≥25% improvement in serum creatinine from baseline, and confirmed by 2 consecutive measurements obtained at least 4 weeks apart.

The secondary efficacy endpoints of the study are the following:
A. Dialysis requirement status;
B. Time to Complete TMA Response;
C. Complete TMA Response status over time;
D. Observed value and change from baseline in eGFR;
E. CKD stage, as evaluated by the Investigator at select target days and classified as improved, stable (no change), or worsened compared to baseline;
F. Observed value and change from baseline in hematologic parameters (platelets, LDH, hemoglobin);
G. Increase in hemoglobin of ≥20 g/L from baseline, sustained for at least 2 consecutive measurements obtained at least 4 weeks apart;
H. Change from baseline in QoL, as measured by EQ-5D-3L (all patients), FACIT Fatigue version 4 (patients ≥18 years of age), and Pediatric FACIT Fatigue (patients <18 years of age) questionnaires.

The Pharmacokinetic (PK) and Pharmacodynamic (PD) endpoints of this study are changes in serum ALXN1210 concentration over time and changes in free C5 concentrations over time.

The safety and tolerability of ALXN1210 is evaluated by physical examinations, vital signs, electrocardiograms (ECGs), laboratory assessments, and incidence of AEs and SAEs. The proportion of patients who develop antidrug antibodies (ADA) are also assessed.

Exploratory biomarkers of PD effect include, but are not limited to, change from baseline in levels of markers of complement dysregulation (e.g., Factor Ba), vascular inflammation (e.g., soluble tumor necrosis factor receptor 1 [sTNFR1]), endothelial activation/damage (eg, soluble vascular adhesion molecule 1 [sVCAM1], thrombomodulin), coagulation (e.g., D-dimer), and renal injury (e.g., cystatin C). Additional assessments may include measurements of ALXN1210 excretion in urine, chicken red blood cell (cRBC) hemolysis, total C5, autoantibodies to complement proteins (e.g., anti-factor H) and APC activity (e.g., Modified Ham's test, complement deposition assays).

Exploratory genetics can be performed to investigate genetic variants in genes known to be associated with aHUS, as well as to identify novel genetic variants associated with aHUS, complement dysregulation, or metabolism or efficacy of ALXN1210. Patients can opt-out from providing a sample for exploratory genetics and still participate in the study.

3. Summary of Study Design

Figure 24:
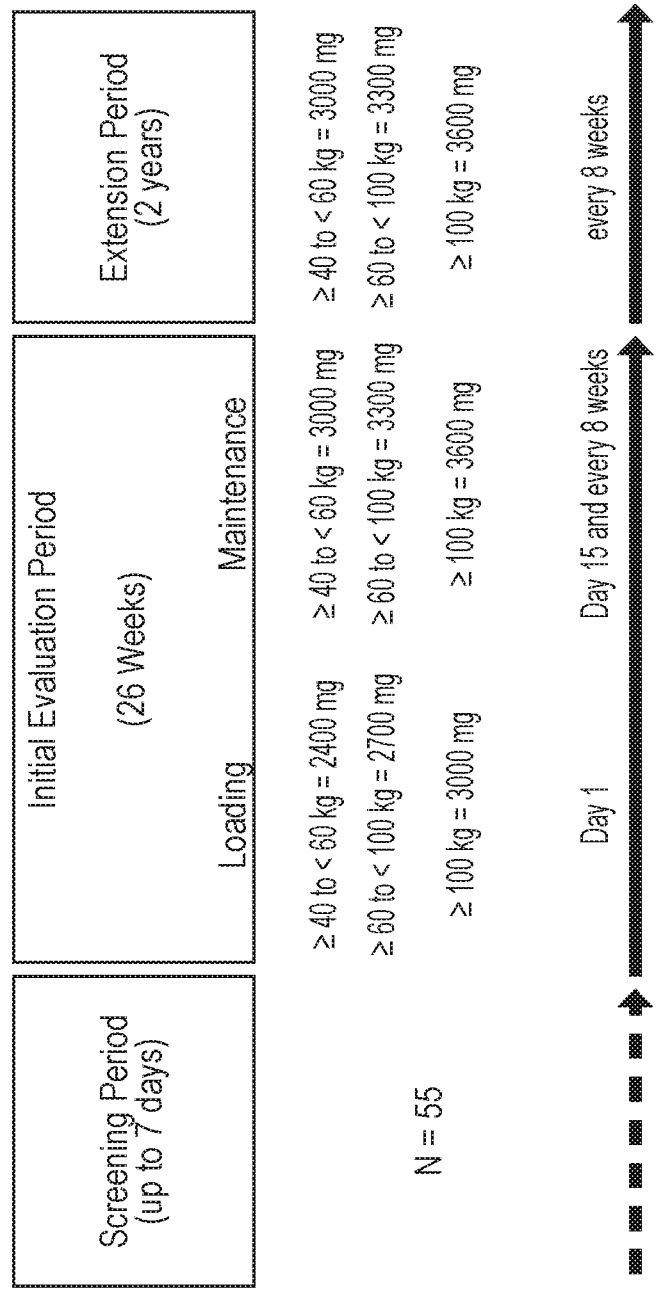
FIG. 24 is a schematic depicting the design for clinical protocol ALXN1210-aHUS-311.

Study ALXN1210-aHUS-311 is a Phase 3, open-label, single arm, multicenter study to evaluate the safety and efficacy of ALXN1210 administered by intravenous (IV) infusion to adolescent (12 to <18 years of age) and adult (≥18 years of age) patients with aHUS. The study is enrolling approximately 55 patients to receive ALXN1210. FIG. 24 illustrates the study design. All patients are naïve to complement inhibitor treatment and include at least 6 and up to 10 adolescent (12 to <18 years of age at Screening) patients and at least 10 and up to 25 patients with prior kidney transplants.

The study consists of an up to 7 day Screening Period, a 26-week Initial Evaluation Period, and an Extension Period of up to 2 years. Dosages are based on the patient's last recorded study visit body weight (Table 27). Patients receive a loading dose of ALXN1210 IV (2400 mg for patients weighing ≥40 to <60 kg, 2700 mg for patients weighing ≥60 to <100 kg, 3000 mg for patients weighing ≥100 kg) on Day 1, followed by maintenance doses of ALXN1210 IV (3000 mg for patients weighing ≥40 to <60 kg, 3300 mg for patients weighing ≥60 to <100 kg, 3600 mg for patients weighing ≥100 kg) on Day 15 and once every 8 weeks (q8w) thereafter for a total of 26 weeks of treatment. After the Initial Evaluation Period, patients enter an Extension Period and receive ALXN1210 until the product is registered or approved (in accordance with country specific regulations) or for up to 2 years, whichever occurs first. The end of trial is defined as the last patient's last visit.

This Phase 3, open-label, single arm study evaluates the safety and efficacy of treatment with ALXN1210. Although no formal comparison analyses are planned for this study, results from ALXN1210 treated patients are evaluated in the context of results observed in a historical control group of patients treated with eculizumab. The historical control group is comprised of patients with aHUS who were treated with eculizumab in the C08-002A/B, C10-003 and C10-004 prospective registrational studies, for which study design and conduct features of interest that might influence the effect size were similar to the current study. In addition, the control group is restricted to patients ≥12 years of age and with 4 weeks or less on PE/PI prior to eculizumab treatment to further align with eligibility criteria for the current study.

The Schedule of Assessments for Screening and the Initial Evaluation Period is shown in Table 23. The Schedule of Assessments for the Extension Period is shown in Table 24. Additional (unscheduled) visits outside the specified visits are permitted at the discretion of the Investigator. Procedures, tests, and assessments are performed at the discretion of the Investigator. Any tests, procedures, or assessments performed at the Unscheduled Visits are recorded on the electronic Case Report Forms (eCRFs). Local laboratory or central laboratory analysis are used for Unscheduled Visit tests. However, if local laboratory tests are to be used, duplicate samples are collected at the Unscheduled Visit for central laboratory testing.

TABLE 23

Schedule of Study Visits and Assessments: Screening Through End of Initial Evaluation Period

| | Screening | \multicolumn{16}{c}{Initial Evaluation Period} |
|---|---|---|---|---|---|---|---|---|---|---|---|---|---|---|---|---|

| | Screening | Initial Evaluation Period | | | | | | | | | | | | | | |
|---|---|---|---|---|---|---|---|---|---|---|---|---|---|---|---|---|
| | \multicolumn{17}{c}{Study Day} |
| | −7 to −1 | 8 | 15 | 22 | 29 | 43 | 57 | 71 | 85 | 99 | 113 | 127 | 141 | 155 | 169 | 183[v]/ET |
| | \multicolumn{17}{c}{Window (day)} |
| | N/A | 1 | ±2 | ±3 | ±3 | ±3 | ±3 | ±3 | ±3 | ±3 | ±5 | ±5 | ±5 | ±5 | ±5 | ±2 |
| Informed consent | X | | | | | | | | | | | | | | | |
| Confirmation or administration of meningococcal vaccination[a] | X | | | | | | | | | | | | | | | |
| Medical history and demographics | X | | | | | | | | | | | | | | | |
| ADAMTS13 | X | | | | | | | | | | | | | | | |
| HIV screen[b] | X | | | | | | | | | | | | | | | |
| Streptococcal pneumoniae HUS testing | X | | | | | | | | | | | | | | | |
| ST-HUS screen[c] | X | | | | | | | | | | | | | | | |
| Height | X | | | | | | | | | | | | | | | |
| Weight | X | X | X | X | X | X | X | X | X | X | X | X | X | X | X | X |
| Pregnancy test[d] | X | X | | X | | | | X | | | X | | | | | X |
| FACIT-Fatigue questionnaire/ Pediatric FACIT-Fatigue questionnaire[e,f] | | X | X | | X | | | X | | | X | | | | | X |
| EQ-5D-3L questionnaire[f] | | X | X | | X | | | X | | | X | | | | | X |
| Patient-reported aHUS symptoms questionnaire[f] | | X | X | X | X | X | X | X | X | X | X | X | X | X | X | X |
| Resource utilization patient questionnaire[f] | | X | | | X | | | X | | | X | | | | | X |
| Physical examination | X | | | | | | | | | | | | | | | X |
| Abbreviated physical examination[g] | | X | X | X | X | X | X | X | X | X | X | X | X | X | X | |
| Assessment of extra-renal signs or symptoms of aHUS | X | X | X | X | X | X | X | X | X | X | X | X | X | X | X | X |
| Vital signs[h] | X | X | X | X | X | X | X | X | X | X | X | X | X | X | X | X |
| Safety 12-Lead ECG[i] | X | | | | | X | | | | | | | | | | X |
| Chemistry[j] | X[u] | X | X | X | X | X | X | X | X | X | X | X | X | X | X | X |
| LDH isozymes[k] | X | X | X | X | X | X | X | X | X | X | X | X | X | X | X | X |
| Hematology including free hemoglobin and coagulation[l] | X[u] | X | X | X | X | X | X | X | X | X | X | X | X | X | X | X |
| Urinalysis and urine chemistry | X | X | | X | | X | | X | | X | | X | | X | | X |
| PK/PD sampling[m] | | X[m] | X[m] | | X[m] | X[m] | X[m] | X[m] | X[m] | X[m] | X[m] | X[m] | X[m] | X[m] | X[m] | X[m] |
| Urine sample[n] | | X | X | X | | X | | | | | | | | | | |

TABLE 23-continued

Schedule of Study Visits and Assessments: Screening Through End of Initial Evaluation Period

| | Screening | Initial Evaluation Period | | | | | | | | | | | | | |
|---|---|---|---|---|---|---|---|---|---|---|---|---|---|---|---|
| | | Study Day | | | | | | | | | | | | | |
| | −7 to −1 | 8 | 15 | 22 | 29 | 43 | 57 | 71 | 85 | 99 | 113 | 127 | 141 | 155 | 169 | 183$^v$/ET |
| | | | | | | | | Window (day) | | | | | | | | |
| | N/A | 1 | ±2 | ±3 | ±3 | ±3 | ±3 | ±3 | ±3 | ±3 | ±5 | ±5 | ±5 | ±5 | ±5 | ±2 |
| Exploratory APC activity$^o$ | | X | | X | | X | X | X | | | X | | X | | | X |
| Exploratory biomarkers$^p$ | | X | X | | | | | X | | | | X | | | | X |
| Exploratory genetic sample$^q$ | | X | | | | | | | | | | | | | | |
| Immunogenicity (ADA)$^r$ | | X | | | | | | X | | | | X | | | | X |
| Review safety card | | X | X | X | X | X | X | X | X | X | X | X | X | X | X | X |
| Concomitant medications$^s$ | | | | | | | | ←Monitor continuously→ | | | | | | | | |
| Record plasma exchange | | | | | | | | ←Monitor continuously→ | | | | | | | | |
| Adverse events | | | | | | | | ←Monitor continuously→ | | | | | | | | |
| ALXN1210 administraten$^t$ | | X | | X | | | | X | | | | X | | | | |

Abbreviations: ADA = antidrug antibody; ADAMTS13 = a disintegrin and metalloproteinase with a thrombospondin type 1 motif, member 13; aHUS = atypical hemolytic uremic syndrome; APC = alternative pathway of complement; ECG = electrocardiogram; EQ-5D-3L = EuroQol5 dimensions 3 level; ET = early termination; FACIT = functional assessment of chronic illness therapy; HUS = hemolytic uremic syndrome; LDH = lactate dehydrogenase; N/A = not applicable; PD = pharmacodynamics; PK = pharmacokinetics; QoL = quality of life; ST-HUS = Shiga toxin-related hemolytic uremic syndrome.

$^a$All patients are vaccinated against meningococcal infections within 3 years prior to, or at the time of, initiating study drug. Patients who initiate study drug treatment less than 2 weeks after receiving a meningococcal vaccine receive treatment with appropriate prophylactic antibiotics until 2 weeks after vaccination. Patients who have not been vaccinated prior to initiating ALXN1210 treatment receive prophylactic antibiotics prior to and for at least 2 weeks after meningococcal vaccination.

$^b$Human Immunodeficiency Virus Type 1 and Human Immunodeficiency Virus Type 2 screening.

$^c$Stool sample for Shiga toxin enzyme immunoassay.

$^d$Female patients of childbearing potential only. Serum pregnancy test at Screening and Day 183; urine pregnancy test at all other required time points. A negative urine test result is required prior to administering study drug to female patients of childbearing potential at the potential study visits.

$^e$FACIT Fatigue version 4 is used for patients ≥18 years of age at Screening. Pediatric FACIT Fatigue is used for patients <18 years of age at Screening.

$^f$On dosing days, patient-reported assessments are performed prior to dosing.

$^g$Abbreviated physical examination consists of a body system relevant examination based upon Investigator (or designee) judgment and patient symptoms. At least 1 body system is checked for an abbreviated exam.

$^h$Vital sign measurements are taken after the patient has been resting for at least 5 minutes and include systolic and diastolic BP (millimeters of mercury [mmHg]), pulse oximetry, heart rate (beats/minute), respiratory rate (breaths/minute), and oral or tympanic temperature (degrees Celsius [° C.] or degrees Fahrenheit [° F.]). On dosing days, vital signs are taken predose.

$^i$Single 12-lead ECG is collected at Screening, predose on Day 57, and Day 183. Patients are supine for approximately 5 to 10 minutes before ECG collection and remain supine but awake during ECG collection.

$^j$Clinical safety laboratory measurements are collected predose on dosing days. LDH for eligibility is determined from the chemistry assessment. Follicle stimulating hormone levels are measured during Screening only in order to confirm postmenopausal status.

$^k$Serum sample for LDH isozyme testing is only collected at selected sites at any/all timepoints prior to ALXN1210 dosing, dependent on sample testing availability.

$^l$Assessment for safety, as well as the primary and secondary endpoints.

$^m$Serum samples for PK/PD analyses are collected predose (within 0.5 hours prior to the start of infusion) and at end of infusion (EOI) (within 0.5 hours after the EOI) on Days 1, 15, 71, and 127; and at any time on Days 29, 43, 57, 85, 99, 113, 141, 155, and 169; and predose on Day 183 (note additional samples for PK/PD are collected on Day 183 as part of the Extension Period). End of infusion samples are drawn from the patient's opposite, noninfused arm. All collection times are recorded in the eCRF.

$^n$Urine sample for drug measurement are collected and at end of infusion (EOI) (within 0.5 hours after the EOI) on Days 1, 15, and 71; and at any time on Day 29.

$^o$Collection of serum samples are predose on days of dosing and for days without dosing at any time of day. All collection times are recorded in the eCRF.

$^p$Collection of serum, plasma and urine for exploratory biomarker analysis is collected at Baseline and at post-treatment timepoints just prior to ALXN1210 dosing.

$^q$A single whole blood collection from those patients who consent to genetic testing can be collected anytime during the study.

$^r$ADA serum samples are collected predose on Days 1, 71, and 127. Day 183 collection occurs prior to first dose in the Extension Period. All collection times are recorded in the eCRF. If results of the test are positive, the test is repeated every 3 months until results become negative or stabilize, based on the measured titer and the safety assessments.

$^s$Concomitant medications must be collected at all study visits and checked against the prohibited medication list.

$^t$The dose of ALXN1210 is based on the patient's last recorded study visit body weight.

$^u$Local laboratory or central laboratory analysis can be used to determine eligibility at Screening. However, if local laboratory tests are used, duplicate samples for LDH, platelet count, hemoglobin, and serum creatinine are collected at this visit for central laboratory testing.

$^v$The primary efficacy endpoint assessment is before dosing on Day 183. Dosing on Day 183 is the start of the Extension Period.

TABLE 24

Schedule of Study Visits and Assessments: Extension Period

| | Extension Period | | | | | | | | | | | | | |
|---|---|---|---|---|---|---|---|---|---|---|---|---|---|---|
| | Study Day | | | | | | | | | | | | | |
| | 183[1] | 239 | 295 | 351 | 407 | 463 | 519 | 575 | 631 | 687 | 743 | 799 | 855 | 911/ET/EOS |
| | Window (day) | | | | | | | | | | | | | |
| | ±2 | ±7 | ±7 | ±7 | ±7 | ±7 | ±7 | ±7 | ±7 | ±7 | ±7 | ±7 | ±7 | ±7 |
| Weight | | X | X | X | X | X | X | X | X | X | X | X | X | X |
| Pregnancy test[a] | | X | X | X | X | X | X | X | X | X | X | X | X | X |
| FACIT-Fatigue questionnaire/ Pediatric FACIT-Fatigue questionnaire[b,c] | | | | X | | | X | | | X | | | | X |
| EQ-5D-3L questionnaire[c] | | | | X | | | X | | | X | | | | X |
| Patient-reported aHUS symptoms questionnaire[c] | | X | X | X | X | X | X | X | X | X | X | X | X | X |
| Resource utilization patient questionnaire[c] | | X | X | X | X | X | X | X | X | X | X | X | X | |
| Physical examination | | | | | | | | | | | | | | X |
| Abbreviated physical examination[d] | | X | X | X | X | X | X | X | X | X | X | X | X | |
| Assessment of extra-renal signs or symptoms of aHUS | | X | X | X | X | X | X | X | X | X | X | X | X | X |
| Vital signs[e] | | X | X | X | X | X | X | X | X | X | X | X | X | X |
| Safety 12-Lead ECG[f] | | | | | | | | | | | | | | X |
| Chemistry | | X | X | X | X | X | X | X | X | X | X | X | X | X |
| Hematology and coagulation[g] | | X | X | X | X | X | X | X | X | X | X | X | X | X |
| Urinalysis and urine chemistry | | X | X | X | X | X | X | X | X | X | X | X | X | X |
| PK/PD sampling[h] | X[h] | | | X[h] | | | X[h] | | | X[h] | | | | X[h] |
| Exploratory biomarkers[i] | | X | X | X | X | X | X | X | X | X | X | X | X | X |
| Immunogenicity (ADA)[j] | | | | X[j] | | | X[j] | | | X[j] | | | | X[j] |
| Review safety card | | X | X | X | X | X | X | X | X | X | X | X | X | X |
| Concomitant medications[k] | ←Monitor continuously→ | | | | | | | | | | | | | |
| Record plasma exchange | ←Monitor continuously→ | | | | | | | | | | | | | |
| Adverse events | ←Monitor continuously→ | | | | | | | | | | | | | |
| ALXN1210 administration[l] | X[l] | X | X | X | X | X | X | X | X | X | X | X | X | |

Abbreviations: ADA = antidrug antibody;
aHUS = atypical hemolytic uremic syndrome;
ECG = electrocardiogram;
EOS = end of study;
EQ-5D = EuroQol five dimensions;
ET = early termination;
FACIT = functional assessment of chronic illness therapy;
PD = pharmacodynamics;
PK = pharmacokinetics;
QoL = quality of life

[a]Female patients of childbearing potential only. Serum pregnancy test at ET only; urine pregnancy test at all other required time points. A negative urine test result is required prior to administering ALXN1210 to female patients of childbearing potential at the indicated study visits.
[b]FACIT Fatigue version 4 is used for patients≥18 years of age at Screening. Pediatric FACIT Fatigue is used for patients <18 years of age at Screening.
[c]On dosing days, patient-reported assessments are performed prior to dosing.
[d]Abbreviated physical examination consists of a body system relevant examination based upon Investigator judgment and patient symptoms.
[e]Vital sign measurements are taken after the patient has been resting for at least 5 minutes and include systolic and diastolic BP (millimeters of mercury [mmHg]), pulse oximetry, heart rate (beats/minute), respiratory rate (breaths/minute), and oral or tympanic temperature (degrees Celsius [° C.] or degrees Fahrenheit [° F.]). On dosing days, vital signs are taken predose.
[f]Single 12-lead ECG is collected at Day 911 or ET. Patients must be supine for approximately 5 to 10 minutes before ECG collection and remain supine but awake during ECG collection.
[g]Assessment for safety, as well as the primary and secondary endpoints.

TABLE 24-continued

Schedule of Study Visits and Assessments: Extension Period

| Period | | | | | | | | | | | | | |
|---|---|---|---|---|---|---|---|---|---|---|---|---|---|
| Extension Period | | | | | | | | | | | | | |
| Study Day | | | | | | | | | | | | | |
| 183[1] | 239 | 295 | 351 | 407 | 463 | 519 | 575 | 631 | 687 | 743 | 799 | 855 | 911/ET/EOS |
| Window (day) | | | | | | | | | | | | | |
| ±2 | ±7 | ±7 | ±7 | ±7 | ±7 | ±7 | ±7 | ±7 | ±7 | ±7 | ±7 | ±7 | ±7 |

[h]Serum samples for PK/PD analysis are collected predose (within 0.5 hours prior to the start of infusion) and EOI (within 0.5 hours after the EOI) on Days 351, 575, and 743; EOI (within 0.5 hours after the EOI) on Day 183; and at any time on Day 911 or ET. End of infusion samples are drawn from the patient's opposite, noninfused arm. All collection times are recorded in the eCRF

[i]Serum, plasma and urine for exploratory biomarker analysis is collected at the indicated timepoints just prior to ALXN1210 dosing; and at any time on Day 911 or ET. All collection times are recorded in the eCRF.

[j]A predose serum sample is collected on Days 351, 575, and 743. A serum sample is also collected at any time on Day 911 or ET. All collection times are recorded in the eCRF. If results of the test are positive, the test is repeated every 3 months until results become negative or stabilize, based on the measured titer and the safety assessments.

[k]Concomitant medications are collected at all study visits and checked against the prohibited medication list.

[l]Extension Period begins at the start of Day 183 dosing. The dose of ALXN 1210 is based on the patient's last recorded study visit body weight.

4. Study Population

A total of approximately 55 patients with documented aHUS are enrolled and assigned to treatment with ALXN1210 at approximately 200 investigative sites globally. The study enrolls at least 6 and up to 10 adolescent (12 to <18 years of age at Screening) patients and at least 10 and up to 25 patients with prior kidney transplants.

Individuals who do not meet the criteria for participation in this study (screen failure) can be rescreened. Patients can be rescreened a maximum of 2 times. Prospective approval of protocol deviations to recruitment and enrollment criteria, also known as protocol waivers or exemptions, is not permitted.

Patients are eligible for enrollment in the study if they meet all of the following criteria and none of the exclusion criteria:

Male or female patients ≥12 years of age and weighing ≥40 kg at the time of consent.
- Evidence of TMA, including thrombocytopenia, evidence of hemolysis, and kidney dysfunction, based on the following Screening Visit laboratory findings: Platelet count <150,000 per microliter (μL), and LDH ≥1.5× upper limit of normal (ULN), and hemoglobin <lower limit of normal (LLN) for age and gender, and serum creatinine level ≥ULN in adults (≥18 years of age), or ≥97.5[w] percentile for age at Screening in adolescents (12 to <18 years of age) (patients who require dialysis for acute kidney injury are also eligible).
- Among patients with a kidney transplant: known history of aHUS prior to current kidney transplant, or no known history of aHUS, and persistent evidence of TMA after suspension of dosing of calcineurin inhibitor ([CNI]; e.g., cyclosporine, tacrolimus) or mammalian target of rapamycin inhibitor ([mTORi]; e.g., sirolimus, everolimus) for a minimum of 4 days and a maximum of 7 days.
- Among patients with onset of TMA postpartum, persistent evidence of TMA for ≥3 days after the day of childbirth.
- To reduce the risk of meningococcal infection (*Neisseria meningitidis*), all patients are be vaccinated against meningococcal infections within 3 years prior to, or at the time of, initiating study drug. Patients who receive a meningococcal vaccine less than 2 weeks before initiating ALXN1210 treatment receive treatment with appropriate prophylactic antibiotics until 2 weeks after vaccination. Patients who have not been vaccinated prior to initiating ALXN1210 treatment receive prophylactic antibiotics prior to and for at least 2 weeks after meningococcal vaccination.
- Patients <18 years of age must have been vaccinated against *Haemophilus influenzae* type b (Hib) and *Streptococcus pneumoniae* according to national and local vaccination schedule guidelines.
- Female patients of childbearing potential and male patients with female partners of childbearing potential must follow protocol-specified guidance for avoiding pregnancy while on treatment and for 8 months after last dose of study drug.
- Willing and able to give written informed consent and comply with the study visit schedule. For patients <18 years of age, patient's legal guardian must be willing and able to give written informed consent and the patient must be willing to give written informed assent.

Samples collected at Screening can be tested at either a local or central laboratory. If local laboratory tests are used for LDH, platelet count, hemoglobin, and serum creatinine, duplicate samples are collected for central laboratory testing to ensure baseline and post-baseline measurements for analyses are resulted from the central laboratory. Although local laboratory results can be used to expedite assessment of eligibility, the final determination of these Inclusion Criteria is be based on the central laboratory results.

Patients are excluded from study enrollment if they meet any of the following criteria:
- A. Known 'a disintegrin and metalloproteinase with a thrombospondin type 1 motif, member 13' (AD-AMTS13) deficiency (activity <5%).
- B. Shiga toxin-related hemolytic uremic syndrome (ST-HUS).
- C. *Streptococcal pneumoniae*-related hemolytic uremic syndrome (HUS), as evidenced by a positive direct Coombs test and infection by Streptococcal *pneumoniae* (e.g., culture, antigen test).
- D. Known Human Immunodeficiency Virus (HIV) infection.
- E. Unresolved systemic meningococcal disease.
- F. Patients with a confirmed diagnosis of ongoing sepsis defined as positive blood cultures within 7 days prior to the start of Screening and untreated with antibiotics.
- G. Presence or suspicion of active and untreated systemic bacterial infection that, in the opinion of the Investigator, confounds an accurate diagnosis of aHUS or impedes the ability to manage the aHUS disease.

H. Pregnancy or lactation.
I. Heart, lung, small bowel, or liver transplant.
J. Among patients with kidney transplant, any of the following:
   a. Acute kidney dysfunction within 4 weeks of transplant consistent with the diagnosis of acute antibody-mediated rejection (AMR) according to Banff 2013 criteria, or
   b. Acute kidney dysfunction within 4 weeks of transplant and a rising donor-specific antibody (DSA) consistent with a clinical diagnosis of acute AMR.
   c. History of polycystic kidney disease.
K. Among patients ≥18 years of age presenting with systolic blood pressure (SBP) ≥170 mmHg, or patients 12 to <18 years of age presenting with a clinical diagnosis of hypertension, any of the following:
   a. Persistent evidence of TMA (inclusion criterion number 2) after less than 4 days of blood pressure (BP) reduction to ≤140 mmHg.
   b. Known left ventricular hypertrophy.
   c. Known small and hyperechoic kidneys on ultrasound.
L. Identified drug exposure-related HUS.
M. Receiving PE/PI, for 28 days or longer, prior to the start of Screening for the current TMA.
N. History of malignancy within 5 years of Screening with the exception of a nonmelanoma skin cancer or carcinoma in situ of the cervix that has been treated with no evidence of recurrence.
O. Bone marrow transplant (BMT)/hematopoietic stem cell transplant (HSCT) within the last 90 days prior to the start of Screening.
P. HUS related to vitamin B12 deficiency.
Q. Known systemic sclerosis (scleroderma), systemic lupus erythematosus (SLE), or antiphospholipid antibody positivity or syndrome.
R. Chronic dialysis (defined as dialysis on a regular basis as renal replacement therapy for ESKD).
S. Patients receiving chronic intravenous immunoglobulin (IVIg) within 8 weeks prior the start of Screening, unless for unrelated medical condition (eg, hypogammaglobinemia); or chronic rituximab therapy within 12 weeks prior to the start of Screening.
T. Patients receiving other immunosuppressive therapies such as steroids, mTORi (e.g., sirolimus, everolimus), CNI (e.g., cyclosporine or tacrolimus) are excluded unless: a) part of an established post-transplant antirejection regime, or b) patient has confirmed anti-complement factor antibodies requiring immunosuppressive therapy, or c) steroids are being used for a condition other than aHUS (e.g., asthma).
U. Participation in another interventional treatment study or use of any experimental therapy within 30 days before initiation of study drug on Day 1 in this study or within 5 half-lives of that investigational product, whichever is greater.
V. Prior use of eculizumab or other complement inhibitors.
W. Hypersensitivity to murine proteins or to one of the excipients.
X. Any medical or psychological condition that, in the opinion of the Investigator, could increase the risk to the patient by participating in the study or confound the outcome of the study.
Y. Known or suspected history of drug or alcohol abuse or dependence within 1 year prior to the start of Screening.

Laboratory results for Exclusion Criterion number 1 may not be available prior to first dose. Later results for Exclusion Criterion number A may lead to discontinuation and replacement of the patient.

A patient has the right to withdraw from the study at any time. If a patient withdraws consent, the assessments specified for the Early Termination (ET) visit are performed. Patients who withdraw from the study are not replaced. A patient can be discontinued from study drug if the Investigator or Sponsor have reason to believe it is in the best interest of the patient to stop treatment.

Patients with prior kidney transplant developing AMR (C4d positive renal biopsy) and for whom rituximab is deemed the appropriate therapy must withdraw from the study and receive standard of care therapy. The primary reason and any other reason(s) for the discontinuation are recorded on the eCRF.

If a patient is discontinued from the study with an ongoing AE or an unresolved laboratory result that is significantly outside of the reference range and clinically significant, the Investigator attempts to provide follow-up until a satisfactory clinical resolution of the laboratory result or adverse event is achieved.

The Sponsor or Competent Authority can terminate the study for reasonable cause. Conditions that warrant termination of the study include, but are not limited to: (1) discovery of an unexpected, serious, or unacceptable risk to patients enrolled in the study, (2) sponsor decision to suspend or discontinue testing, evaluation, or development of the study drug, (3) failure of the Investigator to comply with the approved protocol, pertinent guidelines, and/or regulations, and (4) submission of knowingly false information from the Investigator to the Sponsor and/or regulatory authorities.

If it is determined at any point that a patient's Screening data does not satisfy one or more of the following inclusion/exclusion criteria (Inclusion Criterion number 2 or Exclusion Criterion number 1), after receiving at least 1 dose of investigational product (e.g., patient local laboratory data used to confirm eligibility criteria are subsequently determined by a central laboratory to no longer meet eligibility criteria), the patient is discontinued from the study and can be replaced. Early termination procedures are performed on patients who are terminated early and all AEs are collected until 60 days after the patient's last dose of study drug.

The end of the study is defined as the date of the last patient's last visit in the Extension Period.

5. Study Treatment

ALXN1210, a humanized anti-C5 monoclonal antibody composed of two 448 amino acid heavy chains and two 214 amino acid light chains, is an IgG2/4 kappa immunoglobulin consisting of human constant regions, and murine complementarity-determining regions grafted onto human framework light- and heavy-chain variable regions. ALXN1210 and eculizumab share over 99% primary amino acid sequence identity and have very similar pharmacology.

ALXN1210 drug product is supplied for clinical studies as a sterile, preservative-free 10-mg/mL solution in single-use vials and designed for infusion by diluting into commercially available saline (0.9% sodium chloride injection; country-specific pharmacopeia) for administration via IV infusion. Table 25 and the current IB provide additional information.

TABLE 25

Study Drug

| | |
|---|---|
| Product Name | ALXN1210 |
| Dosage Form | Concentrated solution (10 mg/mL) for infusion |
| Route of Administration | Intravenous infusion |
| Physical Description | Clear to translucent, slight whitish color, practically free from particles |
| Product Name | ALXN1210 |
| Manufacturer | Alexion Pharmaceuticals, Inc. or Contracted Manufacturing Organization |

ALXN1210 is packaged in United States Pharmacopeia (USP)/European Union Pharmacopeia (EP) Type 1 borosilicate glass vials and stoppered with a butyl rubber stopper with an aluminum overseal and a flip-off cap. Study drugs are supplied in kits. ALXN1210 is released to each site upon receipt of all required essential documents based upon applicable regulations.

Upon arrival of the study drugs kits at the study site, the pharmacist (or trained designee) promptly removes the study drug kits from the shipping cooler and stores them in their original cartons under refrigerated conditions at 2° C. to 8° C. (35° F. to 47° F.) and protected from light. ALXN1210 is not frozen. Study drugs are stored in a secure, limited-access storage area, and the temperature is monitored daily.

The drug product is at room temperature prior to administration. The material is not heated (e.g., by using a microwave or other heat source) other than by ambient air temperature.

ALXN1210 is not administered as an IV push or bolus injection. Infusions of study drug are prepared using aseptic technique. The patient's required dose of ALXN1210 is further diluted into commercially available saline (0.9% sodium chloride; country-specific pharmacopeia) at the volume specified in Table 26. ALXN1210 solution in diluent is administered to the patient using an IV tubing administration set via an infusion pump. Use of an in-line filter for infusion is required.

TABLE 26

Dosing Reference Chart for ALXN1210 Dose Preparation

| Dose Type | Body Weight (kg)$^a$ | Dose (mg) | ALXN1210 Vol. (mL) | Saline Vol. (mL) | Total Vol. (mL) | Min. Infusion Duration minutes (hours) | Max. Infusion Rate (mL/hour) |
|---|---|---|---|---|---|---|---|
| Loading | ≥40 to <60 | 2400 | 240 | 240 | 480 | 114 (1.9) | 253 |
| | ≥60 to <100 | 2700 | 270 | 270 | 540 | 102 (1.7) | 333 |
| | ≥100 | 3000 | 300 | 300 | 600 | 108 (1.8) | 333 |
| Maintenance | ≥40 to <60 | 3000 | 300 | 300 | 600 | 138 (2.3) | 267 |
| | ≥60 to <100 | 3300 | 330 | 330 | 660 | 120 (2.0) | 333 |
| | ≥100 | 3600 | 360 | 360 | 720 | 132 (2.2) | 333 |

Refer to the Pharmacy Manual for additional dose preparation instructions.
$^a$Body weight as recorded at the last study visit.

Doses of study drug are only prepared and dispensed by a pharmacist or a medically qualified staff member. Study drug is dispensed only to enrolled patients who are confirmed eligible for participation in this study. Once study drug is prepared for a patient, it is only administered to that patient. Vials of study drug are for one-time use only and any drug product remaining in the vial is not used for another patient. Any drug remaining in the infusion tubing or infusion bag is not used for another patient.

All clinical study material is stored in a secure place, and allocated and dispensed by appropriately trained persons. Detailed records of the amounts of the investigational product received, dispensed, and destroyed are maintained. Unless otherwise notified, empty vials and vials with residual materials are kept for inspection and accountability by the study monitor prior to their destruction or handled per local pharmacy standard operating procedures (SOPs) for clinical study drugs. To satisfy regulatory requirements regarding drug accountability, at the end of the study all remaining ALXN1210 inventory is reconciled and destroyed or returned to Alexion according to applicable regulations.

Patients receive ALXN1210 for 26 weeks. ALXN1210 is administered as a slow IV infusion over approximately 2 hours. ALXN1210 is not administered as an IV push or bolus injection.

The dose regimen for ALXN1210 during the Initial Evaluation Period is based on the patient's last recorded study visit body weight (Table 27). Patients receive a loading dose of ALXN1210 IV on Day 1, followed by maintenance dosing of ALXN1210 IV on Day 15 and q8w (every eight weeks) thereafter.

TABLE 27

Loading and Maintenance Treatment Regimens

| Body Weight$^a$ | Loading Dose (Day 1) | Maintenance Dose (Days 15, 71, and 127) |
|---|---|---|
| ≥40 to <60 kg | 2400 mg | 3000 mg |
| ≥60 to <100 kg | 2700 mg | 3300 mg |
| ≥100 kg | 3000 mg | 3600 mg |

$^a$Body weight as recorded at the last study visit.

After the Initial Evaluation Period, all patients roll over into an Extension Period of up to 2 years during which all patients receive ALXN1210 q8w (every eight weeks). The actual time of all dose administrations is recorded in the patient's eCRF.

This is an open-label study. Patients who meet all criteria for enrollment are assigned to study treatment with ALXN1210 at the Baseline Visit (Day 1). The interactive voice- or web-response system (IxRS) is used to assign vials containing ALXN1210 to each patient.

The weight-based dosages of ALXN1210 in this study (Table 27) are premised on PK/PD data from early development studies in healthy adult volunteers, as well as the available data from patients with PNH in an ongoing Phase 1b dose-finding study (ALXN1210-PNH-103) and an ongoing Phase 2 proof-of-concept study (ALXN1210-PNH-201). The selection of ALXN1210 dose regimen for patients with aHUS is based on targeting immediate, complete and sustained inhibition of terminal complement in patients with PNH, which is expected to correspond to immediate, complete and sustained inhibition of terminal complement in patients with aHUS as has been shown with eculizumab clinical trial data in PNH and aHUS patients.

Infusion of other monoclonal antibodies has been associated with infusion reactions, with onset typically during or shortly after completion of the infusion.

Prior medications (including vitamins and herbal preparations)—including those discussed in the exclusion criteria and procedures (any therapeutic intervention, such as surgery/biopsy or physical therapy) the patient takes or undergoes within 28 days (or 3 years for documentation of meningococcal vaccination) prior to the start of Screening until the first dose of ALXN1210—are recorded on the patient's eCRF.

For analytical purposes, any dialysis in the 14 day period immediately following the first ALXN1210 dose is not considered "new dialysis."

All medication use and procedures undertaken during the study are recorded in the patient's source document/medical chart and eCRF. This record includes all prescription drugs, herbal products, vitamins, minerals, over-the-counter medications, and current medications. Concomitant medications are recorded from the first infusion of study drug through 56 days after the patient's last dose of study drug. Any changes in concomitant medications also are recorded in the patient's source document/medical chart and eCRF. Any concomitant medication deemed necessary for the patient's standard of care during the study, or for the treatment of any AE, along with the allowed medications described below are given at the discretion of the Investigator. However, it is the responsibility of the Investigator to ensure that details regarding all medications are recorded in full in the patient's source document/medical chart and eCRF.

Patients are prohibited from receiving any of the following medications and procedures at any time after the first dose of study drug: eculizumab or other complement inhibitors, use of any other investigational drug or device as part of a clinical trial, IVIg (unless for an unrelated medical need e.g., hypogammaglobinemia), Rituximab, PE/PI after first dose, and new dialysis with the first 48-hour period following the first dose of ALXN1210, unless there is a compelling medical need as assessed by (1) hypervolemia unresponsive to diuretics, (2) refractory electrolyte imbalance, or (3) new-onset uremic encephalopathy. Exceptions must be approved prior to administration of dialysis on a case-by-case basis by the Sponsor.

The following concomitant medications and procedures are allowed under certain circumstances and with the following restrictions: use of other immunosuppressive therapies (such as steroids, mTORi [e.g., sirolimus, everolimus], CNI [e.g., cyclosporine or tacrolimus]) prior to screening or during the study are not allowed unless: a) part of an established post-transplant anti-rejection regime, or b) patient has confirmed anti-complement factor antibodies antibody requiring immunosuppressive therapy, or c) steroids are being used for a condition other than aHUS (e.g., asthma).

Any patients receiving other complement inhibitors (including eculizumab) or undergoing PE/PI after the first dose of study drug are withdrawn from the study.

Due to its mechanism of action, the use of ALXN1210 increases the patient's susceptibility to infection. To reduce the risk of infection, all patients are vaccinated against N. meningitidis, Hib, and Streptococcus pneumoniae.

Patients are vaccinated against N. meningitidis within 3 years prior to, or at the time of, receiving the first dose of ALXN1210. Patients who are treated with drug less than 2 weeks after receiving a meningococcal vaccine receive treatment with appropriate prophylactic antibiotics until 2 weeks after vaccination. Vaccines against serotypes A, C, Y, W135, and B, where available, are recommended to prevent common pathogenic meningococcal serotypes. Patients are vaccinated or revaccinated according to current national vaccination guidelines or local practice for vaccination use with complement inhibitors (e.g., eculizumab).

It is recognized that some patients who have not been vaccinated against N. meningiditis within 3 years prior to receiving the first dose of ALXN1210 may not be able to receive a vaccination at the time of the first dose. Patients who have not been vaccinated prior to initiating ALXN1210 treatment receive prophylactic antibiotics prior to and for at least 2 weeks after meningococcal vaccination.

Vaccination may not be sufficient to prevent meningococcal infection. Consideration should be given per official guidance and local practice on the appropriate use of antibacterial agents. All patients are monitored for early signs of meningococcal infection, evaluated immediately if infection is suspected, and treated with appropriate antibiotics, if necessary. To increase risk awareness and promote quick disclosure of any potential signs or symptoms of infection experienced by the patients during the course of the study, patients are provided a safety card to carry with them at all times. Additional discussion and explanation of the potential risks, signs, and symptoms occur at specific time points as part of the review of the patient safety card and throughout the study as described in the Schedule of Assessments (Table 23 and Table 24).

Patients are vaccinated against Haemophilus influenzae type b (Hib) and Streptococcus pneumoniae according to national and local vaccination schedule guidelines, prior to, or at the time of, receiving the first dose of ALXN1210. Vaccination status for N. meningitidis, Hib, and S. pnemoniae is recorded on the patient's eCRF.

Patients are administered study drug in a controlled setting under the supervision of the Investigator or designee, thereby ensuring compliance with study drug administration. The Investigator or designee ensures that all patients are adequately informed on the specific dosing regimen required for compliance with the study protocol, ensure that the patient receives the appropriate dose at the designated time points during the study and that adequate safety monitoring occurs during the infusion.

Before receiving study drug, female patients who consider themselves to be postmenopausal must provide evidence of menopause based on a combination of amenorrhea for at least 1 year and increased serum follicle-stimulating hormone (FSH) level (>30 IU/L) (e.g., in the absence of hormone replacement therapy, dietary phytoestrogens).

Female patients of childbearing potential use a highly effective method of contraception (as defined below), starting at Screening and continuing for at least 8 months after the last dose of study drug. Highly effective contraceptive methods* include: hormonal contraception associated with inhibition of ovulation, intrauterine device, intrauterine hormone-releasing system, bilateral tubal occlusion, vasectomized partner (provided that the partner is the patient's sole sexual partner), sexual abstinence (defined as refraining from heterosexual intercourse during the entire period of risk associated with the study drug treatment; reliability of sexual abstinence needs to be evaluated in relation to the duration of the clinical study and the preferred and usual lifestyle of the patient), combination of male condom with either cap, diaphragm, or sponge with spermicide (double barrier methods). Male patients with a female spouse/partner of childbearing potential or a pregnant or breastfeeding spouse or partner agree to use double barrier contraception (male condom plus appropriate barrier method for the female partner) while on treatment and for at least 8 months after the last dose of study drug. Double barrier contraception is required even with documented medical assessment of surgical success of a vasectomy.

Male patients do not donate sperm while on treatment and for at least 8 months after the last dose of study drug.

6. Efficacy Assessments

The primary efficacy assessment is Complete TMA Response during the 26-week Initial Evaluation Period. The criteria for Complete TMA Response are (1) normalization of platelet count, (2) normalization of LDH, and (3) ≥25% improvement in serum creatinine from baseline.

Patients who meet all Complete TMA Response criteria, confirmed by 2 consecutive measurements obtained at least 4 weeks apart, are classified as having met the primary efficacy endpoint.

The following secondary efficacy assessments are measured during the study:
  A. Dialysis requirement status
  B. Time to Complete TMA Response
  C. Complete TMA Response status over time
  D. Observed value and change from baseline in eGFR
  E. CKD stage, as evaluated by the Investigator at select target days and classified as improved, stable (no change), or worsened compared to baseline
  F. Observed value and change from baseline in hematologic parameters (platelets, LDH, hemoglobin)
  G. Increase in hemoglobin of ≥20 g/L from baseline, sustained for at least 2 consecutive measurements obtained at least 4 weeks apart
  H. Change from baseline in QoL, as measured by EQ-5D-3L (all patients), FACIT Fatigue Version 4 (patients ≥18 years of age), and Pediatric FACIT Fatigue (patients <18 years of age) questionnaires.

7. Safety Assessments

The Investigator or his/her designee meet with patients to discuss the potential safety risks of ALXN1210 and to give the Investigator the opportunity to address any of the patient's safety concerns regarding the study.

The collection of AEs is monitored from the time informed consent is obtained until study completion. Investigators follow any AEs through to their conclusion (resolution or stabilization). In the event of patient withdrawal from the study, AE monitoring continues through the last patient's last study visit if possible. The timing of the clinical and laboratory assessments is performed per the Schedule of Assessments (Tables 23 and 24). Any clinically significant abnormal results is followed until resolution or stabilization.

A review of demographic parameters, including age, gender, race, and ethnicity is performed. A complete medical history is taken and documented. Weight and height are recorded. Height is measured at Screening only.

The patient's aHUS medical history, including onset of first aHUS symptom and date of diagnosis, is documented at the Screening Visit.

The patient's medical history, including prior and concomitant conditions/disorders, is recorded at the Screening Visit. Medication (prescription or over-the-counter, including vitamins and/or herbal supplements) use over the 28 days (or 3 years for documentation of meningococcal vaccination) prior to the start of Screening is also recorded, in addition to meningococcal vaccination.

A physical examination includes the following assessments: general appearance; skin; head, ear, eye, nose, and throat; neck; lymph nodes; chest; heart; abdominal cavity; limb; central nervous system; and musculoskeletal system. An abbreviated physical examination consists of a body system relevant examination based upon Investigator judgment and patient symptoms. Vital sign measurements are taken after the patient has been resting for at least 5 minutes, and include systolic and diastolic BP (millimeters of mercury [mmHg]), pulse oximetry, heart rate (beats/minute), respiratory rate (breaths/minute), and oral or tympanic temperature (degrees Celsius [° C.] or degrees Fahrenheit [° F.]).

Samples for serum pregnancy, hematology, chemistry, coagulation, and urinalysis are performed at the times specified in the Schedule of Assessments (Tables 23 and 24). Samples for laboratory assessments are collected before each study drug administration.

Samples collected at Screening can be tested at either a local or central laboratory. If local laboratory tests are used for LDH, platelet count, hemoglobin, and serum creatinine, duplicate samples are collected for central laboratory testing to ensure baseline and postbaseline measurements for analyses are resulted from the central laboratory. In the event of duplicate samples from local and central laboratories, central laboratory results are used for analysis.

It is anticipated that some laboratory values may be outside the normal value range due to the underlying disease. The Investigators should use medical judgment when assessing the clinical significance of these values. Clinical significance is defined as any variation in laboratory measurements that has medical relevance and which results in a change in medical care. If clinically significant laboratory changes from baseline value are noted, the changes are documented as AEs on the AE eCRF. The Investigator assesses the relationship to study treatment for all clinically significant out-of-range values. The Investigator continues to monitor the patient through additional laboratory assessments until (1) values have returned to the normal range or baseline level, or (2) in the judgment of the Investigator, values that are outside the normal range are not related to the administration of study drug or other protocol-specific procedures.

For females of childbearing potential, a serum or urine pregnancy test (i.e., beta-human chorionic gonadotropin [β-hCG]) are performed according to the Schedule of Assessments (Tables 23 and 24). Blood samples are analyzed for hematology parameters.

Blood samples are analyzed for the serum chemistry parameters. Indirect bilirubin is calculated from total and direct bilirubin values; therefore, indirect bilirubin results are not available if direct bilirubin is below the limit of quantification. Serum FSH level is measured during Screening for postmenopausal female patients to confirm their postmenopausal status.

Chemistry assessments are performed at the time points specified in the Schedule of Assessments Tables 23 and 24). The eGFR is calculated for all visits at which serum chemistries are collected using the Modification of Diet in Renal Disease formula in patients ≥18 years of age and Modification of Diet in Renal Disease Schwartz formula in patients <18 years of age.

Blood samples are analyzed for coagulation parameters.

Urine samples are analyzed. A microscopic examination of urine samples is performed if the results of the macroscopic analysis are abnormal. Urine samples are also analyzed to measure proteins and creatinine in order to calculate the urine total protein:creatinine ratio.

For each patient, single 12-lead digital ECGs are collected according to the Schedule of Assessments (Tables 23 and 24). Patients must be supine for approximately 5 to 10 minutes before ECG collection and remain supine but awake during ECG collection. The Investigator or designee responsible for reviewing the ECG to assess whether the ECG is within normal limits and to determine the clinical significance of the results. These assessments are indicated on the CRF.

Blood samples are collected to test for presence and titer of ADAs to ALXN1210 in serum prior to study drug administration as indicated in the Schedule of Assessments (see Tables 23 and 24). I f results of the test are positive, the test can be repeated every 3 months until results become negative or stabilize, based on the measured titer and the safety assessments. Further characterization of antibody responses can be conducted as appropriate, including binding and neutralizing antibodies, PK/PD, safety, and activity of ALXN1210.

An AE is any untoward medical occurrence in a patient administered a pharmaceutical product and which does not necessarily have a causal relationship with this treatment. An AE can therefore be any unfavorable or unintended sign (e.g., an abnormal laboratory finding), symptom, or disease temporally associated with the use of a medicinal product, whether or not considered related to the medicinal product.

Situations in which an untoward medical occurrence did not occur (e.g—hospitalization for elective surgery if planned before the start of the study, admissions for social reasons or convenience), and anticipated day-to-day fluctuations of pre-existing disease(s) or condition(s) present or detected at the start of the study that do not worsen are not AEs.

Lack of drug effect is not an AE in clinical studies, because the purpose of the clinical study is to establish drug effect.

A medication error (including intentional misuse, abuse, and overdose of the product) or use other than what is defined in the protocol is not considered an AE unless there is an untoward medical occurrence as a result of a medication error.

Cases of pregnancy that occur during maternal or paternal exposure to investigational product are to be reported within 24 hours of Investigator/site awareness. Data on fetal outcome and breastfeeding is collected for regulatory reporting and safety evaluation.

Adverse events are recorded from the time of signed consent. An AE reported after informed consent but before study drug administration is considered a pretreatment AE.

The following events are important identified risks in this study: Meningococcal infections.

The severity of AEs is graded using Common Terminology Criteria for Adverse Events (CTCAE) version 4.03 or higher. A grading (severity) scale is provided for each AE term. Each CTCAE term is a Lowest Level Term (LLT) per the Medical Dictionary for Regulatory Activities) (MedDRA®). vEach LLT is coded to a MedDRA preferred term. Grade refers to the severity of the AE. The CTCAE assigns a grade of 1 through 5, with unique clinical descriptions of severity for each AE (Table 28).

TABLE 28

Adverse Event Severity Grading Scale

| Grade | Description |
|---|---|
| Grade 1 | Mild; asymptomatic or mild symptoms; clinical or diagnostic observations only; intervention not indicated |

TABLE 28-continued

Adverse Event Severity Grading Scale

| Grade | Description |
|---|---|
| Grade 2 | Moderate; minimal, local or noninvasive intervention indicated; limiting age-appropriate instrumental activities of daily living (ADL)[a] |
| Grade 3 | Severe or medically significant, but not immediately life-threatening; hospitalization or prolongation of hospitalization indicated; disabling; limiting self-care ADL[b] |
| Grade 4 | Life-threatening consequences; urgent intervention indicated. |
| Grade 5 | Death related to AE. |

Abbreviations: ADL = activities of daily living;
AE = adverse event
[a]Instrumental ADL refers to preparing meals, shopping for groceries or clothes, using the telephone, managing money, etc.
[b]Self-care ADL refers to bathing, dressing and undressing, feeding self, using the toilet, taking medications, and not bedridden.

Any change in the severity of an AE is documented based on specific guidelines in the eCRF Completion Guidelines. Severity and seriousness are differentiated: severity describes the intensity of an AE, while the term seriousness refers to an AE that has met specific criteria for a serious adverse event (SAE).

An Investigator must provide a causality assessment (Unrelated, Unlikely, Possible, Probable, or Definite) for all AEs (both serious and nonserious) based upon the Investigator's medical judgment and the observed symptoms associated with the event (Table 29). This assessment is recorded on the eCRF and any additional forms as appropriate.

TABLE 29

Causality Assessment Descriptions

| Assessment | Description |
|---|---|
| Not Related/Unrelated | Suggests that there is no causal association between the investigational product and the reported event. |
| Unlikely Related | Suggests that the clinical picture is highly consistent with a cause other than the investigational product but attribution cannot be made with absolute certainty and a relationship between the investigational product and AE cannot be excluded with complete confidence. |
| Possibly Related | Suggests that treatment with the investigational product may have caused or contributed to the AE (ie, the event follows a reasonable temporal sequence from the time of drug administration and/or follows a known response pattern to the investigational product, but could also have been produced by other factors). |
| Probably Related | Suggests that a reasonable temporal sequence of the event with the investigational product administration exists and the likely causal association of the event with the investigational product. This is based upon the known pharmacological action of the investigational product, known or previously reported adverse reactions to the investigational product or class of drugs, or judgment based on the Investigator's clinical experience. |
| Definitely Related | Temporal relationship to the investigational product, other conditions (concurrent illness, concurrent medication reaction, or progression/expression of disease state) do not appear to explain event, corresponds with the known pharmaceutical profile, improvement on discontinuation, reappearance on rechallenge. |

An serious adverse event (SAE) is any untoward medical occurrence that:
Results in death
Is life-threatening (i.e., patient was at risk of death at the time of the event)

Requires inpatient hospitalization or prolongation of existing hospitalization

Results in persistent or significant disability/incapacity

Is a congenital anomaly/birth defect

Important medical events that may not result in death, be immediately life-threatening, or require hospitalization, may be considered a serious adverse event when, based upon appropriate medical judgment, they may jeopardize the patient or may require intervention to prevent one of the outcomes listed above.

Suspected unexpected serious adverse reactions (SUSARs) are serious events that are not listed in the IB and that the Investigator identifies as related to investigational product or procedure. United States Title 21 Code of Federal Regulations (CFR) 312.32 and European Union Clinical Trial Directive 2001/20/EC and the associated detailed guidances or national regulatory requirements in participating countries require the reporting of SUSARs.

All AEs (serious and nonserious) are collected from the signing of the ICF until 60 days after the last dose of study drug for patients with ET or until 56 days after the last dose of study drug for patients who complete the study. All AEs are recorded on the eCRF upon the Investigator or his/her staff becoming aware of their occurrence.

All SAEs are recorded regardless of the Investigator's assessment of causality. No time limit exists on reporting SAEs that are thought to be causally related to the study drug. Investigators are at liberty to report SAEs irrespective of causality at any time.

For all SAEs, the Investigator must provide the following: appropriate and requested follow-up information, causality of the SAE(s), treatment of/intervention for the SAE(s), outcome of the SAE(s), and supporting medical records and laboratory/diagnostic information.

Pregnancy data is collected during this study for all patients and female spouse/partner of male patients. Exposure during pregnancy (also referred to as exposure in utero) can be the result of either maternal exposure or transmission of drug product via semen following paternal exposure. Pregnancy in itself is not regarded as an AE unless there is a suspicion that the investigational product may have interfered with the effectiveness of a contraceptive medication. However, complications of pregnancy and abnormal outcomes of pregnancy are AEs and may meet the criteria for an SAE (e.g., ectopic pregnancy, spontaneous abortion, intrauterine fetal demise, neonatal death, or congenital anomaly). Elective abortions without complications should not be reported as AEs.

8. Pharmacokinetics and Pharmacodynamics Assessments

Blood samples for determination of serum drug concentrations and PD assessments are collected before and after administration of study drug at the time points indicated in the Schedule of Assessments (see Tables 23 and 24). The actual date and time (24-hour clock time) of each sampling is recorded. The number of PK sampling time points for any given patient does not exceed the currently planned number of time points.

The blood samples for PK and PD assessment are collected from the arm opposite to the arm used for infusing drug. Assessments for PK/PD are as follows: (1) changes in serum ALXN1210 concentration over time and (2) changes in free C5 concentrations.

9. Exploratory Assessments

For exploratory biomarker analyses, summary statistics are presented for actual, change and percentage change from baseline.

The relationship between ALXN1210 concentration and exploratory biomarkers or the correlation between clinical benefit and key exploratory biomarkers can be assessed by graphical display. Exploratory analysis and potential relationships between clinical outcomes, PK/PD, genetic profile, and biomarker levels can also be performed. APC activity and autoantibody results are summarized if evaluated.

Exploratory genetics can be performed to investigate genetic variants in genes known to be associated with aHUS, as well as to identify novel genetic variants associated with aHUS, complement dysregulation, or metabolism or efficacy of ALXN1210.

Genetic mutations of known clinical relevance in aHUS are communicated to the patient or patient's guardian by Investigator together with appropriate genetic counseling. Genetic variants of unknown clinical significance is not be communicated to patients or their Investigator.

Additional signs or symptoms of aHUS are assessed using the Resource Utilization Patient Questionnaire and Patient-reported aHUS Symptoms Questionnaire.

Components of extra-renal signs or symptoms of aHUS, including vital signs and clinical laboratories, can be summarized descriptively at baseline and postbaseline time points and for changes from baseline. By-patient listings can be provided.

Analysis for signs, symptomology, and resource utilization can include standard approaches to categorical outcomes with or without repeated measures.

If a Day 1 assessment is missing, the Screening assessment is used as the baseline assessment.

For evaluation of Complete TMA Response during the 26-week Initial Evaluation Period (primary endpoint), patients missing an efficacy assessment that is part of the definition of Complete TMA Response while still on-study, have their last observation carried forward (LOCF). For patients who have discontinued from the study prior to Week 26, their data up to the time of discontinuation is used to assess Complete TMA Response.

Missing data for QoL instruments is handled as specified in the instructions for each instrument.

An interim analysis is planned for this study at the end of the 26-week Initial Evaluation Period after all patients have completed or withdrawn from the 26-week Initial Evaluation Period. Additionally, a second analysis to summarize long-term efficacy, safety, and PK parameters is performed at the end of the 2-year Extension Period.

Example 4: A Phase 3, Randomized, Open-Label, Active-Controlled Study of ALXN1210 Versus Eculizumab in Adult Patients with Paroxysmal Nocturnal Hemoglobinuria (PNH) Previously Treated with Eculizumab A Phase 3, open-label, randomized, active-controlled, multicenter study was conducted to evaluate the safety and efficacy of ALXN1210 (also known as Ultomiris™, antibody BNJ441, or ravulizumab) versus eculizumab administered by intravenous (IV) infusion to adult patients with PNH who had been treated with eculizumab for at least 6 months.

1. Objectives and Endpoints

The primary objective was to assess the non-inferiority of ALXN1210 (ravulizumab) compared to eculizumab in adult patients with PNH who had been treated with eculizumab for at least 6 months.

Non-inferiority was claimed if after 26 weeks of treatment the upper bound of the 95% confidence interval (CI) for the difference (ALXN1210-eculizumab) in percent change in LDH level (LDH-PCHG) was less than 15%.

Secondary objectives included characterizing the safety and tolerability of ALXN1210 in patients who switched from eculizumab to ALXN1210, evaluating the efficacy of ALXN1210 by additional efficacy measures, characterizing the pharmacokinetics/pharmacodynamics (PK/PD) and immunogenicity of ALXN1210, and evaluating the long-term safety and efficacy of ALXN1210.

The primary efficacy endpoint of the study was hemolysis as directly measured by percent change in lactate dehydrogenase level (LDH-PCHG) from Baseline to Day 183. The key secondary efficacy endpoints of the study (to be tested in a hierarchical manner) were:
1. Proportion of patients with breakthrough hemolysis, defined as at least one new or worsening symptom or sign of intravascular hemolysis (fatigue, hemoglobinuria, abdominal pain, shortness of breath (dyspnea), anemia (hemoglobin <10 g/dL), major adverse vascular event (MAVE) (including thrombosis), dysphagia, or erectile dysfunction) in the presence of elevated LDH ≥2×upper limit of normal (ULN)
2. Change in quality of life (QoL) as assessed via the Functional Assessment of Chronic Illness Therapy (FACIT)-Fatigue Scale, Version 4, from Baseline to Day 183
3. Transfusion avoidance (TA), defined as the proportion of patients who remained transfusion-free and did not require a transfusion as per protocol-specified guidelines from Baseline to Day 183
4. Proportion of patients with stabilized hemoglobin, defined as avoidance of a ≥2 g/dL decrease in hemoglobin level from baseline in the absence of transfusion from Baseline to Day 183

Other secondary efficacy endpoints of the study included assessment of: (1) total number of units of packed red blood cells (pRBCs) transfused from Baseline to Day 183, (2) proportion of patients with LDH in normal range at Day 183, (3) change in the European Organisation for Research and Treatment of Cancer (EORTC) Quality of Life Questionnaire-Core 30 Scale (QLQ-C30), Version 3.0, from Baseline to Day 183, (4) change in clinical manifestations of PNH (fatigue, hemoglobinuria, abdominal pain, shortness of breath, anemia, dysphagia, and erectile dysfunction) from Baseline to Day 183, and (5) proportion of patients experiencing MAVEs from Baseline to Day 183.

Pharmacokinetic and pharmacodynamic endpoints included assessment of: (1) change in serum ALXN1210 and eculizumab concentration over time, (2) change in chicken red blood cell (cRBC) hemolytic activity over time (exploratory), and (3) change in free C5 concentrations over time.

Exploratory endpoints included assessment of patient-reported PNH symptoms and healthcare resource utilization.

The safety and tolerability of ALXN1210 compared with eculizumab was evaluated by physical examinations, vital signs, electrocardiograms (ECGs), laboratory assessments, and incidence of adverse events (AEs) and serious adverse events (SAEs). The proportion of patients who developed antidrug antibodies (ADAs) was also assessed through the end of the study.

2. Study Design

This study was to evaluate the safety and efficacy of ALXN1210 (ravulizumab) versus eculizumab administered by intravenous (IV) infusion to adult patients with PNH who had been treated with eculizumab for at least the past 6 months. The study as designed was expected to include approximately 192 patients (96 patients per treatment group), but ultimately 195 subjects were enrolled in the study and 186 subjects were analyzed as part of the per-protocol analysis. The study comprised a 4-week screening period, a 26-week randomized treatment period, and an extension period of up to 2 years. Patients were stratified into 1 of 2 groups based on their transfusion history (received a transfusion of packed red blood cells (pRBCs) within 12 months prior to Day 1, yes or no). Patients within each of the 2 groups were randomly assigned in a 1:1 ratio to either continue on eculizumab or switch to ALXN1210. 97 patients were assigned to the ALXN1210 group and 98 patients were assigned to the eculizumab group. Upon completion of the study, 191 subjects went on to enroll in the extension study, as 4 subjects (1 in the ALXN1210 group and 3 in the eculizumab group) discontinued treatment.

Prior to randomization and within 5 days prior to study drug administration on Day 1, each patient's hemoglobin was evaluated by either local or central laboratory. If at that time the patient's hemoglobin value met protocol-specified transfusion guidelines, the patient was transfused with pRBCs to a hemoglobin level above the protocol-specified transfusion threshold in order to be eligible for randomization. The patient's post-transfusion hemoglobin value was confirmed by either a local or central laboratory to be above the protocol-specified transfusion threshold.

Day 1 of study treatment occurred 2 weeks from the patient's last dose of eculizumab. Patients randomly assigned to the ALXN1210 group received a loading dose (see Table 7) of ALXN1210 on Day 1, followed by maintenance doses of ALXN1210 on Day 15 and every 8 weeks (q8w) thereafter for a total of 26 weeks of treatment. Patients randomly assigned to the eculizumab group continued to receive the approved dose of eculizumab for the treatment of PNH (900 mg every 2 weeks [q2w]) for a total of 26 weeks of study treatment.

Figure 25:
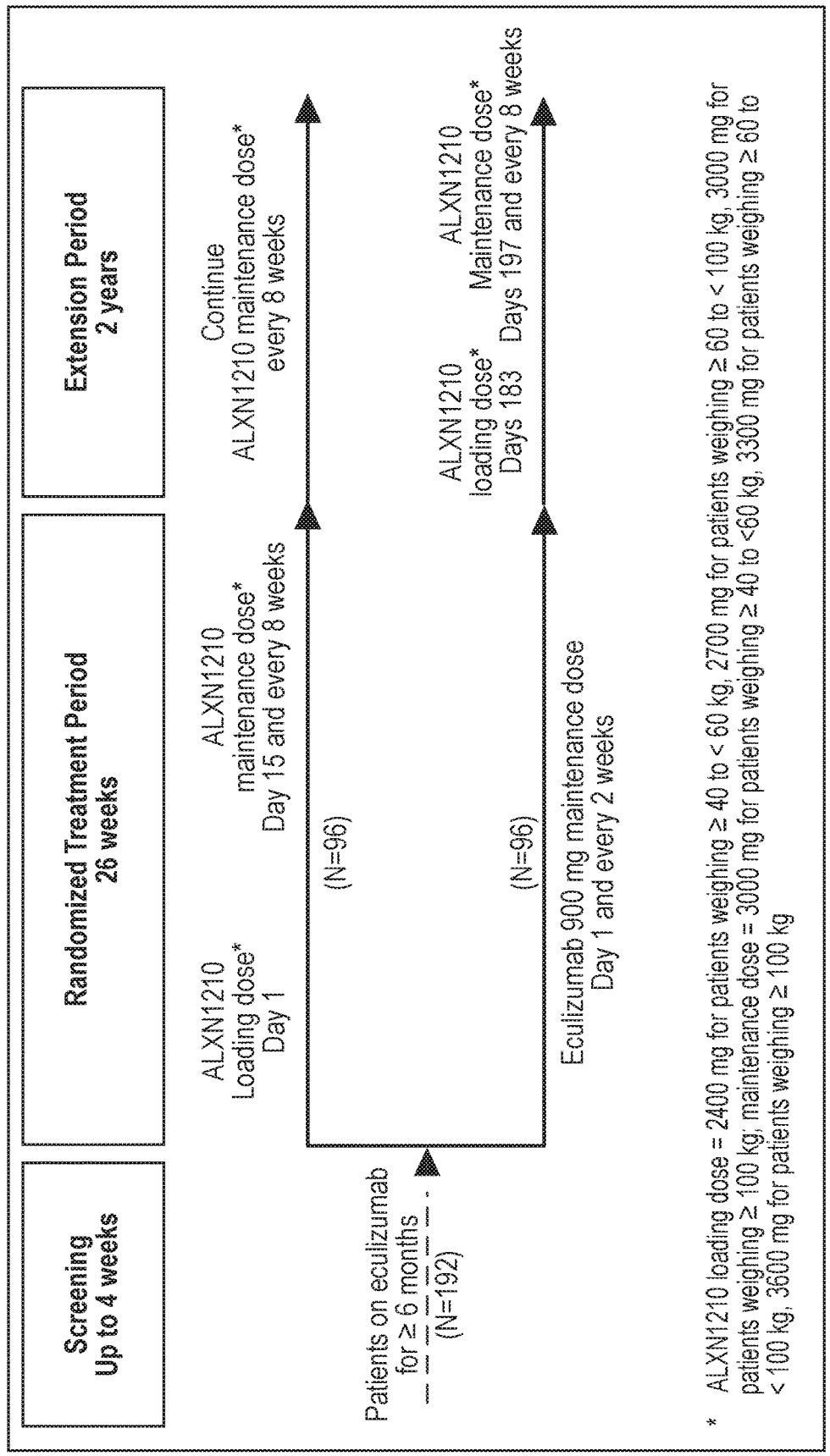
FIG. 25 is a schematic depicting the design of a Phase III ALXN1210-PNH-302 clinical trial in PNH patients who have been treated with eculizumab for at least the past six (6) months, wherein a complement inhibitor other than eculizumab is administered to the patients.
Figure 26:
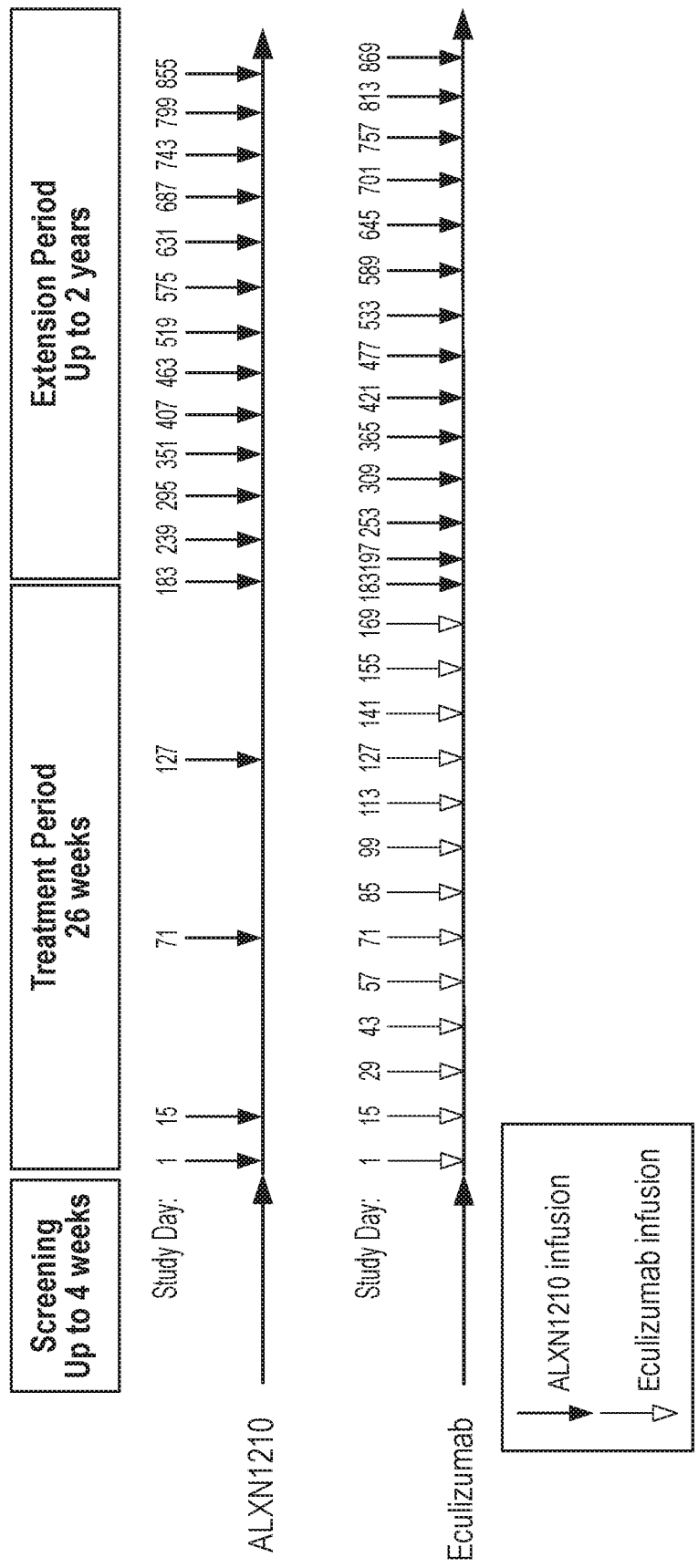
FIG. 26 is a schematic depicting the dosing schedule for patients in the Phase III ALXN1210-PNH-302 clinical trial, including the actual infusion days.

After completion of all assessments on Day 183, patients entered an extension period and received and will continue to receive ALXN1210 until the product is registered or approved (in accordance with country-specific regulations) or for up to 2 years, whichever occurs first. Beginning on Day 183, patients who had been randomized to the ALXN1210 treatment group received a maintenance dose (as described above) of ALXN1210 every 8 weeks (q8w), and patients are randomized to the eculizumab group received a loading dose (as described above) of ALXN1210 followed 2 weeks later and every 8 weeks (q8w) thereafter by a weight-based maintenance dose of ALXN1210. FIGS. 25 and 26 illustrate the study design.

A pRBC transfusion was administered when a patient had a hemoglobin value of 9 g/dL or lower with signs or symptoms of sufficient severity to warrant a transfusion, or a hemoglobin value of 7 g/dL or lower regardless of presence of clinical signs or symptoms.

The Schedule of Assessments is provided in Table 30 for the Screening and Randomized Treatment Period and in Table 31 (patients entering from ALXN1210 group) and Table 32 (patients entering from eculizumab group) for the Extension Period.

Additional (unscheduled) visits outside the specified visits were permitted at the discretion of the Investigator. Procedures, tests, and assessments were performed at the discretion of the Investigator. Any tests, procedures, or assessments performed at the Unscheduled Visits were recorded on the electronic case report forms (eCRFs). Additionally, if a suspected event of breakthrough hemolysis occurred, LDH, PK, and PD parameters were analyzed at the central laboratory. If the suspected event of breakthrough did not occur at a scheduled visit, an unscheduled visit occurred for evaluation of the patient and collection of the required LDH, PK, and PD parameters. For purposes of defining breakthrough hemolysis, assessment of LDH was based on a central laboratory value.

TABLE 30

Schedule of Study Visits and Assessments: Screening Through End of Randomized Treatment Period

| | Period | | | | | | | | | | | | | | | | |
|---|---|---|---|---|---|---|---|---|---|---|---|---|---|---|---|---|---|
| | Screening | Randomized Treatment Period | | | | | | | | | | | | | | | |
| | | Study Day | | | | | | | | | | | | | | | |
| | −28 to −1 | 1 | 8 | 15 | 22 | 29 | 43 | 57 | 71 | 85 | 99 | 113 | 127 | 141 | 155 | 169 | 183/ET |
| | | | | | | | | Window (day) | | | | | | | | | |
| | N/A | ±2 | ±2 | ±2 | ±2 | ±2 | ±2 | ±2 | ±2 | ±2 | ±2 | ±2 | ±2 | ±2 | ±2 | ±2 | ±2 |
| Informed consent | X | | | | | | | | | | | | | | | | |
| Confirmation or administration of meningococcal vaccination[a] | X | X | | | | | | | | | | | | | | | |
| Medical history and demographics | X | | | | | | | | | | | | | | | | |
| HIV testing | X | | | | | | | | | | | | | | | | |
| PNH clone size[b] | X | X | | | | | | | X | | | | | | | | X |
| Height | X | | | | | | | | | | | | | | | | |
| Weight | X | X | X | X | X | X | X | X | X | X | X | X | X | X | X | X | X |
| Pregnancy test[c] | X | X | | X | | | | | X | | | | X | | | | X |
| Record transfusions and transfusion parameters[d] | X[e] | X | X | X | X | X | X | X | X | X | X | X | X | X | X | X | X |
| PNH symptomatology[f,g] | X | X | X | X | X | X | X | X | X | X | X | X | X | X | X | X | X |
| FACIT-Fatigue[g] | X | X | X | | | X | | | X | | | | X | | | | X |
| EORTC QLQ-C30[g] | X | X | X | | | X | | | X | | | | X | | | | X |
| PNH symptoms patient questionnaire[g] | | X | X | X | X | X | X | X | X | X | X | X | X | X | X | X | X |
| Resource utilization patient questionnaire[g] | | X | | | | X | | | X | | | | X | | | | X |
| Physical examination | X | | | | | | | | | | | | | | | | |
| Abbreviated physical examination[h] | | X | | | | | | | X | | | | | | | | X |
| Vital signs[i] | X | X | X | X | X | X | X | X | X | X | X | X | X | X | X | X | X |
| Safety 12-Lead ECG[j] | X | | | | | | | | X | | | | | | | | X |
| Chemistry including LDH[k] | X | X | X | X | X | X | X | X | X | X | X | X | X | X | X | X | X |
| Hematology including free hemoglobin and coagulation[k] | X | X | X | X | X | X | X | X | X | X | X | X | X | X | X | X | X |
| Urinalysis and urine chemistry[k] | X | X | | X | | X | | | X | | | | X | | | | X |
| PK/PD sampling | | X[l] | X[m] | X[l] | X[m] | X[m] | X[m] | X[m] | X[l] | X[m] | X[m] | X[m] | X[l] | X[m] | X[m] | X[m] | X[l] |
| Immunogenicity (ADA)[n] | | X | | | | | | | X | | | | X | | | | X |
| Review safety card | | X | X | X | X | X | X | X | X | X | X | X | X | X | X | X | X |
| Breakthrough hemolysis[o] | | | | | | | | ←Monitor continuously→ | | | | | | | | | |
| Concomitant medications | X | | | | | | | | ←Monitor continuously→ | | | | | | | | |
| Adverse events | X | | | | | | | | ←Monitor continuously→ | | | | | | | | |
| Randomization[p] | | X | | | | | | | | | | | | | | | |
| ALXN1210 administration[q] | | X | | X | | | | | X | | | | X | | | | —[r] |

TABLE 30-continued

Schedule of Study Visits and Assessments: Screening Through End of Randomized Treatment Period

| | Screening | Randomized Treatment Period | | | | | | | | | | | | | | |
|---|---|---|---|---|---|---|---|---|---|---|---|---|---|---|---|---|
| | | Study Day | | | | | | | | | | | | | | |
| | −28 to −1 | 1 | 8 | 15 | 22 | 29 | 43 | 57 | 71 | 85 | 99 | 113 | 127 | 141 | 155 | 169 | 183/ET |
| | | | | | | | | | Window (day) | | | | | | | |
| | N/A | ±2 | ±2 | ±2 | ±2 | ±2 | ±2 | ±2 | ±2 | ±2 | ±2 | ±2 | ±2 | ±2 | ±2 | ±2 | ±2 |
| Eculizumab administration | | X | | X | | X | X | X | X | X | X | X | X | X | X | X | |

Abbreviations: ADA = antidrug antibody;
ECG = electrocardiogram;
EORTC QLQ-C30 = European Organization for Research and Treatment of Cancer, Quality of Life Questionnaire-Core 30 Scale;
ET = early termination;
FACIT-Fatigue = Functional Assessment of Chronic Illness Therapy-Fatigue Scale;
HIV = human immunodeficiency virus;
LDH = lactate dehydrogenase;
N/A = not applicable;
PD = pharmacodynamics;
PK = pharmacokinetics;
PNH = paroxysmal nocturnal hemoglobinuria

[a] All patients were vaccinated against meningococcal infections within 3 years prior to, or at the time of, initiating study drug. Patients who initiated study drug treatment less than 2 weeks after receiving a meningococcal vaccine received treatment with appropriate prophylactic antibiotics until 2 weeks after vaccination.
[b] White blood cell (WBC; granulocyte and monocyte) and red blood cell (RBC) clone size measured by high-sensitivity flow cytometry at Screening and Day 1; RBC clone size only on Day 71 and Day 183.
[c] Female patients of childbearing potential only. Serum pregnancy test at Screening and Day 183; urine pregnancy test at all other required time points. A negative urine test result was required prior to administering ALXN1210 or eculizumab to female patients of childbearing potential at the indicated visits.
[d] Transfusions given during and between visits were recorded.
[e] Prior to randomization and within 5 days prior to study drug administration on Day 1, each patient's hemoglobin was evaluated by either local or central laboratory. If at that time the patient's hemoglobin value met protocol-specified transfusion guidelines, the patient was transfused with pRBCs to a hemoglobin level above the protocol-specified transfusion threshold in order to be eligible for randomization. The patient's post-transfusion hemoglobin value was confirmed by local or central laboratory to be above the protocol-specified transfusion threshold.
[f] Investigator or designee assessment of the following events: fatigue, abdominal pain, dyspnea, dysphagia, chest pain, and erectile dysfunction.
[g] Physician- and patient-reported assessments was performed prior to study drug administration.
[h] Abbreviated physical examination consisted of a body system relevant examination based upon Investigator (or designee) judgment and patient symptoms. At least 1 body system was checked for an abbreviated physical examination.
[i] Vital sign measurements were taken after the patient had been resting for at least 5 minutes and included systolic and diastolic blood pressure (millimeters of mercury [mmHg]), heart rate (beats/minute), respiratory rate (breaths/minute), and temperature (degrees Celsius [° C.] or degrees Fahrenheit [° F.]). On dosing days, vital signs were taken before study drug administration.
[j] Single 12-lead ECG was collected at Screening and predose on Day 57 and Day 183. Patients were supine for approximately 5 to 10 minutes before ECG collection and remained supine but awake during ECG collection.
[k] Clinical laboratory measurements were collected predose on dosing days. Follicle stimulating hormone levels were measured during Screening only in order to confirm postmenopausal status.
[l] Serum samples for PK/PD analyses were collected predose (within 0.5 hours prior to the start of infusion) and at end-of-infusion (within 0.5 hours after the end of infusion). To minimize needle sticks to the patient, the predose sample may have been drawn through the venous access created for the dose infusion, prior to administration of the dose. End-of- infusion samples were drawn from the patient's opposite, noninfused arm. Note that the Day 183 end-of-infusion sample was considered an Extension Period assessment (see Table 31 and Table 32). All collection times were recorded in the eCRF. In the event of breakthrough hemolysis, a serum sample for PK/PD analysis was collected.
[m] Serum samples for PK/PD analyses were collected predose (within 0.5 hours prior to the start of infusion) for eculizumab-treated patients and at any time for ALXN1210-treated patients. All collection times were recorded in the eCRF. In the event of breakthrough hemolysis, a serum sample for PK/PD analysis was collected.
[n] Samples for ADA were collected predose.
[o] If a suspected event of breakthrough hemolysis occurred, LDH, PK, and PD parameters were analyzed at the central laboratory. If the suspected event of breakthrough did not occur at a scheduled visit, an unscheduled visit occurred for evaluation of the patient and collection of the required LDH, PK, and PD parameters.
[p] Patients were randomly assigned to treatment through an interactive voice or web response system (IxRS).
[q] The dose of ALXN1210 was based on the patient's last recorded study visit body weight.
[r] The primary efficacy endpoint assessment was before dosing on Day 183. Dosing on Day 183 was the start of the Extension Period. Please refer to additional Day 183 post dose procedures in Table 31 and Table 32.

TABLE 31

Schedule of Study Visits and Assessments: Extension Period Patients Entering from ALXN1210 Group

| | Extension Period | | | | | | | | | | | | |
|---|---|---|---|---|---|---|---|---|---|---|---|---|---|
| | Study Day | | | | | | | | | | | | |
| | 183[a] | 239 | 295 | 351 | 407 | 463 | 519 | 575 | 631 | 687 | 743 | 799 | 855 | 911 EOS/ET |
| | | | | | | | Window (day) | | | | | | |
| | ±2 | ±7 | ±7 | ±7 | ±7 | ±7 | ±7 | ±7 | ±7 | ±7 | ±7 | ±7 | ±7 | ±7 |
| PNH clone size[b] | | X | X | X | X | X | X | X | X | X | X | X | X | X |
| Weight | | X | X | X | X | X | X | X | X | X | X | X | X | X |
| Pregnancy test[c] | | X | X | X | X | X | X | X | X | X | X | X | X | X |
| Record transfusions and transfusion parameters[d] | | X | X | X | X | X | X | X | X | X | X | X | X | X |
| PNH symptomatology[e] | | X | X | X | X | X | X | X | X | X | X | X | X | X |
| FACIT-Fatigue[f] | | | X | | | | X | | | X | | | | X |

TABLE 31-continued

Schedule of Study Visits and Assessments: Extension Period Patients Entering from ALXN1210 Group

| | Period Extension Period | | | | | | | | | | | | | |
|---|---|---|---|---|---|---|---|---|---|---|---|---|---|---|
| | Study Day | | | | | | | | | | | | | |
| | 183[a] | 239 | 295 | 351 | 407 | 463 | 519 | 575 | 631 | 687 | 743 | 799 | 855 | 911 EOS/ET |
| | Window (day) | | | | | | | | | | | | | |
| | ±2 | ±7 | ±7 | ±7 | ±7 | ±7 | ±7 | ±7 | ±7 | ±7 | ±7 | ±7 | ±7 | ±7 |
| EORTC QLQ-C30[f] | | | | X | | | X | | | X | | | | X |
| PNH symptoms patient questionnaire[f] | | X | X | X | X | X | X | X | X | X | X | X | X | X |
| Resource utilization patient questionnaire[f] | | X | X | X | X | X | X | X | X | X | X | X | X | X |
| Abbreviated physical examination[g] | | X | | X | | X | | X | | X | | X | | X |
| Vital signs[h] | | X | X | X | X | X | X | X | X | X | X | X | X | X |
| Safety 12-Lead ECG[i] | | | | | | | | | | | | | | X |
| Chemistry including LDH[j] | | X | X | X | X | X | X | X | X | X | X | X | X | X |
| Hematology including free hemoglobin and coagulation[j] | | X | X | X | X | X | X | X | X | X | X | X | X | X |
| Urinalysis and urine chemistry[j] | | X | X | X | X | X | X | X | X | X | X | X | X | X |
| PK/PD sampling[k] | X | | | X | | | X | | | X | | | | X |
| Immunogenicity (ADA)[l] | | X | | X | | X | X | | | X | | X | | X |
| Review safety card | | X | X | X | X | X | X | X | X | X | X | X | X | X |
| Breakthrough hemolysis[m] | | | | | | | ←Monitor continuously→ | | | | | | | |
| Concomitant medications | | | | | | | ←Monitor continuously→ | | | | | | | |
| Adverse events | | | | | | | ←Monitor continuously→ | | | | | | | |
| ALXN1210 administration[n] | X | X | X | X | X | X | X | X | X | X | X | X | X | |

Abbreviations: ADA = antidrug antibody;
ECG = electrocardiogram;
EORTC QLQ-C30 = European Organization for Research and Treatment of Cancer, Quality of Life Questionnaire-Core 30 Scale;
EOS = end of study;
ET = early termination;
FACIT-Fatigue = Functional Assessment of Chronic Illness Therapy-Fatigue Scale;
LDH = lactate dehydrogenase;
PD = pharmacodynamics;
PK = pharmacokinetics;
PNH = paroxysmal nocturnal hemoglobinuria

[a]All patients who rolled over into the Extension Period received ALXN1210 on Day 183 after all assessments have been performed.
[b]Granulocyte and red blood cell (RBC) clone size measured by high-sensitivity flow cytometry on Days 351 and 743; RBC clone size only at other visits.
[c]Female patients of childbearing potential only. Serum pregnancy test at ET only; urine pregnancy test at all other time points. A negative urine test result was required prior to administering ALXN1210 to female patients of childbearing potential on dosing days.
[d]Transfusions given during and between visits were recorded.
[e]Investigator or designee assessment of the following events: fatigue, abdominal pain, dyspnea, dysphagia, chest pain, and erectile dysfunction.
[f]Physician- and patient-reported assessments were performed prior to study drug administration.
[g]Abbreviated physical examination consisted of a body system relevant examination based upon Investigator (or designee) judgment and patient symptoms. At least one body system was checked for an abbreviated physical examination.
[h]Vital sign measurements were taken after the patient had been resting for at least 5 minutes and included systolic and diastolic blood pressure (millimeters of mercury [mmHg]), heart rate (beats/minute), respiratory rate (breaths/minute), and temperature (degrees Celsius [° C.] or degrees Fahrenheit [° F.]). Vital signs were taken before each study drug administration.
[i]Single 12-lead ECG was collected at Day 911 or ET. Patients were supine for approximately 5 to 10 minutes before ECG collection and remained supine but awake during ECG collection.
[j]Clinical laboratory measurements were collected predose on dosing days.
[k]Serum samples for PK/PD analyses were collected at end-of-infusion on Day 183; predose (within 0.5 hours prior to the start of infusion) and at end-of-infusion (within 0.5 hours after the end of infusion) on Days 351, 575, and 743; and at any time on Day 911 or ET. To minimize needle sticks to the patient, the predose sample was drawn through the venous access created for the dose infusion, prior to administration of the dose. End-of-infusion samples were drawn from the patient's opposite, noninfused arm. All collection times were recorded in the eCRF. In the event of breakthrough hemolysis, a serum sample for PK/PD analysis was collected.
[l]Samples for ADA were collected predose.
[m]If a suspected event of breakthrough hemolysis occurred, LDH, PK, and PD parameters were analyzed at the central laboratory. If the suspected event of breakthrough did not occur at a scheduled visit, an unscheduled visit occurred for evaluation of the patient and collection of the required LDH, PK, and PD parameters.
[n]The dose of ALXN1210 was based on the patient's last recorded study visit body weight.

TABLE 32

Schedule of Study Visits and Assessments: Extension Period Patients Entering from Eculizumab Group

| | Period |||||||||||||||| 
|---|---|---|---|---|---|---|---|---|---|---|---|---|---|---|---|---|
| | Extension Period ||||||||||||||||
| | Study Day ||||||||||||||||
| | 183[a] | 197 | 225 | 253 | 309 | 365 | 421 | 477 | 533 | 589 | 645 | 701 | 757 | 813 | 869 | 925 EOS/ET |
| | Window (day) ||||||||||||||||
| | ±2 | ±3 | ±7 | ±7 | ±7 | ±7 | ±7 | ±7 | ±7 | ±7 | ±7 | ±7 | ±7 | ±7 | ±7 | ±7 |
| PNH clone size[b] | | X | X | X | X | X | X | X | X | X | X | X | X | X | X | X |
| Weight | | X | X | X | X | X | X | X | X | X | X | X | X | X | X | X |
| Pregnancy test[c] | | X | | X | X | X | X | X | X | X | X | X | X | X | X | X |
| Record transfusions and transfusion parameters[d] | | X | X | X | X | X | X | X | X | X | X | X | X | X | X | X |
| PNH symptomatology[e] | | X | | X | X | X | X | X | X | X | X | X | X | X | X | X |
| FACIT-Fatigue[f] | | | | | | X | | | | X | | | X | | | X |
| EORTC QLQ-C30[f] | | | | | | X | | | | X | | | X | | | X |
| PNH symptoms patient questionnaire[f] | | X | | X | X | X | X | X | X | X | X | X | X | X | X | X |
| Resource utilization patient questionnaire[f] | | X | | X | X | X | X | X | X | X | X | X | X | X | X | X |
| Abbreviated physical examination[g] | | X | X | X | | X | | X | | X | | X | | X | | X |
| Vital signs[h] | | X | X | X | X | X | X | X | X | X | X | X | X | X | X | X |
| Safety 12-Lead ECG[i] | | | | | | | | | | | | | | | | X |
| Chemistry including LDH[j] | | X | X | X | X | X | X | X | X | X | X | X | X | X | X | X |
| Hematology including free hemoglobin and coagulation[j] | | X | X | X | X | X | X | X | X | X | X | X | X | X | X | X |
| Urinalysis and urine chemistry[j] | | X | X | X | X | X | X | X | X | X | X | X | X | X | X | X |
| PK/PD sampling[k] | X | X | X | | | X | | | X | | | | X | | | X |
| Immunogenicity (ADA)[l] | | | | X | | X | | X | | X | | X | | X | | X |
| Review safety card | | X | X | X | X | X | X | X | X | X | X | X | X | X | X | X |
| Breakthrough hemolysis[m] | | | | | | ←Monitor continuously→ ||||||||||
| Concomitant medications | | | | | | ←Monitor continuously→ ||||||||||
| Adverse events | | | | | | ←Monitor continuously→ ||||||||||
| ALXN1210 administration[n] | X | X | | X | X | X | X | X | X | X | X | X | X | X | X | |

Abbreviations: ADA = antidrug antibody;
ECG = electrocardiogram;
EORTC QLQ-C30 = European Organization for Research and Treatment of Cancer, Quality of Life Questionnaire-Core 30 Scale;
EOS = end of study;
ET = early termination;
FACIT-Fatigue = Functional Assessment of Chronic Illness Therapy-Fatigue Scale;
LDH = lactate dehydrogenase;
PD = pharmacodynamics;
PK = pharmacokinetics;
PNH = paroxysmal nocturnal hemoglobinuria

[a] All patients who rolled over into the Extension Period received ALXN1210 on Day 183 after all assessments had been performed.
[b] Granulocyte and red blood cell (RBC) clone size measured by high-sensitivity flow cytometry on Days 365 and 757; RBC clone size only at other visits.
[c] Female patients of childbearing potential only. Serum pregnancy test at ET only; urine pregnancy test at all other time points. A negative urine test result was required prior to administering ALXN1210 to female patients of childbearing potential on dosing days.
[d] Transfusions given during and between visits were recorded.
[e] Investigator or designee assessment of the following events: fatigue, abdominal pain, dyspnea, dysphagia, chest pain, and erectile dysfunction.
[f] Physician- and patient-reported assessments were performed prior to study drug administration.
[g] Abbreviated physical examination consisted of a body system relevant examination based upon Investigator (or designee) judgment and patient symptoms. At least one body system was checked for an abbreviated physical examination.
[h] Vital sign measurements were taken after the patient had been resting for at least 5 minutes and included systolic and diastolic blood pressure (millimeters of mercury [mmHg]), heart rate (beats/minute), respiratory rate (breaths/minute), and temperature (degrees Celsius [° C.] or degrees Fahrenheit [° F.]). Vital signs were taken before each study drug administration.
[i] Single 12-lead ECG was collected at Day 925 or ET. Patients were supine for approximately 5 to 10 minutes before ECG collection and remained supine but awake during ECG collection.
[j] Clinical laboratory measurements were collected predose on dosing days.

TABLE 32-continued

Schedule of Study Visits and Assessments: Extension Period Patients Entering from Eculizumab Group

| | | | | | | | Period | | | | | | | | |
|---|---|---|---|---|---|---|---|---|---|---|---|---|---|---|---|
| | | | | | | | Extension Period | | | | | | | | |
| | | | | | | | Study Day | | | | | | | | |
| 183[a] | 197 | 225 | 253 | 309 | 365 | 421 | 477 | 533 | 589 | 645 | 701 | 757 | 813 | 869 | 925 EOS/ET |
| | | | | | | | Window (day) | | | | | | | | |
| ±2 | ±3 | ±7 | ±7 | ±7 | ±7 | ±7 | ±7 | ±7 | ±7 | ±7 | ±7 | ±7 | ±7 | ±7 | ±7 |

[k]Serum samples for PK/PD analyses were collected predose (within 0.5 hours prior to the start of infusion) and at end-of-infusion (within 0.5 hours after the end of infusion) on Days 197, 365, 589, and 757; at end-of-infusion on Day 183; and at any time on Days 225 and 925 or ET. To minimize needle sticks to the patient, the predose sample was drawn through the venous access created for the dose infusion, prior to administration of the dose. End-of- infusion samples were drawn from the patient's opposite, noninfused arm. All collection times were recorded in the eCRF. In the event of breakthrough hemolysis, a serum sample for PK/PD analysis was collected.
[l]Samples for ADA were collected predose.
[m]If a suspected event of breakthrough hemolysis occurred, LDH, PK, and PD parameters were analyzed at the central laboratory. If the suspected event of breakthrough did not occur at a scheduled visit, an unscheduled visit occurred for evaluation of the patient and collection of the required LDH, PK, and PD parameters.
[n]The dose of ALXN1210 was based on the patient's last recorded study visit body weight.

3. Study Population

A total of 195 patients with documented PNH were enrolled and randomly assigned to treatment with either ALXN1210 (ravulizumab) or eculizumab at approximately 50 investigative sites globally. Individuals who did not meet the criteria for participation in this study (screen failure) could be rescreened. Prospective approval of protocol deviations to recruitment and enrollment criteria, also known as protocol waivers or exemptions, was not permitted.

Patients were eligible for enrollment in the study only if they met all of the following criteria and none of the exclusion criteria:

1. Male or female, 18 years of age or older at the time of consent.
2. Treated with eculizumab according to the labelled dosing recommendation for PNH for at least 6 months prior to Day 1.
3. Lactate dehydrogenase (LDH)≤1.5×ULN at Screening. Sample must have been obtained on a scheduled eculizumab-dosing day prior to dose administration (i.e., at trough eculizumab level) and analyzed by the central laboratory.
4. Documented diagnosis of PNH, confirmed by high-sensitivity flow cytometry evaluation (Borowitz M J et al., Cytometry Part B, 78B:211-230, 2010) of RBCs and white blood cells (WBCs), with granulocyte or monocyte clone size of ≥5%.
5. To reduce the risk of meningococcal infection (*Neisseria meningitidis*), all patients must have been vaccinated against meningococcal infections within 3 years prior to, or at the time of, initiating study drug. Patients who initiated study drug treatment less than 2 weeks after receiving a meningococcal vaccine received treatment with appropriate prophylactic antibiotics until 2 weeks after vaccination.
6. Female patients of childbearing potential and male patients with female partners of childbearing potential were required to follow protocol-specified guidance for avoiding pregnancy while on treatment and for 8 months after last dose of study drug.
7. Patients must have been willing and able to give written informed consent and to comply with all study visits and procedures, including the use of any data collection device(s) to directly record patient data.

Patients were excluded from study enrollment if they met any of the following criteria:

1. LDH value ≥2×ULN in the 6 months prior to Day 1.
2. MAVE in the 6 months prior to Day 1.
3. Platelet count <30,000/mm$^3$ (30×10$^9$/L) at Screening.
4. Absolute neutrophil count <500/μL (0.5×10$^9$/L) at Screening.
5. History of bone marrow transplantation.
6. Body weight <40 kg at Screening.
7. History of *N. meningitidis* infection.
8. History of unexplained, recurrent infection.
9. Active systemic bacterial, viral, or fungal infection within 14 days prior to study drug administration on Day 1.
10. Presence of fever ≥38° C. (100.4° F.) within 7 days prior to study drug administration on Day 1.
11. Human immunodeficiency virus (HIV) infection (evidenced by HIV-1 or HIV-2 antibody titer).
12. Immunized with a live-attenuated vaccine 1 month prior to study drug administration on Day 1.
13. History of malignancy within 5 years of Screening, with the exception of nonmelanoma skin cancer or carcinoma in situ of the cervix that had been treated with no evidence of recurrence.
14. History of or ongoing major cardiac, pulmonary, renal, endocrine, or hepatic disease (e.g., active hepatitis) that, in the opinion of the Investigator or Sponsor, precluded the patient's participation in an investigational clinical trial.
15. Unstable medical conditions (e.g., myocardial ischemia, active gastrointestinal bleed, severe congestive heart failure, anticipated need for major surgery within 6 months of randomization, coexisting chronic anemia unrelated to PNH) that would have made them unlikely to tolerate the requirements of the protocol (e.g., transfusion guidelines).
16. Concomitant use of anticoagulants was prohibited if not on a stable regimen for at least 2 weeks prior to Day 1.
17. History of hypersensitivity to any ingredient contained in the study drug, including hypersensitivity to murine proteins.
18. Females who plan to become pregnant or were currently pregnant or breastfeeding.
19. Females who had a positive pregnancy test result at Screening or on Day 1.
20. Participation in another interventional treatment study or use of any experimental therapy within 30 days before initiation of study drug on Day 1 in this study or within 5 half-lives of that investigational product, whichever was greater.

21. Known or suspected history of drug or alcohol abuse or dependence within 1 year prior to the start of Screening.
22. Known medical or psychological condition(s) or risk factor that, in the opinion of the Investigator, might have interfered with the patient's full participation in the study, posed any additional risk for the patient, or confounded the assessment of the patient or outcome of the study.

A patient had the right to withdraw from the study at any time. If a patient withdrew consent, the assessments specified for the Early Termination (ET) visit were performed. Patients who withdrew from the study were not replaced.

Patients were permanently discontinued from ALXN1210 treatment if any of the following occur during the study:
1. Serious infusion reaction (such as bronchospasm with wheezing or requiring ventilator support or symptomatic hypotension) or serum sickness-like reactions manifesting 1 to 14 days after drug administration;
2. Severe uncontrolled infection;
3. Pregnancy or planned pregnancy; or
4. If it was in the best interest of the patient.

If a patient was discontinued from study drug, the patient was encouraged to return for the remainder of his or her scheduled protocol visits until starting a different complement-targeted therapy.

If a patient was discontinued from the study with an ongoing adverse event or an unresolved laboratory result that, in the opinion of the Investigator, was significantly outside of the reference range and clinically significant, the Investigator attempted to provide follow-up until a satisfactory clinical resolution of the laboratory result or adverse event was achieved. If a female patient was permanently discontinued from ALXN1210 treatment due to pregnancy, the Investigator attempted to follow-up until the outcome of the pregnancy.

The Sponsor or health authority may have terminated the study for reasonable cause. The end of the study was defined as the date of the last patient's last visit in the Extension Period.

6. Study Treatment

The study drugs in this study were ALXN1210 (ravulizumab) and eculizumab (active control). Both ALXN1210 and eculizumab are humanized, anti-C5 monoclonal antibodies.

ALXN1210 and eculizumab drug products were supplied for clinical studies as sterile, preservative-free 10-mg/mL solutions in single-use vials and designed for infusion by diluting into commercially available saline (0.9% sodium chloride injection; country-specific pharmacopeia) for administration via IV infusion (see Table 33).

TABLE 33

| | Study Drug | |
|---|---|---|
| | Study Drug | |
| Product Name | ALXN1210 | Eculizumab |
| Dosage Form | Concentrated solution (10 mg/mL) for infusion | Concentrated solution (10 mg/mL) for infusion |
| Route of Administration | Intravenous infusion | Intravenous infusion |
| Physical Description | Clear to translucent, slight whitish color, practically free from particles | Clear, colorless solution practically free from particles |
| Manufacturer | Alexion Pharmaceuticals, Inc. or Contracted Manufacturing Organization | Alexion Pharmaceuticals, Inc. or Contracted Manufacturing Organization |

ALXN1210 and eculizumab were packaged in US Pharmacopeia/European Pharmacopeia Type 1 borosilicate glass vials and stoppered with a butyl rubber stopper with an aluminum overseal and a flip-off cap. Study drug was supplied in kits. Study drug orders were released to each site upon receipt of all required documents based upon applicable regulations.

Upon arrival of the study drug kits at the study site, the pharmacist or designee promptly removed the study drug kits from the shipping cooler and stored them in their original cartons under refrigerated conditions at 2° C. to 8° C. (35° F. to 47° F.) and protected from light. ALXN1210 and eculizumab were not to be frozen. Study drug was stored in a secure, limited-access storage area, and the temperature was monitored daily.

Eculizumab or ALXN1210 was not administered as an IV push or bolus injection. Infusions of study drug were prepared using aseptic technique. The patient's required dose of ALXN1210 or eculizumab was further diluted into commercially available saline (0.9% sodium chloride; country-specific pharmacopeia) at the volume specified in Table 34 for ALXN1210 or Table 35 for eculizumab (see also approved local labeling or current IB for eculizumab). ALXN1210 or eculizumab admixture was administered to the patient using an IV tubing administration set via an infusion pump. Use of a 0.2 micron filter was required during infusion of ALXN1210.

TABLE 34

Dosing Reference Chart for ALXN1210 Dose Preparation

| Dose Type | Body Weight (kg)[a] | Dose (mg) | ALXN1210 Volume (mL) | Saline Volume (mL) | Total Volume (mL) | Minimum Infusion Duration minutes (hours) | Maximum Infusion Rate (mL/hour) |
|---|---|---|---|---|---|---|---|
| Loading | ≥40 to <60 | 2400 | 240 | 240 | 480 | 114 (1.9) | 253 |
| | ≥60 to <100 | 2700 | 270 | 270 | 540 | 102 (1.7) | 318 |
| | ≥100 | 3000 | 300 | 300 | 600 | 108 (1.8) | 333 |

TABLE 34-continued

Dosing Reference Chart for ALXN1210 Dose Preparation

| Dose Type | Body Weight (kg)[a] | Dose (mg) | ALXN1210 Volume (mL) | Saline Volume (mL) | Total Volume (mL) | Minimum Infusion Duration minutes (hours) | Maximum Infusion Rate (mL/hour) |
|---|---|---|---|---|---|---|---|
| Maintenance | ≥40 to <60 | 3000 | 300 | 300 | 600 | 140 (2.4) | 250 |
|  | ≥60 to <100 | 3300 | 330 | 330 | 660 | 120 (2.0) | 330 |
|  | ≥100 | 3600 | 360 | 360 | 720 | 132 (2.2) | 328 |

Note:
Please refer to the Pharmacy Manual for additional dose preparation instructions.
[a]Body weight as recorded at the last study visit.

TABLE 35

Dosing Reference Chart for Eculizumab Dose Preparation

| Dose Type | Dose (mg) | Eculizumab Volume (mL) | Saline Volume (mL) | Total Volume (mL) | Infusion Duration (minutes) | Approximate Infusion Rate (mL/hour) |
|---|---|---|---|---|---|---|
| Maintenance | 900 | 90 | 90 | 180 | 35 | 300 |

Doses of study drug were only prepared and dispensed by a pharmacist or a medically qualified staff member. Study drug was dispensed only to enrolled patients who were confirmed eligible for participation in this study. Once study drug was prepared for a patient, it was only administered to that patient. Vials of study drug are for one-time use only and any drug product remaining in the vial was not used for another patient. Any drug remaining in the infusion tubing or infusion bag was not used for another patient.

Patients were randomly assigned in a 1:1 ratio to either continue on eculizumab or switch to ALXN1210 for 26 weeks. Study drug was administered as a slow IV infusion (see Table 34 and Table 35). Day 1 of study treatment occurred 2 weeks from the patient's last dose of eculizumab.

The dose regimen for ALXN1210 was a loading dose on Day 1 followed by maintenance doses on Day 15 and every 8 weeks (q8w) thereafter. The dosage of ALXN1210 was based on the patient's last recorded study visit body weight, as indicated in Table 36.

TABLE 36

ALXN1210 Weight-Based Dosages

| ALXN1210 Treatment Group Body Weight | Loading Dose | Maintenance Dose |
|---|---|---|
| ≥40 to <60 kg | 2400 mg | 3000 mg |
| ≥60 to <100 kg | 2700 mg | 3300 mg |
| ≥100 kg | 3000 mg | 3600 mg |

Patients randomly assigned to continue on eculizumab continued to receive eculizumab maintenance dosing according to the approved dosing regimen for the PNH indication, which was 900 mg q2w.

After the randomized treatment period all patients entered the Extension Period and received and will continue to receive ALXN1210 until the product is registered or approved (in accordance with country-specific regulations) or for up to 2 years, whichever occurs first. Beginning on Day 183, patients were randomized to the ALXN1210 treatment group received their weight-based maintenance dose of ALXN1210 every 8 weeks (q8w), and patients randomized to the eculizumab group received a weight-based loading dose of ALXN1210 followed 2 weeks later and every 8 weeks (q8w) thereafter by a weight-based maintenance dose of ALXN1210 (Table 36; FIG. 26). The actual time of all dose administrations was recorded on the patient's electronic case report form (eCRF). Patients who met all criteria for enrollment were randomly assigned to study treatment with ALXN1210 or eculizumab at the Baseline Visit (Day 1). Treatment group assignment was determined by a computer-generated random sequence using an interactive voice- or web-response system (IxRS). The randomization was a stratified randomization. Patients were stratified into 1 of 2 groups based on their transfusion history (received a transfusion of pRBCs within 12 months prior to Day 1, yes or no). Patients within both groups were then randomly assigned in a 1:1 ratio to either continue on eculizumab or switch to ALXN1210 during the 26-week randomized treatment period.

The weight-based dosages of ALXN1210 in this study (Table 36) were premised on PK/PD data from early development studies in healthy adult volunteers, as well as the available data from patients with PNH in an ongoing Phase 1b dose-finding study (ALXN1210-PNH-103) and an ongoing Phase 2 proof-of-concept study (ALXN1210-PNH-201). The selection of ALXN1210 dose regimen was based on targeting immediate, complete and sustained inhibition of terminal complement in patients with PNH.

The eculizumab dosage was the approved dose for the treatment of patients with PNH (Soliris® United States Prescribing Information [USPI] and Summary of Product Characteristics [SmPC]).

Infusion of other monoclonal antibodies had been associated with infusion reactions, with onset typically during or shortly after completion of the infusion. Prior medications (including vitamins and herbal preparations)—including those discussed in the exclusion criteria and procedures (any therapeutic intervention, such as surgery/biopsy or physical therapy) the patient takes or undergoes within 28 days (or 3 years for documentation of meningococcal vaccination) prior to the start of Screening until the first dose of study drug-were recorded on the patient's electronic case report form (eCRF).

Transfusions of pRBCs received within 1 year prior to first study drug administration were recorded on the patient's eCRF.

All medication use and procedures undertaken during the study were recorded in the patient's source document/medical chart and eCRF. This record included all prescription drugs, herbal products, vitamins, minerals, over-the-counter medications, and current medications for PNH. Concomitant medications were recorded from the first infusion of study drug through 56 days after the patient's last dose of study drug. Any changes in concomitant medications also were recorded in the patient's source document/medical chart and eCRF. Any concomitant medication deemed necessary for the patient's standard of care during the study, or for the treatment of any adverse event (AE), along with the allowed medications described below was given at the discretion of the Investigator.

Concomitant use of anticoagulants was prohibited if not on a stable dose regimen for at least 2 weeks prior to Day 1. Use of complement inhibitors other than the patient's assigned study treatment was prohibited.

Due to their mechanism of action, the use of eculizumab or ALXN1210 increases the patient's susceptibility to meningococcal infection (*N. meningitidis*). To reduce the risk of meningococcal infection, all patients were vaccinated against meningococcal infections within 3 years prior to, or at the time of, initiating study drug. Patients who initiated study drug treatment less than 2 weeks after receiving a meningococcal vaccine received treatment with appropriate prophylactic antibiotics until 2 weeks after vaccination. Vaccines against serotypes A, C, Y, W135, and B, where available, were recommended to prevent common pathogenic meningococcal serotypes. Patients were vaccinated or revaccinated according to current national vaccination guidelines or local practice for vaccination use with complement inhibitors (e.g., eculizumab).

Vaccination may not be sufficient to prevent meningococcal infection. Consideration could have been given per official guidance and local practice on the appropriate use of antibacterial agents. All patients could have been monitored for early signs of meningococcal infection, evaluated immediately if infection was suspected, and treated with appropriate antibiotics, if necessary.

7. Efficacy Assessments

A packed red blood cell (pRBC) transfusion was administered when a patient had a
- hemoglobin value of 9 g/dL or lower with signs or symptoms of sufficient severity to warrant a transfusion
- hemoglobin value of 7 g/dL or lower regardless of presence of clinical signs or symptoms Signs or symptoms typically associated with or that precipitate the patient's need for transfusion were documented on the eCRF for each individual patient. Typical anemia-related symptoms warranting transfusions included angina, change in mental status (e.g., syncope, light headedness, confusion, stroke, transient ischemic attack), severe or worsening shortness of breath, and severe or worsening fatigue. Other symptoms precipitating a potential need for transfusion could have been discussed with the Medical Monitor before the transfusion was given.

If a patient met either transfusion criterion during the study, the Investigator determined the appropriate number of units of pRBCs to be transfused. It was recommended that the transfusion be performed within 48 hours of the hemoglobin determination responsible for the transfusion. Administration of a transfusion, including the hemoglobin result and symptoms that triggered the transfusion, and the number of units transfused, were documented in the eCRF.

Prior to randomization and within 5 days prior to study drug administration on Day 1, each patient's hemoglobin was evaluated by either local or central laboratory. If at that time the patient's hemoglobin value met these transfusion guidelines, the patient was transfused with pRBCs to a hemoglobin level above the transfusion threshold in order to be eligible for randomization. The patient's post-transfusion hemoglobin value was confirmed by local or central laboratory to be above the transfusion threshold.

E. LDH and Other Disease-Related Laboratory Parameters

Blood and urine samples were collected. The following disease-related laboratory parameters were measured during the study: LDH, free hemoglobin, occult blood, urine, total C5, haptoglobin, reticulocyte count, PNH RBC clone size evaluated by high-sensitivity flow cytometry, D-dimer concentration, estimated glomerular filtration rate (calculated using the Modification of Diet in Renal Disease formula), spot urine albumin:creatinine ratio, and C-reactive protein.

F. Quality of Life, Additional Signs and Symptoms of PNH, and Resource Utilization Questionnaires.

Two validated QoL scales were administered to patients before study drug administration. The FACIT-Fatigue scale, Version 4.0, is a collection of QoL questionnaires pertaining to the management of fatigue symptoms due to a chronic illness. The FACIT-Fatigue is a 13-item questionnaire that assesses self-reported fatigue and its impact upon daily activities and function over the preceding 7 days. Patients scored each item on a 5-point scale: 0 (Not at all) to 4 (Very much). Total scores ranged from 0 to 52, with higher score indicating better QoL.

The European Organization for Research and Treatment of Cancer (EORTC) Quality of Life Questionnaire-Core 30 Scale (QLQ-C30), Version 3.0, is a questionnaire developed to assess the QoL of cancer patients. The questionnaire includes the following subscales: global health status, functional scales (physical functioning, role functioning, emotional functioning, cognitive functioning, and social activity), symptom scales (fatigue, nausea and vomiting, and pain), and single items (dyspnea, insomnia, appetite loss, constipation, diarrhea, and financial difficulties). Thirty questions related to QoL, with the first 28 questions were scored on a 4-point scale (1=not at all to 4=very much) and the final 2 questions that probe the patient's overall health and QoL were scored on a scale of 1 (very poor) to 7 (excellent). Each subscale had a range of 0 to 100%, with a high score representing a higher response level. Thus, a high score for a functional scale represented a high level of functioning, but a high score for a symptom scale represented a high level of symptomatology/problem.

Two additional questionnaires were completed by patients to assess disease burden. These questionnaires were administered to patients before study drug was infused. The PNH Symptoms Questionnaire listed the following symptoms: yellow discoloration of eyes, discoloration of urine, chest pain, shortness of breath, headache, fatigue, abdominal pain, confusion, erectile dysfunction, trouble swallowing, and other. Patients indicated whether they had experienced each of the symptoms in the past week, and if so, they rated the frequency (4-point scale ranging from rarely to almost constantly), severity (4-point scale ranging from slight to very severe), and extent of distress/bother associated with it (5-point scale ranging from not at all to very much).

The Resource Utilization Questionnaire asked patients to provide the number of times within the past month that they had: visited their health care provider primarily for treatment of their PNH (excluding protocol-specified study visits), gone to an emergency room primarily for treatment of their PNH, been admitted to a hospital primarily for treatment of their PNH, had darkened urine, and/or missed work as a result of symptoms of PNH.

a) Major Adverse Vascular Events

Major adverse vascular events (MAVEs) were assessed as part of the planned evaluation for adverse events (AEs). The description of the MAVE, including the method of diagnosis, and date resolved (or ongoing) were collected on the eCRF as part of the patient's medical history (prior to baseline).

A MAVE was defined as follows: Thrombophlebitis/deep vein thrombosis, Pulmonary embolus, Myocardial infarction, Transient ischemic attack, Unstable angina, Renal vein thrombosis, Acute peripheral vascular occlusion, Mesenteric/visceral vein thrombosis or infarction, Mesenteric/visceral arterial thrombosis or infarction, Hepatic/portal vein thrombosis (Budd-Chiari syndrome), Cerebral arterial occlusion/cerebrovascular accident, Cerebral venous occlusion, Renal arterial thrombosis, Gangrene (nontraumatic; nondiabetic), Amputation (nontraumatic; nondiabetic), and Dermal thrombosis Other.

G. Safety Assessments

The Investigator or his/her designee met with patients to discuss the potential safety risks of ALXN1210 (ravulizumab) and eculizumab and to have given the Investigator the opportunity to have addressed any of the patient's safety concerns regarding the study. Investigators followed any AEs through to their conclusion (resolution or stabilization). The timing of the clinical and laboratory assessments is specified in the Schedule of Assessments. Any clinically significant abnormal results were followed until resolution or stabilization.

A review of demographic parameters, including age, gender, race, and ethnicity was performed. A complete medical history was taken and documented. Weight and height were recorded. Height was measured at screening only.

The patient's PNH medical history, including onset of first PNH symptom, date of diagnosis, PNH clone size, pRBC transfusions, and history of any MAVEs, was documented at the Screening visit.

The patient's medical history, including prior and concomitant conditions/disorders and transfusion history, were recorded at the Screening Visit. Medication (prescription or over-the-counter, including vitamins and/or herbal supplements) use within 28 days prior to the start of Screening and meningococcal vaccination within 3 years prior to the first dose of study drug were also recorded.

A physical examination included the following assessments: general appearance; skin; head, ear, eye, nose, and throat; neck; lymph nodes; chest; heart; abdominal cavity; limb; central nervous system; and musculoskeletal system. An abbreviated physical examination consisted of a body system relevant examination based upon Investigator judgment and patient symptoms.

Vital sign measurements were taken after the patient had been resting for at least 5 minutes, and included systolic and diastolic blood pressure (BP; millimeters of mercury [mmHg]), heart rate (beats/minute), respiratory rate (breaths/minute), and oral or tympanic temperature (degrees Celsius [° C.] or degrees Fahrenheit [° F.]).

Samples for serum pregnancy, hematology, chemistry, coagulation, and urinalysis were taken. Samples for laboratory assessments were collected before each study drug administration. If a suspected event of breakthrough hemolysis occurred, an unscheduled visit would have taken place at which a sample was collected for analysis of LDH and PK/PD by the central laboratory.

It was anticipated that some laboratory values may be outside the normal value range due to the underlying disease. The Investigators used their medical judgment when assessing the clinical significance of these values. Clinical significance was defined as any variation in laboratory measurements that had medical relevance and which resulted in a change in medical care. If clinically significant laboratory changes from baseline value were noted, the changes were documented as AEs on the AE eCRF. The Investigator also assessed the relationship to study treatment for all clinically significant out-of-range values. The Investigator continued to monitor the patient through additional laboratory assessments until (1) values had returned to the normal range or baseline level, or (2) in the judgment of the Investigator, values that were outside the normal range were not related to the administration of study drug or other protocol-specific procedures.

For females of childbearing potential, a serum or urine pregnancy test (i.e., beta-human chorionic gonadotropin [β-hCG]) was performed.

Blood samples were analyzed for serum chemistry parameters. Indirect bilirubin was calculated from total and direct bilirubin values; therefore, indirect bilirubin results were not available if direct bilirubin was below the limit of quantification. Serum FSH levels were measured during Screening for postmenopausal female patients to confirm their postmenopausal status. Chemistry assessments were performed. Estimated glomerular filtration rate was calculated using the Modification of Diet in Renal Disease formula for all visits at which serum chemistries were collected. Blood samples were analyzed for coagulation parameters.

Urine samples were analyzed. A microscopic examination of urine samples was performed if the results of the macroscopic analysis were abnormal. Urine samples were also analyzed to measure proteins and creatinine in order to calculate the urine protein:creatinine ratio.

HIV testing for human immunodeficiency virus type 1 (HIV-1) and human immunodeficiency virus type 2 (HIV-2) was required for all patients prior to enrollment. Known HIV positive patients were not enrolled.

For each patient, single 12-lead digital ECGs were collected. Patients were supine for approximately 5 to 10 minutes before ECG collection and remained supine but awake during ECG collection.

Blood samples were collected to test for presence and titer of ADAs to ALXN1210 or eculizumab in serum prior to study drug administration. Further characterization of antibody responses were conducted as appropriate, including binding and neutralizing antibodies, PK/PD, safety, and activity of ALXN1210 or eculizumab.

An adverse event (AE) was any untoward medical occurrence in a patient administered a pharmaceutical product and which did not necessarily have a causal relationship with this treatment. An AE could therefore be any unfavorable or unintended sign (e.g., an abnormal laboratory finding), symptom, or disease temporally associated with the use of a medicinal product, whether or not considered related to the medicinal product.

Situations in which an untoward medical occurrence did not occur (e.g., hospitalization for elective surgery if planned before the start of the study, admissions for social reasons or for convenience), and anticipated day-to-day fluctuations of pre-existing disease(s) or condition(s) present or detected at the start of the study that do not worsen were not AEs.

Lack of drug effect was not an AE in clinical studies, because the purpose of the clinical study was to establish drug effect.

A medication error (including intentional misuse, abuse, and overdose of the product) or use other than what was defined in the protocol was not considered an AE unless there was an untoward medical occurrence as a result of a medication error.

Cases of pregnancy that occurred during maternal or paternal exposure to investigational product were reported within 24 hours of Investigator/site awareness. Data on fetal outcome and breastfeeding was collected for regulatory reporting and safety evaluation.

Adverse events were recorded from the time of signed consent. An AE reported after informed consent but before study drug administration was considered a pretreatment AE.

C5 inhibition is known to increase susceptibility to infections caused by encapsulated bacteria, particularly *N. meningitidis*. The following events were important identified risks in this study: meningococcal infections, sepsis, serious infections, *aspergillus* infection, infusion reactions. Additional events of interest in this study included the following: serious cutaneous adverse reactions, cardiac disorders (including ventricular fibrillation), and angioedema.

The severity of adverse events (AEs) was graded using Common Terminology Criteria for Adverse Events (CTCAE) version 4.03 or higher. A grading (severity) scale was provided for each AE term. Each CTCAE term was a Lowest Level Term (LLT) per the Medical Dictionary for Regulatory Activities (MedDRA®). Each LLT was coded to a MedDRA preferred term (PT).

Grade referred to the severity of the AE. The CTCAE assigned a grade of 1 through 5, with unique clinical descriptions of severity for each AE (Table 37).

TABLE 37

Adverse Event Severity Grading Scale

| Grade | Description |
|---|---|
| Grade 1 | Mild; asymptomatic or mild symptoms; clinical or diagnostic observations only; intervention not indicated |
| Grade 2 | Moderate; minimal, local or noninvasive intervention indicated; limiting age-appropriate instrumental activities of daily living (ADL)[a] |
| Grade 3 | Severe or medically significant, but not immediately life-threatening; hospitalization or prolongation of hospitalization indicated; disabling; limiting self-care ADL[b] |
| Grade 4 | Life-threatening consequences; urgent intervention indicated. |
| Grade 5 | Death related to AE. |

Abbreviations: ADL = activities of daily living;
AE = adverse event
[a]Instrumental ADL referred to preparing meals, shopping for groceries or clothes, using the telephone, managing money, etc.
[b]Self-care ADL referred to bathing, dressing and undressing, feeding self, using the toilet, taking medications, and not bedridden.

Any change in the severity of an AE was documented based on specific guidelines in the eCRF Completion Guidelines. Severity and seriousness was differentiated: severity described the intensity of an AE, while the term seriousness referred to an AE that had met specific criteria for an SAE.

An Investigator must have provided a causality assessment (Unrelated, Unlikely, Possible, Probable, or Definite) for all AEs (both serious and nonserious) based upon the Investigator's medical judgment and the observed symptoms associated with the event (Table 38). This assessment was recorded on the eCRF and any additional forms as appropriate.

TABLE 38

Causality Assessment Descriptions

| Assessment | Description |
|---|---|
| Not Related/Unrelated | Suggests that there is no causal association between the investigational product and the reported event. |
| Unlikely Related | Suggests that the clinical picture is highly consistent with a cause other than the investigational product but attribution cannot be made with absolute certainty and a relationship between the investigational product and AE cannot be excluded with complete confidence. |
| Possibly Related | Suggests that treatment with the investigational product may have caused or contributed to the AE (i.e., the event follows a reasonable temporal sequence from the time of drug administration and/or follows a known response pattern to the investigational product, but could also have been produced by other factors). |
| Probably Related | Suggests that a reasonable temporal sequence of the event with the investigational product administration exists and the likely causal association of the event with the investigational product. This is based upon the known pharmacological action of the investigational product, known or previously reported adverse reactions to the investigational product or class of drugs, or judgment based on the Investigator's clinical experience. |
| Definitely Related | Temporal relationship to the investigational product, other conditions (concurrent illness, concurrent medication reaction, or progression/expression of disease state) do not appear to explain event, corresponds with the known pharmaceutical profile, improvement on discontinuation, reappearance on rechallenge. |

A serious adverse event (SAE) was any untoward medical occurrence that:
1. Resulted in death
2. Was life-threatening (i.e., patient was at risk of death at the time of the event)
3. Required inpatient hospitalization or prolongation of existing hospitalization
4. Resulted in persistent or significant disability/incapacity
5. Was a congenital anomaly/birth defect Important medical events that may not have resulted in death, been immediately life-threatening, or required hospitalization may have been considered a serious adverse event when, based upon appropriate medical judgment, they jeopardized the patient or required intervention to prevent one of the outcomes listed above.

Suspected unexpected serious adverse reactions (SUSARs) were serious events that were not listed in the IB and that the Investigator identified as related to investigational product or procedure.

All AEs (serious and nonserious) were collected from the signing of the ICF until 56 days after the last dose of study drug for patients with ET or until 56 days after the last dose of study drug for patients who completed the study.

(i) Pharmacokinetics and Pharmacodynamics

Blood samples for determination of serum drug concentrations and PD assessments were collected before and after administration of study drug. The actual date and time (24-hour clock time) of each sampling was recorded. The number of PK sampling time points for any given patient did not exceed the currently planned number of time points. In the event of breakthrough hemolysis, an additional PK/PD sample was required.

End of infusion blood samples for PK and PD assessment were collected from the arm opposite to the arm used for infusing drug.

Assessments for PK/PD were as follows: change in serum ALXN1210 and eculizumab concentration over time, change in cRBC hemolytic activity over time (exploratory), and change in free and total C5 concentrations over time.

(ii) Statistical Methods and Planned Analyses

All data collected was presented in summary tabulations. All data, as well as any outcomes derived from the data, was presented in detailed data listings. Graphical displays were also provided, when appropriate. All analyses were performed using SAS® release, version 9.4 or higher (SAS Institute Inc., Cary, NC, USA) or other validated statistical software. Continuous variables were summarized using descriptive statistics, including number of observations and mean, standard deviation, median, minimum, and maximum values. Categorical variables were summarized by frequency counts and percentage of patients. All statistical tests performed were based on a 2-sided 5% level of significance unless otherwise specified. Any and all exclusions were documented in patient listings.

Details of the statistical analyses described below were specified in a separate Statistical Analysis Plan (SAP) before database lock and analysis. Any change to the data analysis methods described in the protocol required an amendment only if it changed the primary or key secondary objectives or the study conduct. Any other change to the data analysis methods described in the protocol or SAP, and the justification for making the change, was described in the clinical study report (CSR). Additional exploratory analyses of the data were conducted as deemed appropriate.

A CSR is produced based on efficacy, safety, PK, and PD, and immunogenicity data when all patients who remain on study have completed the 26-week randomized treatment period. A final CSR to summarize long-term efficacy, safety, PK, and PD, and immunogenicity data are produced at study completion.

195 patients were randomly assigned in a 1:1 ratio to continue on eculizumab (N=98) or switch to ALXN1210 (N=97) to ensure at least 172 evaluable patients (assumes no more than a 10% dropout rate). The sample size estimation was based on a non-inferiority design comparing patients treated with ALXN1210 to those treated with eculizumab. The primary endpoint of hemolysis as directly measured by LDH-PCHG from Baseline through Day 183 was used to assess non-inferiority.

TABLE 39

Summary of Parameters Used in Estimating Sample Size

| Parameters | Percent Change in LDH |
|---|---|
| Power | 90% |
| Type I error | 1-sided 0.025 |
| Noninferiority margin | 0.15 |
| Allocation ratio | 1:1 |
| Standard deviation of eculizumab/ALXN1210 response | 0.30/0.30 |
| Assumed treatment difference | 0 |
| Estimated sample size (SS) | 172 |
| Adjusted SS for 10% dropouts | 192 |

Note:
Software package: Hintze, J. (2011). PASS 11. NCSS, LLC. Kaysville, Utah, US. www.ncss.com.

Efficacy analyses were performed on the Full Analysis Set (FAS). The primary efficacy endpoint analysis, as well as key secondary endpoint analyses, were also performed on the Per Protocol (PP) set. The FAS was the primary population for all efficacy analyses. The FAS included all patients who received at least 1 dose of ALXN1210 or eculizumab.

The PP set, which was finalized prior to database lock, consisted of FAS patients who met all of the following criteria:
- Missed no doses of ALXN1210 or no more than 1 dose of eculizumab during the 26-week randomized treatment period
- Met inclusion criteria #2, 3, and 4
- Did not meet exclusion criteria #1, 2, 3, 4, or 5
- Never received the wrong randomized treatment
- Followed the protocol-specified transfusion guidelines Safety analyses were performed on the Safety Set, defined as all patients who received at least 1 dose of ALXN1210 or eculizumab. Pharmacokinetic and PD analyses were performed on all patients who received at least 1 dose of study drug and who had evaluable PK and PD data. Patient demographic and baseline characteristics, including medical history and transfusion history, were summarized by treatment group and overall for the FAS, and Safety sets. The number of infusions received per patient was tabulated by treatment group for the FAS and Safety sets.

The primary efficacy endpoint was the difference between treatment arms in LDH-PCHG from Baseline to Day 183. Baseline was defined as the average of all assessments analyzed by the central laboratory prior to first study drug administration.

The percentage change in LDH was analyzed using a mixed model for repeated measures (MMRM) with the fixed, categorical effects of treatment, study visit, and study visit by treatment group interaction as well as the continuous, fixed covariate of baseline LDH and the stratification randomization indicator of pRBC transfusion history (yes/no within 12 months prior to Day 1). The Kenward-Roger approximation was used to estimate denominator degrees of freedom. A difference in LDH-PCHG between the ALXN1210 and eculizumab treatment groups along with a two-sided 95% CI were calculated.

If the upper bound of the 95% CI for the difference (ALXN1210-eculizumab) was less than the NIM of 15%, then ALXN1210 treatment was concluded to be non-inferior to eculizumab. If non-inferiority is established and a larger effect for ALXN1210 was observed, then superiority was assessed using a two-sided 5% test.

The key secondary efficacy endpoints of proportion of patients with breakthrough hemolysis, change from baseline in FACIT-Fatigue, proportion of patients who did not require a transfusion, and proportion of patients with stabilized hemoglobin were summarized by treatment group. The percentage of patients with breakthrough hemolysis were computed for both the ALXN1210 and eculizumab treatment groups. A difference in the percentage of patients with breakthrough hemolysis in the 2 treatment groups was calculated, along with a 95% CI for the difference. The 95% CI for the difference between ALXN1210 and eculizumab treatment groups were calculated using the Newcombe confidence interval method. The same approach was employed for transfusion avoidance and stabilized hemoglobin. Transfusion avoidance was achieved only by those patients who did not receive a transfusion and did not meet the protocol-specified guidelines for transfusion. For change from baseline in FACIT-Fatigue, the same approach used for the primary endpoint was employed.

These key secondary endpoints were tested in a hierarchical manner provided that non-inferiority was declared for the primary endpoint. If non-inferiority was established for a key secondary endpoint and a larger effect for ALXN1210 was observed, then superiority was assessed using a 2-sided 0.05 test for each parameter.

When performing the analyses for the key secondary efficacy endpoints, a closed-testing procedure was used; lack of significance of a test precluded assessment of subsequent tests. Estimates and CIs were computed for all key secondary efficacy endpoints, regardless of whether a lack of significance of a test precluded assessment of subsequent tests.

1. If the upper bound of the 95% CI for the difference between the ALXN1210 and eculizumab treatment groups in the proportion of patients with breakthrough hemolysis was less than the NIM of 20%, then ALXN1210 was declared non-inferior for this parameter and the next parameter was tested.
2. If the lower-bound of the 95% CI for the difference between the ALXN1210 and eculizumab treatment groups in change from baseline in FACIT-Fatigue was greater than the NIM of −3, then ALXN1210 was declared non-inferior for this parameter and the next parameter was tested.
3. If the lower bound of the 95% CI for the difference between the ALXN1210 and eculizumab treatment groups for TA was greater than the NIM of −20%, then ALXN1210 was declared to be non-inferior to eculizumab and the next parameter was tested.
4. If the lower bound of the 95% CI for the difference between the ALXN1210 and eculizumab treatment groups in the proportion of patients with stabilized hemoglobin was greater than the NIM of −20%, then ALXN1210 was declared non-inferior for this parameter.

Total number of units of pRBCs transfused during treatment and the number (%) of patients with LDH within the normal range at each study visit was computed for both ALXN1210 and eculizumab treatment groups. Changes from baseline in EORTC-QLQ-C30 was summarized by treatment group at baseline and at the study visits where these assessments were collected. Shifts from baseline in clinical manifestations of PNH were summarized by treatment group and at the study visits where these assessments were collected. The number of any treatment-emergent MAVEs (n) and number of patients with events (n, %) were displayed by treatment group.

All safety analyses were performed for the Safety set, defined as all patients who receive at least 1 dose of ALXN1210 or eculizumab. Safety results were reported by treatment group.

The following definitions were used for AEs:
Pretreatment adverse events: Any AE that started after providing informed consent, but before the first infusion of study drug.
Treatment-emergent adverse event (TEAE): Any AE that started during or after the first infusion of study drug.
The incidence of TEAEs, TEAEs leading to withdrawal from the study, TEAEs leading to study treatment discontinuation, drug-related TEAEs, TEAEs during study drug administration, severe TEAEs, and SAEs were summarized. All AEs were coded using MedDRA version 18 or higher, and were summarized by system organ class (SOC) and PT.
Adverse changes from Baseline in physical examination findings were classified as AEs and analyzed accordingly.

Vital signs were summarized descriptively at Baseline and post-baseline time points and for changes from Baseline by treatment group.

Observed values and changes from baseline in clinical chemistry, hematology, and urinalysis were summarized descriptively at baseline and at each post-baseline time point. For laboratory results that can be classified as normal, low, or high based on normal range values, shifts from baseline in classification was summarized for all study visits.

By-patient data listings of ECG parameters were provided. Changes from baseline in electrocardiogram intervals (PR, RR, QT, and QTcF) were provided by treatment group. QT interval was corrected for heart rate using Fridericia's formula (QTcF).

Abnormal immunogenicity findings, including the incidence and titers for ADAs to ALXN1210 or eculizumab, were summarized in tabular format by treatment group. The proportion of patients ever positive and the proportion of patients always negative could have been explored.

Individual serum concentration data for all patients who received at least 1 dose of study drug (i.e., ALXN1210 or eculizumab) and who had evaluable PK data were used to derive PK parameters for ALXN1210 and eculizumab.

Graphs of mean serum concentration-time profiles were constructed. Graphs of serum concentration-time profiles for individual patients could have also been provided. Actual dose administration and sampling times were used for all calculations. Descriptive statistics were calculated for serum concentration data at each sampling time, as appropriate. Assessment of population-PK could have been considered using data from this study or in combination with data from other studies.

Descriptive statistics were presented for all ALXN1210 and eculizumab PD endpoints at each sampling time. The PD effects of ALXN1210 and eculizumab administered IV were evaluated by assessing the absolute values and changes and percentage changes from baseline in total and free C5 serum concentrations and cRBC hemolysis over time, as appropriate. Assessments of ALXN1210 PK/PD relationships could have been explored using data from this study or in combination with data from other studies.

If a Day 1 assessment was missing, the Screening assessment was used as the Baseline assessment. Missing data for QoL instruments were handled as specified in the instructions for each instrument.

Example 5: Results from Phase 3, Randomized, Open-Label, Active-Controlled Study of ALXN1210 Versus Eculizumab in Adult Patients with Paroxysmal Nocturnal Hemoglobinuria (PNH) Previously Treated with Eculizumab The following is a summary of data obtained from an ongoing open-label, phase 3 clinical study conducted according to the protocol described above in Example 4. A summary of the efficacy and safety results are presented below.

1. Summary of Trial

This phase 3 human clinical trial was an open-label, randomized, active-controlled, multicenter study conducted to evaluate the safety and efficacy of ALXN1210 (also known as Ultomiris™, antibody BNJ441, or ravulizumab) versus eculizumab (Souris®) administered by intravenous (IV) infusion to adult patients with PNH who had been treated with eculizumab for at least 6 months. The study enrolled 195 patients in total. A total of 191 patients completed the study and 186 of these patients were included in this per-protocol analysis. Only 4 subjects discontinued during the course of the study (1 from the ALXN1210 group and 3 from the eculizumab group).

This phase 3 study met its primary objective and demonstrated that ALXN1210 (ravulizumab) was noninferior to eculizumab. Specifically, the study met the pre-designated non-inferiority margins (NIM) for LDH percent change (LDH-PCHG) from baseline by better than the 15% margins required by the FDA and as specified in the protocol, but did not quite achieve superiority in this study (p<0.0583). In addition, all 4 key secondary endpoints favored ALXN1210 and demonstrated non-inferiority to eculizumab. Breakthrough hemolysis (BTH) also demonstrated a numerical trend favoring ALXN1210 to eculizumab by 0% versus 5.1% respectively. In fact, no patients on ALXN1210 experienced BTH compared to 5 for eculizumab (1 eculizumab patient had 3 BTH events). Importantly, the sensitivity analysis demonstrated robust results on all efficacy endpoints. The data is presented in the attached Figures and Tables and discussed more fully below.

The design of the non-inferiority study comparing ALXN1210 and eculizumab is shown in FIG. 25. The study compared a personalized weight based dosing scheme for ALXN1210 to the existing approved dosing scheme for eculizumab in PNH in an attempt to show non-inferiority in PNH patients who had received eculizumab for at least 6 months prior to starting this study. The dose chosen for ALXN1210 was weight based and comprised a loading dose (2400 mg for patients ≥40 kg to <60 kg, 2700 mg for patients ≥60 kg to <100 kg, 3000 mg for patients ≥100 kg) on day 1, followed by maintenance doses of ALXN1210 (3000 mg for patients ≥40 kg to <60 kg, 3300 mg for patients ≥60 to <100 kg, 3600 mg for patients ≥100 kg) on day 15 and every 8 weeks thereafter. See FIG. 25. In contrast, the eculizumab dose comprises a maintenance dose of 900 mg administered IV on day 1 and every 2 weeks thereafter. See FIG. 25. Following completion of the study, both subjects in both the ALXN1210 and eculizumab groups entered an extension period, as described in Example 4. During the extension period, the ALXN1210 group continued to receive ALXN1210 every 8 weeks. The eculizumab group received an ALXN1210 loading dose (2400 mg for patients ≥40 kg to <60 kg, 2700 mg for patients ≥60 kg to <100 kg, 3000 mg for patients ≥100 kg) on day 183, followed by maintenance doses of ALXN1210 (3000 mg for patients ≥40 kg to <60 kg, 3300 mg for patients ≥60 to <100 kg, 3600 mg for patients ≥100 kg) on day 197 and every 8 weeks thereafter. The full dosing schematic for both the ALXN1210 and eculizumab groups is shown in FIG. 26.

Figure 27:
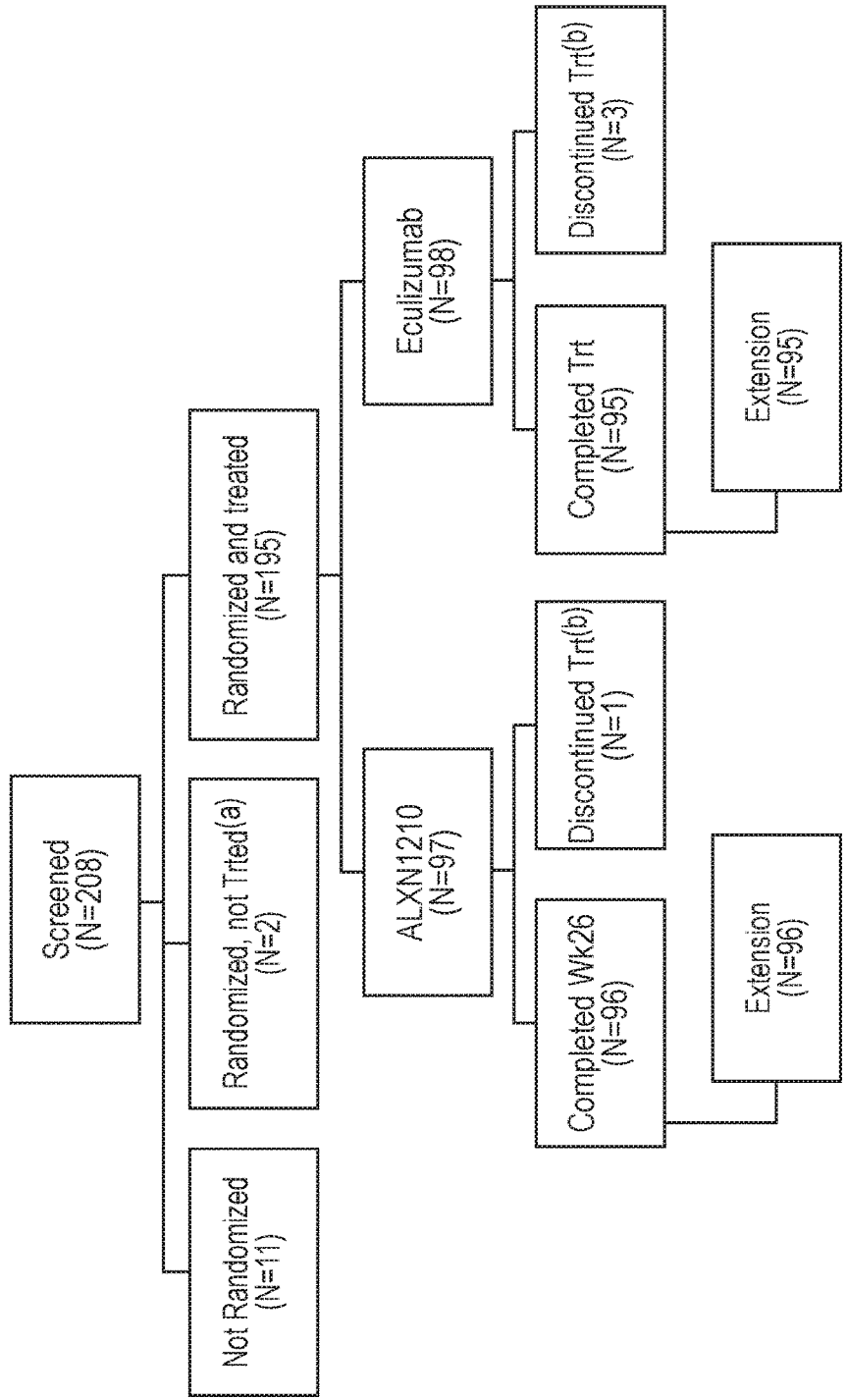
FIG. 27 is a schematic showing the disposition of patients enrolled in the Phase III ALXN1210-PNH-302 clinical trial.

The study enrolled more patients than originally planned. Specifically, 195 patients enrolled in the study and were randomized to either the ALXN1210 group or the eculizumab group (see FIG. 27). A total of 13 subjects failed the screening. Of the 195 patients to enter and complete the 26 week treatment period, 191 proceeded into the ongoing extension study (see FIG. 27). The baseline characteristics and demographics of the study population are shown in FIG. 28. The baseline characteristics of the disease are shown in FIG. 29.

Of the 197 randomized patients, 195 treated patients (97 patients in the ALXN1210 group and 98 patients in the eculizumab group) were included in the FAS and Safety Set, as set forth below in Table 40.

TABLE 40

Analysis Data Sets (All Randomized Patients)

| | ALXN1210 n (%) | Eculizumab n (%) | Total n (%) |
|---|---|---|---|
| Number of randomized patients | 98 (100) | 99 (100) | 197 (100) |
| Number of patients in the FAS | 97 (99.0) | 98 (99.0) | 195 (99.0) |
| Number of patients excluded from the FAS | 1 (1.0) | 1 (1.0) | 2 (1.0) |
| Number of patients in the PP Set | 93 (94.9) | 93 (93.9) | 186 (94.4) |
| Number of patients excluded from the PP Set | 5 (5.1) | 6 (6.1) | 11 (5.6) |
| Number of patients in the Safety Set | 97 (99.0) | 98 (99.0) | 195 (99.0) |
| Number of patients excluded from the Safety Set | 1 (1.0) | 1 (1.0) | 2 (1.0) |
| Number of patients in the PK Analysis Set | 97 (99.0) | 98 (99.0) | 195 (99.0) |
| Number of patients excluded from the PK Analysis Set | 1 (1.0) | 1 (1.0) | 2 (1.0) |

Abbreviations: FAS = Full Analysis Set;
PP = Per Protocol

Eleven patients were excluded from the PP Set (ALXN1210: n=5, eculizumab, n=6). The following were reasons for exclusion. Two patients were randomized but were not treated due to patient withdrawal prior to first dose (see Table 41). Two patients in the ALXN1210 group were determined to not meet the criteria of being treated with eculizumab according to the labelled dosing recommendation for PNH (eculizumab every 14±2 days) within 6 months prior to Day 1, since some of the eculizumab doses were administered outside of the ±2 day window. Two patients in the eculizumab group were determined to have had an LDH value >2×ULN within 6 months prior to Day 1. Five patients (ALXN1210: n=2, eculizumab: n=3) met the protocol-specified criteria for pRBC transfusion (hemoglobin ≤7 g/dL), but were not transfused at that time or at any other time during the Primary Evaluation Period. Although other patients met the transfusion criteria at a particular visit, but did not receive a transfusion, these patients were included in the PP Set because they received at least 1 transfusion according to the transfusion criteria.

Three differences in the actual stratification at the time of randomization compared to the observed stratification for transfusion history occurred in this study, as set forth in Table 41. Of the 24 patients stratified to transfusion history "Yes", 1 patient was determined to have no history of transfusion. Of the 173 patients stratified as transfusion history "No", 2 patients had a history of prior transfusion.

TABLE 41

Stratification Groups at Randomization and Observed (All Randomized Patients)

| Stratification Groups at Randomization | Observed Stratification Groups | ALXN1210 (N = 98) | Eculizumab (N = 99) | Total (N = 197) |
|---|---|---|---|---|
| Transfusion History, n (%) | | | | |
| Yes | Yes | 12 (12.2) | 11 (11.1) | 23 (11.7) |
| Yes | No | 0 | 1 (1.0) | 1 (0.5) |

TABLE 41-continued

Stratification Groups at Randomization and Observed (All Randomized Patients)

| Stratification Groups at Randomization | Observed Stratification Groups | ALXN1210 (N = 98) | Eculizumab (N = 99) | Total (N = 197) |
|---|---|---|---|---|
| No | Yes | 1 (1.0) | 1 (1.0) | 2 (1.0) |
| No | No | 85 (86.7) | 86 (86.9) | 171 (86.8) |

Note:
Baseline was defined as the last non-missing value prior to first dose of study drug. The ULN for LDH is 246 U/L.

In the study population of patients with stable disease, only 12.8% had a history of pRBC transfusions in the year prior to first dose of study drug, as shown in Table 42. The mean number of transfusions within 1 year of first dose was higher in the ALXN1210 group than in the eculizumab group, as was the mean number of units transfused. This difference is attributable to 2 heavily transfusion-dependent ALXN1210 patients.

TABLE 42

Red Blood Cell Transfusions within 12 Months Prior to First Dose (Full Analysis Set)

| Variable Category | ALXN1210 (N = 97) | Eculizumab (N = 98) | Total (N = 195) |
|---|---|---|---|
| Number of patients with pRBC/whole blood transfusions within 1 year prior to first dose, n (%) | 13 (13.4) | 12 (12.2) | 25 (12.8) |
| pRBC/whole blood transfusions within 1 year prior to first dose | | | |
| Total | 64 | 30 | 94 |
| Mean (SD) | 4.9 (5.51) | 2.5 (2.32) | 3.8 (4.38) |
| Median | 3.0 | 1.5 | 2.0 |
| Min, max | 1, 17 | 1, 8 | 1, 17 |
| Units of pRBC/whole blood transfused within 1 year prior to first dose | | | |
| Total | 103 | 50 | 153 |
| Mean (SD) | 7.9 (8.78) | 4.2 (3.83) | 6.1 (7.00) |
| Median | 4.0 | 2.5 | 3.0 |
| Min, max | 1, 32 | 2, 15 | 1, 32 |

Abbreviations: max = maximum;
min = minimum;
pRBC = packed red blood cells;
SD = standard deviation The types of PNH symptoms that patients experienced prior to informed consent were similar between the treatment groups, with the most common (>20% of all patients) being fatigue or asthenia (generalized weakness), red or dark urine, abdominal pain shortness of breath (dyspnea), CNS-related symptoms such as headache, dizziness, or difficulty concentrating, jaundice (yellowing of skin or eyes), and dysphagia.

In the total population, 95.4% of patients had documented PNH-associated conditions that were diagnosed prior to informed consent as set forth in Table 43. Of note, 37.4% of patients had a history of aplastic anemia, 9.2% of patients had a history of renal failure, and 4.6% of patients had myelodysplastic syndrome.

TABLE 43

PNH-Associated Conditions Diagnosed at Any Time Prior to Informed Consent (Full Analysis Set)

| PNH-Associated Conditions, n (%) | ALXN1210 (N = 97) | Eculizumab (N = 98) | Total (N = 195) |
|---|---|---|---|
| Patients with any PNH conditions prior to informed consent | 90 (92.8) | 96 (98.0) | 186 (95.4) |
| Anemia | 64 (66.0) | 67 (68.4) | 131 (67.2) |
| Hematuria or hemoglobinuria | 47 (48.5) | 48 (49.0) | 95 (48.7) |
| Aplastic anemia | 34 (35.1) | 39 (39.8) | 73 (37.4) |
| Renal failure | 11 (11.3) | 7 (7.1) | 18 (9.2) |
| Pregnancy complication | 4 (4.1) | 9 (9.2) | 13 (6.7) |
| Myelodysplastic syndrome | 3 (3.1) | 6 (6.1) | 9 (4.6) |
| Other[a] | 14 (14.4) | 14 (14.3) | 28 (14.4) |

Note:
Conditions as documented in patient medical record. Patients could have been counted in more than one category.
[a]"Other" category included neutropenia (n = 3), proteinuria, renal dysfunction (n = 3), lymphoid hyperplasia, pancytopenia (n = 2), thrombopenia (n = 3), iron defficiency anemia (n = 2), non-severe aplasia, splenomegaly, hepatic cytolisis Grade 1 (n = 2), hemolytic anemia, haptoglobin collapse, pulmonary hypertension, monosomy 7, mildly hypocellular mallow, reduced trilineage haematopoies, medular hypoplasia, haptoglobin deficiency and hyper reticulocytosis, leucopenia, dysgranulopoiesis, dyserythropoiesis, dysplasia dyserythropoiesis, relapse of idiopathic medullary aplasia, thrombocytosis, thrombocytopenia, leukocytosis, muscle aches and pains and gallstones.
Abbreviation: PNH = paroxysmal nocturnal hemoglobinuria A history of one or more MAVEs was reported for 25.6% of patients overall, as set forth below in Table 44.

TABLE 44

Major Adverse Vascular Events History (Full Analysis Set)

| MAVE Categories | ALXN1210 (N = 97) | Eculizumab (N = 98) | Total (N = 195) |
|---|---|---|---|
| Patients with a history of MAVE | 28 (28.9) | 22 (22.4) | 50 (25.6) |
| Thrombophlebitis/deep vein thrombosis | 11 (11.3) | 5 (5.1) | 16 (8.2) |
| Hepatic/portal vein thrombosis (Budd-Chiari syndrome) | 8 (8.2) | 6 (6.1) | 14 (7.2) |
| Cerebral arterial occlusion/cerebrovascular accident | 5 (5.2) | 6 (6.1) | 11 (5.6) |
| Cerebral venous occlusion | 3 (3.1) | 2 (2.0) | 5 (2.6) |
| Mesenteric/visceral arterial thrombosis or infarction | 2 (2.1) | 3 (3.1) | 5 (2.6) |
| Mesenteric/visceral vein thrombosis or infarction | 1 (1.0) | 4 (4.1) | 5 (2.6) |
| Pulmonary embolus | 5 (5.2) | 0 (0.0) | 5 (2.6) |
| Dermal thrombosis | 2 (2.1) | 0 (0.0) | 2 (1.0) |
| Transient ischemic attack | 1 (1.0) | 1 (1.0) | 2 (1.0) |
| Myocardial infarction | 1 (1.0) | 0 (0.0) | 1 (0.5) |
| Acute peripheral vascular occlusion | 0 (0.0) | 0 (0.0) | 0 (0.0) |
| Amputation (non-traumatic; non-diabetic) | 0 (0.0) | 0 (0.0) | 0 (0.0) |
| Gangrene (non-traumatic; non-diabetic) | 0 (0.0) | 0 (0.0) | 0 (0.0) |
| Renal arterial thrombosis | 0 (0.0) | 0 (0.0) | 0 (0.0) |
| Renal vein thrombosis | 0 (0.0) | 0 (0.0) | 0 (0.0) |
| Unstable angina | 0 (0.0) | 0 (0.0) | 0 (0.0) |
| Other[a] | 2 (2.1) | 3 (3.1) | 5 (2.6) |

Note:
Patients could have been counted in more than one category.
[a]"Other" category included recurrent thrombosis of transjugular intrahepatic portosystemic shunt, inferior vena caval thrombosis, retinal vein thrombosis, thrombus left atrium, superficial thrombosis left lower leg, ischemic enteritis.
Abbreviation: MAVE = major adverse vascular event As required, all 195 patients had a history of eculizumab use. Two patients in the ALXN1210 group were not vaccinated for meningococcal infection within 3 years prior to or at the time of initiating study drug. All other patients received meningococcal vaccine no later than Day 1.

The most commonly reported (≥10% of patients) groupings of prior medications other than meningococcal vaccine were vitamin B12 and folic acid (59.5%), beta-lactam antibacterials (penicillins) (43.1%), antithrombotic agents (19.0%), drugs for peptic ulcer and gastro-esophageal reflux disease (15.4%), and other analgesics and antipyretics (12.8%). Overall, 97.9% of patients (97.9% in the ALXN1210 group and 98.0% in the eculizumab group) took at least one concomitant medication. The most commonly reported (≥10% of patients) groupings of concomitant medications were vitamin B12 and folic acid (62.1%), beta-lactam antibacterials (penicillins) (52.8%), other analgesics and antipyretics (36.9%), bacterial vaccines (29.2%), antithrombotic agents (22.6%), viral vaccines (19.5%), drugs for peptic ulcer and gastro-esophageal reflux disease (19.0%), quinolone antibacterials (16.4%), anti-inflammatory and antirheumatic products, nonsteroids (13.3%) and opioids (10.3%). During the study, a total of 30.3% patients underwent a nonpharmacologic medical procedure.

2. Primary/Secondary Endpoints and Disease-Related Parameters

Figure 30:
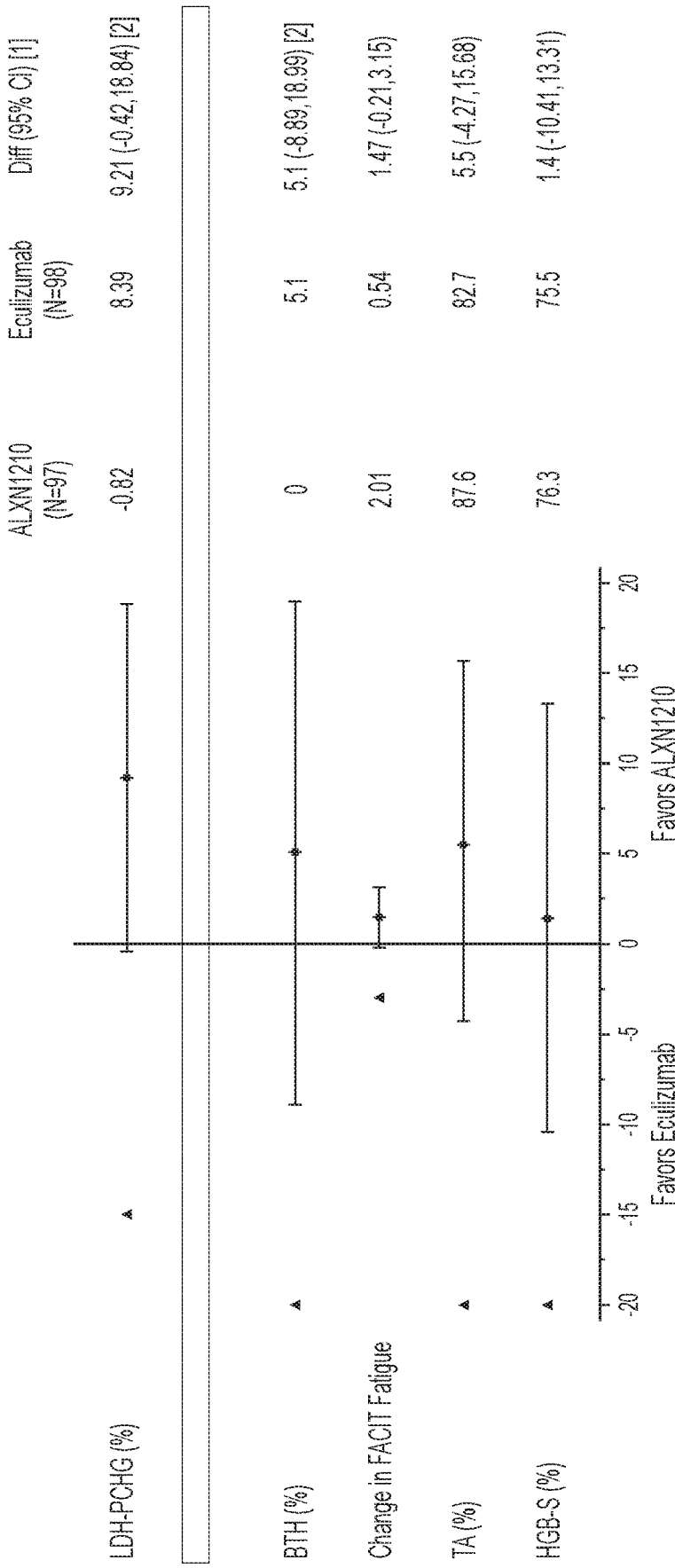
FIG. 30 is a graphical schematic showing the key efficacy results of the primary and secondary endpoints from the Phase III ALXN1210-PNH-302 clinical trial.

ALXN1210 achieved statistically significant noninferiority compared to eculizumab for the primary endpoint, percent change in LDH (LDH-PCHG) from baseline to Day 183, for the FAS. Specifically, the primary efficacy endpoint of LDH percent change (LDH-PCHG) was very clearly met and exceeded as shown in FIG. 30. The red triangle in FIG. 30 indicates the non-inferiority margin required by the FDA and as specified in the protocol. For the LDH-PCHG endpoint, the 15% non-inferiority margins were exceeded substantially and achieved a non-inferiority margin of better than 1%. See FIG. 30.

The key secondary endpoints breakthrough hemolysis (BTH), change in FACIT fatigue score, transfusion avoidance (TA) and hemoglobin stabilization (HGB-S) were also positive and favored ALXN1210 over eculizumab (see FIG. 30). Moreover, not only did all the secondary endpoints favor ALXN1210, but they all substantially exceeded the non-inferiority margins shown by the red triangles in the graph (see FIG. 30).

The key primary and secondary endpoints are tabulated in FIG. 31. Also shown is the treatment effect for each endpoint in favor of ALXN1210 over that for eculizumab. For example the first row shows that the treatment effect for LDH percent change (LDH-PCHG) for ALXN1210 over eculizumab was −9.2%, much greater than the 15% required non-inferiority margin and renders a clear finding of non-inferior. Likewise, all the primary and secondary endpoints led to the same conclusion of non-inferior for ALXN1210 over eculizumab. Stated another way, ALXN1210 was found to be better than eculizumab; conclusions of statistical superiority were unable to be reached, likely due to the sample size (see FIG. 31).

The efficacy data from this study for LDH-PCHG was subjected to multiple different sensitivity analyses. The results are shown in FIG. 32. For example, the treatment effect (point estimate) for 1210 was −9.2% better than for eculizumab, with a 95% confidence intervals (CI) of −18.8% to 0.42%. The 0.42% number is substantially better that the predefined non-inferiority margin of 15%. This table shows a variety of sensitivity analysis, which all support the robust finding of the primary analysis. It is worth noting that this consistency is unusual for a clinical trial of this type and supports the idea that this study was conducted with very high quality.

Figure 33:
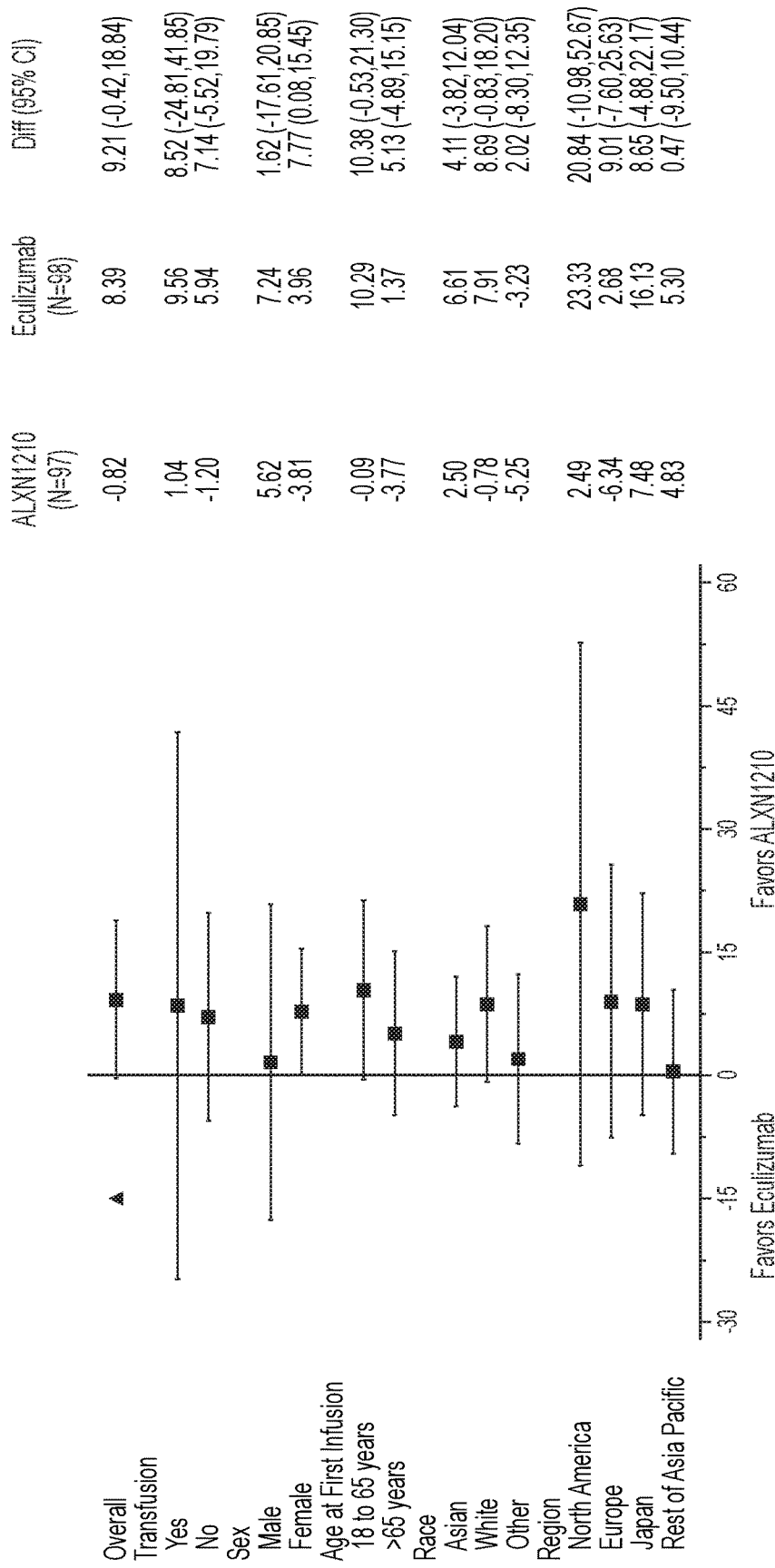
FIG. 33 is a graphical display showing efficacy results for subgroups for the primary endpoint from the Phase III ALXN1210-PNH-302 clinical trial.

The efficacy results for the LDH-PCHG primary endpoint were analyzed as subgroups of the patient population and are shown in FIG. 33. LDH-PCHG (lactate dehydrogenase percent change) refers to percentage change in LDH from baseline to day 183. Subgroup analyses for LDH-PCHG revealed that the preponderance of evidence favored ALXN1210. Grey lines are 95% confidence intervals and blue squares are point estimates. Estimation was based on a generalized estimating equation (GEE) approach. The model included the following terms: treatment group, history of transfusion and baseline LDH levels. Estimates to the right of 1 favor ALXN1210 and estimates to the left favor eculizumab. All point estimates were to right of the pre-defined non inferiority margin (red triangle) (15%) No endpoints clearly favored eculizumab. In conclusion, all of the subgroups favored ALXN1210 over eculizumab (see FIG. 33).

Figure 34:
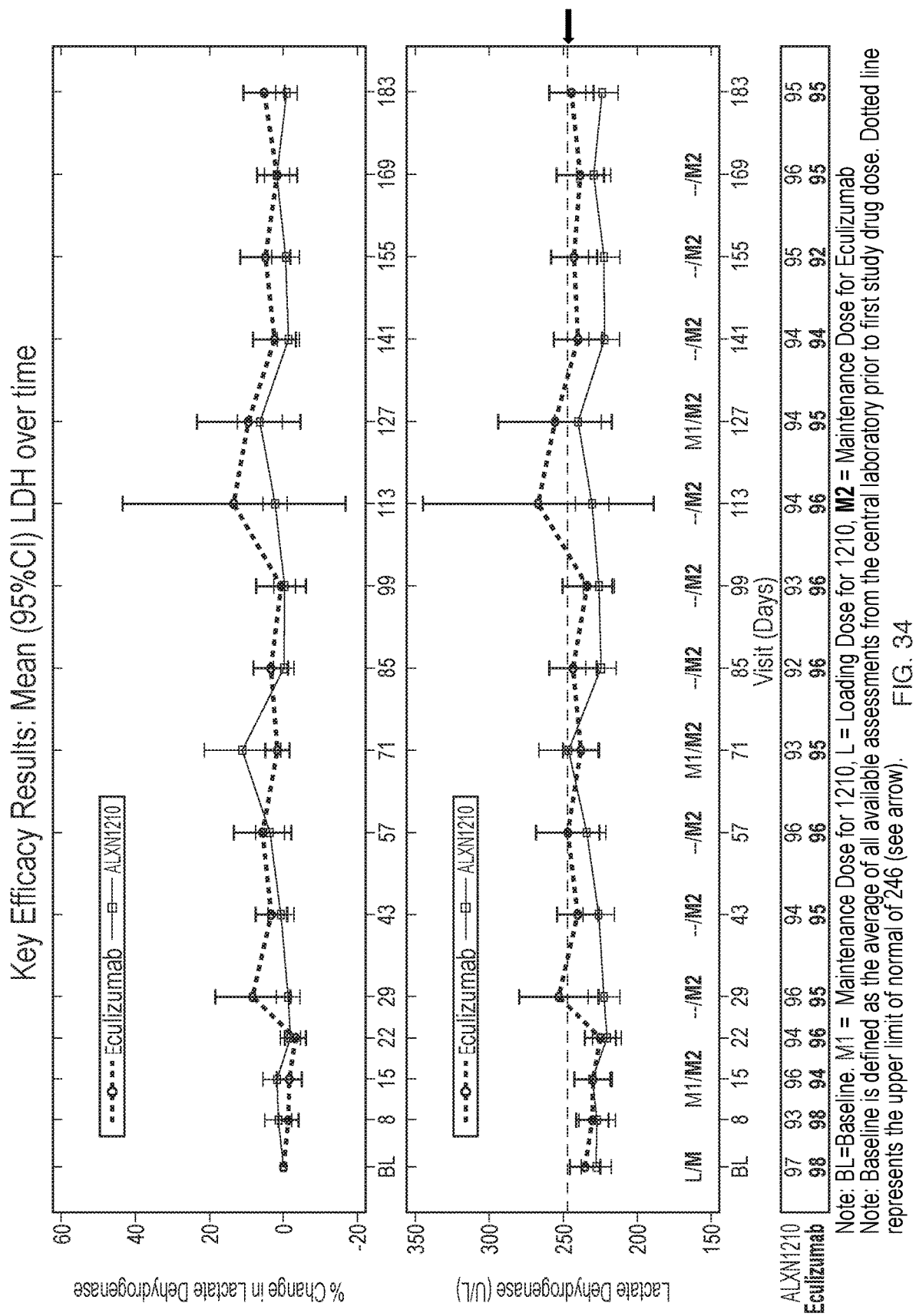
FIG. 34 is a graphical display of the mean LDH levels over time for patients enrolled in the Phase III ALXN1210-PNH-302 clinical trial.
Figure 35:
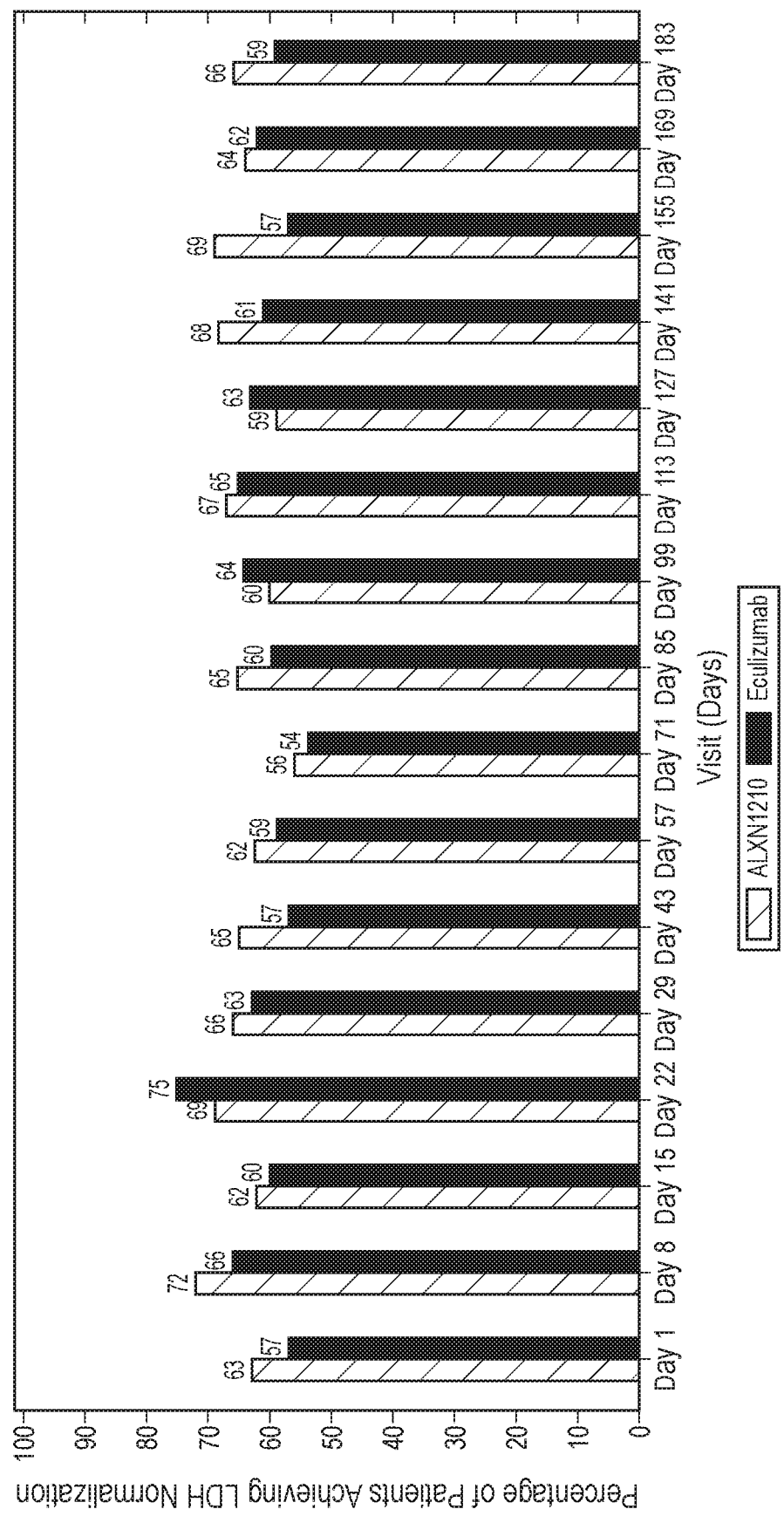
FIG. 35 is a graphical display of the percentage of patients achieving normalized LDH during the Phase III ALXN1210-PNH-302 clinical trial.
Figure 36:
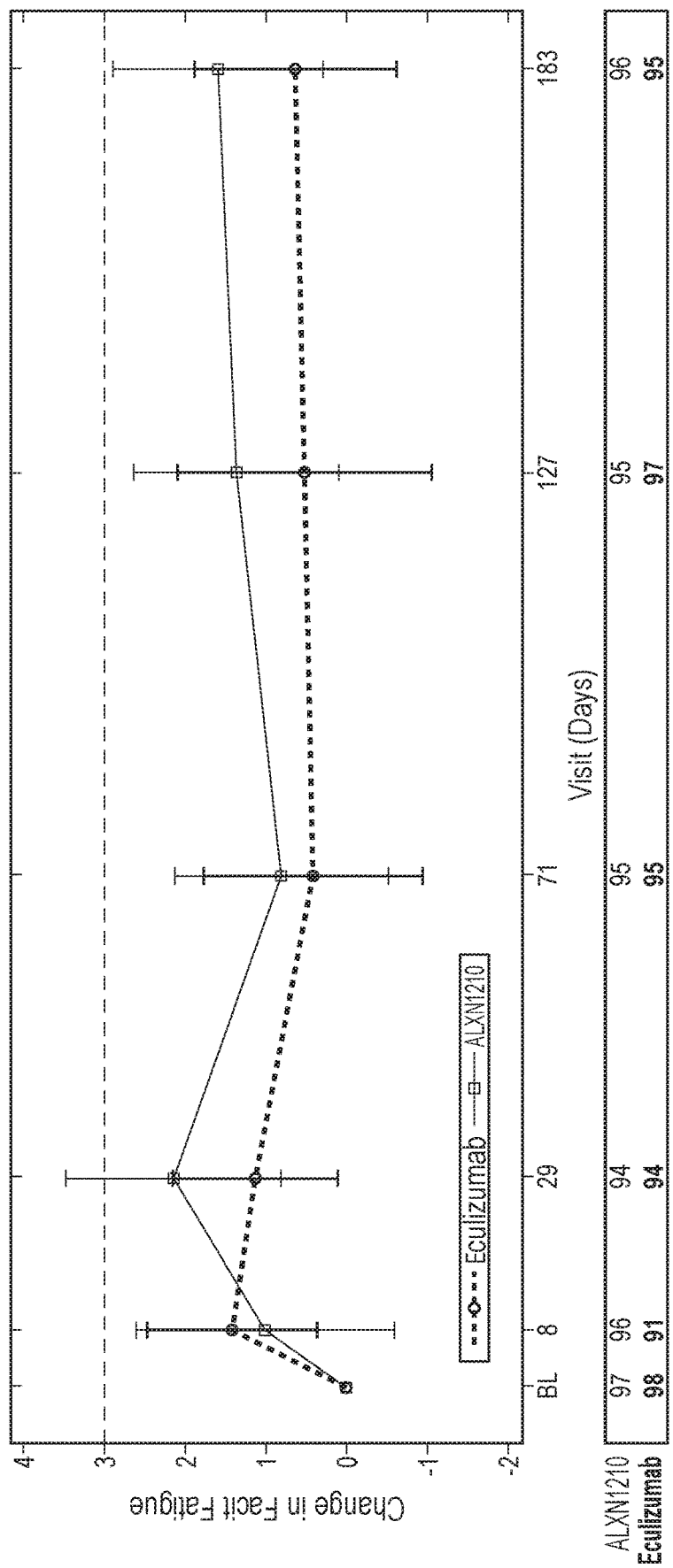
FIG. 36 is a graphical display of the mean change as compared to baseline in quality of life over time for patients enrolled in the Phase III ALXN1210-PNH-302 clinical trial, as assessed using the Functional Assessment of Chronic Illness Therapy (FACIT)-Fatigue scale.
Figure 37:
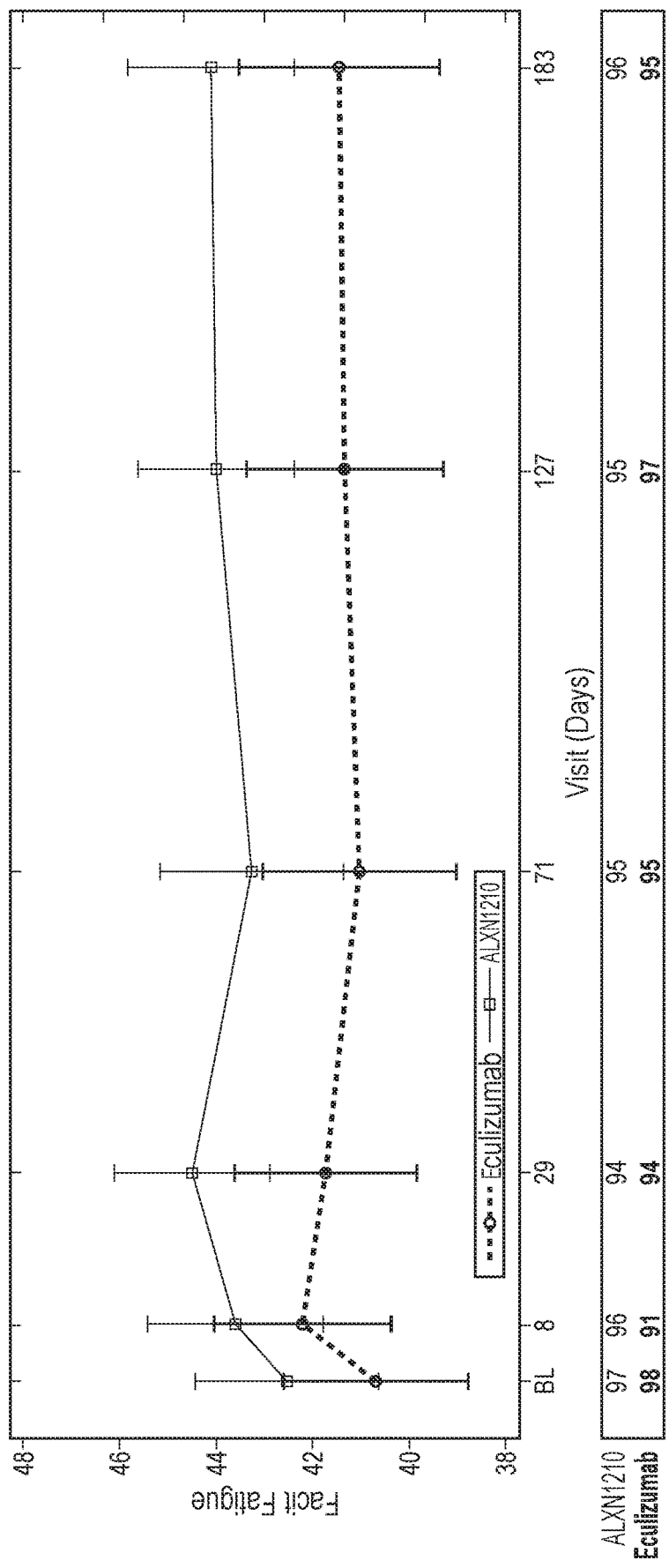
FIG. 37 is a graphical display of the mean value for the quality of life over time for patients enrolled in the Phase III ALXN1210-PNH-302 clinical trial, as assessed using the Functional Assessment of Chronic Illness Therapy (FACIT)-Fatigue scale.

FIG. 34 shows both the mean values for percent change from baseline (top panel) and total level (bottom panel) of LDH over time. As shown in FIG. 34, the mean values for LDH level were within the normal range for the patient population at the beginning of the study and remained less than the upper limit of normal (1×ULN LDH) throughout the entirety of the study for the ALXN1210-treated group. In contrast, the mean LDH level exceeded this upper limit of normal in the eculizumab-treated group on day 29, 113 and 127. The dotted line in FIG. 34 shows the value of the upper limit of normal for LDH or 1×ULN LDH. The box below the graph shows the number of patients in each group that contributed to the mean on that day. In conclusion, it is clear the mean value of LDH in patients on ALXN1210 remained below the critical level of 1.5×ULN (see FIG. 34). The percentage of patients maintaining LDH normalization at various time points during the course of the study is shown in FIG. 35. Greater than 50% of both ALXN1210 and eculizumab patients stayed in the normal range throughout the study (see FIG. 35). FIG. 36 shows the mean change from baseline of quality of life assessed via the Functional Assessment of Chronic Illness Therapy (FACIT)-Fatigue Scale, Version 4, over time. FIG. 37 shows the mean assessed value for FACIT fatigue over time. As shown in FIG. 36, the mean change from baseline showed improvement for the ALXN1210-treated group throughout the study and at most timepoints trended higher than the improvement seen for the eculizumab-treated group. However, despite the improvement in FACIT fatigue scores over baseline, neither group demonstrated a mean increase greater than 3 points (>3 points) as indicated by the dashed line. The box below the graph shows the number of patients in each group that contributed to the mean on that day. As shown in FIG. 37, which shows the mean assessed scores on the FACIT fatigue scale (0-52 with a higher score indicating less fatigue), the ALXN1210-treated group showed higher mean FACIT fatigue scores than the eculizumab-treated group at all timepoints.

In addition to the primary and secondary endpoints, the following disease-related laboratory parameters were measured during the study: free hemoglobin, occult blood in urine, total C5, haptoglobin, reticulocyte count, PNH RBC clone size, D-dimer concentration, eGFR, spot urine albumin:creatinine ratio, and C-reactive protein. Total PNH RBC clone size was similar between treatment groups at baseline, with no notable changes in either group during the study. There was no apparent trend in mean free hemoglobin change from baseline over time was observed in either treatment groups. Mean D dimer levels decreased from baseline at most post-baseline study visits in either treatment group. Mean haptoglobin was low (reference range: 0.4 2.4 g/L) at baseline and throughout the 26 week treatment period in both treatment groups (ALXN1210: 0.283 g/L to 0.298 g/L; eculizumab: 0.255 g/L to 0.257 g/L from baseline to Day 183). Urinary occult blood was negative in the majority of patients in both the ALXN1210 and eculizumab treatment groups, and remained negative during the treatment period. The reticulocytes/erythrocytes ratio was stable and consistent in both groups throughout the 26 week treatment period (ALXN1210: 5.70% to 6.54%; eculizumab: 5.54% to 5.87% from baseline to Day 183). No notable change from baseline in mean urine microalbumin: creatinine ratio was observed over time in both treatment groups. Mean C reactive protein levels were similar between treatment groups at baseline with little change noted over time in either treatment group.

3. Safety

FIG. 38 is a tabulation of the key safety results in the Phase III ALXN1210-PNH-301 clinical trial. Overall safety differences in adverse events (AEs) were observed at generally similar rates between ALXN1210 and eculizumab and there were no discontinuations due to AEs or deaths observed during the primary evaluation period (see FIG. 38). Serious adverse events (SAEs) were less frequent for ALXN1210 as compared to eculizumab (4% v. 8%), as shown in FIG. 39. The most frequent AEs were headache (27% v. 17%) and nasopharyngitis (22% v. 20%), as shown in FIGS. 40 and 41. Further, there were no meningococcal infections during the primary evaluation period (see FIG. 42).

There were no observations of treatment emergent cases of anti-drug antibody (ADA) observed ALXN1210 and there was 1 case observed for eculizumab. No neutralizing antibodies were produced and there was no apparent effect on PK/PD, efficacy or safety.

Drug compliance was perfect for this clinical trial, demonstrating a 100% drug compliance over the 6 month treatment period (see FIG. 43).

2. Pharmacokinetic Results

Pharmacokinetic parameters for ALXN1210 are summarized below in Tables 45 and 46 for the first (induction) and last (maintenance) doses, respectively. The geometric mean (geometric CV %) $C_{max}$ and $C_{trough}$ of ALXN1210 following the first dose in all patients was 822.3 (22.03) and 390.9 (26.78) µg/mL, respectively. Following the last dose of ALXN1210, the geometric mean (% CV) $C_{max}$ and $C_{trough}$ in all patients were 1359.3 (19.50) and 479.8 (30.68) µg/mL, respectively.

TABLE 45

ALXN1210 Pharmacokinetic Parameters ($C_{max}$ and $C_{trough}$) Following the First (Loading) Dose of ALXN1210 (Pharmacokinetic Analysis Set)

| Parameter | Statistics | All Patients (N = 96) | ≥40 to <60 kg (N = 26) | ≥60 to <100 kg (N = 63) | ≥100 kg (N = 7) |
|---|---|---|---|---|---|
| $C_{max}$ (µg/mL) | n | 95 | 26 | 62 | 7 |
| | Mean | 842.9 | 903.2 | 823.1 | 794.7 |
| | SD | 203.47 | 150.42 | 216.00 | 239.70 |
| | CV % | 24.14 | 16.65 | 26.24 | 30.16 |
| | Median | 811.0 | 893.0 | 779.5 | 802.0 |
| | Minimum | 511 | 656 | 536 | 511 |
| | Maximum | 1750 | 1450 | 1750 | 1240 |
| | Geometric mean | 822.3 | 892.6 | 801.0 | 765.1 |
| | Geometric CV % | 22.03 | 15.41 | 22.77 | 30.39 |

TABLE 45-continued

ALXN1210 Pharmacokinetic Parameters ($C_{max}$ and $C_{trough}$) Following the First (Loading) Dose of ALXN1210 (Pharmacokinetic Analysis Set)

| Parameter | Statistics | All Patients (N = 96) | ≥40 to <60 kg (N = 26) | ≥60 to <100 kg (N = 63) | ≥100 kg (N = 7) |
|---|---|---|---|---|---|
| $C_{trough}$ (µg/mL) | n | 96 | 26 | 63 | 7 |
| | Mean | 405.4 | 448.2 | 394.5 | 344.3 |
| | SD | 121.24 | 151.41 | 108.28 | 50.29 |
| | CV % | 29.91 | 33.78 | 27.45 | 14.61 |
| | Median | 384.0 | 440.5 | 373.0 | 352.0 |
| | Minimum | 197 | 219 | 197 | 294 |
| | Maximum | 1040 | 1040 | 896 | 421 |
| | Geometric mean | 390.9 | 428.6 | 382.1 | 341.2 |
| | Geometric CV % | 26.78 | 30.34 | 25.37 | 14.61 |

Abbreviations: $C_{max}$ = maximum serum concentration;
$C_{trough}$ = trough serum concentration;
CV = coefficient of variation;
SD = standard deviation

TABLE 46

ALXN1210 Pharmacokinetic Parameters ($C_{max}$ and $C_{trough}$) Following the Final Maintenance Dose of ALXN1210 (Pharmacokinetic Analysis Set)

| Parameter | Statistics | All Patients (N = 96) | ≥40 to <60 kg (N = 27) | ≥60 to <100 kg (N = 61) | ≥100 kg (N = 8) |
|---|---|---|---|---|---|
| $C_{max}$ (µg/mL) | n | 96 | 27 | 61 | 8 |
| | Mean | 1384.5 | 1561.1 | 1347.4 | 1071.1 |
| | SD | 267.61 | 261.30 | 231.75 | 115.87 |
| | CV % | 19.33 | 16.74 | 17.20 | 10.82 |
| | Median | 1395.0 | 1520.0 | 1360.0 | 1040.0 |
| | Minimum | 902 | 1040 | 902 | 924 |
| | Maximum | 2320 | 2320 | 1850 | 1240 |
| | Geometric mean | 1359.3 | 1540.8 | 1327.6 | 1065.8 |
| | Geometric CV % | 19.50 | 16.57 | 17.60 | 10.68 |
| $C_{trough}$ (µg/mL) | n | 95 | 27 | 60 | 8 |
| | Mean | 500.8 | 560.7 | 484.1 | 423.5 |
| | SD | 143.17 | 135.18 | 143.05 | 108.74 |
| | CV % | 28.59 | 24.11 | 29.55 | 25.68 |
| | Median | 508.0 | 542.0 | 472.5 | 472.5 |
| | Minimum | 232 | 340 | 240 | 232 |
| | Maximum | 854 | 854 | 853 | 520 |
| | Geometric mean | 479.8 | 544.9 | 462.9 | 408.9 |
| | Geometric CV % | 30.68 | 25.00 | 31.38 | 30.43 |

Abbreviations: $C_{max}$ = maximum serum concentration;
$C_{trough}$ = trough serum concentration;
CV = coefficient of variation;
SD = standard deviation Noncompartmental PK parameters following the last maintenance dose of ALXN1210 are presented in Table 47. ALXN1210 PK steady state was achieved following multiple dose administration for all weight-based maintenance doses (Table 48).

TABLE 47

Summary of ALXN1210 Noncompartmental Analysis Pharmacokinetic Parameters Following the Last ALXN1210 Maintenance Dose (Pharmacokinetic Analysis Set)

| PK Parameter (Units) | All Patients (N = 96) Mean ± SD (% CV) | ≥40 to <60 kg (N = 27) Mean ± SD (% CV) | ≥60 to <100 kg (N = 61) Mean ± SD (% CV) | ≥100 kg (N = 8) Mean ± SD (% CV) |
|---|---|---|---|---|
| $t_{max}$ (h)[a] | 2.42 (2.0, 307.0) | 2.58 (2.3, 3.5) | 2.32 (2.0, 307.0) | 2.43 (2.3, 2.8) |
| $C_{max}$ (μg/mL) | 1384.5 ± 267.6 (19.3) | 1561.1 ± 261.3 (16.7) | 1347.4 ± 231.8 (17.2) | 1071.1 ± 115.9 (10.8) |
| $C_{trough}$ (μg/mL) | 500.8 ± 143.2 (28.6) | 560.7 ± 135.2 (24.1) | 484.1 ± 143.1 (29.6) | 423.5 ± 108.7 (25.7) |
| $AUC_\tau$ (h · μg/mL) | 1043617.0 ± 205648.0 (19.7) | 1178769.2 ± 185661.1 (29.8) | 1004866.7 ± 192953.0 (19.2) | 895000.0 ± 137834.3 (15.4) |
| CL (L/h) | 0.0015 ± 0.0006 (35.8) | 0.0019 ± 0.0004 (29.0) | 0.002 ± 0.0007 (34.5) | 0.0022 ± 0.0007 (33.1) |
| $V_z$ (L) | 3.0 ± 0.7 (22.7) | 2.4 ± 0.4 (18.2) | 3.2 ± 0.5 (17.3) | 3.8 ± 0.9 (23.7) |

Note:
Mean half-life could not be reliably estimated due to continuous therapeutic maintenance dosing.
[a]$t_{max}$ values are presented as median (minimum, maximum).
Abbreviations: $AUC_\tau$ = area under the serum concentration versus time curve over the dosing interval; $C_{max}$ = maximum observed serum concentration; $C_{trough}$ = concentrations at the end of the dosing interval; CL = total clearance; CV = coefficient of variation; SD = standard deviation; $t_{max}$ = time to maximum observed serum concentration; $V_z$ = volume of distribution at steady state.

TABLE 48

Assessment of ALXN1210 Pharmacokinetic Steady State Attainment (Pharmacokinetic Analysis Set)

| Steady State Attainment | Maintenance Dose in mg (Body Weight Group) | Slope | Lower 95% CI | Upper 95% CI | Steady State Reached? |
|---|---|---|---|---|---|
| Days 15, 71, 127, 183 | 3000 (≥40 to <60 kg) | −0.00001448 | −0.00019039 | 0.00016143 | Yes |
| Days 15, 71, 127, 183 | 3300 (≥60 to <100 kg) | 0.00003648 | −0.00006497 | 0.00013793 | Yes |
| Days 15, 71, 127, 183 | 3600 (≥100 kg) | −0.00001702 | −0.00021949 | 0.00018545 | Yes |
| Days 15, 71, 127, 183 | All patients | 0.00001648 | −0.00007798 | 0.00011093 | Yes |

Abbreviations: CI = confidence interval.

Figure 44:
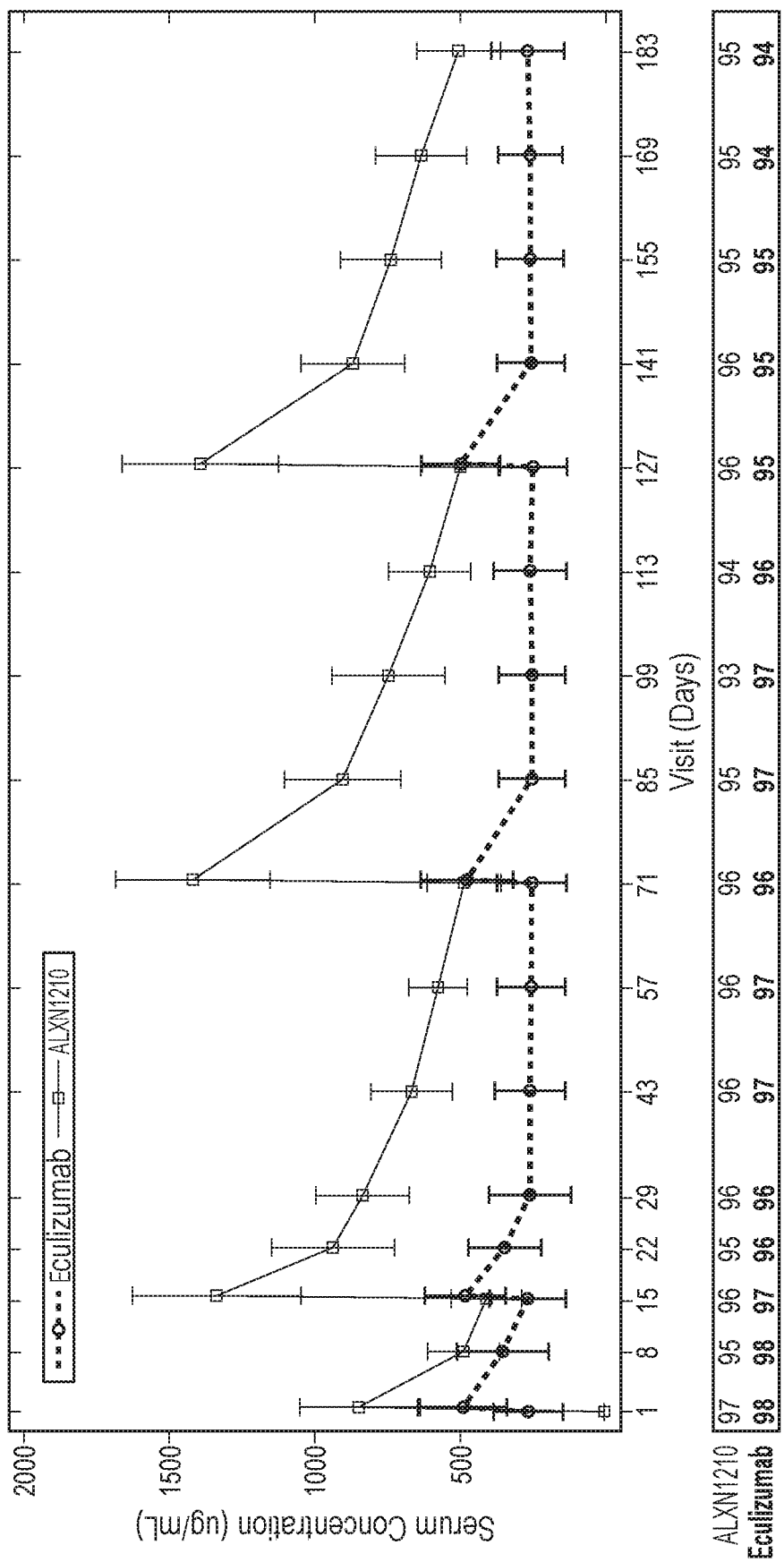
FIG. 44 is a graphical depiction of the pharmacokinetics (PK) of ALXN1210 and eculizumab showing the serum concentration of each drug over time.

FIG. 44 shows the mean serum concentration of each study drug, ALXN1210 and eculizumab, throughout the study. Weight based dosing every 8 weeks resulted in maximal steady state and trough exposures, as shown in FIG. 44. In addition, serum concentrations of ALXN1210 were consistently higher than the corresponding concentrations of eculizumab at each time point (see FIG. 44).

4. Pharmacodynamics

Figure 45:
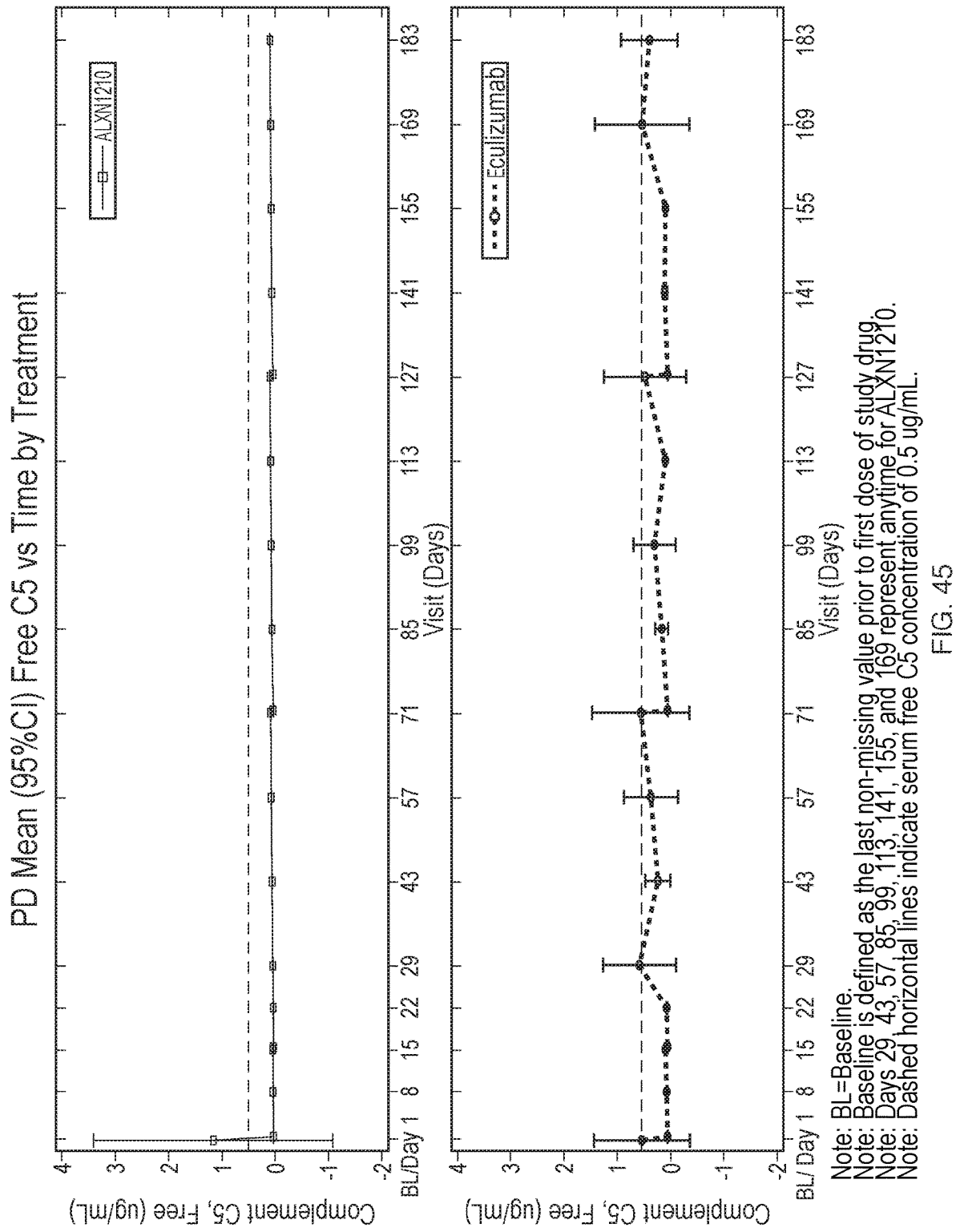
FIG. 45 is a graphical depiction of the pharmacodynamics (PD) of ALXN1210 and eculizumab showing the mean C5 concentration in the presence of each drug over time.

Treatment with ALXN1210 resulted in sustained and complete complement C5 inhibition throughout the trial and each dosing interval, as compared to the greater fluctuations as seen for the eculizumab treatment group, as shown in FIG. 45. Table 49 summarizes the mean serum free C5 concentration and the number (%) of patients with serum free C5 concentration ≥0.5 μg/mL over time following treatment with ALXN1210 (body weight based dose q8w) or eculizumab (900 mg q2w). The mean free C5 levels were inhibited by greater than 99% by the end of the first infusion with ALXN1210 and remained inhibited by greater than 99% for the duration of the study treatment period (see FIG. 45, Top panel). In contrast, the free C5 did not remain inhibited by greater than 99% at all times in the eculizumab group (see FIG. 45, bottom panel).

TABLE 49

Mean Serum Free C5 Concentration and Number (Percentage) of Patients With Serum Free C5 Concentration ≥0.5 μg/mL Over Time (Full Analysis Set)

| | ALXN1210 (N = 97) | | | Eculizumab (N = 98) | | |
|---|---|---|---|---|---|---|
| Visit | n | Mean Serum Free C5 Conc., μg/mL | n (%) of Patients With Serum Free C5 Conc. ≥0.5 μg/mL | n | Mean Serum Free C5 Conc., μg/mL | n (%) of Patients With Serum Free C5 Conc. ≥0.5 μg/mL |
| Baseline | 96 | 0.02 | 0 | 97 | 0.05 | 0 |
| Day 1, EOI | 97 | 0.01 | 0 | 98 | 0.02 | 0 |
| Day 8 | 95 | 0.02 | 0 | 98 | 0.03 | 0 |
| Day 15, predose | 96 | 0.02 | 0 | 96 | 0.06 | 1 (1.0) |
| Day 15, EOI | 93 | 0.01 | 0 | 94 | 0.02 | 0 |
| Day 2 | 95 | 0.02 | 0 | 96 | 0.03 | 0 |
| Day 29 | 95 | 0.02 | 0 | 96 | 0.55 | 2 (2.1) |

TABLE 49-continued

Mean Serum Free C5 Concentration and Number (Percentage) of Patients With Serum Free C5 Concentration ≥0.5 µg/mL Over Time (Full Analysis Set)

|  | ALXN1210 (N = 97) | | | Eculizumab (N = 98) | | |
|---|---|---|---|---|---|---|
| Visit | n | Mean Serum Free C5 Conc., µg/mL | n (%) of Patients With Serum Free C5 Conc. ≥0.5 µg/mL | n | Mean Serum Free C5 Conc., µg/mL | n (%) of Patients With Serum Free C5 Conc. ≥0.5 µg/mL |
| Day 43 | 96 | 0.04 | 0 | 97 | 0.20 | 3 (3.1) |
| Day 57 | 96 | 0.05 | 0 | 97 | 0.33 | 2 (2.1) |
| Day 71, predose | 96 | 0.06 | 0 | 96 | 0.52 | 2 (2.1) |
| Day 71, EOI | 94 | 0.02 | 0 | 92 | 0.02 | 0 |
| Day 85 | 95 | 0.04 | 0 | 97 | 0.12 | 2 (2.1) |
| Day 99 | 93 | 0.05 | 0 | 96 | 0.26 | 3 (3.1) |
| Day 113 | 94 | 0.06 | 0 | 96 | 0.06 | 1 (1.0) |
| Day 127, predose | 96 | 0.08 | 0 | 95 | 0.44 | 1 (1.1) |
| Day 127, EOI | 95 | 0.02 | 0 | 91 | 0.02 | 0 |
| Day 141 | 96 | 0.05 | 0 | 95 | 0.07 | 1 (1.1) |
| Day 155 | 95 | 0.06 | 0 | 95 | 0.06 | 1 (1.1) |
| Day 169 | 95 | 0.07 | 0 | 94 | 0.49 | 1 (1.1) |
| Day 183 | 95 | 0.08 | 0 | 94 | 0.36 | 3 (3.2) |

Figure 46:
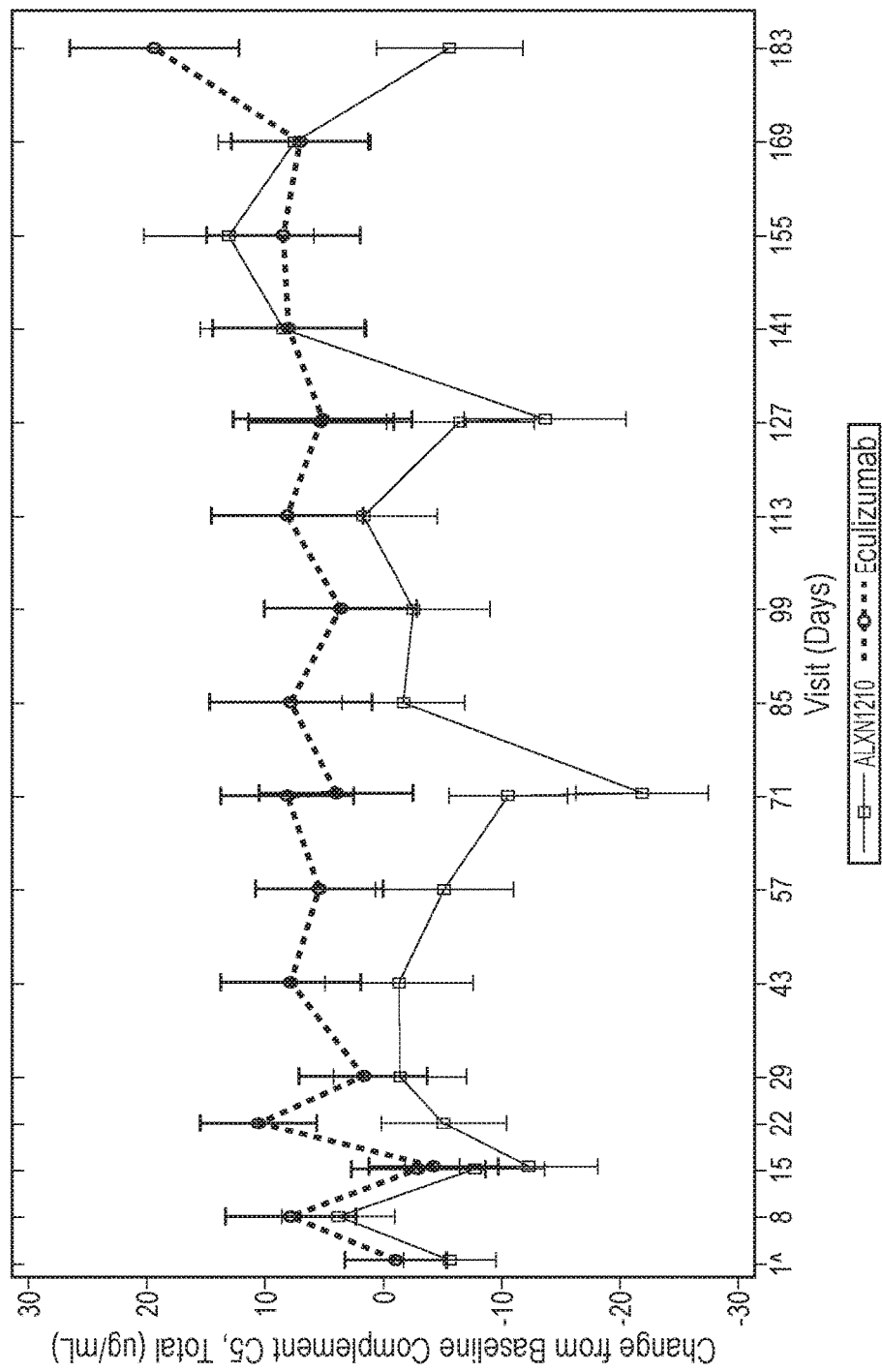
FIG. 46 is a graphical depiction of ALXN1210 and eculizumab showing the mean (±95% CI) change from baseline for total serum C5 concentration in the presence of each drug over time.

Note:
One Day 1 baseline free C5 sample from each treatment group were excluded as the data were considered biologically implausible. The exclusion was corroborated with the paired PK data, as the PK and free C5 samples were collected from the same draw.
Note:
Days 29, 43, 57, 85, 99, 113, 141, 155, and 169 represent anytime for ALXN1210 and predose for eculizumab.
For free C5, BLOQ/2 = 0.00915 µg/mL was utilized for results that were BLOQ. Percentages were calculated using n as denominator.
The ALXN1210 and eculizumab free C5 data are generated from different bioanalytical assays.
Abbreviations: BLOQ = below the limit of quantification;
C5 = complement component 5;
EOI = end of infusion The mean (±95% CI) change from baseline for total serum C5 concentration versus time profile is shown in FIG. 46. The serum total C5 values were similar at baseline between treatments and remained relatively stable throughout the treatment period, with transient decreases in total C5 concentrations observed for ALXN1210 at EOI following all infusions.

Example 6

Descriptive statistics of pharmacokinetic parameters of ravulizumab from the Phase 3 ALXN-PNH-301 and ALXN-PNH-302 described above are set forth below in Table 50.

TABLE 50

Summary of the Population of PK Model Parameters for Ravulizumab in Phase 3 Studies (ALXN-PNH-301 and ALXN-PNH-302).

| Dose Group | Arithmetic Mean (SD) Median [2.5$^{th}$-97.5$^{th}$ percentile] | | | | | |
|---|---|---|---|---|---|---|
|  | CL (L/h) | Q (L/h) | Vc (L) | Vp (L) | Vss (L) | t½β (days) |
| 2400/3000 mg (N = 68) | 0.00266 (0.000544) 0.00260 [0.00172-0.00388] | 0.0131 (0.000803) 0.0133 [0.0114-0.0141] | 2.87 (0.401) 2.86 [2.18-3.76] | 1.55 (0.121) 1.58 [1.28-1.78] | 4.42 (0.475) 4.47 [3.52-5.34] | 50.6 (8.38) 50.9 [38.0-64.3] |
| 2700/3300 mg (N = 141) | 0.00354 (0.000897) 0.00341 [0.00220-0.00584] | 0.0165 (0.00140) 0.0162 [0.0144-0.0196] | 3.65 (0.529) 3.61 [2.63-4.71] | 2.02 (0.216) 1.98 [1.68-2.45] | 5.67 (0.668) 5.69 [4.44-6.92] | 49.5 (9.25) 48.9 [33.5-69.2] |
| 3000/3600 mg (N = 13) | 0.00441 (0.000964) 0.00440 [0.00334-0.00608] | 0.0208 (0.00108) 0.0202 [0.0199-0.0231] | 4.28 (0.709) 4.08 [3.30-5.58] | 2.48 (0.221) 2.42 [2.20-2.94] | 6.77 (0.830) 6.53 [5.71-8.34] | 47.1 (8.29) 50.3 [34.5-58.2] |
| All Phase 3 Patients (N = 222) | 0.00332 (0.000941) 0.00320 [0.00190-0.00576] | 0.0157 (0.00236) 0.0155 [0.0118-0.0203] | 3.45 (0.652) 3.44 [2.41-4.75] | 1.91 (0.321) 1.88 [1.38-2.50] | 5.35 (0.916) 5.35 [3.74-7.06] | 49.7 (8.94) 49.5 [34.2-66.1] |

Abbreviations: CL = clearance; CV = coefficient of variation; PK = pharmacokinetics; Q = intercompartmental clearance; SD = standard deviation; t½β = terminal elimination half-life; Vc = volume of distribution in the central compartment; Vp = volume of distribution in the peripheral compartment.

The mean estimate of clearance (CL) for ravulizumab was 0.00332 L/h (standard deviation (SD), 0.00094). The mean SD clearance was 0.00266 L/h (0.00054) for patients with body weight of ≥40 to <60 kg, 0.00354 L/h (0.00090) for patients with body weight of ≥60 to <100 kg, and 0.00441 L/h (0.00096) for patients with body weight of ≥100 kg. The mean (SD) terminal elimination half-life of ravulizumab in 222 Phase 3 patients with PNH was 1193 hours or 49.7 (8.94) days. The mean (SD) Vss of ravulizumab was 5.35 (0.916) L.

Summaries of the individual Bayesian estimates for a Phase 3 study using eculizumab (ECU-MG-301) are set forth below in Table 51.

TABLE 51

Summaries of Individual Bayesian Estimates of Final Population of Pharmacokinetic Model (Run 72) for Study ECU-MG-301

|  | CL (L/h) | V1 (L) | V2 (L) | Q (L/h) | Observed Cmax (ug/mL) | SS Cmax (ug/mL) | SS Ctrough (ug/mL) | Term life (h) | AUC SS (ug*h/ |
|---|---|---|---|---|---|---|---|---|---|
| Mean | 0.0106 | 2.54 | 2.73 | 0.251 | 939 | 845 | 348 | 436 | 154000 |
| SD | 0.00783 | 0.758 | 0.554 | 0.107 | 353 | 295 | 180 | 152 | 68600 |
| Median | 0.00785 | 2.44 | 2.61 | 0.218 | 912 | 878 | 348 | 453 | 153000 |
| Min | 0.00362 | 1.32 | 1.76 | 0.0956 | 265 | 253 | 29.6 | 136 | 26800 |
| Max | 0.0448 | 5.25 | 4.26 | 0.605 | 1640 | 1580 | 831 | 952 | 331000 |

SS = steady state; SD = standard deviation; AUCss calculated as: DOSE/CLi where DOSE is the study specific maintenance dose (1200 mg for ECU-MG-301) and CLi is the individual posthoc clearance.

For eculizumab, the mean terminal elimination half-life for the Phase 3 ECU-MG-301 study was 436 hours or 18.1 days.

A patient having a complement-associated disorder (e.g., PNH or aHUS) is treated with a first anti-C5 antibody and then switched to treatment with a second different anti-C5 antibody. In a preferred embodiment, the second anti-C5 antibody binds to a different epitope than the first anti-C5 antibody. To ensure that the first anti-C5 antibody is cleared (e.g., "washed out") from the patient before the second (different) anti-C5 antibody is administered (e.g., to avoid issues associated with aggregation, immune complex formation, etc.), the half-life of the first anti-C5 antibody is taken into consideration. In one embodiment, the second (different) anti-C5 antibody is not administered until a duration of time corresponding to 2, 2.5, 3, 3.5, 4, 4.5, 5, 5.5, 6, 6.5, 7, or 7.5 times the half-life of the first anti-C5 antibody has passed after the final administration of the first anti-C5 antibody.

In one instance, the patient has previously been treated with eculizumab and then is switched to treatment with a different anti-C5 antibody (e.g., ravulizumab, 7086 antibody, 8110 antibody, 305LO5 antibody, SKY59 antibody, or REGN3918 antibody). When eculizumab is the first administered antibody, the second (different) anti-C5 antibody is not administered, for example, until at least 36, 45, 54, 63, 72, 81, 90, 99, 108, 117, or 126 days have passed after the final administration of eculizumab.

In another instance, the patient has previously been treated with ravulizumab and then is switched to treatment with a different anti-C5 antibody (e.g., eculizumab, 7086 antibody, 8110 antibody, 305LO5 antibody, SKY59 antibody, or REGN3918 antibody). When ravulizumab is the first administered antibody, the second (different) anti-C5 antibody is not administered, for example, until at least 100, 125, 150, 175, 200, 225, 250, 275, 300, 325, 375, or 400 days have passed after the final administration of ravulizumab.

Additionally or alternatively, techniques are used to clear or enhance clearance of the first anti-C5 antibody before switching to treatment with a second (different) anti-C5 antibody. Exemplary techniques include, but are not limited to, plasmapheresis, blood transfusions, or administering an antibody against the first anti-C5 antibody (e.g., an anti-eculizumab antibody, an anti-ravulizumab antibody, an anti-7086 antibody, an anti-8110 antibody, an anti-305LO5 antibody, an anti-SKY59 antibody, or an anti-REGN3918 antibody) to clear or enhance clearance of the first anti-C5 antibody before a second (different) anti-C5 antibody is administered.

SEQUENCE SUMMARY

SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQ ID NO: 6
QNVLNTPLT

SEQ ID NO: 7
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTVSS

SEQ ID NO: 8
DIQMTQSPSSLSASVGDRVTITCGASENIYGALNWYQQKPGKAPKLLIYG
ATNLADGVPSRFSGSGSGTDFTLTISSLQPEDFATYYCQNVLNTPLTFGQ
GTKVEIK

SEQ ID NO: 9
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDP
EVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGN
VFSCSVMHEALHNHYTQKSLSLSLGK

SEQ ID NO: 10
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTVSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP

KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK

SEQ ID NO: 11
DIQMTQSPSSLSASVGDRVTITCGASENIYGALNWYQQKPGKAPKLLIYG
ATNLADGVPSRFSGSGSGTDFTLTISSLQPEDFATYYCQNVLNTPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

SEQ ID NO: 12
QVQLVQSGAEVKKPGASVKVSCKASGHIFSNYWIQWVRQAPGQGLEW
MGEILPGSGHTEYTENFKDRVTMTRDTSTSTVYMELSSLRSEDTAVYYC
ARYFFGSSPNWYFDVWGQGTLVTSS

SEQ ID NO: 13
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSQEDP
EVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVLHEALHSHYTQKSLSLSLGK

SEQ ID NO: 14
QVQLVQSGAEVKKPGASVKVSCKASGHIFSNYWIQWVRQAPGQGLEWM
GEILPGSGHTEYTENFKDRVTMTRDTSTSTVYMELSSLRSEDTAVYYCAR
YFFGSSPNWYFDVWGQGTLVTSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVLHEALHSHYTQKSLSLSLGK

SEQ ID NO: 15
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLYITREPEVTCVVVDVSHEDP
EVQFNWYVDGMEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK

SEQ ID NO: 16
QVQLVQSGAEVKKPGASVKVSCKASGYIFSNYWIQWVRQAPGQGLEWM
GEILPGSGSTEYTENFKDRVTMTRDTSTSTVYMELSSLRSEDTAVYYCAR
YFFGSSPNWYFDVWGQGTLVTSSASTKGPSVFPLAPCSRSTSESTAALG
CLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKP
KDTLYITREPEVTCVVVDVSHEDPEVQFNWYVDGMEVHNAKTKPREEQ
FNSTFRVVSVLTVVHQDWLNGKEYKCKVSNKGLPAPIEKTISKTKGQPRE
PQVYTLPPSREEMTKNQVSLTCLVKGFYPSDIAVEWESNGQPENNYKTTP
PMLDSDGSFFLYSKLTVDKSRWQQGNVFSCSVMHEALHNHYTQKSLSLS
PGK

SEQ ID NO: 17
GASENIYHALN

SEQ ID NO: 18
EILPGSGHTEYTENFKD

SEQ ID NO: 19
GHIFSNYWIQ

SEQ ID NO: 20
QVQLVQSGAEVKKPGASVKVSCKASGHIFSNYWIQWVRQAPGQGLEW
MGEILPGSGHTEYTENFKDRVTMTRDTSTSTVYMELSSLRSEDTAVYYC
ARYFFGSSPNWYFDVWGQGTLVTSSASTKGPSVFPLAPCSRSTSESTAA
LGCLVKDYFPEPVTVSWNSGALTSGVHTFPAVLQSSGLYSLSSVVTVPSS
NFGTQTYTCNVDHKPSNTKVDKTVERKCCVECPPCPAPPVAGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSL
GK

SEQ ID NO: 21
SYAIS

SEQ ID NO: 22
GIGPFFGTANYAQKFQG

SEQ ID NO: 23
DTPYFDY

SEQ ID NO: 24
SGDSIPNYYVY

SEQ ID NO: 25
DDSNRPS

SEQ ID NO: 26
QSFDSSLNAEV

SEQ ID NO: 27
QVQLVQSGAEVKKPGSSVKVSCKASGGTFSSYAISVWRQAPGQGLEWMGG
IGPFFGTANYAQKFQGRVTITADESTSTAYMELSSLRSEDTAVYYCARDT
PYFDYWGQGTLVTSS

SEQ ID NO: 28
DIELTQPPSVSVAPGQTARISCSGDS1PNYYVYWYQQKPGQAPVLVIYDD
SNRPSGIPERFSGSNSGNTATLTISGTQAEDEADYYCQSFDSSLNAEVFG
GGTKLTVL

SEQ ID NO: 29
NYIS

SEQ ID NO: 30
IIDPDDSYTEYSPSFQG

SEQ ID NO: 31
YEYGGFDI

SEQ ID NO: 32
SGDNIGNSYVH

SEQ ID NO: 33
KDNDRPS

SEQ ID NO: 34
GTYDIESYV

SEQ ID NO: 35
EVQLVQSGAEVKKPGESLKISCKGSGYSFTNYISWVRQMPGKGLEWMGII
DPDDSYTEYSPSFQGQVTISADKSISTAYLQWSSLKASDTAMYYCARYEY
GGFDIWGQGTLVTSS

SEQ ID NO: 36
SYELTQPPSVSVAPGQTARISCSGDNIGNSYVHWYQQKPGQAPVLVIYKD
NDRPSGIPERFSGSNSGNTATLTISGTQAEDEADYYCGTYDIESYVFGGG
TKLTVL

SEQ ID NO: 37
SSYYVA

SEQ ID NO: 38
AIYTGSGATYKASWAKG

SEQ ID NO: 39
DGGYDYPTHAMHY

SEQ ID NO: 40
QASQNIGSSLA

SEQ ID NO: 41
GASKTHS

SEQ ID NO: 42
QSTKVGSSYGNH

| SEQUENCE SUMMARY |
|---|
| SEQ ID NO: 43<br>QVQLVESGGGLVQPGGSLRLSCAASGFTSHSSYYVAWVRQAPGKGLEWVG<br>AIYTGSGATYKASWAKGRFTISKDTSKNQVVLTMTNMDPVDTATYYCASD<br>GGYDYPTHAMHYWGQGTLVTVSS |
| SEQ ID NO: 44<br>DVVMTQSPSSLSASVGDRVTITCQASQNIGSSLAWYQQKPGQAPRLLIYG<br>ASKTHSGVPSRFSGSGSGTDFTLTISSLQPEDVATYYCQSTKVGSSYGNH<br>FGGGTKVEIK |
| SEQ ID NO: 45<br>QVQLVESGGGLVQPGRSLRLSCAASGFTVHSSYYMAWVRQAPGKGLEWVG<br>AIFTGSGAEYKAEWAKGRVTISKDTSKNQVVLTMTNMDPVDTATYYCASD<br>AGYDYPTHAMHYWGQGTLVTVSSASTKGPSVFPLAPSSKSTSGGTAALGC<br>LVKDYFPEPVTVSWNSGALTSGVHTFPAVLQSSGLYSLSSVVTVPSSSLG<br>TQTYICNVNHKPSNTKVDKKVEPKSCDKTHTCPPCPAPELRRGPKVFLFP<br>PKPKDTLMISRTPEVTCVVVDVSHEDPEVKFNWYVDGVEVHNAKTKPREE<br>QYNSTYRVVSVLTVLHQDWLNGKEYKCKVSNKGLPSSIEKTISKAKGQPR<br>EPQVYTLPPSREEMTKNQVSLTCLVKGFYPSDIAVEWESNGQPENNYKTT<br>PPVLDSDGSFFLYSKLTVDKSRWQQGNVFSCSVLHEALHAHYTRKELSLS<br>P |
| SEQ ID NO: 46<br>DIQMTQSPSSLSASVGDRVTITCRASQGISSSLAWYQQKPGKAPKLLIYG<br>ASETETESGVPSRFSGSGSGTDFTLTISSLQPEDFATYYCQNTKVGSSYGNT<br>FGGGTKVEIKRTVAAPSVFIFPPSDEQLKSGTASVVCLLNNFYPREAKVQ<br>WKVDNALQSGNSQESVTEQDSKDSTYSLSSTLTLSKADYEKHKVYACEVT<br>HQGLSSPVTKSFNRGEC |
| SEQ ID NO: 47<br>QVQLQESGPGLVKPSETLSLTCTVSGDSVSSSYWTWIRQPPGKGLEWIGY<br>IYYSGSSNYNPSLKSRATISVDTSKNQFSLKLSSVTAADTAVYYCAREGN<br>VDTTMIFDYWGQGTLVTVSS |
| SEQ ID NO: 48<br>AIQMTQSPSSLSASVGDRVTITCRASQGIRNDLGWYQQKPGKAPKLLIYA<br>ASSLQSGVPSRFAGRGSGTDFTLTISSLQPEDFATYYCLQDFNYPWTFGQ<br>GTKVEIK |
| SEQ ID NO: 49<br>QVQLQESGPGLVKPSETLSLTCTVSGDSVSSSYWTWIRQPPGKGLEWIGY<br>IYYSGSSNYNPSLKSRATISVDTSKNQFSLKLSSVTAADTAVYYCAREGN<br>VDTTMIFDYWGQGTLVTVSSASTKGPSVFPLAPCSRSTSESTAALGCLVK<br>DYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLFPPKPKDT<br>LMISRTPEVTCVVVDVSQEDPEVQFNWYVDGVEVHNAKTKPREEQFNSTY<br>RVVSVLTVLHQDWLNGKEYKCKVSNKGLPSSIEKTISKAKGQPREPQVYT<br>LPPSQEEMTKNQVSLTCLVKGFYPSDIAVEWESNGQPENNYKTTPPVLDS<br>DGSFFLYSRLTVDKSRWQEGNVFSCSVMHEALHNHYTQKSLSLSLGK |
| SEQ ID NO: 50<br>AIQMTQSPSSLSASVGDRVTITCRASQGIRNDLGWYQQKPGKAPKLLIYA<br>ASSLQSGVPSRFAGRGSGTDFTLTISSLQPEDFATYYCLQDFNYPWTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGEC |

What is claimed is:

1. A method of treating a human patient with Paroxysmal Nocturnal Hemoglobinuria (PNH) or atypical hemolytic uremic syndrome (aHUS), the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, and CDR1, CDR2, and CDR3 light chain sequences as set forth in SEQ ID NOs:4, 5, and 6, respectively, wherein the anti-C5 antibody, or antigen binding fragment thereof, is administered:

(a) once on Day 1 of the administration cycle at a dose of:
      2400 mg to a patient weighing ≥40 to <60 kg, 2700 mg to a patient weighing ≥60 to <100 kg, or 3000 mg to a patient weighing ≥100 kg; and
   (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

2. A method of treating a human patient with Paroxysmal Nocturnal Hemoglobinuria (PNH) or atypical hemolytic uremic syndrome (aHUS), the method comprising administering to the patient during an administration cycle an effective amount of an anti-C5 antibody, or antigen binding fragment thereof, comprising CDR1, CDR2, and CDR3 heavy chain sequences as set forth in SEQ ID NOs:19, 18, and 3, respectively, CDR1, CDR2, and CDR3 light chain sequences as set forth in SEQ ID NOs:4, 5, and 6, respectively, and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434 of a native human IgG Fc constant region, each in EU numbering, wherein the anti-C5 antibody, or antigen binding fragment thereof, is administered:
  (a) once on Day 1 of the administration cycle at a dose of: 2400 mg to a patient weighing ≥40 to <60 kg, 2700 mg to a patient weighing ≥60 to <100 kg, or 3000 mg to a patient weighing ≥100 kg; and
  (b) on Day 15 of the administration cycle and every eight weeks thereafter at a dose of 3000 mg to a patient weighing ≥40 to <60 kg, 3300 mg to a patient weighing ≥60 to <100 kg, or 3600 mg to a patient weighing ≥100 kg.

3. The method of claim 1, wherein the patient has previously been treated with eculizumab.

4. The method of claim 1, wherein the administration cycle starts at least two weeks after the patient's last dose of eculizumab.

5. The method of claim 1, wherein the patient has been treated with eculizumab:
  (a) for at least 6 months prior to Day 1 of the administration cycle; and/or
  (b) at a dose of 900 mg every 2 weeks.

6. The method of claim 1, wherein the anti-C5 antibody, or antigen-binding fragment thereof, comprises:
  (a) a heavy chain variable region depicted in SEQ ID NO:12 and a light chain variable region depicted in SEQ ID NO:8;
  (b) a heavy chain constant region depicted in SEQ ID NO:13; and/or
  (c) a heavy chain polypeptide comprising the amino acid sequence depicted in SEQ ID NO:14 and a light chain polypeptide comprising the amino acid sequence depicted in SEQ ID NO:11.

7. The method of claim 1, wherein the anti-C5 antibody, or antigen-binding fragment thereof, binds to human C5:
  (a) at pH 7.4 and 25° C. with an affinity dissociation constant ($K_D$) that is in the range 0.1 nM ≤$K_D$≤1 nM; or
  (b) at pH 6.0 and 25° C. with a $K_D$≥10 nM.

8. The method of claim 1, wherein the treatment:
  (a) maintains a serum trough concentration of the anti-C5 antibody, or antigen binding fragment thereof, of 100 μg/ml or greater during the administration cycle;
  (b) maintains a serum trough concentration of the anti-C5 antibody, or antigen binding fragment thereof, of 200 μg/ml or greater during the administration cycle;
  (c) maintains a free C5 concentration of 0.309 to 0.5 μg/mL or below;
  (d) reduces free C5 concentration by greater than 99% throughout the treatment period; and/or
  (e) reduces free C5 concentration by greater than 99.5% throughout the treatment period.

9. The method of claim 1, wherein the anti-05 antibody, or antigen binding fragment thereof, is administered at a dose of 3000 mg, 3300 mg, or 3600 mg every eight weeks after the administration cycle for up to two years.

10. The method of claim 1, wherein the anti-C5 antibody, or antigen binding fragment thereof, is formulated for intravenous administration.

11. The method of claim 1, wherein the administration cycle is a total of 26 weeks of treatment.

12. The method of claim 1, wherein the treatment results in:
  (a) terminal complement inhibition;
  (b) a reduction of hemolysis as assessed by lactate dehydrogenase (LDH) levels;
  (c) normalization of LDH levels;
  (d) normalization of LDH levels by at least day 24 of treatment;
  (e) a percent change in LDH levels (LDH-PCHG) of less than 15% as compared to treatment with eculizumab;
  (f) a reduction in breakthrough hemolysis relative to treatment with eculizumab;
  (g) an elimination of breakthrough hemolysis during the treatment period;
  (h) a reduction of breakthrough hemolysis compared to pretreatment baseline amount of breakthrough hemolysis;
  (i) at least one therapeutic effect selected from the group consisting of a reduction or cessation in abdominal pain, dyspnea, dysphagia, chest pain, erectile dysfunction;
  (j) a shift toward normal levels of a hemolysis-related hematologic biomarker selected from the group consisting free hemoglobin, haptoglobin, reticulocyte count, PNH red blood cell (RBC) clone and D-dimer;
  (k) at least one therapeutic effect selected from the group consisting of a reduction or cessation in severe hypertension, proteinuria, uremia, lethargy, fatigue, irritability, thrombocytopenia, microangiopathic hemolytic anemia, and renal function impairment;
  (l) a shift toward normal levels of Factor Ba, soluble tumor necrosis factor receptor 1 (sTNFR1), soluble vascular adhesion molecule 1 (sVCAM1), thrombomodulin, D-dimer, and cystatin C;
  (m) an increase in hemoglobin stabilization from the pretreatment baseline;
  (n) a reduction in the need for blood transfusions;
  (o) a greater than 70% increase in transfusion avoidance;
  (p) a reduction in major adverse vascular events (MAVEs);
  (q) a shift toward normal levels of a chronic disease associated biomarker selected from the group consisting estimated glomerular filtration rate (eGFR) and spot urine:albumin:creatinine and plasma brain natriuretic peptide (BNP);
  (r) a change from baseline in quality of life, assessed via the Functional Assessment of Chronic Illness Therapy (FACIT)-Fatigue Scale, version 4 and the European Organisation for Research and Treatment of Cancer, Quality of Life Questionnaire-Core 30 Scale; and/or
  (s) a change from baseline in quality of life, assessed via the Functional Assessment of Chronic Illness Therapy (FACIT)-Fatigue Scale, version 4 and the European Organisation for Research and Treatment of Cancer, Quality of Life Questionnaire-Core 30 Scale by at least 7 points from the patient's untreated baseline score.

* * * * *